US008252841B2

(12) United States Patent
Sperandio et al.

(10) Patent No.: US 8,252,841 B2
(45) Date of Patent: Aug. 28, 2012

(54) METHODS OF INHIBITING BACTERIAL VIRULENCE AND COMPOUNDS RELATING THERETO

(75) Inventors: Vanessa Sperandio, Flower Mound, TX (US); John R. Falck, Dallas, TX (US); Donald R. Stewart, Fort Worth, TX (US)

(73) Assignees: The Board of Regents of the University of Texas System, Austin, TX (US); OMM Scientific Inc., Dallas, TX (US)

( * ) Notice: Subject to any disclaimer, the term of this patent is extended or adjusted under 35 U.S.C. 154(b) by 614 days.

(21) Appl. No.: 12/254,690

(22) Filed: Oct. 20, 2008

(65) Prior Publication Data

US 2010/0048573 A1 Feb. 25, 2010

Related U.S. Application Data

(60) Provisional application No. 60/999,637, filed on Oct. 19, 2007.

(51) Int. Cl.
*A61K 31/17* (2006.01)
(52) U.S. Cl. .................................. 514/586; 514/585
(58) Field of Classification Search ................... 514/585, 514/586
See application file for complete search history.

(56) References Cited

U.S. PATENT DOCUMENTS

| 4,412,992 A | 11/1983 | Chan | 514/150 |
|---|---|---|---|
| 6,214,880 B1 * | 4/2001 | Houze | 514/595 |
| 2003/0236306 A1 | 12/2003 | Chen et al. | 514/534 |

FOREIGN PATENT DOCUMENTS

| JP | 11-268421 | 10/1999 |
|---|---|---|
| JP | 03-843586 | 11/2006 |
| WO | WO 99/45136 | 9/1999 |
| WO | WO 02/070467 | 9/2002 |
| WO | WO 03/028762 | 4/2003 |
| WO | WO 2005/016873 | 2/2005 |

OTHER PUBLICATIONS

Bacca-DeLancey et al., "*Echerichia coli* genes regulated by cell-to-cell signaling," *Proc. Natl. Acad Sci., USA*, 96:4610-4614, 1999.
Bearson and Bearson, "The role of the QseC quorum-sensing sensor kinase in colonization and norepinephrine-enhanced motility of *Salmonella enterica* serovar Typhimurium," *Microb. Pathog.*, 44:271-8, 2007.
Boyle et al., "Salmonella: from pathogenesis to therapeutics," *J. Bacteriol.*, 189:1489-1495, 2007.
Chen et al., "Structural identification of a bacterial quorum-sensing signal containing boron," *Nature*, 415:545-549, 2002.
Clarke and Sperandio, "Transcriptional autoregulation by quorum sensing *Escherichia coli* regulators B and C (QseBC) in enterohaemorrhagic *E. coli* (EHEC)," *Mol. Microbiology*, 58:441-455, 2005.

(Continued)

*Primary Examiner* — Shengjun Wang
(74) *Attorney, Agent, or Firm* — Fulbright & Jaworski

(57) ABSTRACT

The present invention relates to compounds and methods for the treatment of bacterial infections. Because their mechanism of action does not involve killing of bacteria or inhibiting their growth, the potential for these compounds to induce drug resistance in bacteria is minimized. Through inhibiting bacterial virulence, the present invention provides a novel means of treating bacterial infections.

18 Claims, 23 Drawing Sheets

OTHER PUBLICATIONS

Clarke and Sperandio, "Transcriptional regulation of flhDC by QseBC and sigma (FliA) in enterohaemorrhagic *Escherichia coli*," *Mol. Microbiology*, 57:1734-1749, 2005.

Clarke et al., "The QseC sensor kinase: a bacterial adrenergic receptor," *PNAS*, 103:10420-10425, 2006.

Crump et al., "Reevaluating fluoroquinolone breakpoints for *Salmonella enterica* serotype Typhi and for non-Typhi salmonellae," *Clin. Infect. Dis.*, 37:75-81, 2003.

Davis et al., "Changes in antimicrobial resistance among *Salmonella enterica* Serovar typhimurium isolates from humans and cattle in the Northwestern United States, 1982-1997," *Emerg. Infect. Dis.*, 5:802-806, 1999.

de Kievit and Iglewski, "Bacterial quorum sensing in pathogenic relationships," *Infect. Immun.*, 68(9):4839-4849, 2000.

Ge et al., "Identification of *Escherichia* colo O157:H7 and other enterohemorrhagic serotypes by EHEC-hly A targeting, strand displacement amplificiation, and fluorescence polarization," *Molecular and Cellular Probes*, 16:85-92, 2002.

Golovliov et al., "Identification of proteins of *Francisella tularensis* induced during growth in macrophages and cloning of the gene encoding a prominently induced 23-kilodalton protein," *Infect. Immun.*, 65:2183-2189, 1997.

Jarvis et al., "Enteropathogenic *Escherichia coli* contains a putative type III secretion system necessary for the export of proteins involved in attaching and effacing lesion formation," *Proc. Natl. Acad. Sci., USA*, 92:7996-8000, 1995.

Jorgensen and Slots, "Practical antimicrobial periodontal therapy," *Compend. Contin. Educ. Dent.*, 21:111-4, 2000 (Abstract).

Kansagra et al., "Azetidinones from ρ, ρ'-N-aminophenylacetamidobenzenesulphonamide: a dye intermediate as antimicrobial agents," *Oriential Journal of Chemistry*, 19:209-212, 2003.

Kaper and O'Brien, In: *Escherichia coli O157:H7 and other Shiga toxin producing E. coli strains*, 1$^{st}$ Ed., ASM Press, Washington, DC, 1998.

Kimmitt et al., "Induction of type 2 Shiga toxin synthesis in *Escherichia coli* O157 by 4-quinolones," *Lancet*, 353:1588-1589, 1999.

Kimmitt et al., "Toxin gene expression by shiga toxin-producing *Escherichia coli*: the role of antibiotics and the bacterial SOS response," *Emerg. Infect. Dis.*, 6:458-465, 2000.

Lyon and Muir, "Chemical signaling among bacteria and its inhibition," *Chem. Biol.*, 10:1007-1021, 2003.

Lyte et al., "Norepinephrine induced growth and expression of virulence associated factors in enterotoxigenic and enterohemorrhagic strains of *Escherichia coli*," *Adv. Exp. Med. Biol.*, 412:331-9, 1997.

Maris et al., "Alpha- and beta-adrenergic receptor blockade protect against mortality during muirne *Escherichia coli* peritonitis by different mechanisms," *Abstr. Intersci. Conf. Antimicrob. Agents Chemother.*, 42: (Abstract No. B-1418), 2002.

Miller et al., "Substituted sulfanilamides. I. N$^4$-acyl derivatives," *J. Am. Chem. Soc.*, 61:1198-1200, 1939.

Nakaya et al., "Life-threatening infantile diarrhea from fluoroquinolone-resistant *Salmonella enterica* typhimurium with mutations in both gyrA and parC," *Emerg. Infect. Dis.*, 9:255-257, 2003.

Plant et al., "Are the Lsh and Ity disease resistance genes at one locus on mouse chromosome 1?" *Nature*, 297:510-511, 1982.

Rasko et al., "Targeting QseC signaling and virulence for antibiotic development," *Science*, 321:1078-1080, 2008.

Rasmussen and Gibskov, "Quorum sensing inhibitors: a bargain of effects," *Microbiology*, 152:895-904, 2006.

Samrakandi et al., "Genome diversity among regional populations of *Francisella tularensis* subspecies *tularensis* and *Francisella tularensis* subspecies *holarctica* isolated from the US," *FEMS Microbiol. Lett.*, 237:9-17, 2004.
Schauder et al., "The LuxS family of bacterial autoinducers: biosynthesis of a novel quorum-sensing signal molecule," *Mol. Microbiol.*, 41(2):463-476, 2001.
Sharp and Sperandio, "QseA directly activates transcription of LEE1 in enterohemorrhagic *Escherichia coli*," *Infect. Immun.*, 75:2432-2440, 2007.
Shehata et al., "Sulfamido-o-toluic acid azide and its urea and urethane derivatives," *Proceedings of the Indian National Science Academy, Part A: Physical Sciences*, 52:1413-19, 1986.
Sperandio et al., "Bacteria-host communication: the language of hormones," *Proc. Natl. Acad. Sci. USA*, 100:8951-6, 2003.
Sperandio et al., "Quorum sensing controls expression of the type III secretion gene transcription and protein secretion in enterohemorrhagic and enteropathogenic *Escherichia coli*," *Proc Natl. Acad. Sci. USA*, 96:15196-201, 1999.
Sperandio et al., "Quorum-sensing *Escherichia coli* regulator A: a regulator of the LysR family involved in the regulation of the locus of enterocyte effacement pathogenicity island in enterohemorrhagic *E. coli*," *Infection and Immunity*, 70:3085-3093, 2002.
Sperandio et al., "Quorum sensing *Escherichia coli* regulators B and C (QseBC): a novel two-component regulatory system involved in the regulation of flagella and motility by quorum sensing in *E. coli*," *Mol. Microbiol.*, 43:809-23, 2002.
Sperandio et al., "Quorum sensing is a global regulatory mechanism in enterohemorrhagic *Escherichia coli* O157:H7," *J. Bacteriology*, 183(17):5187-5197, 2001.
Surette and Bassler, "Quorum sensing in *Escherichia coli* and *Salmonella typhimurium*," *Proc. Natl. Acad Sci., USA*, 95:7046-7050, 1998.
Tannock et al., "Ecological behavior of *Lactobacillus reuteri* 100-23 is affected by mutation of the luxS gene," *Appl. Environ. Microbiol.*, 71:8419-25, 2005.
von Bodman et al., "Quorum sensing in plant-pathogenic bacteria," *Ann. Rev. Phytopath.*, 41:455-482, 2003.
Walters and Sperandio, "Autoinducer 3 and epinephrine signaling in the kinetics of locus of enterocyte effacement gene expression in enterohemorrhagic *Escherichia coli*," *Infect. Immun.*, 74:5445-5455, 2006.
Walters et al., "AI-3 synthesis is not dependent on luxS in *Escherichia coli*," *J. Bacter.*, 188:5668-5681, 2006.
Weill et al., "Ciprofloxacin-resistant *Salmonella* Kentucky in travelers," *Emerg. Infect. Dis.*, 12:1611-1612, 2006.
Weiss et al., "In vivo negative selection screen identifies genes required for *Francisella* virulence," *Proc. Natl. Acad. Sci. USA*, 104:6037-6042, 2007.
International Search Report and Written Opinion, issued in Application No. PCT/US2008/080533, mail date Nov. 23, 2009.
"The Merck Index," Merck & Co., Inc., Whitehouse Station, New Jersey, pp. 1721, compound 9727, 2001.
Database accession No. RN: 5779-20-4, Nov. 1984.
Database accession No. RN: 6986-80-7, Nov. 1984.
Fujikawa et al., "Chemotherapeutic agents against *Mycobacterium tuberculosis* XXVI. Synthesis and antituberculous activity of phenylthiourea, p-ethoxyphenylthiourea and 3-bromo-3-ethoxyphenylthiourea derivatives," Database accession No. 1971:141216, May 1984.
Gernez-Rieux and Devulder, "Comparative investigation in vitro of the sensibility of atypical mycobacteria to cycloserine and to other antibacterial substances," *Scandinavian Journal of Respiratory Diseases*, 71:22-34, 1970.
Lesieur, "Antiseptics: classification and mode of action," *Bulletin De La Societe De Pharmacie De Lille*, 32:233-261, 1976.
Pitea et al., "Studies on some p-substituted benzenesulfonamide derivatives," *Arch. Pharm.*, 309:586-591, 1976.
Xuong, "Tuberculostatic activity of some p-sulphonamidothiocarbanilides," *Comptes Rendus De L'Academie Des Sciences*, 240:1378-1380, 1955.
Invitation to Pay Additional Fees (partial search report), issued in Application No. PCT/US2008/080533, mail date Sep. 18, 2009.
Beaver et al., "The preparation and bacteriostatic activity of substituted ureas," *Journal of American Chemical Society*, 79:1236-1245, 1957.
Chough and Ko, "Synthetic studies on chemotherapeutic agents. II. Synthesis, antibacterial, and antitubercular activity of N,N'-disubstituted thiourea derivatives," *Journal of the Pharmaceutical Society of Korea*, 15:87-92, 1971.

El-Gaby et al., "Preparation of some hithero unknown thiosemicarbazide, thiourea, bisthiourea, benzoazole derivatives bearing quinoxalin-2-yl moiety and evaluate their biological activity," *Afindad*, 60:358-368, 2003.

Gheorghiu et al., "Sulfonamides. V. The antituberculous action of certain new thioureas, sulfonamide derivatives, and of aromatic amino acids," *Studii Si Cercetari De Chimie*, 4:47-56, 1956.

Ivanov and Popov, "1-Phenyl and u-allyl-3-sulfamoylthioureas," Chemical Abstracts Service, Columbus, Ohio, Database accession No. 1968:68626, May 12, 1984.

English Translation of Office Communication issued in Chinese patent application No. 200880120028.1, dated Dec. 7, 2011.

* cited by examiner

Table S1. QseC Homologs

| Organism | Annotation | GenBank Accession | Similarity | Identity |
|---|---|---|---|---|
| Shigella flexneri 2a str. 301 | sensor protein QseC | NP_708838.1 | 93 | 92 |
| Citrobacter koseri ATCC BAA-895 | hypothetical protein CKO_04415 | YP_001455907.1 | 89 | 80 |
| Enterobacter sp. 638 | sensor protein QseC | YP_001178140.1 | 83 | 69 |
| Salmonella typhimurium LT2 | sensor protein QseC | NP_462093.1 | 87 | 79 |
| Salmonella enterica subsp. enterica serovar Typhi str. CT18 | sensor protein QseC | NP_457571.1 | 87 | 78 |
| Yersinia mollaretii ATCC 43969 | COG0642: Signal transduction histidine kinase | ZP_00825878.1 | 75 | 61 |
| Klebsiella pneumoniae subsp. pneumoniae MGH 78578 | putative 2-component sensor protein | YP_001337067.1 | 83 | 71 |
| Haemophilus influenzae PittGG | sensor protein QseC | YP_001291883.1 | 66 | 44 |
| Pasteurella multocida subsp. multocida str. Pm70 | YgiY | NP_245152.1 | 65 | 46 |
| Coxiella burnetii RSA 493 | sensor histidine kinase | NP_820223.1 | 49 | 32 |
| Burkholderia phymatum STM815 | periplasmic sensor signal transduction histidine kinase | ZP_01500068.1 | 53 | 36 |
| Ralstonia eutropha H16 | signal transduction histidine kinase | YP_725931.1 | 58 | 37 |
| Legionella pneumophila str. Paris | hypothetical protein lpp1254 | YP_123578.1 | 54 | 30 |
| Bordetella parapertussis 12822 | two-component system histidine kinase | NP_884854.1 | 56 | 37 |
| Francisella tularensis subsp. tularensis SCHU S4 | sensor histidine kinase | YP_169166.1 | 57 | 32 |
| Pseudomonas aeruginosa | probable two-component sensor | AAG08163.1 | 51 | 31 |
| Pseudomonas fluorescens Pf-5 | sensor histidine kinase | YP_260953.1 | 52 | 31 |
| Vibrio sp. | signal transduction histidine kinase | VVA0112 | 48 | 29 |
| Erwinia carotovora subsp. atroseptica SCRI1043 | sensor protein QseC | YP_048139.1 | 69 | 56 |
| Actinobacillus pleuropneumoniae serovar 1 str. 4074 | COG0642: Signal transduction histidine kinase | ZP_00204505.1 | 61 | 38 |
| Yersinia pestis CO92 | two-component system sensor protein | CAL22096.1 | 50 | 33 |
| Yersinia pseudotuberculosis IP 32953 | two-component system sensor protein | CAH19708.1 | 50 | 32 |
| Yersinia enterocolitica subsp. enterocolitica 8081 | sensor protein BasS/PmrB | YP_001004792.1 | 50 | 31 |
| Chromobacterium violaceum ATCC 12472 | sensor protein qseC | NP_900562.1 | 58 | 42 |

FIG. 2

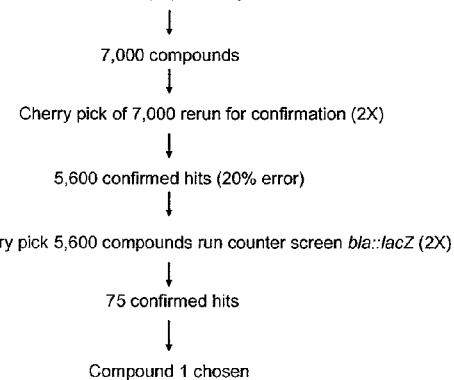
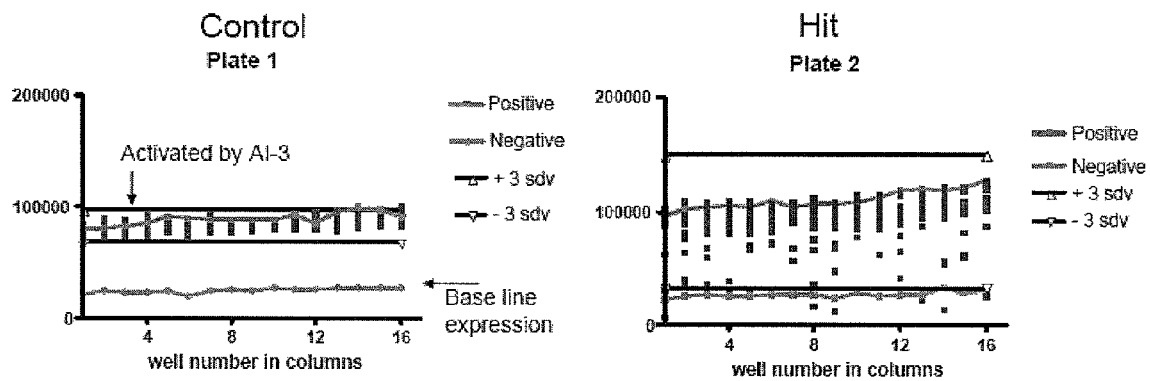
FIG. 5

A

B

A

B

C

D

E

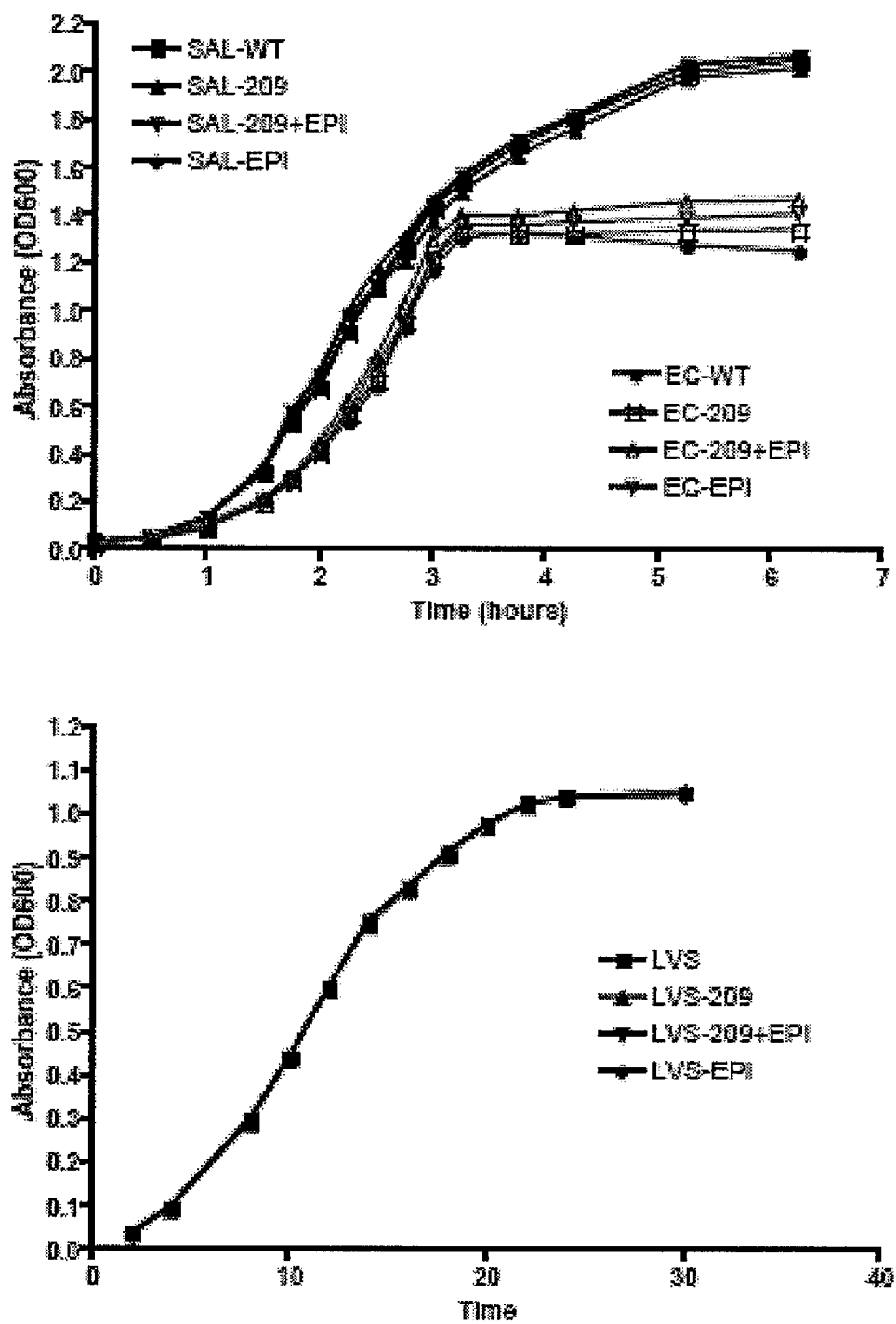
FIG. 8F (top and bottom)

A

B

C

D

E

| Blood Chemistry | CONTROL | | | | | LED209 | | | | |
|---|---|---|---|---|---|---|---|---|---|---|
| | 2781C | 2782C | 2783C | Average | Stdev | 2784 | 2785 | 2786 | Average | Stdev |
| CHOL (mg/dl) | 144.0 | 109.0 | 93.0 | 115.3 | 26.1 | 84.0 | 137.0 | 145.0 | 122.0 | 33.2 |
| TRG (mg/dl) | 75.0 | 157.0 | 67.0 | 99.7 | 49.8 | 94.0 | 101.0 | 103.0 | 99.3 | 4.7 |
| GGT (u/l) | NT | NT | NT | | | NT | NT | NT | | |
| ALT (u/l) | 31.0 | 35.0 | 27.0 | 31.0 | 4.0 | 33.0 | 27.0 | 35.0 | 31.7 | 4.2 |
| AST (u/l) | 112.0 | 96.0 | 106.0 | 104.7 | 8.1 | 130.0 | 135.0 | 96.0 | 120.3 | 21.2 |
| ALK (u/l) | 102.0 | 88.0 | 124.0 | 104.7 | 18.1 | 129.0 | 123.0 | 172.0 | 141.3 | 26.7 |
| TBIL (mg/dl) | 0.2 | 0.3 | 0.2 | 0.2 | 0.1 | 0.2 | 0.2 | 0.2 | 0.2 | 0.0 |
| GLU (mg/dl) | 215.0 | 241.0 | 238.0 | 231.3 | 14.2 | 261.0 | 275.0 | 325.0 | 287.0 | 33.6 $p=0.058$ |
| PHOS (mg/dl) | 11.3 | 9.5 | 8.3 | 9.7 | 1.5 | 10.5 | 11.5 | 11.1 | 11.0 | 0.5 |
| TPR (g/dl) | 4.5 | 4.4 | 4.3 | 4.4 | 0.1 | 4.5 | 4.3 | 4.3 | 4.4 | 0.1 |
| CAL (mg/dl) | 9.2 | 9.5 | 9.4 | 9.4 | 0.2 | 9.6 | 9.5 | 9.7 | 9.6 | 0.1 |
| BUN (mg/dl) | 25.0 | 29.0 | 25.0 | 26.3 | 2.3 | 19.0 | 15.0 | 23.0 | 19.0 | 4.0 $p=0.051$ |
| CRE (mg/dl) | 0.2 | 0.2 | 0.2 | 0.2 | 0.0 | 0.1 | 0.2 | 0.2 | 0.2 | 0.1 |
| ALB (g/dl) | 2.7 | 2.6 | 2.6 | 2.6 | 0.1 | 2.7 | 2.6 | 2.5 | 2.6 | 0.1 |
| NA (meq/l) | QNS | QNS | QNS | | | QNS | QNS | QNS | | |
| K (meq/l) | QNS | QNS | QNS | | | QNS | QNS | QNS | | |
| CL (meq/l) | QNS | QNS | QNS | | | QNS | QNS | QNS | | |
| CBC and Differential | CONTROL | | | | | LED209 | | | | |
| | 2781C | 2782C | 2783C | Average | Stdev | 2784 | 2785 | 2786 | Average | Stdev |
| WBC (K/uL) | 1.42 | 1.4 | 1.32 | 1.4 | 0.1 | 1.44 | 1.8 | 1.22 | 1.5 | 0.3 |
| NE (K/uL) | 0.19 | 0.13 | 0.05 | 0.1 | 0.1 | 0.11 | 0.17 | 0.12 | 0.1 | 0.0 |
| LY (K/uL) | 1.13 | 1.16 | 1.14 | 1.1 | 0.0 | 1.17 | 1.51 | 0.99 | 1.2 | 0.3 |
| MO (K/uL) | 0.08 | 0.1 | 0.13 | 0.1 | 0.0 | 0.15 | 0.11 | 0.09 | 0.1 | 0.0 |
| EO (K/uL) | 0.01 | 0 | 0 | 0.0 | 0.0 | 0 | 0 | 0.02 | 0.0 | 0.0 |
| BA (K/uL) | 0 | 0 | 0 | 0.0 | 0.0 | 0 | 0 | 0 | 0.0 | 0.0 |
| NE (%) | 13.44 | 9.53 | 3.88 | 9.0 | 4.8 | 7.83 | 9.69 | 10.24 | 9.3 | 1.3 |
| LY (%) | 79.33 | 83.16 | 86.08 | 82.9 | 3.4 | 81.18 | 83.86 | 80.99 | 82.0 | 1.6 |
| MO (%) | 5.97 | 7.19 | 9.9 | 7.7 | 2.0 | 10.75 | 6.36 | 7.14 | 8.1 | 2.3 |
| EO (%) | 1.02 | 0.12 | 0.13 | 0.4 | 0.5 | 0.23 | 0.09 | 1.63 | 0.7 | 0.9 |
| BA (%) | 0.24 | 0 | 0 | 0.1 | 0.1 | 0 | 0 | 0 | 0.0 | 0.0 |
| RBC (M/uL) | 6.78 | 7.61 | 7.65 | 7.3 | 0.5 | 7.49 | 8.64 | 6.21 | 7.4 | 1.2 |
| Hb (g/dL) | 10.4 | 13 | 11.6 | 11.7 | 1.3 | 12.3 | 13.9 | 9.9 | 12.0 | 2.0 |
| HCT (%) | 31.8 | 42.5 | 35 | 36.4 | 5.5 | 41.5 | 43.1 | 30.9 | 38.5 | 6.6 |
| MCV (fL) | 46.9 | 55.9 | 45.8 | 49.5 | 5.5 | 55.4 | 49.9 | 49.7 | 51.7 | 3.2 |
| MCH (pg) | 15.3 | 17.1 | 15.2 | 15.9 | 1.1 | 16.4 | 16.1 | 15.9 | 16.1 | 0.3 |
| MCHC (g/dL) | 32.7 | 30.6 | 33.1 | 32.1 | 1.3 | 29.6 | 32.3 | 32 | 31.3 | 1.5 |
| RDW (%) | 17.2 | 16.2 | 16.7 | 16.7 | 0.5 | 17.3 | 18 | 17.6 | 17.6 | 0.4 |
| PLT (K/uL) | 873 | 1132 | 1096 | 1033.7 | 140.3 | 1320 | 766 | 1139 | 1075.0 | 282.5 |
| MPV (fL) | 5.4 | 4.7 | 4.7 | 4.9 | 0.4 | 5.1 | 5 | 5 | 5.0 | 0.1 |

FIG. 18

METHODS OF INHIBITING BACTERIAL VIRULENCE AND COMPOUNDS RELATING THERETO

The present application claims benefit of U.S. Provisional Application Ser. No. 60/999,637, filed Oct. 19, 2007, the entire contents of which are hereby incorporated by reference.

This invention was made with government support under grant numbers 1-RO3-NS053582-01 and RO1 GM31278 awarded by the National Institutes of Health (NIH). The government has certain rights in the invention.

BACKGROUND OF THE INVENTION

1. Field of the Invention

The present invention generally relates to the fields of bacteriology and infectious diseases. More specifically, it relates to inhibitors of certain bacterial signaling mechanisms and bacterial infection treatments using these inhibitors.

2. Description of Related Art

Treatment of bacterial infections typically involves administration of one or more antibiotics. These agents, while often initially effective, may cause development of bacterial resistance to one or more types of antibiotics. Indeed, multi-drug resistant bacterial infections are a significant health concern throughout the world. Treatment methods that effectively eliminate bacterial infections without inducing bacterial resistance are therefore needed.

Quorum sensing (QS) is a mechanism that allows bacteria to respond to hormone-like molecules called autoinducers (AI) and is responsible for controlling a plethora of virulence genes in several bacterial pathogens. Because QS is not directly involved in essential processes such as growth of the bacteria, inhibition of QS should not yield a selective pressure for development of resistance (Rasmussen and Givskov, 2006).

The present inventors have previously reported that a signaling cascade in enterohemorrhagic *E. coli* O157:H7 (EHEC) is involved with QS by signaling with autoinducer-3 (AI-3) (Clarke et al., 2006). The AI-3/epinephrine (epi)/norepinephrine (NE) inter-kingdom signaling cascade activates expression of the flagella regulon (necessary for the bacteria to swim through the mucus layer, and reach the epithelial barriers), the LEE genes (encodes a specialized secretory pathway, through which bacteria secrete toxins to the mammalian cells, which culminate in diarrhea) and Shiga toxin genes (responsible for hemolytic uremic syndrome (HUS)) in EHEC (Sperandio et al., 2003; Clarke et al., 2006; Walters et al., 2006). AI-3 and epinephrine/NE are agonistic signals, and response to both signals can be blocked by adrenergic antagonists such as phentolamine or propranolol (Sperandio et al., 2003; Clarke et al., 2006; Walters et al., 2006; Walter and Sperandio, 2006). These signals are sensed by sensor kinases in the membrane of EHEC that relay this information through a complex regulatory cascade that activates the expression of the flagella regulon, the LEE genes and Shiga toxin. QseC (Quorum sensing *E. coli* regulator C) is one of these sensor kinases. QseC specifically senses AI-3/epinephrine and NE to augment its phosphorylation state, and that QseC directly binds to NE (Clarke et al., 2006). QseC's recognition of these signals can be blocked with the α-adrenergic antagonist phentolamine (Clarke et al., 2006). The QseC regulon is very complex and is intrinsically involved in the regulation of all known, and potentially several unknown, EHEC virulence genes.

Manipulation of QseC and/or the AI-3/epi/NE signaling cascade may offer a means of controlling bacterial virulence and thus, bacterial infections. Such means may minimize the probability of inducing bacterial resistance relative to conventional antibiotics. Agents that modulate these systems therefore merit investigation.

SUMMARY OF THE INVENTION

The present invention is based on the discovery that certain compounds inhibit bacterial virulence by interfering with bacterial host communication. In general, these compounds do not kill or inhibit bacterial growth, but instead interfere with the bacteria's ability to recognize signals to activate its virulence genes. This is a novel strategy to fight bacterial infection: instead of "attacking" the bacterial cell, these compounds "confuse" communication to render the cell "blind" to the host. Because this strategy does not attack the bacteria per se as do conventional antibiotics, the evolutionary pressure for bacteria to evolve resistance mechanisms to this type of treatment is low. This approach has broad applicability as it is useful not only for certain mammalian bacterial pathogens, but also certain plant bacterial pathogens, such as *Erwinia* and *Ralstonia*. Indeed, compounds of the present invention may be applied in any number of medical (e.g., infection treatment), agricultural (e.g., plant disease eradication), or environmental (e.g., elimination of environmentally destructive species) purposes.

Accordingly, compounds of the present invention may, in certain embodiments, be inhibitors of quorum sensing that would otherwise lead to pathogenesis or virulence. Thus, compounds of the present invention, in certain embodiments, inhibit virulence. Compounds of the present invention may, in certain embodiments, be inhibitors of AI-3/epinephrine/NE signaling, such as in EHEC, *Salmonella* and *F. tularensis* pathogenesis. For example, in certain embodiments, compounds of the present invention inhibit Shiga toxin production. In certain embodiments, the compounds of the present invention inhibit QseC (Quorum sensing *E. coli* regulator C), a histidine sensor kinase. Compounds of the present invention may also be used to treat infections in plants. In certain embodiments, compounds of the present invention inhibit virulence but do not kill bacteria (ie., they are not bacteriocidal) nor are they bacteriostatic. Other methods of the present invention are described herein.

Compounds of the present invention that may be employed in any method of the present invention are described herein. In certain embodiments, a non-limiting compound of the present invention is one that falls into a category represented by the following table:

TABLE 1

Non-limiting examples of compounds of the present invention.

| A (bound to A) | B (may be ortho, meta, or para to D when C is a 6-membered ring) | C 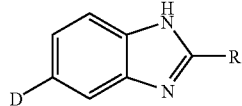 | D | E (bound to D) |
|---|---|---|---|---|
| alkyl<br>aryl<br>aralkyl<br>H<br>polymer tail<br>polymer backbone<br>linker-polymer backbone | urea<br>thiourea<br>—C(O)NR—<br>—NRC(O)—<br>—NRC(O)C(O)—NR—<br>—ROC(O)NR—<br>—RN(R)C(O)O— | the aryl ring is substituted by at least B and D; remaining ring atoms may be optionally substituted by alkyl and/or wherein B and D are ortho and further comprise a heterocycle fused to the ring, such as shown below, wherein R = E: | —SO$_2$NR—<br>—NRSO$_2$—<br>—S(O)$_2$—<br>—S(O)—<br>—N(R)R—<br>—RN(R)—<br>—C(O)NR—<br>—NRC(O)— | alkyl<br>aryl<br>aralkyl<br>H<br>polymer tail<br>polymer<br>backbone<br>linker-polymer backbone | wherein R is H or alkyl, or together with the nitrogen(s) forms a cyclic group, and wherein each R may be the same or different In certain embodiments of compounds of Table 1, only ortho B/D substituents are contemplated. In certain embodiments, only meta B/D substituents are contemplated. In certain embodiments, only para B/D substituents are contemplated.

Compounds of formula (V), below, may be employed in any method described herein. For example, the present invention contemplates a method of treating or preventing bacterial infection in a subject, comprising administering to the subject an effective amount of a compound of formula (V):

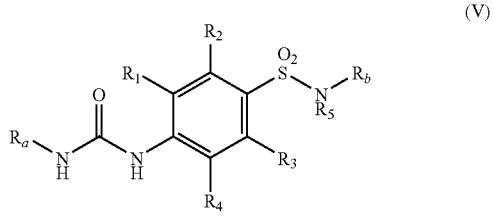

(V)

wherein: $R_a$ and $R_b$ are each independently aryl or aralkyl, such as

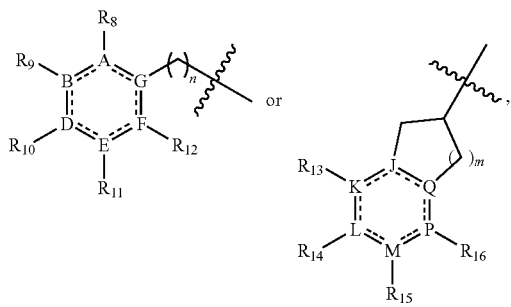

wherein: the dotted lines represent single or double bonds; A, B, D, E, F, G, J, K, L, M, P and Q are each independently carbon or nitrogen; $R_8$-$R_{16}$ are each H, alkyl, alkylamino, dialkylamino, trialkylammonium, alkoxy, halo, hydroxy, thiol, —NO$_2$, —CO$_2$H, —SO$_2$NH-aryl, —C(O)CH$_3$, —OCH$_3$, —OCF$_3$—CF$_3$, —NH$_2$, or wherein two consecutive R groups together form a 1,3-dioxolanyl group; m is 1 or 2; and n is 0-3; $R_1$-$R_5$ are each independently H or alkyl; or $R_5$ and $R_b$, together with the nitrogen to which they are attached, form one of the following groups:

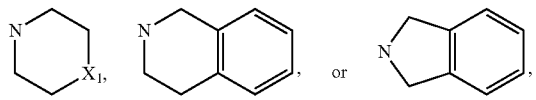

wherein $X_1$ is oxygen or alkylamino. In certain embodiments, $R_8$-$R_{16}$ are each independently H, unsubstituted alkyl, unsubstituted alkylamino, unsubstituted dialkylamino, unsubstituted trialkylammonium, or unsubstituted alkoxy. In certain embodiments, $R_8$-$R_{16}$ are each independently H, substituted alkyl, substituted alkylamino, substituted dialkylamino, substituted trialkylammonium, or substituted alkoxy. In certain embodiments, each substituent of substituted alkyl, substituted alkylamino, substituted dialkylamino, or substituted alkoxy is independently —CH$_3$, halo, hydroxy, thiol, —NO$_2$, —CO$_2$H, —SO$_2$NH-aryl, —C(O)CH$_3$, —OCH$_3$, —OCF$_3$, —CF$_3$, —NH$_2$, or morpholinyl, or any other substituent described herein. In certain embodiments, $R_8$-$R_{16}$ are each independently lower alkyl, lower alkylamino, lower dialkylamino, lower trialkylammonium, or lower alkoxy. In certain embodiments, $R_5$ is lower alkyl or unsubstituted alkyl. In certain embodiments, $R_1$-$R_4$ are each independently H or lower alkyl. In certain embodiments, $X_1$ is substituted lower alkylamino. Non-limiting examples of substituents of the —SO$_2$NH-aryl, alkyl, aryl, aralkyl, alkylamino, dialkylamino, trialkylammonium and alkoxy groups and lower versions thereof, and substituents comprising these groups, as noted, of compounds of formula (V) include —CH$_3$, halo, hydroxy, thiol, —NO$_2$, —CO$_2$H, —SO$_2$NH-aryl, —C(O)CH$_3$, —OCH$_3$, —OCF$_3$—CF$_3$, and —NH$_2$. Non-limiting examples of compounds of formula (V) include:

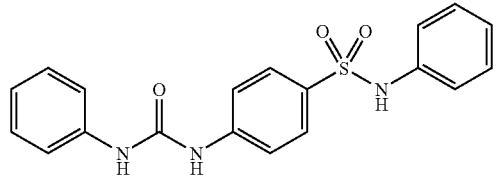

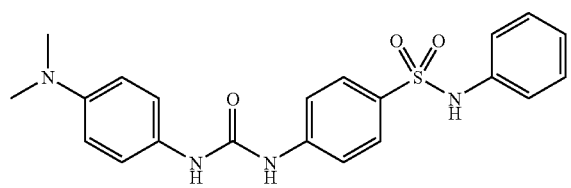
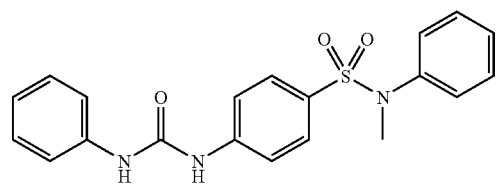
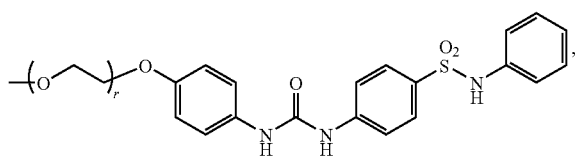
wherein r = 3-100;
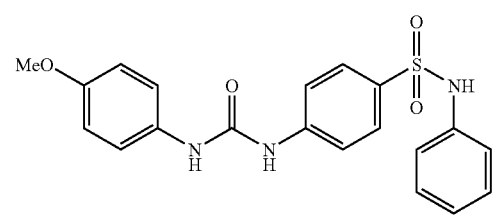
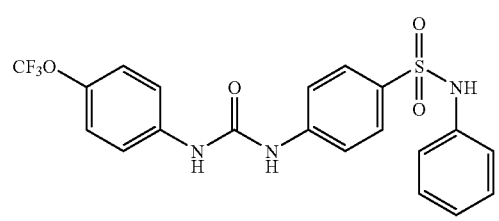
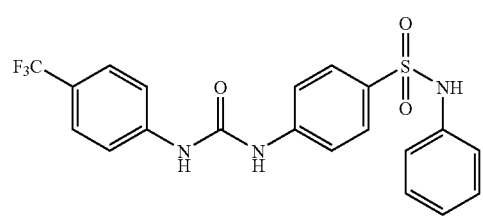
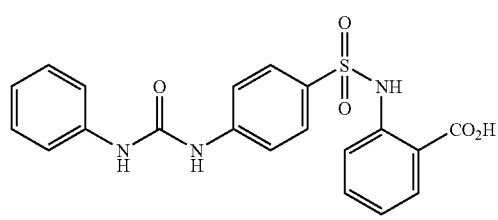
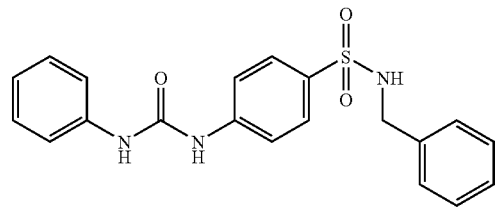
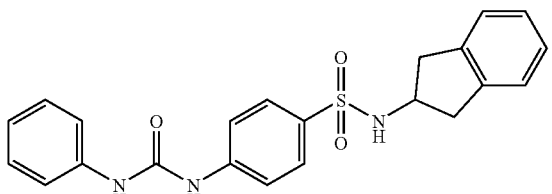
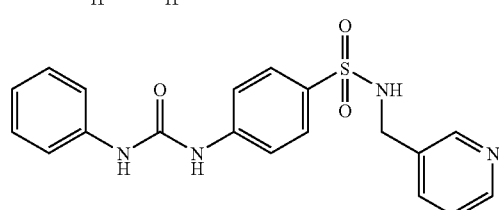
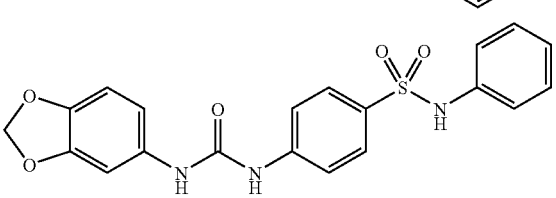
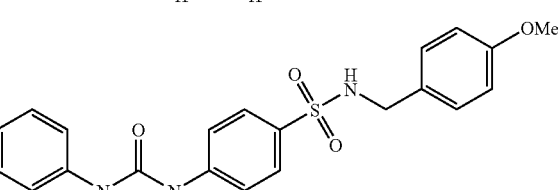
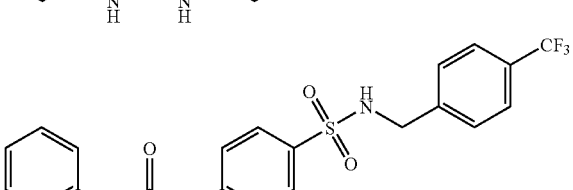
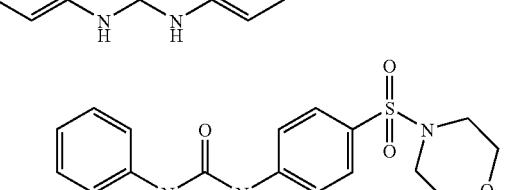
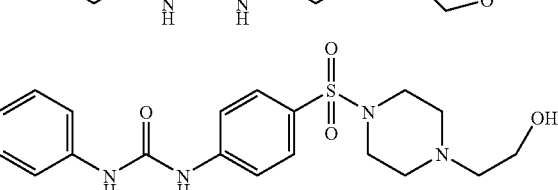
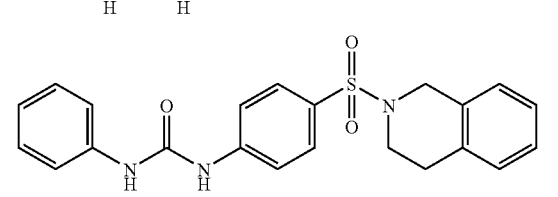
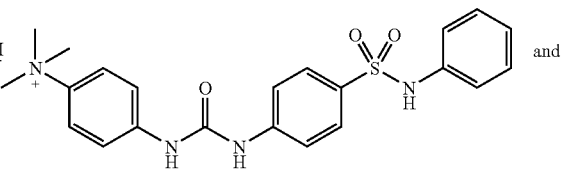
and

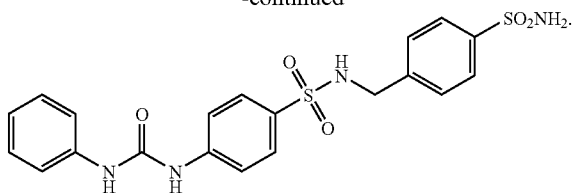

Compounds of formula (VI), below, may be employed in any method described herein. For example, the present invention contemplates a method of treating or preventing bacterial infection in a subject, comprising administering to the subject an effective amount of a compound of formula (VI):

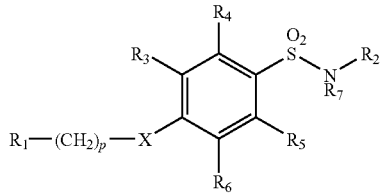

(VI)

wherein: $R_1$ and $R_2$ are each independently aryl or aralkyl, such as

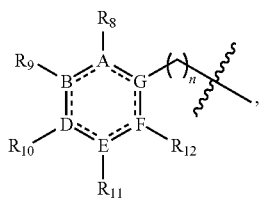

wherein A, B, D, E, F and G are each independently carbon or nitrogen; $R_8$-$R_{12}$ are each independently H, alkyl, alkoxy; —$CH_3$, halo, hydroxy, thiol, —$NO_2$, —$CO_2H$, —$SO_2NH$-Aryl, —$C(O)CH_3$, —$OCH_3$, —$OCF_3$—$CF_3$, or —$NH_2$; and n is 0-3; $R_3$-$R_6$ are each independently H, alkyl, alkoxy; —$CH_3$, halo, hydroxy, thiol, —$NO_2$, —$CO_2H$, —$SO_2NH$-aryl, —$C(O)CH_3$, —$OCH_3$, —$OCF_3$—$CF_3$, or —$NH_2$; $R_7$ is H or alkyl; X is —$C(O)NR_{13}$— or —$NR_{13}C(O)$—, wherein $R_{13}$ is H or alkyl; and p is 0-3. In certain embodiments, $R_8$-$R_{12}$ are each independently H, unsubstituted alkyl, or unsubstituted alkoxy. In certain embodiments, $R_8$-$R_{12}$ are each independently H, substituted alkyl, or substituted alkoxy. The substituents of substituted alkyl, or substituted alkoxy, may, for example, each independently be —$CH_3$, halo, hydroxy, thiol, —$NO_2$, —$CO_2H$, —$C(O)CH_3$, —$OCH_3$, —$CF_3$, —$NH_2$, or morpholinyl, or any other substituent described herein. In certain embodiments, $R_8$-$R_{12}$ are each independently H, lower alkyl, or lower alkoxy. $R_7$ and $R_{13}$ are each independently lower unsubstituted alkyl, in certain embodiments. In certain embodiments, $R_3$-$R_6$ are each independently H or lower alkyl. Non-limiting examples of substituents of alkyl, aryl, aralkyl, alkoxy, lower versions of these groups, and substituents comprising these groups, as noted, of compounds of formula (VI) include —$CH_3$, halo, hydroxy, thiol, —$NO_2$, —$CO_2H$, —$SO_2NH$-aryl, —$C(O)CH_3$, —$OCH_3$, —$OCF_3$—$CF_3$, and —$NH_2$. Non-limiting examples of compounds of formula (VI) include:

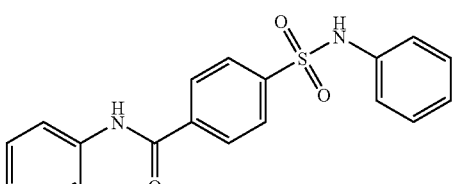

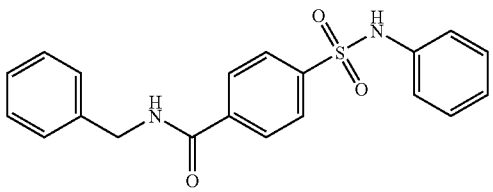

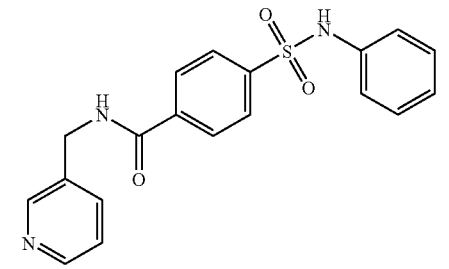

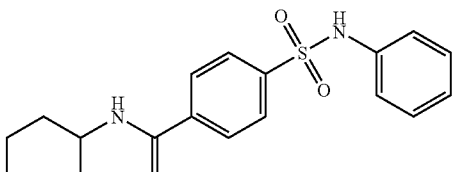

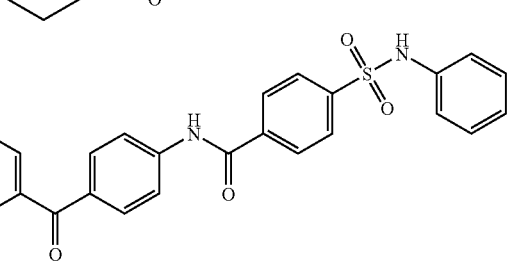

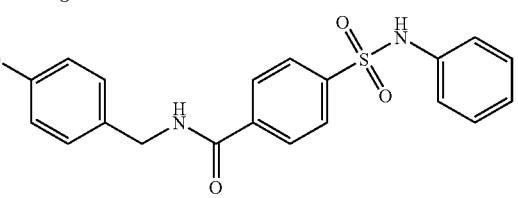

and

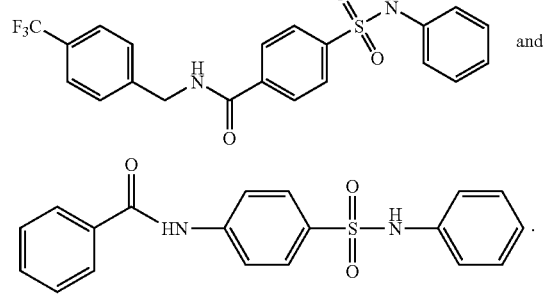

Compounds of formula (VII), below, may be employed in any method described herein. For example, the present invention contemplates a method of treating or preventing bacterial infection in a subject, comprising administering to the subject an effective amount of a compound of formula (VII):

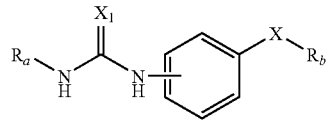

(VII)

wherein the moiety comprising —NHC($X_1$)NHR$_a$ may be ortho, meta, or para to the —XR$_b$ substituent: R$_a$ and R$_b$ are each independently aralkyl, or aryl such as

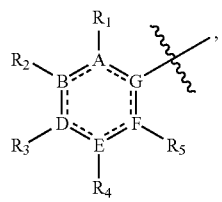

wherein: A, B, D, E, F and G are each independently carbon or nitrogen; and $R_1$-$R_5$ are each independently H, alkyl, alkoxy; —CH$_3$, halo, hydroxy, thiol, —NO$_2$, —CO$_2$H, —SO$_2$NH-aryl, —C(O)CH$_3$, —OCH$_3$, —OCF$_3$—CF$_3$, or —NH$_2$; X is —NR$_7$—, —SO$_2$NR$_7$—, —NR$_7$SO$_2$—, or —S(O)$_2$—, wherein R$_7$ is H or alkyl; and $X_1$ is O or S. In certain embodiments regarding compounds of formula (VII), there is the proviso that if the substituents on the phenyl ring shown in formula (VII) are para, then X is —NH—, —S(O)$_2$— or —NHSO$_2$—. In certain embodiments, $R_1$-$R_5$ are each independently H, unsubstituted alkyl or unsubstituted alkoxy. In certain embodiments, $R_1$-$R_5$ are each independently H, substituted alkyl or substituted alkoxy. In certain embodiments, each substituent of substituted alkyl or substituted alkoxy is independently —CH$_3$, halo, hydroxy, thiol, —NO$_2$, —CO$_2$H, —C(O)CH$_3$, —OCH$_3$, —CF$_3$, —NH$_2$, or morpholinyl, or any other substituent described herein. In certain embodiments, $R_1$-$R_5$ are each independently H, —CH$_3$, halo, hydroxy, thiol, —NO$_2$, —CO$_2$H, —C(O)CH$_3$, —OCH$_3$, —CF$_3$, or —NH$_2$; or lower alkyl or lower alkoxy, wherein lower alkyl or lower alkoxy may optionally comprise —CH$_3$, halo, hydroxy, thiol, —NO$_2$, —CO$_2$H, —SO$_2$NH-aryl, —C(O)CH$_3$, —OCH$_3$, —OCF$_3$—CF$_3$, or —NH$_2$. In particular embodiments, R$_7$ is H or lower unsubstituted alkyl. Non-limiting examples of substituents of the alkyl, aryl, aralkyl and alkoxy, and lower version of these groups, and substituents comprising these groups, as noted, of compounds of formula (VII) include —CH$_3$, halo, hydroxy, thiol, —NO$_2$, —CO$_2$H, —SO$_2$NH-aryl, —C(O)CH$_3$, —OCH$_3$, —OCF$_3$—CF$_3$, and —NH$_2$. Non-limiting examples of compounds of formula (VII) include.

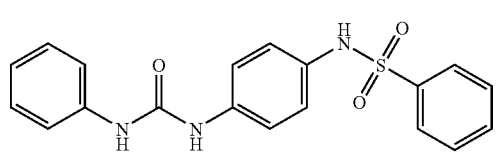

-continued

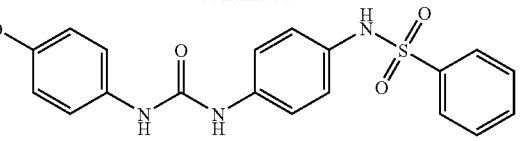

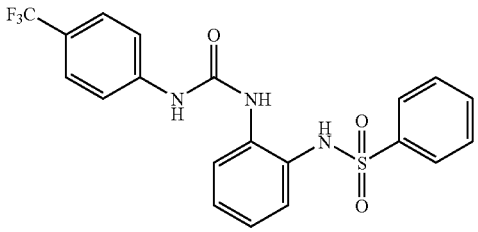

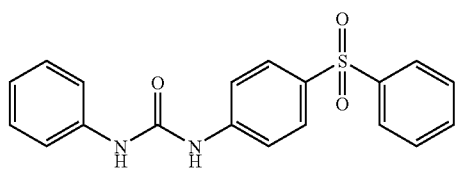

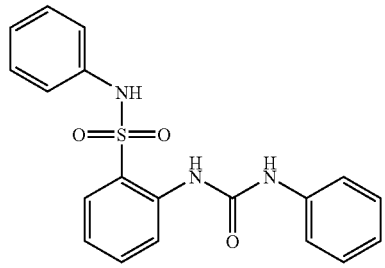

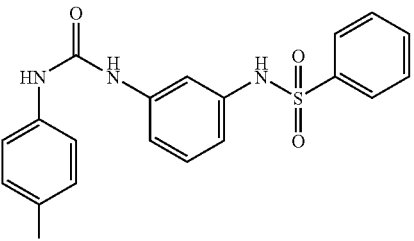

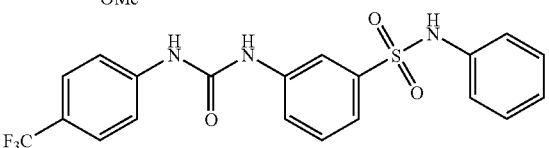

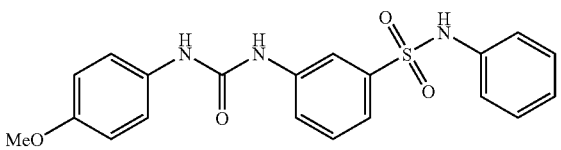

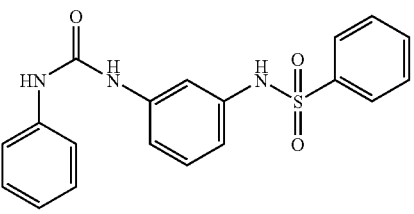

-continued

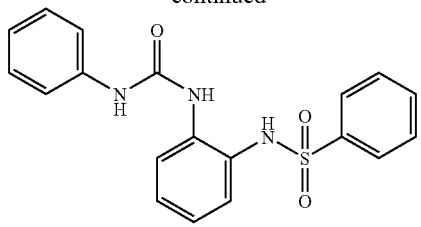

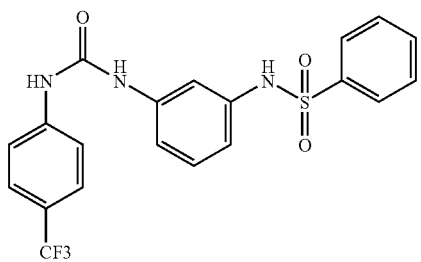

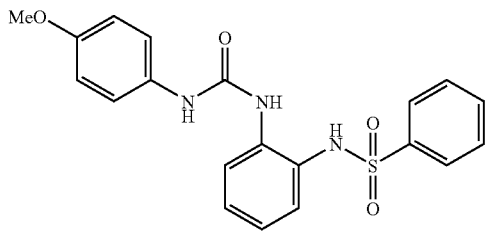

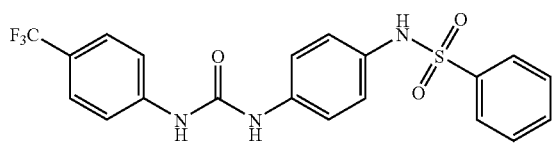

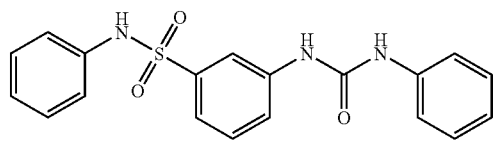

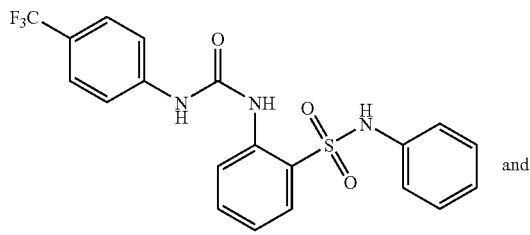 and

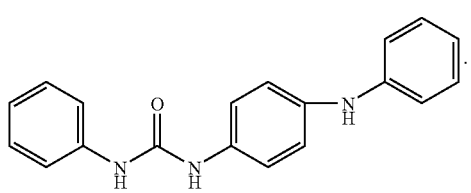.

Compounds of formula (VIII), below, may be employed in any method described herein. For example, the present invention contemplates a method of treating or preventing bacterial infection in a subject, comprising administering to the subject an effective amount of a compound of formula (VIII):

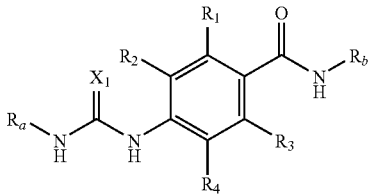

wherein: $R_a$ and $R_b$ are each independently aralkyl, or aryl, such as

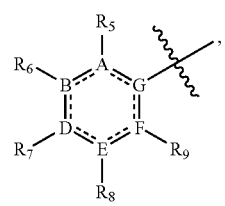

wherein A, B, D, E, F and G are each independently carbon or nitrogen; and $R_5$-$R_9$ are each independently H, alkyl, or alkoxy; $R_1$-$R_4$ are each independently H or alkyl; and $X_1$ is O or S. In certain embodiments, $R_5$-$R_9$ are each independently H, unsubstituted alkyl, or unsubstituted alkoxy. In certain embodiments, $R_5$-$R_9$ are each independently H, substituted alkyl, or substituted alkoxy. In certain embodiments, the substituents of substituted alkyl or substituted alkoxy are selected from the group consisting of halo, substituted alkyl, —$CH_3$, hydroxy, thiol, —$NO_2$, —$CO_2H$, —C(O)$CH_3$, —$OCH_3$, —$CF_3$, and —$NH_2$, or are any other substituent described herein. In certain embodiments, $R_5$-$R_9$ are each independently lower alkyl or lower alkoxy. $R_1$-$R_4$, may, for example, each independently H or lower alkyl. Non-limiting examples of substituents of the alkyl, aryl, aralkyl and alkoxy groups, and lower versions thereof, and substituents comprising these groups, as noted, of compounds of formula (VIII) include —$CH_3$, halo, hydroxy, thiol, —$NO_2$, —$CO_2H$, —$SO_2NH$-aryl, —C(O)$CH_3$, —$OCH_3$, —$OCF_3$—$CF_3$, and —$NH_2$. Non-limiting examples of compounds of formula (VIII) include:

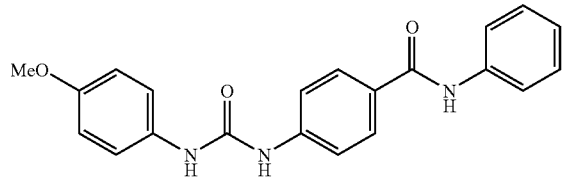

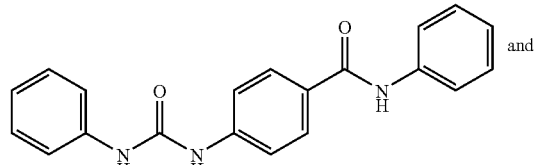 and

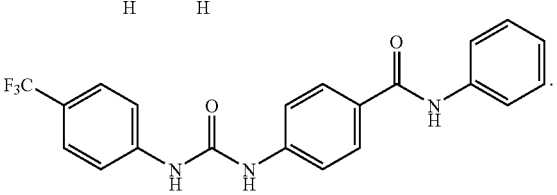.

Compounds of formula (IX), below, may be employed in any method described herein. For example, the present invention contemplates a method of treating or preventing bacterial infection in a subject, comprising administering to the subject an effective amount of a compound of formula (IX):

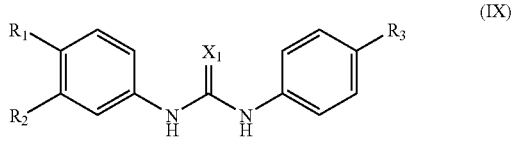

wherein: $R_1$ and $R_2$ are each H or $R_1$ and $R_2$ together form a 1,3-dioxolanyl group; $R_3$ is H, —OH, —SO$_2$NH$_2$, —SO$_2$NH-alkyl, or dialkylamino; and $X_1$ is O or S. In certain embodiments, alkyl group of —SO$_2$NH-alkyl is substituted alkyl. In certain embodiments, the substituent of substituted alkyl is —OH. In certain embodiments, each alkyl group of the dialkylamino group of $R_3$ is independently unsubstituted lower alkyl. Non-limiting examples of substituents of the alkyl, —SO$_2$NH-alkyl, dialkylamino and lower versions thereof, and substituents comprising these groups, as noted, of compounds of formula (IX) include —CH$_3$, halo, hydroxy, thiol, —NO$_2$, —CO$_2$H, —SO$_2$NH-aryl, —C(O)CH$_3$, —OCH$_3$, —OCF$_3$—CF$_3$, and —NH$_2$. Non-limiting examples of compounds of formula (IX) include:

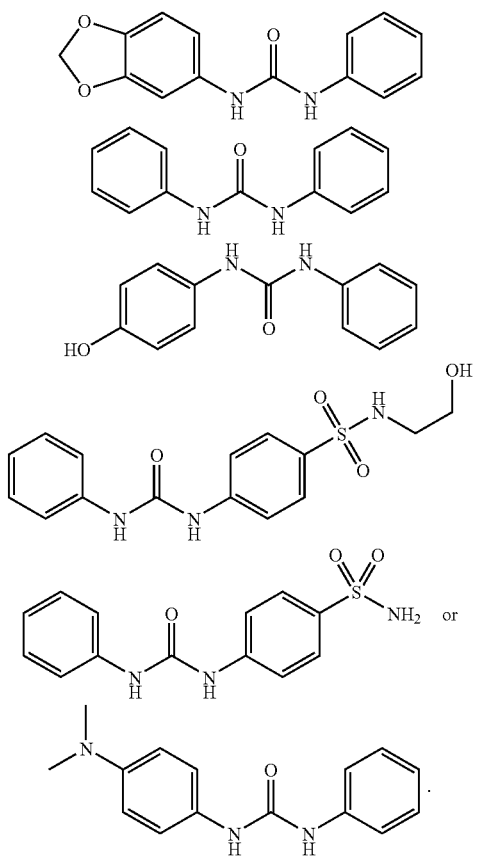

Also contemplated by the present invention is a compound of the following formula:

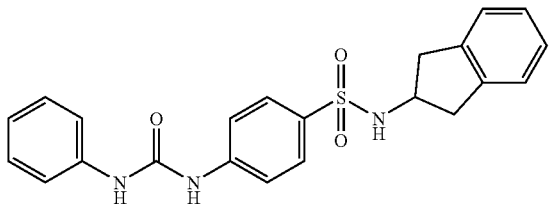

and pharmaceutical compositions comprising such a compound.

Compounds of the present invention that may be employed in any method herein also contemplate compounds of formula (X):

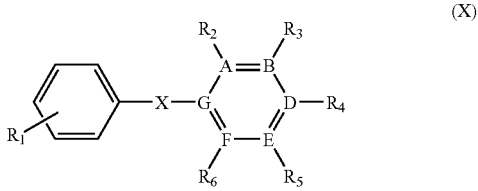

wherein: A, B, D, E, F and G are each independently carbon or nitrogen; $R_1$ is H, —NH$_2$, alkylamino, dialkylamino, or —CO$_2$H; $R_2$-$R_6$ are each independently H or alkyl; and X is —NR$_7$—, —SO$_2$NR$_7$—, —NR$_7$SO$_2$—, —S(O)$_2$—, —C(O)NR$_7$—, or —NR$_7$C(O)—, wherein $R_7$ is H or alkyl. In certain embodiments, $R_1$ is unsubstituted alkylamino or unsubstituted dialkylamino. In certain embodiments, $R_1$ is lower alkylamino or lower dialkylamino. In certain embodiments, $R_2$-$R_7$ are each independently unsubstituted alkyl. $R_2$-$R_7$ may be, in certain embodiments, each independently lower alkyl. Non-limiting examples of compounds of formula (X) include:

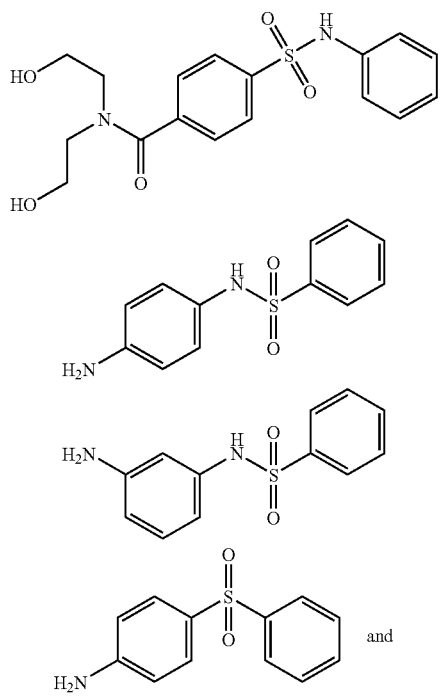

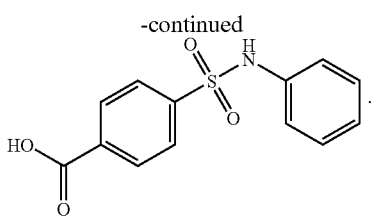

Another aspect of the present invention contemplates a method of treating or preventing a bacterial infection in a subject, comprising administering to the subject an effective amount of a compound of formula (I):

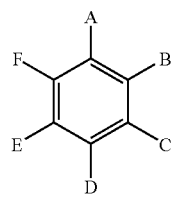

(I)

wherein A, C, D and F are each independently H, lower alkyl, —OH, —NH$_2$, lower alkoxy, a polymer tail, a polymer backbone, or a linker-polymer backbone; B is H, —SO$_2$NH$_2$, —SO$_2$(NR$_1$)alkyl, or —SO$_2$(NR$_1$)aryl, wherein R$_1$ is H, lower alkyl, a polymer tail, a polymer backbone, or a linker-polymer backbone; and E is —NH$_2$ or —NH—C(O)R$_2$, wherein R$_2$=lower alkyl or aryl, or E is a substituent having the formula (II):

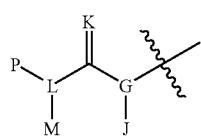

(II)

wherein G and L are each independently N or O but do not form a carbonate; J and M are each independently H, lower alkyl, —NH$_2$, —OH, lower alkoxy, a polymer tail, a polymer backbone, or a linker-polymer backbone; K is —CH$_2$, O or S; and P is H, lower alkyl, or aryl. The subject in this or any other embodiment of the present invention may be an animal, such as a mammal (e.g., mouse, rabbit, or human). A subject in this or any other embodiment of the present invention may be a plant.

In certain embodiments, the compound of formula (I) is a compound of formula (III):

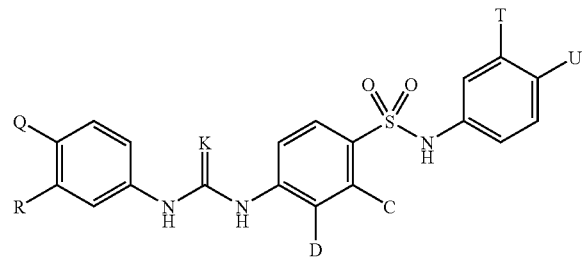

(III)

wherein Q, R, C, D, T and U are each independently H, alkyl, —NH$_2$, —CH$_2$NH$_2$, —CH$_2$NH— (lower alkyl), a polymer tail, a polymer backbone, or a linker-polymer backbone; and K is C, S, or O. In certain embodiments regarding Q, R, C, D, T and U, alkyl is unsubstituted alkyl. In certain embodiments, alkyl is substituted alkyl. In certain embodiments, the substituent of substituted alkyl is hydroxy. In certain embodiments, the substituted alkyl is lower substituted alkyl, wherein the substituent is hydroxy.

In certain embodiments, the compound of formula (I) is a compound of formula (IV):

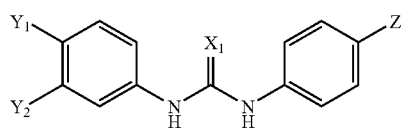

(IV)

wherein X$_1$ is O or S; Y$_1$ and Y$_2$ are each independently H, a polymer tail, a polymer backbone, or a linker-polymer backbone; and Z is H,

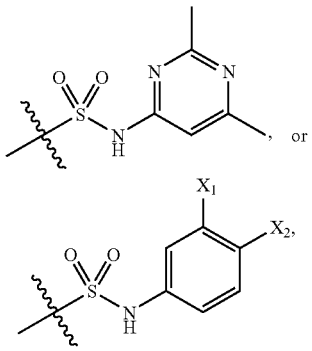

, or wherein X$_1$ and X$_2$ are each independently H, a polymer tail, a polymer backbone, or a linker-polymer backbone. In certain embodiments, X$_1$ is S. In particular embodiments, the lower alkyl of A, C, D, F, J and M are each independently —CH$_2$NH$_2$ or —CH$_2$NHCH$_3$. In particular embodiments, B is —SO$_2$(NH)aryl. In certain embodiments, the aryl group is phenyl. The aryl group may be a six-membered ring wherein two of the ring atoms are nitrogen and four of the ring atoms are carbon. In certain embodiments, the aryl group is a di-substituted aryl group. In certain embodiments, the aryl group is substituted with a polymer tail, a polymer backbone, or a linker-polymer backbone, as described below. In particular embodiments, E is —NH$_2$ or —NHAc. In particular embodiments, E is a substituent having formula (II). In such embodiments, G and L are each N, and J and M are each H. In certain embodiments regarding compounds comprising a substituent having formula (II), K is S and optionally, the aryl group of formula (II) is a phenyl group, which may or may not be substituted with a polymer tail, a polymer backbone, or a linker-polymer backbone.

In certain embodiments, compounds of formula (I) are further defined as any one or more of the following groups:

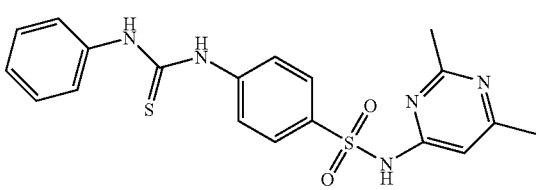

-continued
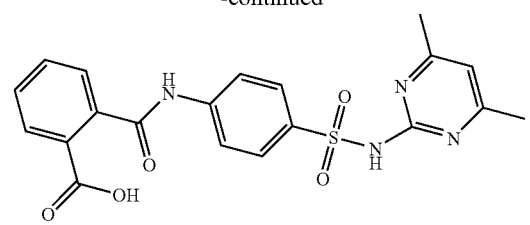
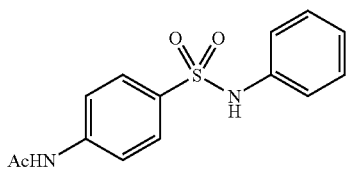
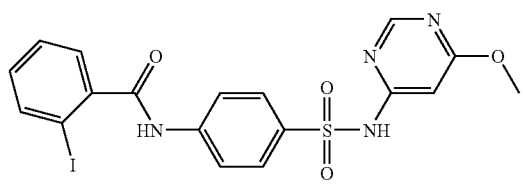
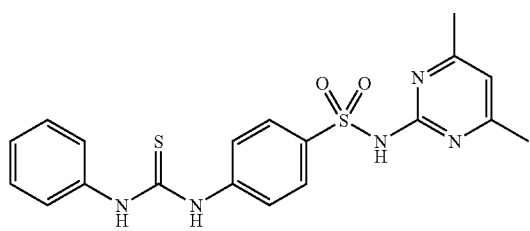
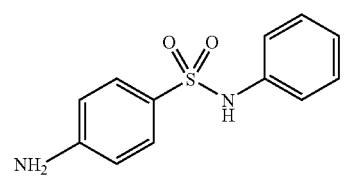
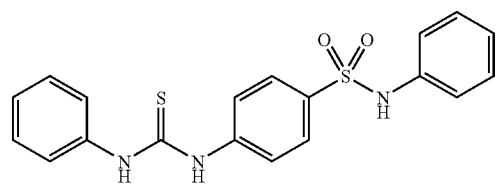
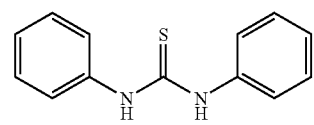
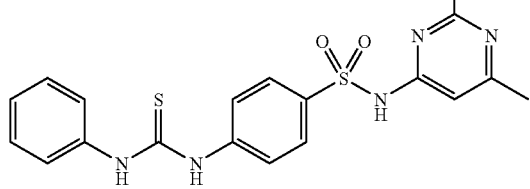
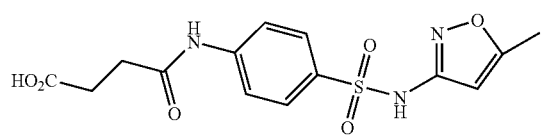
-continued
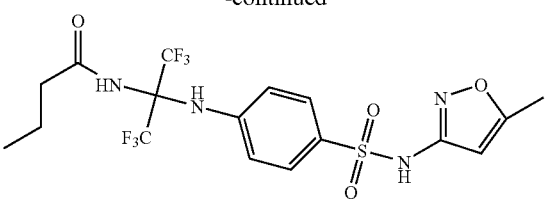
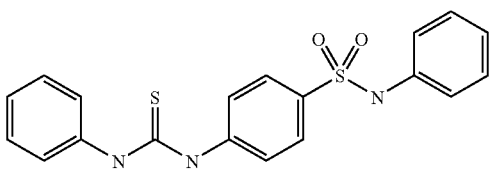
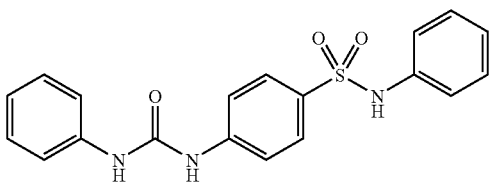
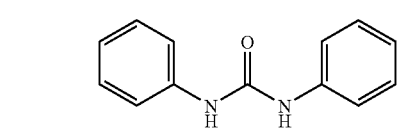
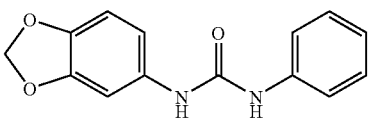
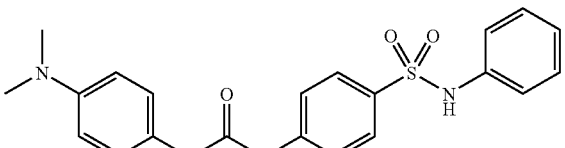
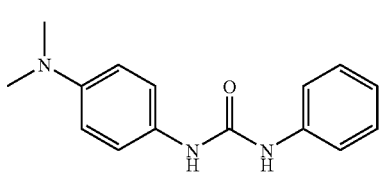
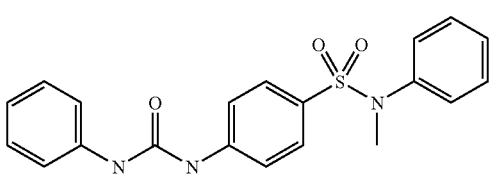
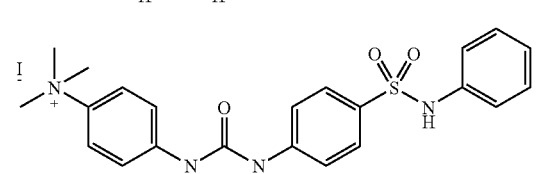
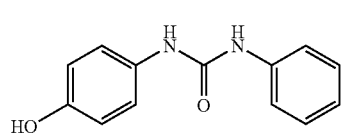

-continued

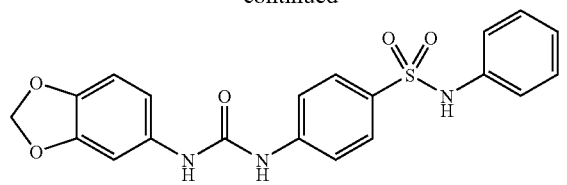

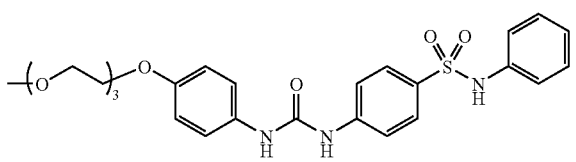

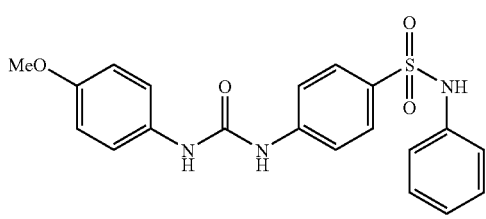

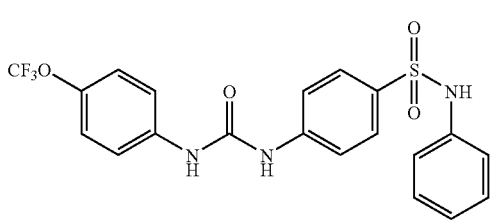

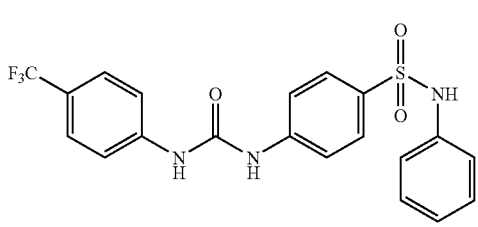

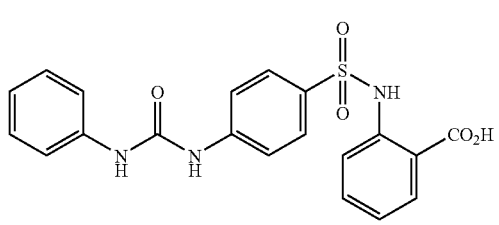

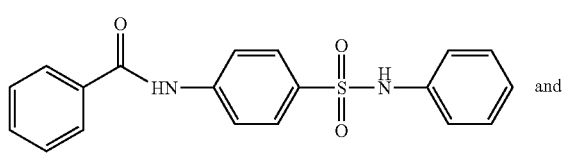

and

-continued

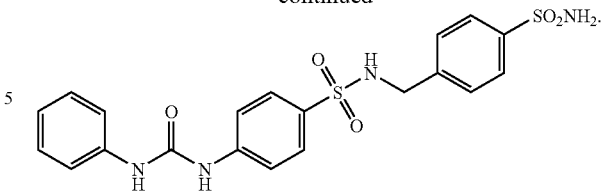

Any compound of the present invention, such as a compound of formula (I), (III), (IV), (V), (VI), (VII), (VIII), (IX), or (X), may be administered to a subject via any method known to those of skill in the art. In particular embodiments, a compound of the present invention is administered orally. Dosage amounts are described elsewhere in this application, but in certain embodiments, a compound of the present invention is administered in an amount of about 0.1 to about 50 mg/kg body weight. In certain embodiments, a compound of the present invention is administered in an amount of about 10 to about 30 mg/kg body weight. Compounds of the present invention may also be administered via inhalation, intraperitoneally, intravenously, intramuscularly, rectally, buccally (e.g., via a mouth wash), transdermally, vaginally, or via eye or ear drops.

In certain embodiments, bioavailable compounds of the present invention exhibiting a calculated water solubility of less than 1 mg/mL are preferred. Such values may be calculated by known in silico methods (e.g., Benchware™ HTS DataMiner, Tripos, Inc.). In certain embodiments, it is preferable that a compound of the present invention is comprised in a composition, such as a pharmaceutically acceptable composition, that is nonabsorbable. A nonabsorbable composition is one that is not, for the most part, absorbed by the body or any particular part of the body. That is, such compositions are not absorbed or metabolized by the body in any meaningful manner or to any meaningful degree. In certain embodiments, a compound is nonabsorbable from the gut, lumen of the GI tract, the nasal passage, the mouth cavity, the skin, the ear canal, and/or the vagina. Such compositions may be useful for targeting infections in the gut, for example (e.g., certain stages of *Salmonella* or EHEC infections), the ear (e.g., *Haemophilus influenzae*) or the vagina (e.g., *Staphylococcus aureus* (*Staphylococcus epidermiditis*, a close homolog of *S. aureus*, induces biofilm formation in the presence of norepinephrine)). In certain embodiments, a compound of the present invention may be conjugated to a carrier that is nonabsorbable, and then administered to a subject. An absorbable compound is also considered a bioavailable compound.

Such carriers include certain polymers, such nonabsorbable ones that are insoluble at the low pH of the stomach (pH 1-2) but readily dissolve at the pH of the intestine (pH>6.5) to release an encapsulated drug or expose a conjugated one. One specific class is the Eudragits™, as shown below. Eudragits™ are completely nonabsorbable. When taken orally, they appear in the feces.

Conjugation of a compound of the present invention to a nonabsorbable carrier such as a Eudragit™ or a cyclodextrin is one way to make a compound of the present invention completely nonabsorbable. Structural design of compounds may achieve this goal as well. An example of how a compound of the present invention, LED209 (also called compound 5) could be conjugated to a nonabsorbable carrier is shown below.

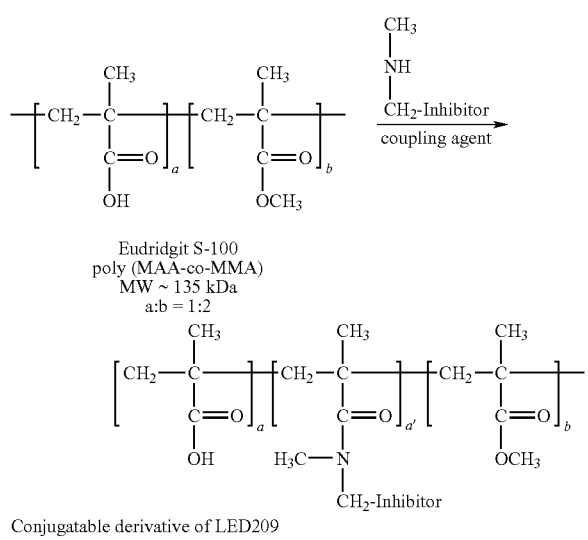

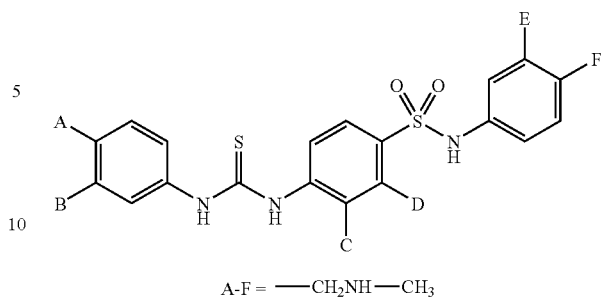

A-F = —CH₂NH—CH₃

Derivatives at sites A-F can be easily prepared with, for example, —CH$_2$NH—CH$_3$, that can then be used to couple to the carrier through a portion of its —CO$_2$H groups. The resulting N-methyl 'peptide' bond is an enzymatically stable tertiary amide. Other methods of coupling to a carrier are known to those with skill in the art, as described herein.

In any embodiment herein, the polymer tail of a compound of the present invention may be

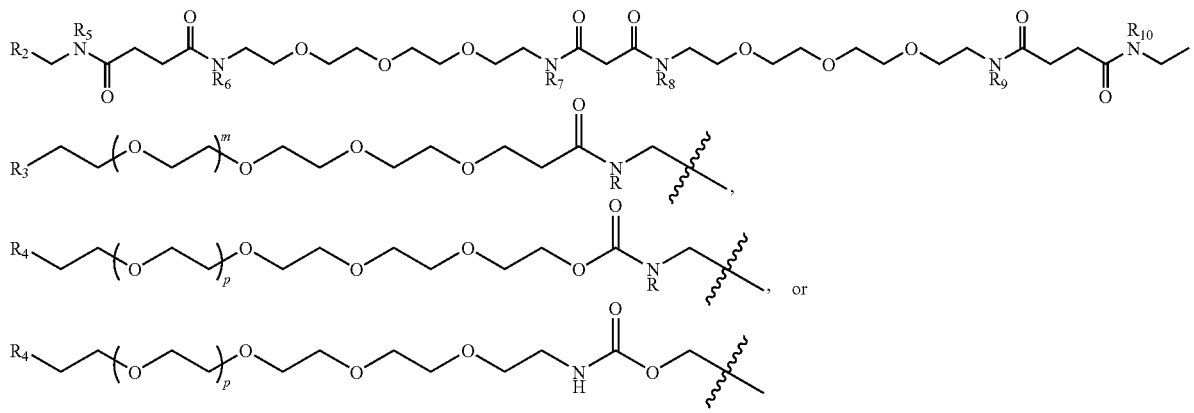

wherein R, R$_5$, R$_6$, R$_7$, R$_8$, R$_9$ and R$_{10}$ are each independently H or lower alkyl; R$_2$ is the same moiety found at the opposite end of the polymer tail; R$_3$ and R$_4$ are each independently H, lower alkyl, CH$_2$OH, hydroxylated lower alkyl, —NH$_2$, —CH$_2$NH$_2$, —CH$_2$NHCH$_3$, —OH, or lower alkoxy; and n, m and p are each independently an integer ranging from 2-200, or any range derivable therein. It is also specifically contemplated that the —NR$_{10}$C(O) or —NRC(O)— linkage shown in these moieties above may be an ether linkage, a urea linkage, a carbamate linkage or a carboxamide linkage, as those linkages are described herein.

In any embodiment herein, the polymer backbone or linker-polymer backbone of a compound of the present invention may comprise any of the following copolymers:

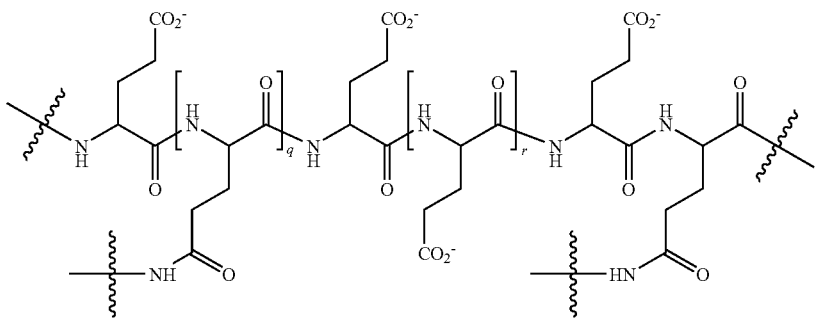

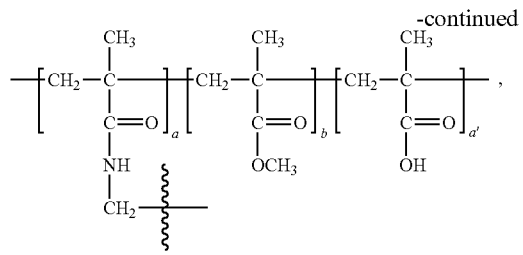
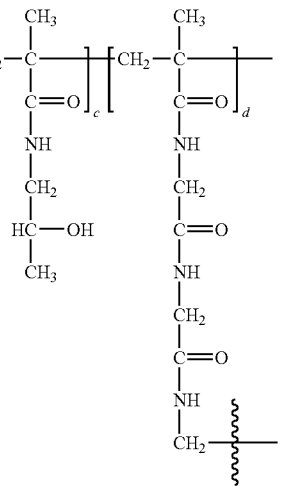

wherein a, a', b, c and d are each independently chosen such that the molecular weight of the polymer is about or at least about 125 kDa. For example, the molecular weight of the polymer may be about or at least about 500. In certain embodiments, the molecular weight of the polymer ranges between about 500 and about 2500. The order of subunits in each type of copolymer is random. In certain embodiments, the ratio of a:b is about 1:2. In certain embodiments, the ratio of c:d is about 9:1. In particular embodiments, the ratio of a:b is about 1:2 and the ratio of c:d is about 9:1. In certain embodiments, (a+a')/b=0.25 to 2.0, or any fraction therein. In certain embodiments, the ratio of d/c is 0.01-0.25, or any fraction therein. In certain embodiments, d+c=about 70 to about 700. The terminal groups of such copolymers may be any terminal group known to those of skill in the art. For example, a terminal group may comprise an alkoxy or hydroxyl (from, e.g., laurel peroxide, benzoyl peroxide, or a persulfate) or a dialkyl cyano group. Terminal groups may vary with respect to the type of initiator, monomer, solvent(s) and radical chain transfer agents or terminators present in the reaction, as is known to those of skill in the art.

In certain embodiments, a compound of the present invention may be immobilized on a substrate or a medical device that is then inserted into a subject. A compound of the present invention may be chemically modified such that immobilizing the compound on a substrate or medical device is facilitated. In particular embodiments, a compound of the present invention comprises one or more polymer backbones, such as a linker-polymer backbone, and/or polymer tails that may then be used for immobilization purposes. Methods of immobilizing bioactive molecules onto such devices are well-known in the art. See, e.g., U.S. Pat. Nos. 5,811,151, 5,281,170, 6,024,918 and 7,256,259, each of which is incorporated by reference in its entirety. Substrates onto which compounds of the present invention may be immobilized may, in certain embodiments, be substantially insoluble in body fluids and that are generally designed and constructed to be placed in or onto the body or to contact fluid of the body. Non-limiting examples of medical devices include prostheses, stents, implants and ports.

In certain aspects of the present invention, any compound of the present invention, such as a compound of formula (I), (III), (IV), (V), (VI), (VII), (VIII), (IX), or (X), minimally affects adrenergic receptor activity. Methods of determining adrenergic receptor activity are well-known to those of skill in the art (see, e.g., Azzi et al., 2001; Sen et al., 2002; Zimmerman et al, 1998) and at least one method is set forth in the Examples below. The phrase "minimally affects adrenergic receptor activity" refers to increasing or decreasing adrenergic receptor activity by about 1% or less.

In any method described herein, the bacterial infection may be caused by bacteria that have a QseC kinase or QseC kinase homolog. In any method described herein, the bacterial infection may be caused by bacteria that sense AI-3/epinephrine/NE. Methods of determining whether bacteria contain a QseC kinase and/or sense AI-3/epinephrine/NE are well-known to those of skill in the art. See, e.g., Clarke et al., 2006. Particular bacteria that contain a QseC kinase and that sense AI-3/epinephrine/NE include EHEC, EPEC, UPEC, K-12, *Klebsiella pneumoniae, Acinetobacter baumannii, Shigela flexneri, Salmonella enterica typhi* and *typhimurium, Yersinia pestis, Yersinia enterocolitica, Yersinia. pseudotuberculosis, Erwinia carotovora, Pasteurella multocida, Haemophilus influenzae, Actinobacillus pleuroneumoniae, Chromobacterium violaceum, Pseudomonas aeruginosa, Pseudomonas fluorescens, Burkholderia cepacia, Coxiella burnetti, Ralstonia solanacenarum* and *Francisella tularensis*. Any QseC homologs listed in FIG. 2 are also contemplated by the present invention. It is contemplated that certain bacteria both contain QseC and detect AI-3/epinephrine/NE and certain bacteria either contain QseC or detect AI-3/epinephrine/NE.

In any embodiment discussing bacteria, pathogenic bacteria are specifically contemplated.

In any method described herein, a bacterial infection may be caused by a mammalian bacterial pathogen. In any method described herein, a bacterial infection may be caused by a plant bacterial pathogen. Non-limiting examples of such pathogens are described herein.

In any method described herein, the bacterial infection may be caused by at least one of the following organisms: *Actinobacillus pleuropneumoniae, Burkholderia cepacia, Chromobacter violaceum, Coxiella burnetti, E. coli, Erwinia carotovora, Francisella tularensis, Haemophilus influenzae, Pasteurella multocida, Pseudomonas aeruginosa, Pseudomonas fluorescens, Ralstonia solanacearum, Shigella flexneri, Salmonella typhi, Salmonella typhimurium, Staphylococcus aureus, Vibrio cholerae, Vibrio parahaemoliticus, Vibrio vulnificus, Yersinia pestis,* or *Yersinia pseudotuberculosis*. Other organisms are described herein. In particular embodiments, the organism is pathogenic *E. coli*, such as enterohemorrhagic *E. coli* or is uropathogenic *E. coli*. Other *E. coli* organisms are discussed herein. In particular embodiments, the organism is *Francisella tularensis*. In particular embodiments, the organism is *Salmonella typhimurium*. In particular embodiments, the organism is *Salmonella typhi*. In particular embodiments, the organism is *Pseudomonas aeruginosa*. In particular embodiments, the organism is *Staphylococcus aureus*. In particular embodiments, the organism is *Haemophilus influenza*. Regarding the latter organism, ear infections and meningitis are two non-limiting examples of *Haemophilus influenza* infections that may be treated with a compound of the present invention.

Moreover, the bacterial infection may be caused by at least one of the following organisms: enteropathogenic *E. coli* (EPEC), enterotoxigenic *E. coli* (ETEC), enteroaggregative *E. coil* (EAEC), enteroinvasive *E. coli* (EIEC), diffuse adhering *E. coli* (DAEC), uropathogenic *E. coil* (UPEC), *E. coli* K1, *Acinetobacter, Bordetella parapertussis, Burkolderia phymatum, Citrobacter, Enterobacter, Klebsiella pseumonia, Legionella pneumophila, Ralstonia euthropha, Salmonella enterica typhimurium, Salmonella enterica typhi, Yersinia enterocolitica,* or *Yersinia mollareti*. In certain embodiments, the *Acinetobacter* organism is *Acinetobacter baumannii*.

In any method described herein, the bacterial infection may be caused by a multi-drug resistant bacteria. Non-limiting examples of such bacteria include *Salmonella* and *Staphylococci*, and others are well-known to those of skill in the art. Also envisioned are multi-drug resistant bacteria that develop in the future. Furthermore, in any method described herein, an infection may be caused by any organism discussed herein.

Any compound of the present invention, such as a compound of formula (I), (III), (IV), (V), (VI), (VII), (VIII), (IX), or (X), may be comprised in a pharmaceutically acceptable composition. Such pharmaceutically acceptable compositions may be used in any method described herein. In certain embodiments, the pharmaceutically acceptable composition is absorbable. In certain embodiments, the pharmaceutically acceptable composition is nonabsorbable. In certain embodiments, the pharmaceutically acceptable composition comprises an enteric coating. Such coatings are well-known to those of skill in the art, and are described further herein.

Also contemplated by the present invention is a method of treating or preventing bacterial infection in a subject, comprising administering to the subject an effective amount of a compound of formula (III), (IV), (V), (VI), (VII), (VIII), or (IX), wherein the subject is an animal or a plant.

Other aspects of the present invention contemplate a method of treating or preventing hemolytic uremic syndrome in a subject, comprising administering to the subject an effective amount of a compound of formula (I):

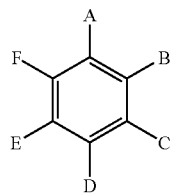

wherein A, B, C, D, E and F are as described above. In certain embodiments, the compound of formula (I) is a compound of formula (III):

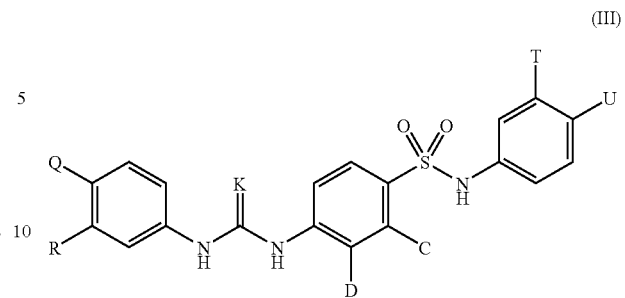

wherein K, Q, R, C, D, T and U are as described above. In particular embodiments regarding the compound of formula (III), C, D, Q, R, T and U are each hydrogen and K is S, as shown below:

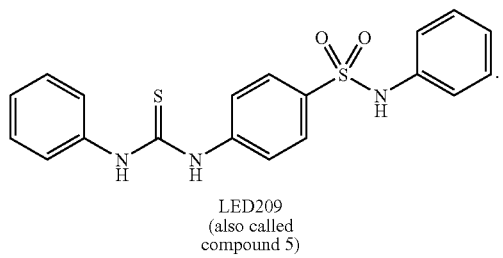

LED209
(also called
compound 5)

In certain embodiments, the compound of formula (I) is a compound of formula (IV):

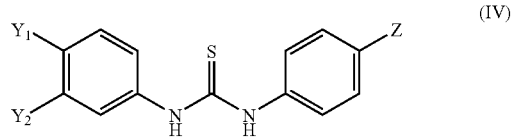

wherein $Y_1$, $Y_2$ and Z are as described above. Compounds of formula (V), (VI), (VII), (VIII), (IX), or (X) may also be employed in such methods, in certain embodiments.

Other aspects of the present invention encompass a method of treating or preventing a bacterial infection in a subject, comprising administering to the subject an effective amount of a compound of formula (IV):

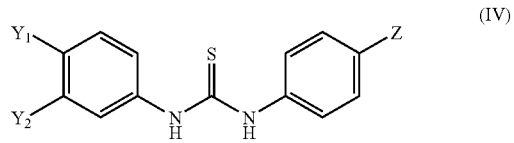

wherein $Y_1$, $Y_2$ and Z are as described above.

Other compounds of the present invention that may be used in the methods discussed here include any one or more of the following:

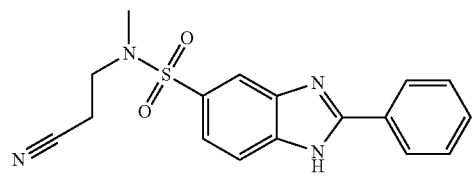

27
-continued
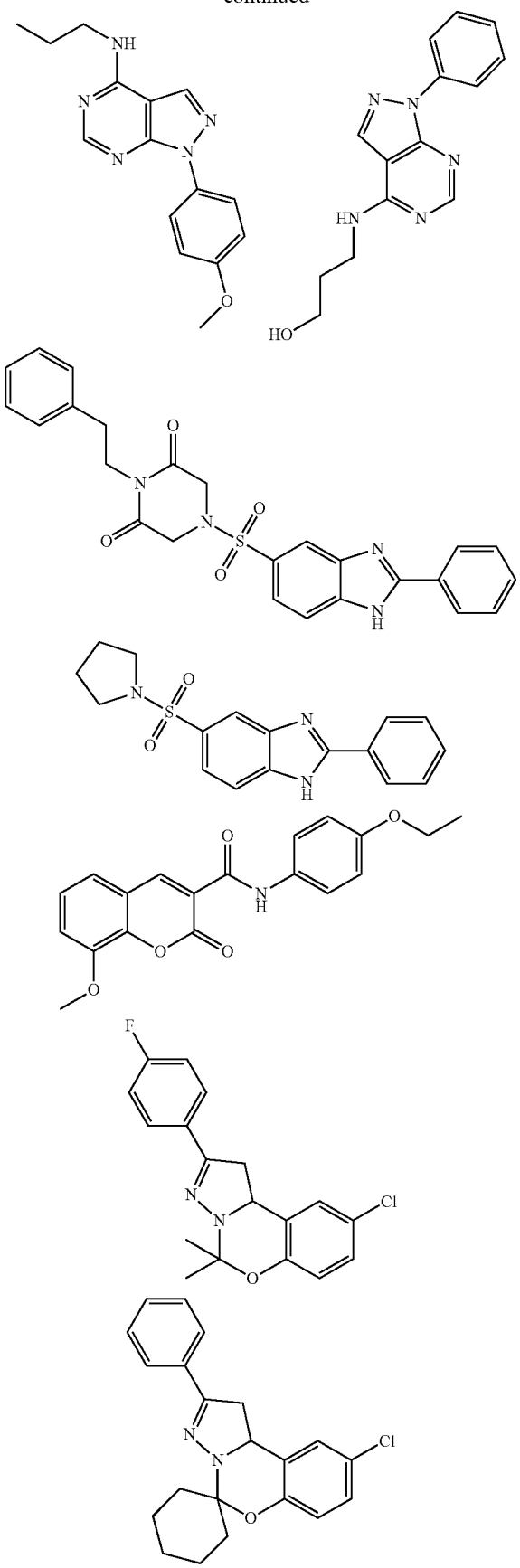
28
-continued
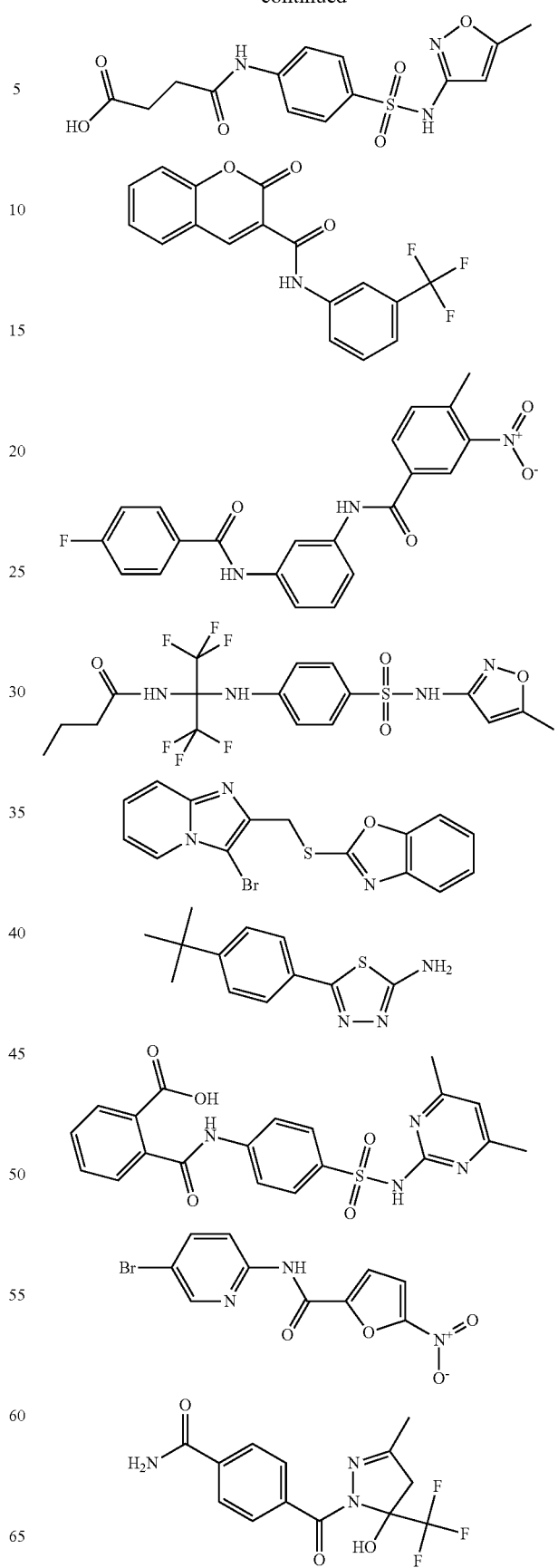

29
-continued
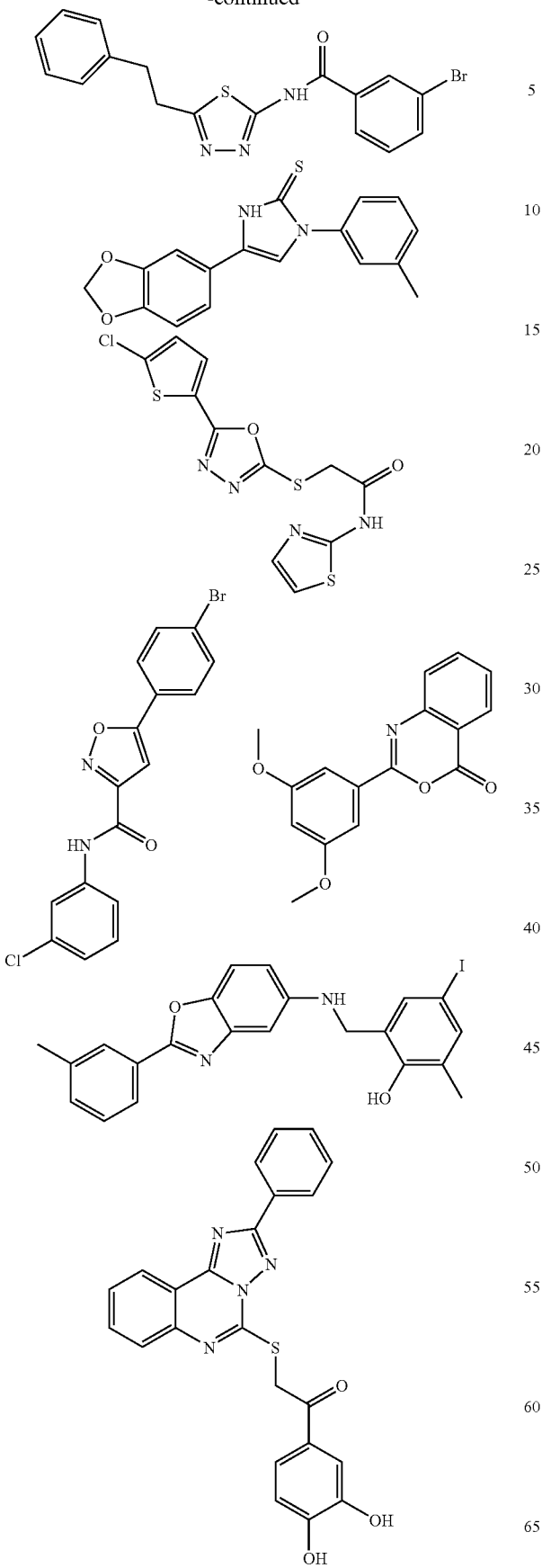
30
-continued
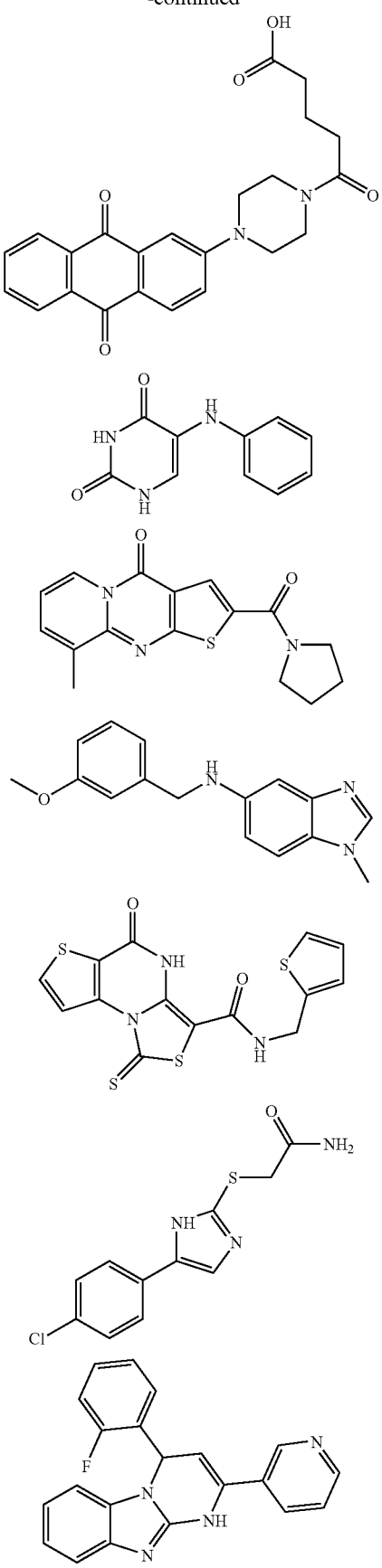

-continued

33
-continued
34
-continued
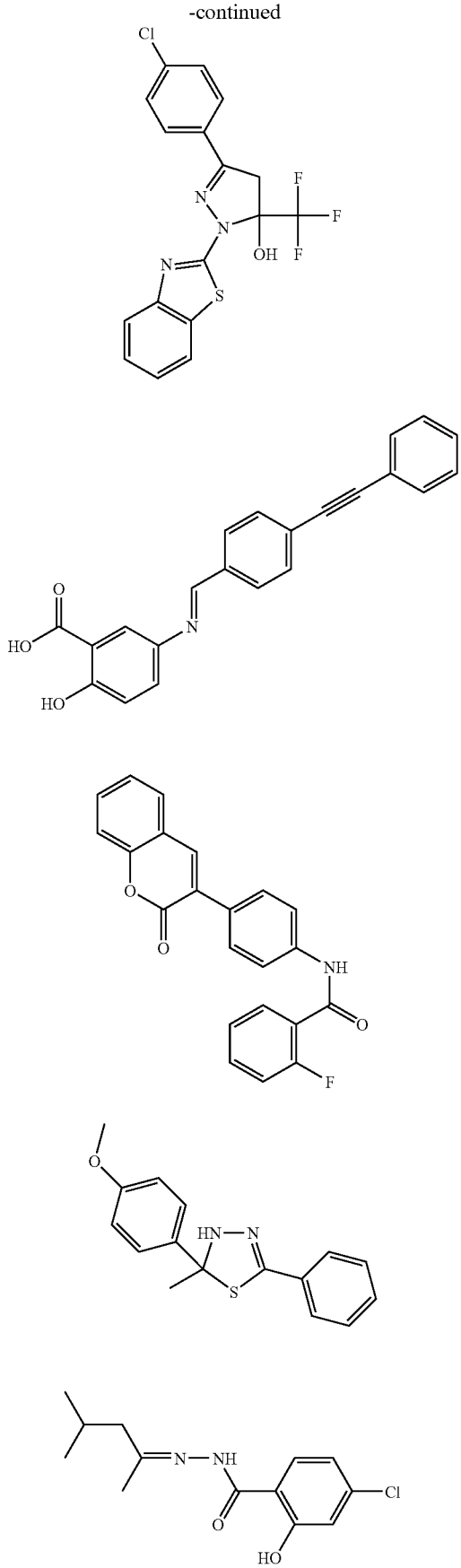
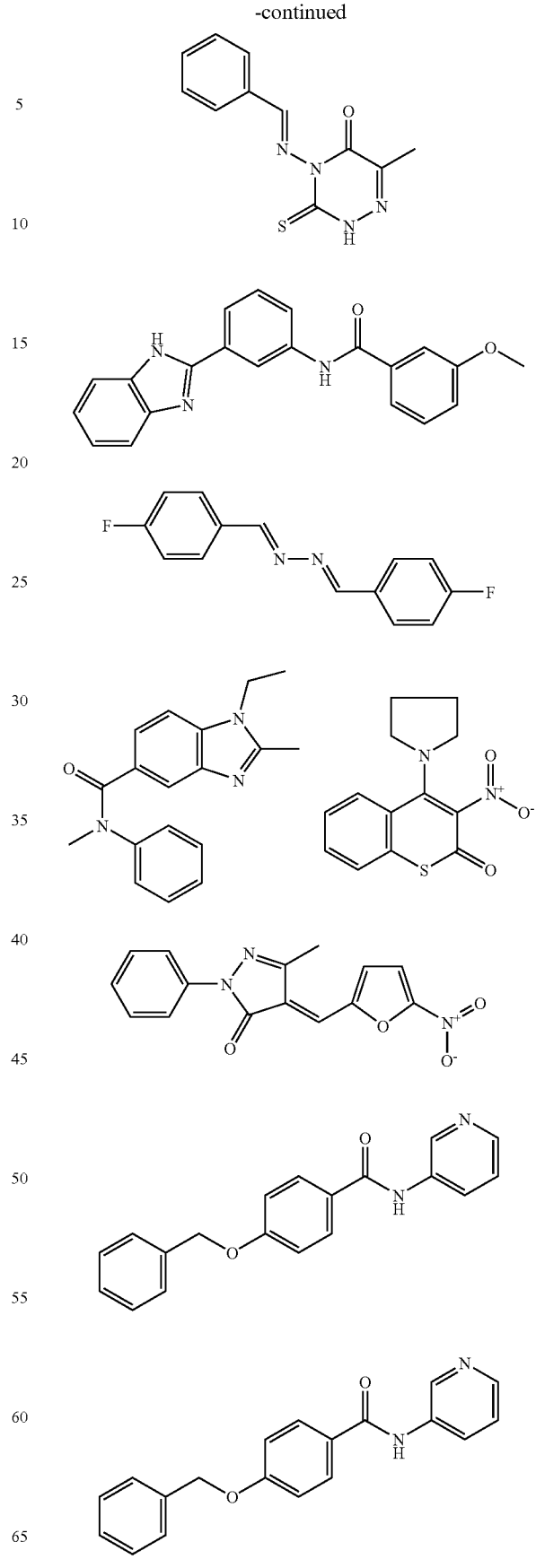

35
-continued
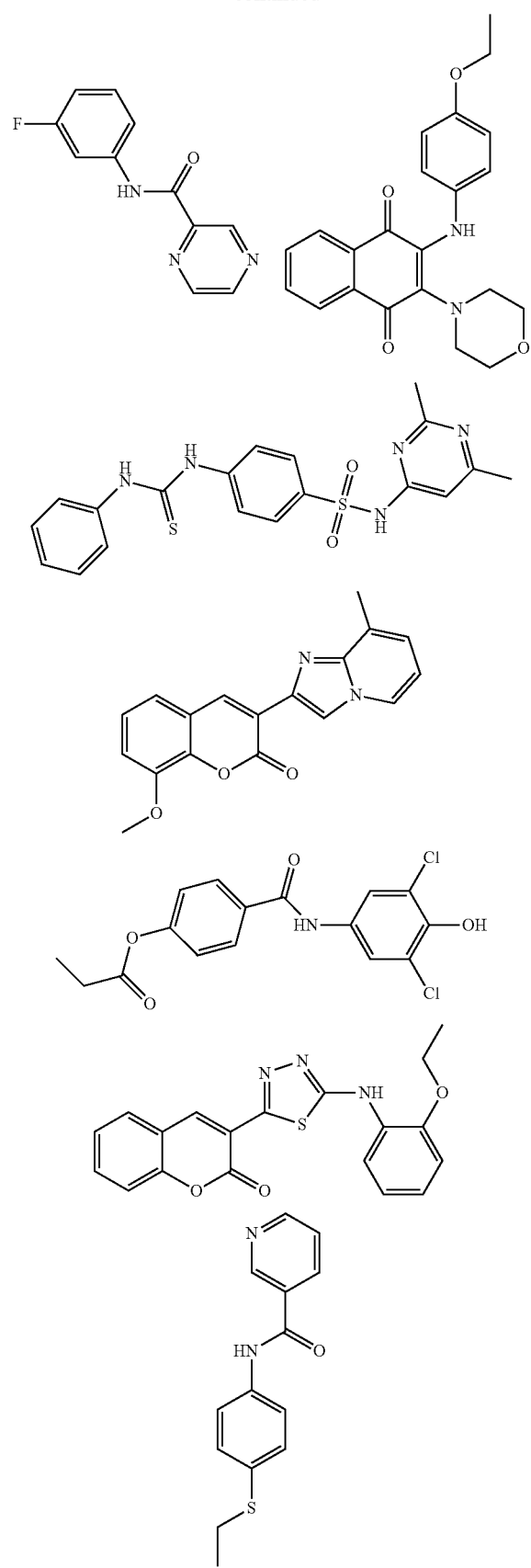
36
-continued
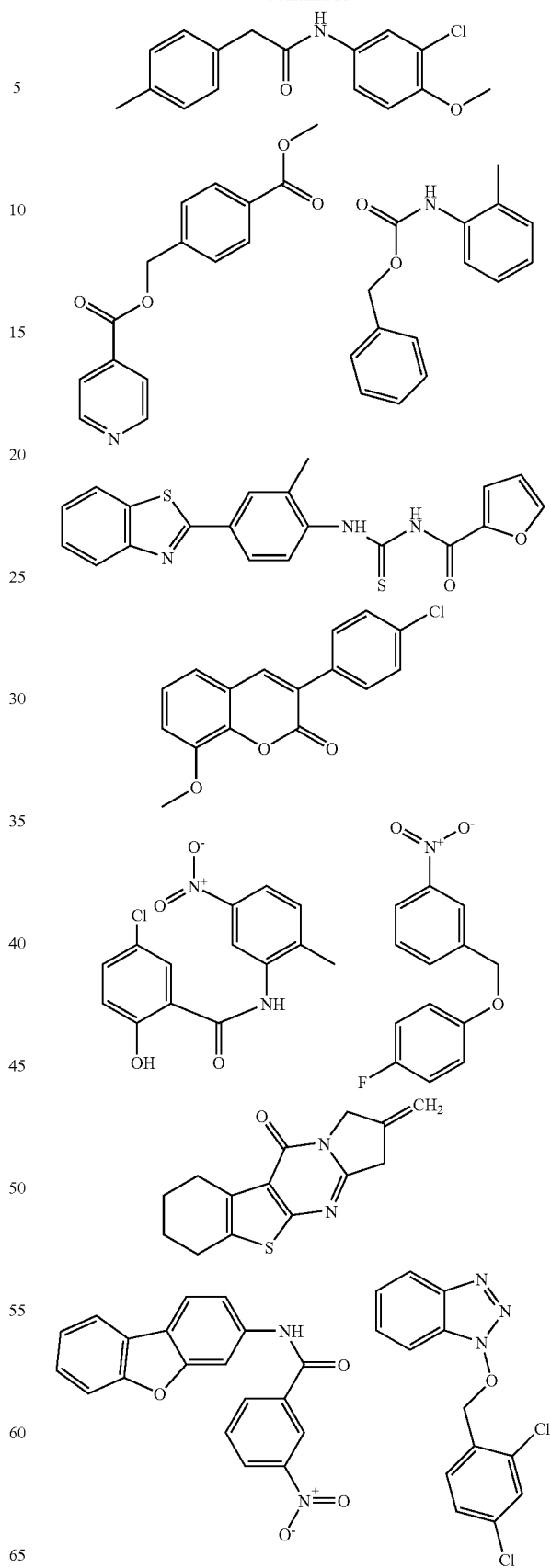

It is specifically contemplated that any specific compound discussed herein may, in certain embodiments, be excluded from a generic compound discussed herein. It is further contemplated that any compounds discussed in the following references may, in certain embodiments, be excluded from the generic compounds discussed herein: WO 2002/070467, WO 2003/028762, WO 2005/016873 and Shehata et al., 1986, each of which is incorporated herein by reference in its entirety.

Another aspect of the present invention contemplates a method of treating or preventing periodontal disease in a subject, comprising administering to the subject an effective amount of a compound of the present invention, such as a compound of formula (I), (III), (IV), (V), (VI), (VII), (VIII), (IX), or (X). As used herein "periodontal disease" refers to an above-normal rate of collagen degradation associated with the periodontium, which may include collagen degradation in the gingiva, the periodontal ligament, the cementum, and the alveolar bone. Periodontal diseases include, for example, gingivitis, chronic inflammatory periodontal disease, prepubertal periodontitis, juvenile periodontitis, and rapidly progressive periodontitis. Biofilms relating to periodontal disease are also specifically contemplated. Biofilms have been implicated in, for example, periodontal disease, tooth decoy, prostate infections, kidney stones, tuberculosis, Legionnaire's disease and some infections of the middle ear. Each of these indications may also be treated using methods and compounds of the present invention.

It is specifically contemplated that for every generic or specific compound disclosed herein that comprises a group comprising C(O)NR or $SO_2NR$, the reverse linkage of that group (e.g., NRC(O) or $NRSO_2$) also constitutes an embodiment of the present invention (wherein R is H or as otherwise shown herein). Moreover, for any aryl ring comprised in any generic or specific compound of the present invention that comprises an ortho, meta, or para substituent, it is specifically contemplated that the ortho, meta, or para substituent may be moved around the ring, and that more than one such substituent may be moved around a ring (e.g., an ortho group may be moved to the para position, and/or a para group may be moved to a meta position). In certain embodiments, for example, an $NHSO_2$ moiety may be exchanged for $SO_2NH$, and then the $NHSO_2$ moiety may be moved to an alternate position on an aryl ring.

The term "effective," as that term is used in the specification and/or claims (e.g., "an effective amount," means adequate to accomplish a desired, expected, or intended result.

"Treatment" and "treating" as used herein refer to administration or application of a therapeutic agent to a subject or performance of a procedure or modality on a subject for the purpose of obtaining a therapeutic benefit of a disease or health-related condition. For example, a subject (e.g., a mammal, such as a human) having a bacterial infection may be subjected to a treatment comprising administration of a compound of the present invention. Alternatively, a subject of the present invention may be a plant, such that the plant may be treated with a compound of the present invention to obtain a beneficial result (e.g., reduction of an infection).

The term "therapeutic benefit" or "therapeutically effective" as used throughout this application refers to anything that promotes or enhances the well-being of the subject with respect to the medical treatment of a condition. This includes, but is not limited to, a reduction in the frequency or severity of the signs or symptoms of a disease. For example, a therapeutically effective amount of a compound of the present invention may be administered to a subject having a bacterial infection, such that the infection is mitigated or eliminated.

The term "subject" as used herein refers to an animal or plant, such as an infected animal or plant, or an animal or plant that is suspected of being infected or susceptible to infection. Animals include, for example, mammals, birds, fish, reptiles, amphibians, and any other vertebrates or invertebrates, such as those of economic, environmental, and/or other significant importance. Mammals include, but are not limited to, humans, livestock, and pets. Without limitation, "livestock" includes economically important animals such as cattle, sheep, goats, rabbits and horses. Birds include without limitation chickens, turkeys, ducks and geese. The term "plants", without limitation, may refer to, for example, plants that produce fruits, vegetables, grains, tubers, legumes, flowers, and leafs such as spinach or tobacco leaf, or any other economically or environmentally important plant.

The term "virulence" as used throughout this application refers to expression control of genes, proteins, or the exhibition of certain behaviors that allow infection of a host or the inhibition of treatment for infections. This includes, but is not limited to, production of toxins; production of proteins or other factors that allow the formation of lesions on subjects' cells or invasion of subjects' cells or tissues; formation of biofilms that resist treatment; formation of plaques in the oral cavity that lead to periodontal disease; and/or inhibition or displacement of commensal or probiotic organisms normally found in healthy subjects.

As used herein, "bacteriocidal" refers to killing of bacteria.

As used herein, "bacteriostatic" refers to inhibiting the growth or reproduction of bacteria.

It is specifically contemplated that any limitation discussed with respect to one embodiment of the invention may apply to any other embodiment of the invention. Furthermore, any composition of the invention may be used in any method of the invention, and any method of the invention may be used to produce or to utilize any composition of the invention.

The use of the term "or" in the claims is used to mean "and/or" unless explicitly indicated to refer to alternatives only or the alternative are mutually exclusive, although the disclosure supports a definition that refers to only alternatives and "and/or."

Throughout this application, the term "about" is used to indicate that a value includes the standard deviation of error for the device and/or method being employed to determine the value.

As used herein the specification, "a" or "an" may mean one or more, unless clearly indicated otherwise. As used herein in the claim(s), when used in conjunction with the word "comprising," the words "a" or "an" may mean one or more than one. As used herein "another" may mean at least a second or more.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following figures form part of the present specification and are included to further demonstrate certain aspects of the present invention. The invention may be better understood by reference to one or more of these drawings in combination with the detailed description of specific embodiments presented herein.

FIG. 2. List of QseC homologs in other bacteria compared to EHEC QseC.

FIG. 5. High throughput screen for AI-3 antagonists. (top) Flow chart depicting the screening. (bottom) One DMSO plate (control) and one 384-well plate (Hit) containing 320 chemical compounds from the UT Southwestern Medical Center (Dallas, Tex.) HTS compound file with positive and negative controls in the outside columns were screened with the HTS assay described above. Each compound well value is plotted on the graph in horizontal blue lines. The horizontal lines on the graphs represent + and − three standard deviations from the compound or DMSO means. Positive controls are samples treated with conditioned medium. Negative controls are samples treated with unconditioned DMEM.

FIG. 6A: Basal cAMP levels in HEK293 cells. FIG. 6B: β2 adrenergic-stimulated cAMP levels in HEK293 cells.

FIG. 7A. Binding to QseC of: tritiated norepinephrine 5 μM (NE); 5 μM tyrosine (tyrosine is a negative control, not a signal to QseC); binding of NE to QseC is inhibited by phentolamine (PE) but not propranolol (PO); 5 pM of LED209 inhibits binding of 5 μM NE to QseC, but 5 fM LED209 does not. FIG. 7B. QseC autophosphorylation in the absence of signal (NT no-treat), with 50 μM epinephrine (Epi) and with 50 μM epinephrine and 5 pM LED209.

FIGS. 8A-8F. FIG. 8A. qRT-PCR of LEE1 gene ler, fliC and stx2A in WT EHEC with self-produced AI-3 (black bars) and AI-3 plus 50 μM epinephrine (white bars), the qseC mutant in with self-produced AI-3 (dark gray bars) and AI-3 plus 50 μM epinephrine (light gray bars). FIG. 8B. qRT-PCR of ler without signals (NT no-treat) (white bar), with 50 μM epinephrine (black bar), and with 50 μM epinephrine plus 5 pM LED209. FIG. 8C. qRT-PCR of LEE genes ler and eae, flagella genes flhDC and stx2A in WT with self-produced AI-3 (black bars) and AI-3 plus 5 pM of LED209 (white bars). FIG. 8D. Western blot of secreted proteins of EHEC (EspA and EspB) with 50 μM epinephrine, 50 μM epinephrine plus 5 nM LED209 and 50 μM epinephrine plus 5 pM LED209 (cross-reactive band as loading control). FIG. 8E. Inhibition of the AE lesions by LED209 (5 μM and 5 pM). Cell nuclei and bacterial cells are stained in red (propidium iodide), the cytoskeleton is stained green (FITC-phalloidin). EHEC forms AE lesions atop the green stained pedestals. There are no pedestals with LED209. *$p<0.05$; $p<0.001$; *$p<0.0001$. FIG. 8F. LED209 does not hinder growth of Salmonella typhimurium, EHEC and F. tularensis. (top) Growth curves of Salmonella typhimurium strain SL1344 (SAL) in LB media in the absence and presence of 1 μM of LED209 (209), 50 μM epinephrine (EPI), and 50 μM epinephrine plus 1 μM LED209 (209+EPI). (top) Growth curves of EHEC strain 8624 (EC-WT) in DMEM in the absence and presence of 1 μM of LED209 (209), 50 μM epinephrine (EPI), and 50 μM epinephrine plus 1 μM LED209 (209+EPI). (bottom) Growth curves of F. tularensis strain LVS (LVS was used for growth curves because with this attenuated strain, these experiments could be performed in a BSL-2 laboratory; all of the experiments with SCHU S4 were conducted within BSL-3 containment) in Mueller Hinton in the absence and presence of 1 μM of LED209 (209), 50 μM epinephrine (EPI), or 50 μM epinephrine plus 1 μM LED209 (209+EPI).

FIG. 10A. The ability of LED209 to interfere with β adrenergic receptor-regulated cAMP generation was assessed in HEK293 cells expressing either β2 (endogenous) (Black bars) or exogenously expressed β1 (white bars) or β3 (gray bars) adrenergic receptors. LED209 does not activate any of the 3 classes of β adrenergic receptors nor does it block the activation by β-adrenergic-specific agonists (β1: dob=dobutamine, β2: terb=terbulaline, or β3: BRL= BRL37344). FIG. 10B. CD-1 female mice were dosed with 20 mg/kg LED209 as an IV bolus or by oral gavage. At various times post-dosing, groups of three animals each were subject to a terminal bleed. Plasma was isolated and frozen at −80° C. for later analysis. Protein was precipitated from 100 μl of plasma with 200 μl of acetonitrile containing 20 ng of an internal standard. Samples were spun in a microcentrifuge to isolate free compound and subject to electrospray LC/MS/MS analysis as described in Materials and Methods. Samples were quantified using a standard curve prepared as described above in blank plasma. The data were evaluated using the noncompartmental model in WinNonLin (Pharsight). Bioavailability was calculated as $AUC_{oral}/AUC_{IV} \times Dose_{IV}/Dose_{oral}$. FIG. 10C. Preliminary toxicology assessment for LED209: the compound was dosed daily for 5 days by oral gavage at 20 mg/kg in 3 female CD-1 mice in comparison to 3 mice given the buffer only by gavage. There were no significant differences in the organ weights of any of these mice.

FIG. 11A. qRT PCR of sifA in vitro in WT and a qseC mutant (ΔqseC) of S. typhimurium the absence and in the presence of 50 μM NE. FIG. 11B. Mice (129×1/SvJ) survival plot upon intraperitonial infection with $10^8$ cfu of wild-type (WT) S. typhimurium strain SL1344, or the qseC isogenic mutant, or upon oral treatment with LED209 (20 mg/kg) alone, and intraperitonial infection with $10^8$ cfu of S. typhimurium strain SL1433 plus LED209 (20 mg/kg).

FIG. 13A. cfus of S. typhimurium harvested from liver and spleens of mice infected intraperitonially with $10^8$ cfu of S. typhimurium strain SL1344, and intraperitonial infection with $10^8$ cfu of S. typhimurium strain SL1433 plus LED209 (20 mg/kg) 48 hours post-infection. FIG. 13B. qRT PCR of expression of the flagella regulator (flhDC) and sifA in vitro in the absence (black bars) and presence (5 pM) of LED209 (white bars).

FIG. 14A. The *E. coli* fliC::lacZ fusion was introduced into WT *E. coli*, the qseC *E. coli* mutant, and the qseC *E. coli* mutant complemented with *F. tularensis* qseC (qseC pFTQseC) in the absence and presence of 5 pM LED209. The *F. tularensis* QseC has been tagged with a His-Tag and the inlet shows that the *F. tularensis* QseC is expressed in the *E. coli* qseC mutant. FIG. 14B. Infection of J774 murine macrophages with *F. tularensis* SCHU S4 in the absence and presence (5 nM) of LED209. FIG. 14C. qRT PCR of *F. tularensis* virulence genes in the absence (gray bars) and presence (5 pM) of LED209 (white bars). FIG. 14D. qRT-PCR measuring expression of qseC in SCHU S4 during growth in vitro and in vivo (spleen, liver and lungs). These data were collected from 5 C3H HeN mice intranasally infected with 30 cfu of SCHU S4. qRT-PCR of qseC was normalized against rpoA. Y-axis: fold-change. FIG. 14E. Mice (C3H HeN) survival plot upon oral treatment with LED209 (20 mg/kg) alone, intranasal infection with 30 cfu of SCHU S4, and intranasal infection with 30 cfu of SCHU S4 plus LED209 (20 mg/kg). *$p<0.01$; $p<0.001$; *$p<0.0001$.

FIG. 18. Blood chemistry and complete blood counts of mice treated with vehicle or LED209.

DESCRIPTION OF ILLUSTRATIVE EMBODIMENTS

Figure 1:
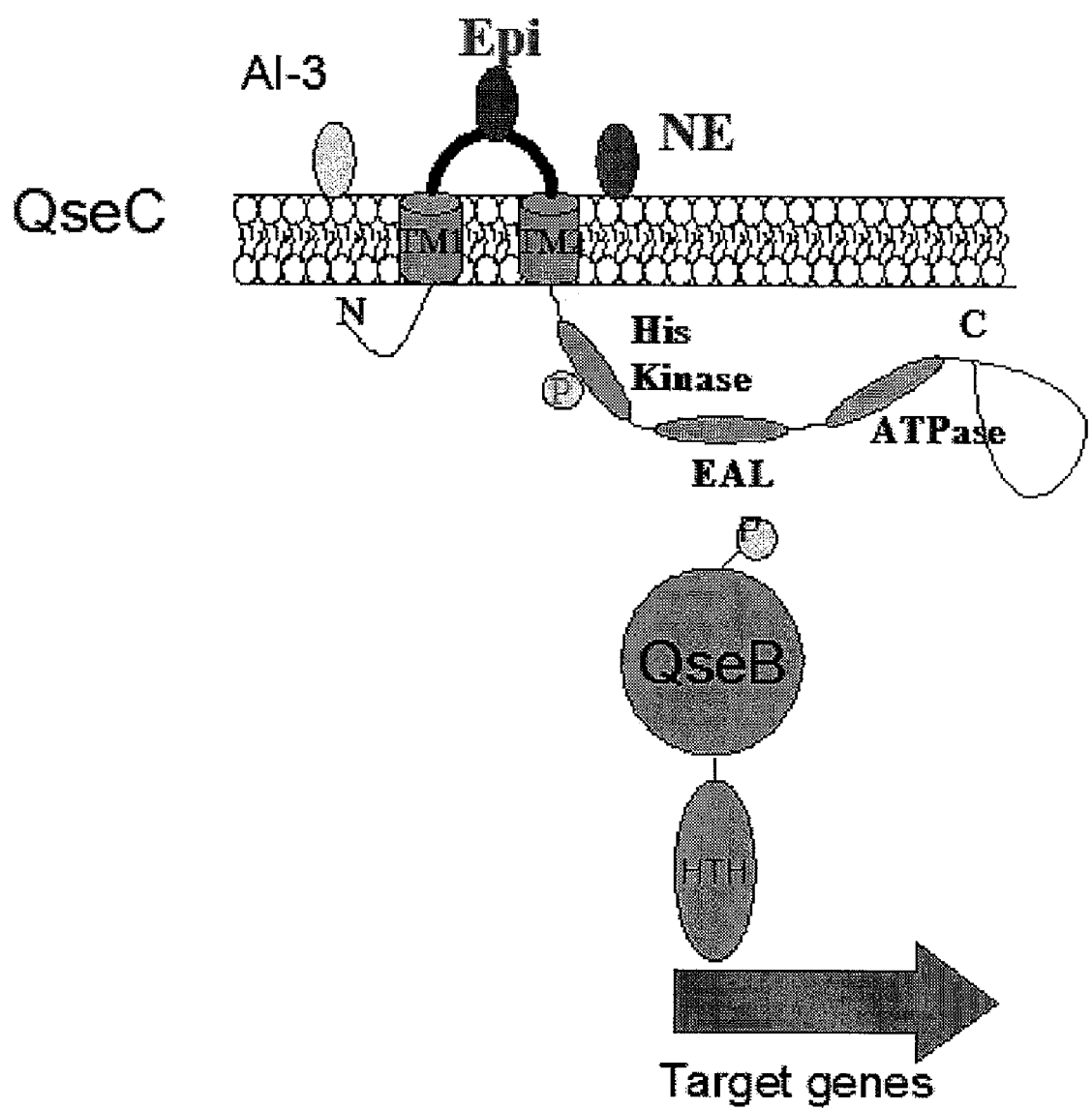
FIG. 1. Schematic autophosphorylation of QseC in response to signals and phosphotransfer to QseB.

The present invention overcomes the deficiencies of the prior art by providing compounds that, unlike antibiotics, do not kill or hinder bacterial growth but still may be used to treat bacterial infection. These compounds are not as susceptible to inducing bacterial resistance and thus present a novel avenue for bacterial infection treatment.

A. Bacteria and Bacterial Infections

1. Enterohemorrhagic *E. coli* (EHEC) Serotype O157:H7

EHEC, a category B biothreat agent, is a food born pathogen responsible for major outbreaks of bloody diarrhea and hemolytic uremic syndrome (HUS), a type of kidney failure, throughout the world. Annually in the United States, EHEC is responsible for an estimated 73,000 illnesses, 1,800-3,600 hospitalizations and from 61-541 deaths with combined annual economic costs exceeding $400 million (world wide web at .cdc.gov) (Kapper and O'Brien, 1998). In Argentina, Chile and Uruguay, EHEC is responsible for 40% of the cases of bloody diarrhea. In the U.K., EHEC incidence has increased over the years to 2.7/100,000. In an outbreak in 1996 in Sakai, Japan, there were over 7,500 cases (CDC webpage).

EHEC has a very low infectious dose (as low as 50 colony forming units (cfu)), which is one of the major contributing factors to EHEC outbreaks. EHEC colonizes the large intestine where it causes attaching and effacing (AE) lesions on intestinal epithelial cells. The AE lesion is characterized by the destruction of the microvilli of the colon epithelium and the rearrangement of the cytoskeleton to form a pedestal-like structure, which cups the bacterium individually. The genes involved in the formation of the AE lesion are encoded within a chromosomal pathogenicity island named the locus of enterocyte effacement (LEE).

The mortality associated with EHEC infections stems from the production and release of a potent toxin, named Shiga toxin (Stx), by these bacteria. This potent inhibitor of protein synthesis can be absorbed systemically where it binds to receptors found in the kidneys and central nervous system (CNS), causing HUS, seizures, cerebral edema, and/or coma, Shiga toxin has the same potency and mechanism of action as the plant toxin ricin: it causes cell death in endothelial cells, primarily in the urinary tract that leads to HUS, whose most common outcome is death. The genes encoding Shiga toxin are located within the late genes of a λ-like bacteriophage, and are transcribed when the phage enters its lytic cycle. Disturbances in bacterial envelope, DNA replication, or protein synthesis (which are targets of conventional antibiotics) trigger an SOS response in the bacterial EHEC cells that signals the bacteriophage to enter the lytic cycle. The phage replicates, Shiga toxin is produced, and the phage lyses the bacteria, thereby releasing Shiga toxin in the host. Consequently, treatment of EHEC infections with conventional antimicrobials is highly controversial, and can do more harm than good. In fact, antibiotics promote the expression and release of Shiga toxins, thereby increasing the occurrence and severity of HUS and CNS involvement (Kimmitt et al, 1999; Kimmitt et al., 2000). Currently, there is no treatment for HUS other than plasmaphoresis of this toxin. Consequently, innovative, cost-effective EHEC treatments are urgently needed to address this significant unmet healthcare need.

2. Salmonella

*Salmonella enterica*, another category B biothreat agent, includes significant human pathogens responsible for food poisoning and enteric or typhoid fever (Boyle et al, 2007). Nontyphoidal *Salmonella* infections (i.e., 'food poisoning' or Salmonellosis) result in mild to moderate diarrhea, fever, nausea, and cramps which normally resolve without treatment in 4-7 days. Nevertheless, nontyphoidal infections have a large health impact with an estimated ~1.4 million infections, 16,000 hospitalizations, and 400-600 deaths annually in the U.S. In economic terms, the impact has been estimated at $2.4 billion for 2005 (Frenzen, P., 2006). *Salmonella* nomenclature and species identification are complicated. Most food poisonings are caused by *Salmonella enterica* serovar *typhimurium* (*S. typhimurium*) or *Salmonella enterica* serovar *Enteritidis* (*S. Enteritidis*). The latter is often associated with eggs and poultry. By contrast, typhoid fever is caused by *Salmonella enterica* serovar *typhi* (*S. typhi*) but is rare in the U.S. Over 2600 *Salmonella enterica* serovars have been identified (Todar, K. 2005). Studies from around the world show that *Salmonella* has become increasingly resistant to many antibiotics (Crump et al., 2003; Davis et al., 1999; Plant et al., 1982; Nakaya et al., 2003; Samrakandi et al., 2004; Weill et al., 2006). Clearly new treatments for *Sal-* monella infections are needed now. Ideally, any new drugs would target new mechanisms and avoid resistance.

3. *Francisella tularensis*

*Francisella tularensis* is a category A biothreat agent that has to be handled within Biosafety Level 3 (BSL-3) plus containment. Tularemia is classically considered a zoonotic disease and the incidence of human infection is low. *F. tularensis* is a highly infectious pathogen, with as few as 10 organisms being capable of causing disease in humans (Golovliov et al., 1997). The disease can have a number of clinical presentations (Prior et al., 2001; Pullen and Stuart, 1945; Stuart and Pullen, 1945; Syrjala et al., 1986). Due to its high infectivity and lethality in humans, *F. tularensis* has been classified as a high-risk agent for bioterrorism. Furthermore, there is very little information on *F. tularensis* pathogenesis, and the only vaccine, *F. tularensis* live vaccine strain (LVS), is not readily available and poorly characterized (Sandstrom, 1994). Although natural infections with *F. tularensis* can be readily treated with antibiotic, this may not be the case with weaponized multi-antibiotic resistant strains—thus, alternative therapeutics are required (Checroun et al, 2006; Clemens et al., 2005; Clemens et al., 2004; Fortier et al., 1995; Lee et al., 2006; Tarnvik, 1999).

4. Plant Pathogens

Quorum sensing, described in more detail below, plays a role in the activity of certain plant pathogenic bacteria. Bacterial plant pathogens produce an array of enzymes which attack host cell components, and these enzymes play important roles in suppression of host defense response and establishment of infection. Compounds of the present invention may thus be used to treat infected plants or pre-treat plants to prevent such infections.

Bacterial pathogens such as *Erwinia carotovora* produce virulence factors, such as degradative enzymes, which assist the bacteria in entering plant cells and degrading plant tissues. The production of these factors is controlled by quorum sensing. See Pirhonen et al., 1993; von Bodman et al., 2003. Several groups of signal molecules are involved in different microbial quorum sensing systems. See Fuqua et al., 1996; Robson et al, 1997. Among them, the best characterized are the N-acyl homoserine lactones (AHLs), also known as autoinducers (AIs) (a term throughout this application). AHLs are members of a family of widely conserved signal molecules used in the quorum sensing systems of many Gram-negative bacteria. They also are involved in regulation of a diverse range of biological activities including expression of virulence genes of bacterial pathogens such as *Erwinia carotovora, Erwinia chrysanthemi* and *Erwinia stewartii*.

Certain gram-positive bacteria are also affected by quorum sensing. Non-limiting examples of quorum sensing pathogenic bacteria that may cause plant diseases treatable by compounds of the present invention include *Agrobacterium tumefaciens, Pantoea stewartii, Erwinia carotovora, Erwinia chrysanthemi, Erwinia stewartii, Ralstonia solanacearum, Pseudomonas syringae, Pseudomonas aeruginosa* and *Xanthomonas campestris*.

i. *Erwinia*

*Erwinia* is a genus of Enterobacteriaceae bacteria containing mostly plant pathogenic species. It is a gram-negative bacterium related to *E. coli, Shigella, Salmonella* and *Yersinia*. A well-known member of this genus is the species *Erwinia amylovora*, which causes fireblight on apple, pear, and other Rosaceous crops. *Erwinia carotovora* is another plant pathogen. This pathogen, which possesses a QseC sensor, boasts a wide host range (carrot, potato, tomato, leafy greens, squash and other cucurbits, onion, green peppers, etc.) and is able to cause disease in almost any plant tissue it invades. It is a very economically important pathogen in terms of postharvest losses, and a common cause of decay in stored fruits and vegetables. Decay caused by *Erwinia carotovora* is often referred to as bacterial soft rot (BSR). Most plants or plant parts can resist invasion by the bacteria, unless some type of wound is present. high humidity and temperatures around 30° C. favor development of decay. Mutants can be produced which are less virulent. Virulence factors include: pectinases, cellulases, (which degrade plant cell walls), and also proteases, lipases, xylanases and nucleases. Other pathogenic *Erwinia* species include *Erwinia chrysanthemi* (causes BSR of corn in the field and in storage) and *Erwinia stewartii* (causes Stewart's wilt in corn).

ii. *Ralstonia*

*Ralstonia* is a genus of proteobacteria, previously included in the genus *Pseudomonas*. One notorious species is *Ralstonia solanacearum*, the causal agent of bacterial wilt. *Ralstonia solanacearum* infects over 100 plant species, such as tomatoes, egg plants, green peppers, tobacco plants, Japanese radishes and strawberries (Kelman, 1953). Ginger, mulberry, banana are also susceptible as well as ornamental plants (e.g., geraniums) (Daughtrey, 2003). The species has been subclassified into at least five races and five biovars. Each race affects a different subset of plants.

*Ralstonia solanacearum* race 3 bv 2 is a strain that has become adapted to temperate climates (Haywood et al., 1998; Stead et al., 1996). Other biovars of *Ralstonia solanacearum* can infect potatoes; however, bv 2 is by far the most destructive biovar in temperate areas. The organism has a narrow host range primarily infecting potato (Hayward, 2000). Brown rot has emerged recently as a serious disease of potato in Western Europe (Stead et al., 1996) and *Ralstonia solanacearum* bv 2 is listed as a zero tolerance quarantine organism in the European Union (EU) (Official J. Eur. Communities, 1998). In those countries affected by brown rot, the costs of disease surveillance and eradication have become considerable. The pathogen has been reported in potato in Turkey; but it has not yet been observed in potato in the continental U.S. where no regulation in potato currently exists. However, the report of finding bv 2 in geranium in Wisconsin (Williamson et al., 2001; Kim et al., 2002) could result in movement of the pathogen into potato. Other Ralstonia species contemplated by the present invention include *Ralstonia eutropha* and *Ralstonia metallidurans*.

5. Biofilms

The term "biofilm" as used herein refers to a material which naturally develops when microbes attach to a support that is made of a material including but not limited to stone, metal, plastic, glass and wood. "Biofilm" also refers to filamentous and non-filamentous bacteria that produce an extracellular polysaccharide and proteinaceous material that act as a natural glue to immobilize the cells. In nature, nonfilament-forming microorganisms stick to the biofilm surface, locating within an area of the biofilm that provides an optimal growth environment with respect to pH, dissolved oxygen, and nutrients. Since nutrients tend to concentrate on solid surfaces, including porous surfaces and wet, dry surfaces, a microorganism saves energy through cell adhesion to a solid surface rather than by growing unattached.

Single-celled organisms generally exhibit two distinct modes of behavior. The first is the familiar free floating, or planktonic, form in which single cells float or swim independently in some liquid medium. The second is an attached state in which cells are closely packed and firmly attached to each other and usually a solid surface. The change in behavior is triggered by many factors, including quorum sensing (described below), as well as other mechanisms that vary between species. When a cell switches modes, it undergoes a phenotypic shift in behavior in which large suites of genes are up- and down-regulated.

Biofilms have been found to be involved in a wide variety of microbial infections in the body, perhaps as high as 80% of all infections. The achievements of medical care in industrialized societies are markedly impaired due to chronic opportunistic infections that have become increasingly apparent in immunocompromised patients and the ageing population. Chronic infections remain a major challenge for the medical profession and are of great economic relevance because traditional antibiotic therapy is usually not sufficient to eradicate these infections. One major reason for persistence seems to be the capability of the bacteria to grow within biofilms that protects them from adverse environmental factors. *Pseudomonas aeruginosa*, for example, is not only an important opportunistic pathogen and causative agent of emerging nosocomial infections, but can also be considered a model organism for the study of diverse bacterial mechanisms that contribute to bacterial persistence. *Pseudomonas aeruginosa* is also responsible for biofilm formed in the lungs of cystic fibrosis patients.

Other infectious processes in which biofilms have been implicated include common problems such as urinary tract infections, catheter infections, middle-ear infections, formation of dental plaque, gingivitis, coating contact lenses, and less common but more lethal processes such as endocarditis, infections in cystic fibrosis, and infections of permanent indwelling devices such as joint prostheses and heart valves. It has recently been shown that biofilms are present on the removed tissue of 80% of patients undergoing surgery for chronic sinusitis. Biofilms are also present on the teeth of most animals as dental plaque, where they may become responsible for tooth decay. Compounds of the present invention may be employed to treat any condition associated with biofilms formed by quorum sensing bacteria.

B. Bacterial Signaling

Microbes and mammals communicate with each other through an array of hormone and hormone-like chemical compounds. These "signals" however, are highjacked by bacterial pathogens, such as enterohemorrhagic *E. coli* (EHEC) O157:H7, to activate its virulence genes. EHEC senses three signals to activate its virulence genes: one is a bacterial aromatic autoinducer (AI-3) produced by the normal human gastrointestinal (GI) microbial flora; and the other two are the host hormones epinephrine/norepinephrine (NE) produced by the host (Sperandio et al., 2003). Recognition of these three signals is essential for virulence in two different animal models, as determined in the laboratory of one of the present inventors (Clarke et al., 2006).

AI-3 is a quorum sensing (QS) signal produced by several species of bacteria, including commensal *E. coli*, as well as several other intestinal bacterial species (EPEC E2348/69, EHEC O26:H11, EPEC O111:H9, *Klebsiella pneumoniae*, *Shigella* sp., *Salmonella* sp., *Lactobacillus reuteri*, and *Enterobacter cloacae*) (Walters et al., 2006; Tannock et al., 2005). The wide variety of bacteria able to produce AI-3 suggests that it may serve as a general inter-species QS signal. The bacterial QS AI-3 signal cross-signals with the host hormones epinephrine and norepinephrine (NE). Both epinephrine and NE are present in the GI tract. Both hormones modulate intestinal smooth muscle contraction, submucosal blood flow, and chloride and potassium secretion in the intestine. Epinephrine and NE are recognized by adrenergic receptors in mammalian cells.

The AI-3/epinephrine/NE inter-kingdom signaling cascade is present in several important bacterial pathogens of animals and plants (e.g., enterohemorrhagic *E. coli* (EHEC), uropathogenic *E. coli* (UPEC), *Shigella flexneri*, *Salmonella typhi* and *typhimurium*, *Erwinia carotovora*, *Pasteurella multocida*, *Haemophilus influenzae*, *Actinobacillus pleuropneumoniae*, *Chromobacter violaceum*, *Pseudomonas aeruginosa*, *Pseudomonas fluorescens*, *Burkholderia cepacia*, *Coxiella burnetti*, *Yersinia pseudotuberculosis*, *Yersinia pestis*, *Francisella tularensis* and *Ralstonia solacearum*) suggesting that this inter-kingdom cross-signaling is not restricted to *E. coli*. The lack of efficient treatments for various bacterial infections caused by these pathogens, due to the controversy posed by administration of conventional antibiotics in certain situations, combined with the growing challenge of antimicrobial resistance and the scarcity of novel antibiotics, highlight the importance of understanding this signaling cascade to design and generate new classes of antimicrobials.

C. The QseC Receptor

QseC is a membrane bound histidine sensor kinase (see FIG. 1). Typically, these sensor kinases constitute two-component systems, acting in concert with response regulators. In response to the environmental signal, the sensor autophosphorylates its own conserved histidine residue. Subsequently, the histidine-bound phosphoryl group of the sensor kinase is transferred onto a specific aspartate residue on the cognate response regulator for activation. The activated response regulator then directly regulates transcription of its target genes. In bacteria, two-component systems are the major system of signal transduction (Igo et al., 1989). Importantly mammals do not harbor histidine sensor kinases, making inhibitors of bacterial histidine kinases as attractive potential novel therapeutics due to their selective toxicity (Lyon and Muir, 2003; Roychoudhury et al., 1993).

QseC is a receptor for the AI-3/Epi/NE signals and is central for the pathogenesis of certain bacteria, such as EHEC, *Salmonella* and *Francisella tularensis*. QseC will directly bind these signals, and in response, augment its autophosphorylation (Clarke et al., 2006). Subsequently, QseC transfers this phosphate to its cognate response regulator QseB (a transcription factor) which then regulates gene expression.

Figure 3:
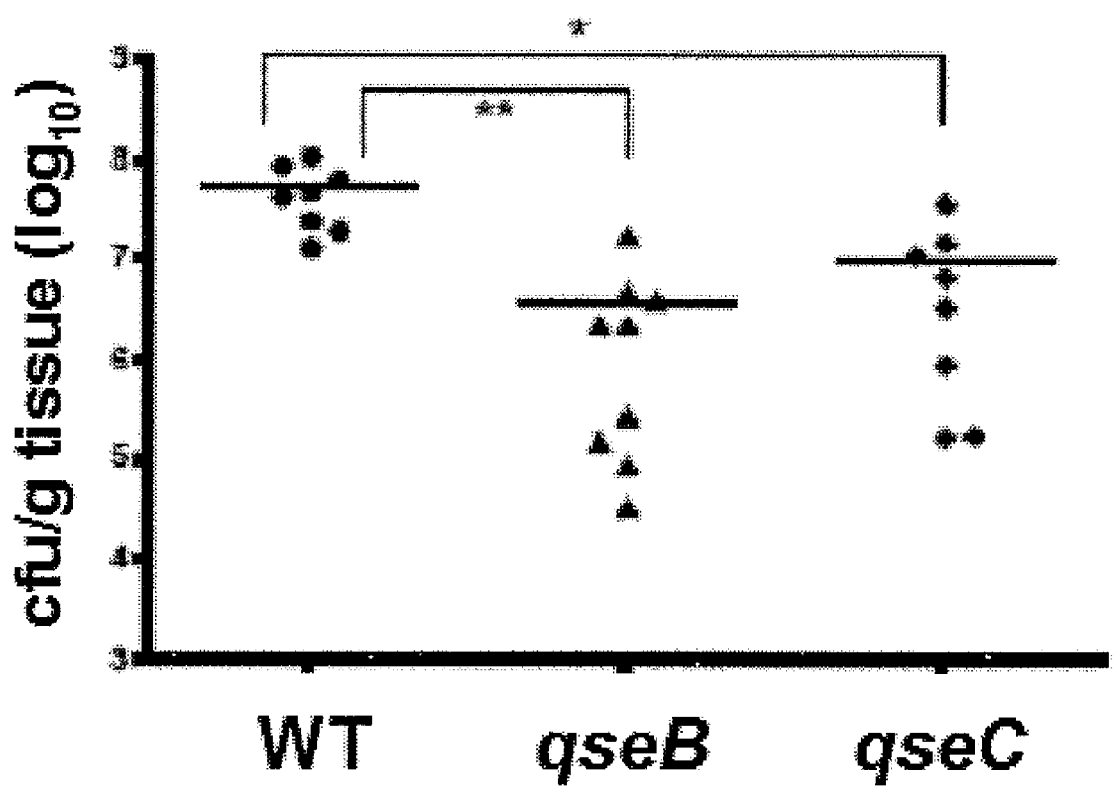
FIG. 3. Colonization of the colon of infant rabbits by WT EHEC, the qseC and qseB mutants (colony forming units/gram of tissue).
Figure 4:
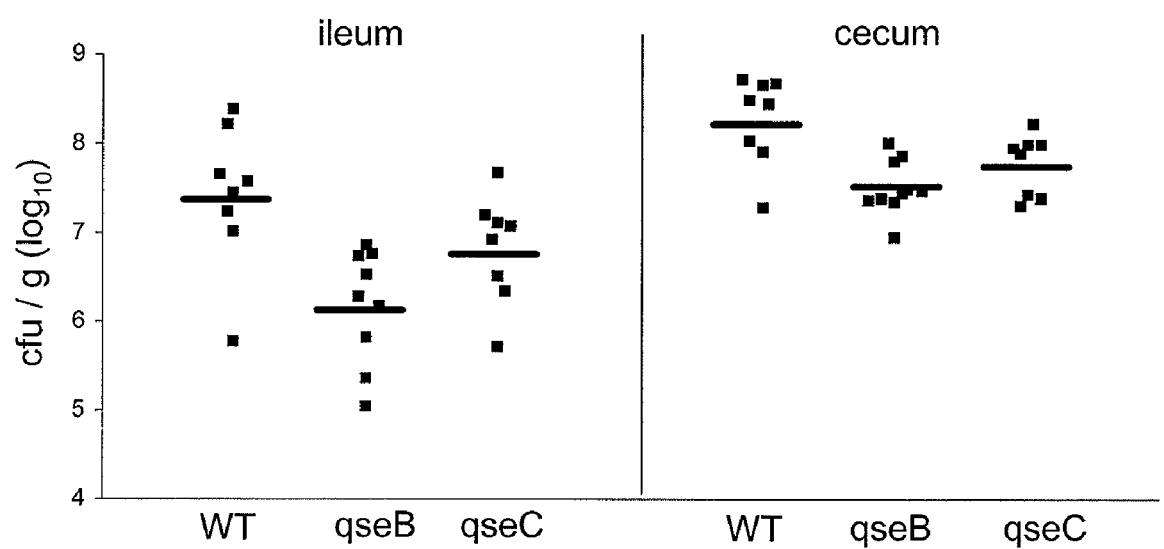
FIG. 4. Colonization of the ileum and cecum of infant rabbits by WT EHEC, the qseC and qseB mutants (results are expressed as colony forming units/gram of tissue).
Figure 19:
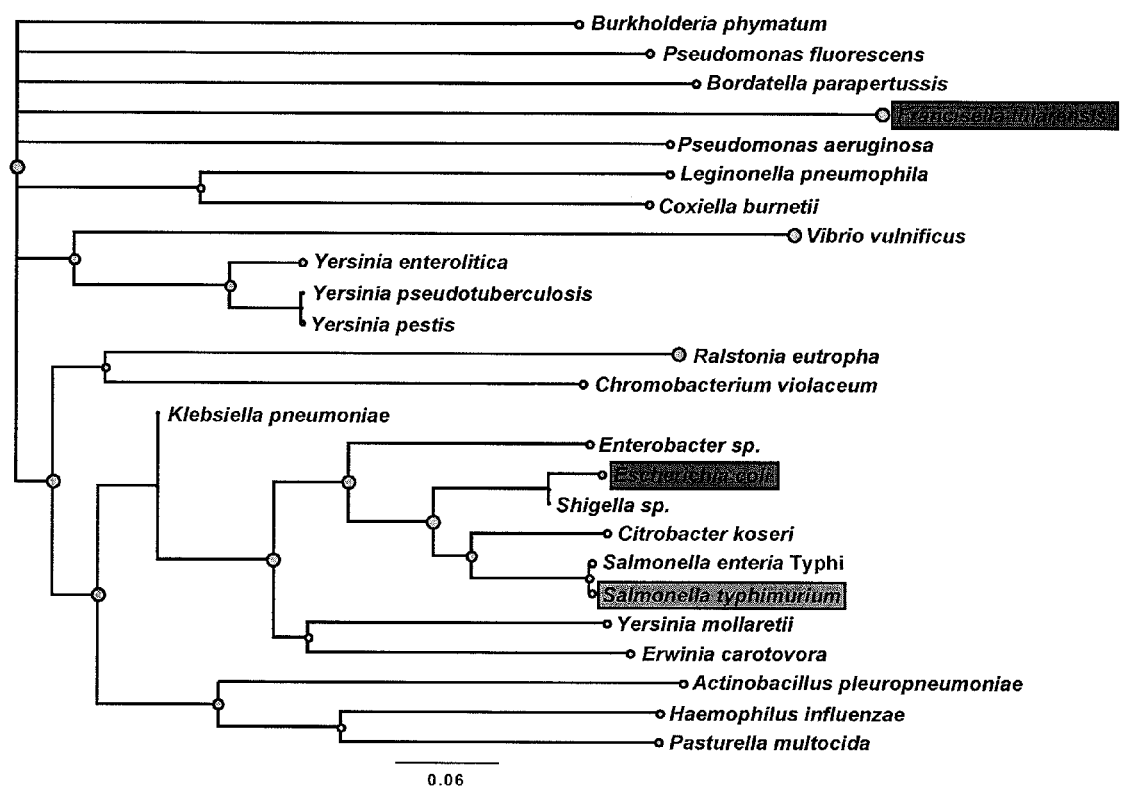
FIG. 19. Neighbor-Joining Tree of QseC homologs. The consensus Neighbor-joining tree was built using a Jukes Cantor genetic distance model with 1000 bootstraps.

QseC homologs are present in several bacterial pathogens including EHEC, EPEC, UPEC, K-12, *Klebsiella pneumoniae*, *Acinetobacter baumannii*, *Shigela flexneri*, *Salmonella enterica typhi* and *typhimurium*, *Yersinia pestis*, *Y. enterocolitica*, *Y. pseudotuberculosis*, *Erwinia carotovora*, *Pasteurella multocida*, *Haemophilus influenzae*, *Actinobacillus pleuroneumoniae*, *Chromobacter violaceum*, *Pseudomonas aeruginosa*, *Pseudomonas fluorescens*, *Burkholderia cepacia*, *Coxiella burnetti*, *Ralstonia solacenarum* and *Francisella tularensis*. See FIGS. 2 and 19. qseC mutants of enterohemorrhagic *E. coli* (EHEC) (Clarke et al., 2006 and FIG. 3 and FIG. 4), *Salmonella typhimurim* (Bearson and Bearson, 2007 and FIG. 11B), and *Francisella tularensis* (Weiss et al., 2007) are attenuated in animal models of infection. Finally, QseC is involved in quorum sensing (QS) signaling, and this signaling is not directly involved in processes essential for bacterial growth. Thus, in theory, inhibitors of QS signaling would not induce selective pressures promoting evolution of bacterial resistance.

Examples of QseC polypeptides include, but are not limited to polypeptides having the amino acid sequence provided in the following database accession numbers: YP_169166, YP_514393, YP_899230, YP_001121274, YP_764109.1, YP_001891028, YP_001677727, YP_123578, YP_095321, YP_126604, YP_286016, NP_820223, YP_001115442, ZP_02062557, YP_981771, YP_001862321, YP_001140960, YP_02843268, NP_439849, YP_001341184, YP_249422, YP_001898056, ZP_00943152, YP_001291883, ZP_01787351, ZP_02007463, ZP_01791137, ZP_02478656, YP_001857419, YP_002258797, ZP_00203211, YP_432917, YP_857714, YP_932480, NP_518670, ZP_01793303, YP_157647, YP_786825, YP_002232952, YP_002256398, ZP_01518082, YP_114371, ZP_01308375, YP_001862413, ZP_02885351, NP_884854, NP_881175, YP_001898159, YP_160589, YP_088436, YP_283657, ZP_03268795, YP_001790728, ZP_03267145, YP_001816214, NP_880853, YP_102133, ZP_00439965, ZP_02446165, YP_002107737, ZP_02884581, NP_885061, NP_889719, YP_582619, NP_840430, YP_725059, YP_558955, ZP_03268804, ZP_00349512, YP_001856676, YP_001100931, YP_001895813, YP_001795885, YP_560317, YP_294751, CAL62240, YP_001100363, YP_284407, YP_984175, YP_001896912, YP_265358, ZP_01915254, YP_001354611, YP_285095, YP_001895822, ZP_01999348, YP_284799, ZP_01224171, YP_367461, YP_001630663, ZP_02842897, YP_001171444, ZP_02886774, NP_253465, YP_545417, YP_001985138, YP_001860133, ZP_02843728, ZP_02906088, YP_690440, YP_542429, NP_417498, YP_001881794, ZP_03069017, YP_001723674, ZP_03034105, ZP_03003495, YP_001745294, ZP_03063918, YP_409231, YP_001464488, YP_001791653, ZP_02885393, YP_001767156, YP_001862321, ZP_02886774, YP_001816214, and ZP_01308375; each of which is incorporated herein by reference as of the filing date of this application. In certain aspects the polypeptide targets of the invention will comprise a HisKA and/or a HARPase_c domain.

Embodiments of the invention include QseC kinase homolog compositions that may include a polypeptide or protein that is or is at least 40%, 50%, 60% 70%, 75%, 80%, 85%, 90%, 95%, 96%, 97%, 98%, or 99% identical or similar, including all values and ranges there between, to QseC kinase as long as key regions, such as its histidine kinase and transmembrane regions, are conserved. Sequence identity and/or similarity can be determined using standard techniques known in the art, such as a Jukes Cantor genetic distance model with 1000 bootstraps (see Yang and Zhang Nucleic Acids Res. 2008 March; 36(5), Cantor and Jukes, Biochem Biophys Res Commun. 1966 May 3; 23(3):319-23). Percent identity and percent similarity may be calculated by using alignment tools known to and readily ascertainable to those of skill in the art.

D. Multidrug-Resistant Bacteria

At least since the early 1980s, studies from around the world show that *Salmonella* has become increasingly resistant to many antibiotics (Davis et al., 1999). Whereas a tiny fraction of isolates were resistant in the early 80's, by the mid-90's nearly 20% were resistant (Glynn et al, 1998). This is attributed in large part to the widespread use of antibiotics as growth agents in livestock, which are the primary reservoir for non-typhoidal *Salmonella*. In the late 90's, the DT104 strain of *S. typhimurium* was shown to be resistant to five agents including ampicillin, chloramphenicol, streptomycin, sulfonamides, and tetracycline. Whereas nalidixic acid was the treatment of choice up to the early 90's, it is seldom used due to the prevalence of resistance strains (Crump et al, 2003). More recently, several ciproflaxin and ceftriaxone resistant strains have emerged (Nakaya et al., 2003; Samrakandi et al., 2004; Weill et al., 2006) as well. Other bacteria have also become resistant to various antibiotics, such as *Staphylococcus, Enterococcus*, and *Streptococcus*.

The growing worldwide challenge of antimicrobial resistance and the paucity of novel antibiotics underscore the urgent need for innovative therapeutics. The increasing understanding of bacterial pathogenesis and inter-cellular communication, when combined with contemporary drug discovery tools and technologies, provides a powerful platform for translating such basic science into therapeutic applications to combat bacterial infections. Interference with bacterial cell-to-cell signaling via the quorum-sensing (QS) pathway constitutes an especially compelling and novel strategy since it also obviates the development of bacterial resistance. QS allows bacteria to respond to hormone-like molecules called autoinducers and is responsible for controlling a plethora of virulence genes in several bacterial pathogens. Because QS is not directly involved in essential processes such as growth of the bacteria, inhibition of QS should not yield a selective pressure for development of resistance. QS antagonists confuse or obfuscate signaling between bacteria and, unlike antibiotics, do not kill or hinder bacterial growth. Hence, QS antagonists should be viewed as blockers of pathogenicity rather than as antimicrobials.

The innovative approach discovered by the present inventors builds on recently obtained insights into the mechanisms of pathogenicity of enterohemorrhagic *E. coli* O157:H7 (EHEC), *Salmonella* (class B biothreat agents) and *Francisella tularensis* (class A biothreat agent). As determined by the present inventors, these diverse pathogens all sense any one or more three signals to activate transcription of their virulence genes (Clarke et al., 2006). These include a bacterial autoinducer (autoinducer-3, AI-3) produced by these pathogens and the normal gastrointestinal flora (in the case of the enteric pathogens) as well as epinephrine/norepinephrine (epi/NE) hormones produced by the host. Importantly, all of these signaling molecules can trigger the QseC membrane bound sensor kinase present in these three pathogens (and in at least 15 other important human and plant pathogens) thereby relaying the presence of these chemical signals to a complex regulatory cascade leading to transcription of key virulence genes. These transcriptional events enable these three pathogens to infect the host. Because of the central role of the AI-3/epi/NE receptor and its signaling system in bacterial pathogenesis and the presence of this system in a broad array of important animal and plant pathogens, compounds of the present invention that act as inhibitors of this receptor system provide an attractive avenue for drug development.

E. Chemical Definitions

The term "alkyl" includes straight-chain alkyl, branched-chain alkyl, cycloalkyl (alicyclic), cyclic alkyl, heteroatom-unsubstituted alkyl, heteroatom-substituted alkyl, heteroatom-unsubstituted $C_n$-alkyl, and heteroatom-substituted $C_n$-alkyl. In certain embodiments, lower alkyls are contemplated. The term "lower alkyl" refers to alkyls of 1-6 carbon atoms (that is, 1, 2, 3, 4, 5 or 6 carbon atoms). The term "heteroatom-unsubstituted $C_n$-alkyl" refers to a radical, having a linear or branched, cyclic or acyclic structure, further having no carbon-carbon double or triple bonds, further having a total of n carbon atoms, all of which are nonaromatic, 3 or more hydrogen atoms, and no heteroatoms. For example, a heteroatom-unsubstituted $C_1$-$C_{10}$-alkyl has 1 to 10 carbon atoms. The groups, —$CH_3$ (Me), —$CH_2CH_3$ (Et), —$CH_2CH_2CH_3$ (n-Pr), —$CH(CH_3)_2$ (iso-Pr), —$CH(CH_2)_2$ (cyclopropyl), —$CH_2CH_2CH_2CH_3$ (n-Bu), —$CH(CH_3)CH_2CH_3$ (sec-butyl), —$CH_2CH(CH_3)_2$ (iso-butyl), —$C(CH_3)_3$ (tert-butyl), —$CH_2C(CH_3)_3$ (neo-pentyl), cyclobutyl, cyclopentyl, and cyclohexyl, are all non-limiting examples of heteroatom-unsubstituted alkyl groups. The term "heteroatom-substituted $C_n$-alkyl" refers to a radical, having a single saturated carbon atom as the point of attachment, no carbon-carbon double or triple bonds, further having a linear or branched, cyclic or acyclic structure, further having a total of n carbon atoms, all of which are nonaromatic, 0, 1, or more than one hydrogen atom, at least one heteroatom, wherein each heteroatom is independently selected from the group consisting of N, O, F, Cl, Br, I, Si, P, and S. For example, a heteroatom-substituted $C_1$-$C_{10}$-alkyl has 1 to 10 carbon atoms. The following groups are all non-limiting examples of heteroatom-substituted alkyl groups: trifluoromethyl, —$CH_2F$, —$CH_2Cl$, —$CH_2Br$, —$CH_2OH$, —$CH_2OCH_3$, —$CH_2OCH_2CF_3$, —$CH_2OC(O)CH_3$, —$CH_2NH_2$, —$CH_2NH$-(lower alkyl), such as —$CH_2NHCH_3$ and —$CH_2N(CH_3)_2$, —$CH_2CH_2Cl$, —$CH_2CH_2OH$, $CH_2CH_2OC(O)CH_3$, —$CH_2CH_2NHCO_2C(CH_3)_3$, —$CH_2Si(CH_3)_3$, imidazolidinyl, pyrazolidinyl, morpholinyl, piperazinyl, and thiomorpholinyl. In certain embodiments, lower alkyl refers to —$CH_2NH_2$ or —$CH_2NH$-(lower alkyl), such as —$CH_2NHCH_3$ and —$CH_2N(CH_3)_2$.

In general, the term "lower," as applied to alkyl-containing substituents, refers to the number of carbon atoms being 1-6, e.g., 1, 2, 3, 4, 5, or 6, or any range derivable therein. This term may apply to any alkyl-containing substituent described herein (e.g., alkyl, alkylthio, alkanediyl, aralkyl, alkylamino, dialkylamino, trialkylammonium, etc.)

The term "alkylthio" refers to —S-alkyl, wherein alkyl is defined above. Lower alkylthio is contemplated for any embodiment, wherein the alkyl moiety comprises 1-6 carbon atoms (that is, 1, 2, 3, 4, 5 or 6 carbon atoms).

The term "alkanediyl" refers to both substituted and unsubstituted alkanediyl. When used without the "substituted" modifier, alkanediyl refers to a non-aromatic divalent group, wherein the alkanediyl group is attached with two σ-bonds, with one or two saturated carbon atom(s) as the point(s) of attachment, a linear or branched, cyclo, cyclic or acyclic structure, no carbon-carbon double or triple bonds, and no atoms other than carbon and hydrogen. The groups, —$CH_2$— (methylene), —$CH_2CH_2$—, —$CH_2C(CH_3)_2CH_2$—, —$CH_2CH_2CH_2$—, and

, are non-limiting examples of alkanediyl groups. The term "substituted alkanediyl" refers to a non-aromatic monovalent group, wherein the alkynediyl group is attached with two σ-bonds, with one or two saturated carbon atom(s) as the point(s) of attachment, a linear or branched, cyclo, cyclic or acyclic structure, no carbon-carbon double or triple bonds, and at least one atom independently selected from the group consisting of N, O, F, Cl, Br, I, Si, P, and S. The following groups are non-limiting examples of substituted alkanediyl groups: —CH(F)—, —$CF_2$—, —CH(Cl)—, —CH(OH)—, —$CH(OCH_3)$—, and —$CH_2CH(Cl)$—.

The term "aryl" includes heteroatom-unsubstituted aryl, heteroatom-substituted aryl, heteroatom-unsubstituted $C_n$-aryl, heteroatom-substituted $C_n$-aryl, heteroaryl, heterocyclic aryl groups, carbocyclic aryl groups, biaryl groups, and single-valent radicals derived from polycyclic fused hydrocarbons (PAHs). The term "heteroatom-unsubstituted $C_n$-aryl" refers to a radical, having a single carbon atom as a point of attachment, wherein the carbon atom is part of an aromatic ring structure containing only carbon atoms, further having a total of n carbon atoms, 5 or more hydrogen atoms, and no heteroatoms. For example, a heteroatom-unsubstituted $C_6$-$C_{10}$-aryl has 6 to 10 carbon atoms. Non-limiting examples of heteroatom-unsubstituted aryl groups include phenyl (Ph), methylphenyl, (dimethyl)phenyl, —$C_6H_4CH_2CH_3$, —$C_6H_4CH_2CH_2CH_3$, —$C_6H_4CH(CH_3)_2$, —$C_6H_4CH(CH_2)_2$, —$C_6H_3(CH_3)CH_2CH_3$, —$C_6H_4CH=CH_2$, —$C_6H_4CH=CHCH_3$, —$C_6H_4C\equiv CH$, —$C_6H_4C\equiv CCH_3$, naphthyl, and the radical derived from biphenyl. The term "heteroatom-substituted $C_n$-aryl" refers to a radical, having either a single aromatic carbon atom or a single aromatic heteroatom as the point of attachment, further having a total of n carbon atoms, at least one hydrogen atom, and at least one heteroatom, further wherein each heteroatom is independently selected from the group consisting of N, O, F, Cl, Br, I, Si, P, and S. For example, a heteroatom-unsubstituted $C_1$-$C_{10}$-heteroaryl has 1 to 10 carbon atoms. Non-limiting examples of heteroatom-substituted aryl groups include the groups: —$C_6H_4F$, —$C_6H_4Cl$, —$C_6H_4Br$, —$C_6H_4I$, —$C_6H_4OH$, —$C_6H_4OCH_3$, —$C_6H_4OCH_2CH_3$, —$C_6H_4OC(O)CH_3$, —$C_6H_4NH_2$, —$C_6H_4NHCH_3$, —$C_6H_4N(CH_3)_2$, —$C_6H_4CH_2OH$, —$C_6H_4CH_2OC(O)CH_3$, —$C_6H_4CH_2NH_2$, —$C_6H_4CF_3$, —$C_6H_4CN$, —$C_6H_4CHO$, —$C_6H_4CHO$, —$C_6H_4C(O)CH_3$, —$C_6H_4C(O)C_6H_5$, —$C_6H_4CO_2H$, —$C_6H_4CO_2CH_3$, —$C_6H_4CONH_2$, —$C_6H_4CONHCH_3$, —$C_6H_4CON(CH_3)_2$, furanyl, thienyl, pyridyl, pyrrolyl, pyrimidyl, pyrazinyl, quinolyl, indolyl, and imidazoyl. A "di-substituted aryl group" refers to an aryl group that is substituted by two substituents: the substituents may be heteroatom-unsubstituted or heteroatom-substituted. Additional aryl groups include oxazolyl, isoxazolyl, thiazolyl, isothiazolyl, pyrazolyl, oxadiazolyl, thiadiazolyl, triazolyl, benzofuranyl, benzothienyl, indolizinyl, isoindolyl, isoindolinyl, indolinyl, benzoxazolyl, benzisoxazolyl, benzthiazolyl, benzisothiazolyl, benzimidazolyl, indazolyl, carbazolyl, dibenzofuranyl, dibenzothienyl, fluorenyl, pyridazinyl, triazinyl, tetrazinyl, pentazinyl, isoquinolinyl, quinolizinumyl, quinazolinyl, cinnolinyl, quinoxalinyl, phthalazinyl, napthyridinyl, pteridinyl, purinyl, adeninyl, guaninyl, acridinyl, phenazinyl, anthyridinyl, phenanthrolinyl, phenanthridinyl, phenothienyl, phenoxazinyl, anthracenyl, naphthyridinyl, azepinyl, oxepinyl, thiepinyl, diazepinyl, dioxepinyl, dithiepinyl, triazepinyl, oxazepinyl, thiazepinyl, thiadiazepinyl, tetrazepinyl, thiatriazepinyl, azocinyl, oxocinyl, thiocinyl, diazocinyl, oxazocinyl, and triazocinyl.

Aryl groups (including aryl groups comprised in aralkyl groups) that are optionally mono-, di-, tri-, tetra- or pentasubstituted are discussed throughout this disclosure and each specific compound or generic compound of the present invention that comprises an aryl group is specifically contemplated as being optionally mono-, di-, tri-, tetra- or pentasubstituted. Substituents may comprise any aryl substituent recited or shown herein. Non-limiting examples of substituents include halo, —OH, —$CO_2H$, —$C(O)NH_2$, —CN, trihalomethyl, trihalomethoxy, —$NH_2$, —$NO_2$, alkyl (e.g., lower unsubstituted or substituted alkyl), alkoxy (e.g., lower unsubstituted or substituted alkoxy), alkylamino (alkyl-N—), dialkylamino ((alkyl)$_2$N—) and trialkylammonium ((alkyl)$_3$-N(+)), wherein the alkyl groups may be the same or different). In addition, substituted alkyl and substituted alkoxy groups may optionally comprise one, two, three, or more of these substituents. Other substituents are described herein.

The term "aralkyl" refers to substituted and unsubstituted aralkyl. When used without the "substituted" modifier, aralkyl refers to the monovalent group—alkanediyl-aryl, in which the terms alkanediyl and aryl are each used in a manner consistent with the definitions provided herein. Non-limiting examples of aralkyls are: phenylmethyl (benzyl, Bn), 1-phenyl-ethyl, 2-phenyl-ethyl, indenyl and 2,3-dihydro-indenyl, provided that indenyl and 2,3-dihydro-indenyl are only examples of aralkyl in so far as the point of attachment in each case is one of the saturated carbon atoms. When the term "aralkyl" is used with the "substituted" modifier, either one or both the alkanediyl and the aryl is substituted. Non-limiting examples of substituted aralkyls are: (3-chlorophenyl)-methyl, 2-oxo-2-phenyl-ethyl(phenylcarbonylmethyl), 2-chloro-2-phenyl-ethyl, chromanyl where the point of attachment is one of the saturated carbon atoms, and tetrahydroquinolinyl where the point of attachment is one of the saturated atoms.

The term "alkoxy" includes straight-chain alkoxy, branched-chain alkoxy, cycloalkoxy, cyclic alkoxy, heteroatom-unsubstituted alkoxy, heteroatom-substituted alkoxy, heteroatom-unsubstituted $C_n$-alkoxy, and heteroatom-substituted $C_n$-alkoxy. In certain embodiments, lower alkoxys are contemplated. The term "lower alkoxy" refers to alkoxys of 1-6 carbon atoms (that is, 1, 2, 3, 4, 5 or 6 carbon atoms). The term "heteroatom-unsubstituted $C_n$-alkoxy" refers to a group, having the structure —OR, in which R is a heteroatom-unsubstituted $C_n$-alkyl, as that term is defined above. Heteroatom-unsubstituted alkoxy groups include: —OCH$_3$, —OCH$_2$CH$_3$, —OCH$_2$CH$_2$CH$_3$, —OCH(CH$_3$)$_2$, and —OCH(CH$_2$)$_2$. The term "heteroatom-substituted $C_n$-alkoxy" refers to a group, having the structure —OR, in which R is a heteroatom-substituted $C_n$-alkyl, as that term is defined above. For example, —OCH$_2$CF$_3$ is a heteroatom-substituted alkoxy group.

The term "acyl" includes both substituted and unsubstituted acyl. When used without the "substituted" modifier, acyl refers to a monovalent group, having a carbon atom of a carbonyl group as the point of attachment, further having a linear or branched, cyclo, cyclic or acyclic structure, farther having no additional atoms that are not carbon or hydrogen, beyond the oxygen atom of the carbonyl group. The groups, —CHO, —C(O)CH$_3$, —C(O)CH$_2$CH$_3$, —C(O)CH$_2$CH$_2$CH$_3$, —C(O)CH(CH$_3$)$_2$, —C(O)CH(CH$_2$)$_2$, —C(O)C$_6$H$_5$, —C(O)C$_6$H$_4$CH$_3$, —C(O)C$_6$H$_4$CH$_2$CH$_3$, —COC$_6$H$_3$(CH$_3$)$_2$, and —C(O)CH$_2$C$_6$H$_5$, are non-limiting examples of acyl groups. The term "acyl" therefore encompasses, but is not limited to groups sometimes referred to as "alkyl carbonyl" and "aryl carbonyl" groups. The term "substituted acyl" refers to a monovalent group, having a carbon atom of a carbonyl group as the point of attachment, further having a linear or branched, cyclo, cyclic or acyclic structure, further having at least one atom, in addition to the oxygen of the carbonyl group, independently selected from the group consisting of N, O, F, Cl, Br, I, Si, P, and S. The groups, —C(O)CH$_2$CF$_3$, —CO$_2$H, —CO$_2$CH$_3$, —CO$_2$CH$_2$CH$_3$, —CO$_2$CH$_2$CH$_2$CH$_3$, —CO$_2$C$_6$H$_5$, —CO$_2$CH(CH$_3$)$_2$, —CO$_2$CH(CH$_2$)$_2$, —C(O)NH$_2$ (carbamoyl), —C(O)NHCH$_3$, —C(O)NHCH$_2$CH$_3$, —CONHCH(CH$_3$)$_2$, —CONHCH(CH$_2$)$_2$, —CON(CH$_3$)$_2$, —CONHCH$_2$CF$_3$, —CO-pyridyl, —CO-imidazoyl, and —C(O)N$_3$, are non-limiting examples of substituted acyl groups. The term "substituted acyl" encompasses, but is not limited to, "heteroaryl (e.g., pyridinyl) carbonyl" groups.

Compounds of the present invention may contain one or more asymmetric centers and thus can occur as racemates and racemic mixtures, single enantiomers, diastereomeric mixtures and individual diastereomers. In certain embodiments, a single diastereomer is present. All possible stereoisomers of the macromolecules of the present invention are contemplated as being within the scope of the present invention. However, in certain aspects, particular diastereomers are contemplated. The chiral centers of the macromolecules of the present invention can have the S- or the R-configuration, as defined by the IUPAC 1974 Recommendations. In certain aspects, certain compounds of the present invention may comprise S- or R-configurations at particular carbon centers.

Linkers may connect two moieties within a compound of the present invention. For example, a linker may connect a polymer backbone to the rest of the molecule to form a linker-polymer backbone. Linkers that may be employed for such uses are well known to those of skill in the art. For example, the amino portion of a —CH$_2$NHCH$_3$ moiety may react with an available carboxylic acid to form a tertiary amide as shown below, wherein the inhibitor is a compound of the present invention:

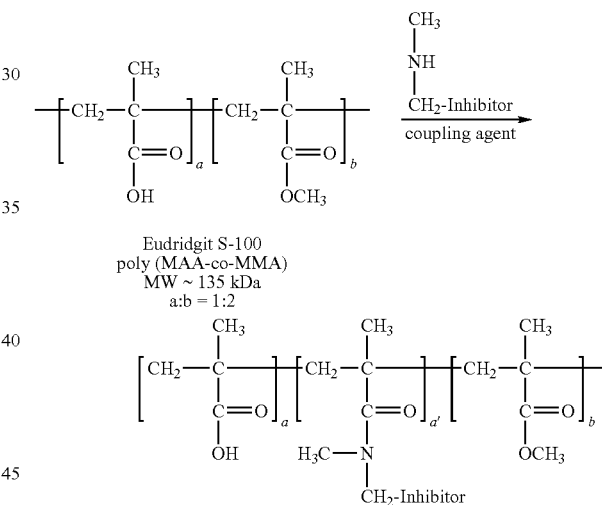

Conjugatable derivative of LED209

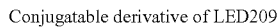

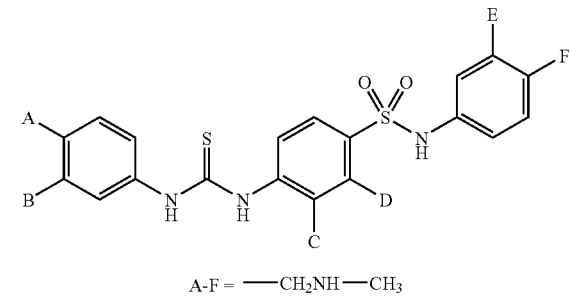

Other linkers include, but are not limited to, ethylenediamine, amino propanol, diethylenetriamine, polypeptides such as glycylglycine or GlyPheLeuGly, aspartic acid, polyaspartic acid, glutamic acid, polyglutamic acid, polyethylene glycol, diamino polyethylene glycol, or lysine. For example, U.S. Pat. No. 6,737,247 discloses several linkers which may be used with the present invention and is hereby incorporated by reference in its entirety without disclaimer. More than one linker may be utilized within a compound of the present invention, and more than one type of linker may be employed. Two linkers, either the same or different in nature, may be joined together to form a longer linker as well. In certain embodiments, a single linker joins a polymer backbone to the rest of the molecule.

Modifications or derivatives of the compounds, agents, and active ingredients disclosed throughout this specification are contemplated as being useful with the methods and compositions of the present invention. Derivatives may be prepared and the properties of such derivatives may be assayed for their desired properties by any method known to those of skill in the art.

In certain aspects, "derivative" refers to a chemically modified compound that still retains the desired effects of the compound prior to the chemical modification ("the parent compound"). Such effects may be enhanced (e.g., slightly more effective, twice as effective, etc.) or diminished (e.g., slightly less effective, 2-fold less effective, etc.) relative to the parent compound, but may still be considered a derivative. Such derivatives may have the addition, removal, or substitution of one or more chemical moieties on the parent molecule. Non-limiting examples of the types of modifications that can be made to the compounds and structures disclosed herein include the addition or removal of lower unsubstituted alkyls such as methyl, ethyl, propyl, or substituted lower alkyls such as hydroxymethyl or aminomethyl groups; carboxyl groups and carbonyl groups; hydroxyls; nitro, amino, amide, imide and azo groups; sulfate, sulfonate, sulfono, sulfhydryl, sulfenyl, sulfonyl, sulfoxido, sulfonamido, phosphate, phosphono, phosphoryl groups, and halide substituents. Additional modifications can include an addition or a deletion of one or more atoms of the atomic framework, for example, substitution of an ethyl by a propyl; substitution of a phenyl by a larger or smaller aromatic group. Alternatively, in a cyclic or bicyclic structure, heteroatoms such as N, S, or O can be substituted into the structure instead of a carbon atom.

For any specific or generic compound that comprises a linkage as in one of the following, it is specifically contemplated that an alternative linkage from this same group may be substituted: —SO$_2$NR—, —NRSO$_2$—, —S(O)$_2$—, —S(O)—, —N(R)R—, —RN(R)—, —C(O)NR— and —NRC(O)—, wherein R is H or as otherwise shown herein.

For any urea linkage (—NRC(O)NR—) represented in a generic or specific compound herein, it is specifically contemplated that a thiourea, oxamide (—NRC(O)C(O)—NR—), or carbamate (—ROC(O)NR— or —RN(R)C(O)O—) linkage may be employed, wherein R is H or as otherwise shown herein.

As discussed herein, various chemical groups may be substituted or unsubstituted. For any such substituted group, such as substituted alkyl or substituted aryl, or any group that comprises an alkyl or aryl group (e.g., an alkoxy, alkylamino, dialkylamino, alkylthio, or aralkyl group) the substituent may be any such substituent as known to those of skill in the art. Non-limiting examples of substituents include halo, alkyl, aryl, aralkyl, acyl, alkoxy, alkylthio, alkylamino, dialkylamino, a polymer tail, a polymer backbone, or a linker-polymer backbone, or wherein two consecutive R groups of an alkyl or aryl moiety together form an aryl group or a 1,3-dioxolanyl group. Additional non-limiting examples of substituents include —CH$_3$, —F, —Cl, —Br, —I, hydroxy, thiol, —NO$_2$, —CO$_2$H, —C(O)CH$_3$, —OCH$_3$, —CF$_3$, —NH$_2$—N$_3$, —CN, —NHOH, =NH, —SiH$_3$, —SO$_2$NH$_2$, —SO$_2$NH-alkyl, —SO$_2$NH-aryl, morpholinyl (substituted or unsubstituted),

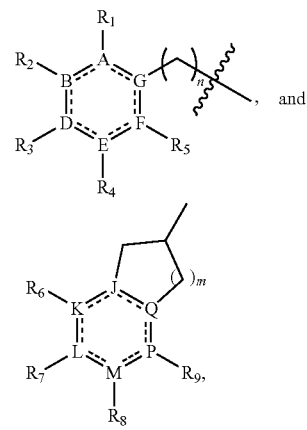

, and wherein A, B, D, E, F, G, J, K, L, M, P and Q are each carbon or nitrogen, and R$_1$-R$_9$ are each independently H or a substituent, such as those described in this paragraph, in is 1 or 2 and n is 0-3. In certain embodiments, —SO$_2$NH$_2$ is excluded as a substituent.

Prodrugs and solvates of the compounds of the present invention are also contemplated herein. The term "prodrug" as used herein, is understood as being a compound which, upon administration to a subject, such as a mammal, undergoes chemical conversion by metabolic or chemical processes to yield a compound any of the formulas herein, or a salt and/or solvate thereof (Bundgaard, 1991; Bundgaard, 1985). Solvates of the compounds of the present invention are preferably hydrates.

Compounds of the present invention may be obtained from commercial sources (e.g., Chembridge Corp., San Diego, Calif.) or synthesized using conventional organic chemistry methods (see, e.g., Example 2). Solvent choices for the methods of making compounds of the present invention will be known to one of ordinary skill in the art. Solvent choices may depend, for example, on which one(s) will facilitate the solubilizing of all the reagents or, for example, which one(s) will best facilitate the desired reaction (particularly when the mechanism of the reaction is known). Solvents may include, for example, polar solvents and non-polar solvents. Solvents choices include, but are not limited to, tetrahydrofuran, dimethylformamide, dimethylsulfoxide, dioxane, methanol, ethanol, hexane, methylene chloride and acetonitrile. More than one solvent may be chosen for any particular reaction or purification procedure. Water may also be admixed into any solvent choice. Further, water, such as distilled water, may constitute the reaction medium instead of a solvent.

Persons of ordinary skill in the art will be familiar with methods of purifying compounds of the present invention. One of ordinary skill in the art will understand that compounds of the present invention can generally be purified at any step, including the purification of intermediates as well as purification of the final products. In preferred embodiments, purification is performed via silica gel column chromatography, TLC, or HPLC using a bonded stationary phase.

The term "functional group" generally refers to how persons of skill in the art classify chemically reactive groups. Examples of functional groups include hydroxyl, amine, sulfhydryl, amide, carboxyls, carbonyls, etc.

As used herein, "protecting group" refers to a moiety attached to a functional group to prevent an otherwise unwanted reaction of that functional group. Protecting groups are well-known to those of skill in the art. Non-limiting exemplary protecting groups fall into categories such as hydroxy protecting groups, amino protecting groups, sulfhydryl protecting groups and carbonyl protecting groups. Such protecting groups may be found in Greene and Wuts, 1999. Compounds of the present invention are specifically contemplated wherein one or more functional groups are protected by a protecting group.

F. Pharmaceutical Preparations

Certain of the methods set forth herein pertain to methods involving the administration of a pharmaceutically and/or therapeutically effective amount of a compound of the present invention for purposes of treating bacterial infections.

In certain embodiments, a compound of the present invention may be administered to inhibit bacterial virulence by any method that allows contact of the active ingredient with a bacteria. A compound of the present invention to be administered by any conventional methods available for use in conjunction with pharmaceuticals, either as an individual therapeutically active ingredient or in a combination of therapeutically active ingredients. A compound of the present invention may be administered alone, but will generally be administered with a pharmaceutically acceptable carrier selected on the basis of the chosen route of administration and standard pharmaceutical practice.

In certain embodiments, a compound of the present invention may be given to a subject who has not responded, or who has negatively responded, to the administration of conventional antibiotics. In certain embodiments, a compound of the present invention is administered to a subject who harbors a multi-drug resistant bacteria or who is suspected of being exposed to a multi-drug resistant bacteria. A compound of the present invention may, in certain embodiments, be administered to a subject who may be threatened with exposure to a multi-drug resistant bacteria. In certain embodiments, a compound of the present invention is administered to a subject who harbors a bacteria containing a QseC sensor or who is suspected of being exposed to a bacteria containing a QseC sensor. A compound of the present invention may, in certain embodiments, be administered to a subject who may be threatened with exposure to a bacteria containing a QseC sensor.

A compound of the present invention may be extensively purified and/or dialyzed to remove undesired small molecular weight molecules and/or lyophilized for more ready formulation into a desired vehicle, where appropriate. Such methods are well-known in the art. The active compounds will then generally be formulated for administration by any known route, such as oral or parenteral administration. Methods of administration are discussed in greater detail below.

Aqueous compositions of the present invention will typically have an effective amount of a compound of the present invention to inhibit bacterial virulence.

Moreover, it will be generally understood that a compound of the present invention can be provided in prodrug form, also discussed above, meaning that an environment to which a compound of the present invention is exposed alters the prodrug into an active, or more active, form. It is contemplated that the term "precursor" covers compounds that are considered "prodrugs."

1. Pharmaceutical Formulations and Routes for Administration to Subjects

Any compound discussed herein is contemplated as comprised in a pharmaceutical composition. Pharmaceutical compositions of the present invention comprise an effective amount of one or more candidate substances (e.g., a compound of the present invention) or additional agents dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that contains at least one candidate substance or additional active ingredient will be known to those of skill in the art in light of the present disclosure, as exemplified by Remington's Pharmaceutical Sciences, 18$^{th}$ Ed. Mack Printing Company, 1990, incorporated herein by reference. Moreover, for animal (e.g., human) administration, it will be understood that preparations should meet sterility, pyrogenicity, general safety and purity standards as required by the FDA's Center of Drug Evaluation and Research.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, pp 1289-1329, 1990). Except insofar as any conventional carrier is incompatible with the active ingredient, its use in the therapeutic or pharmaceutical compositions is contemplated.

The candidate substance may comprise different types of carriers depending on whether it is to be administered in solid, liquid or aerosol form, and whether it needs to be sterile for such routes of administration as injection. The present invention can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intramuscularly, subcutaneously, subconjunctival, intravesicularlly, mucosally, buccally, transdermally, intrapericardially, intraumbilically, intraocularally, orally, locally, via inhalation (e.g., aerosol inhalation), via injection, via infusion, via continuous infusion, via localized perfusion bathing target cells directly, via a catheter, via eye or ear drops, via a lavage, in cremes, in lipid compositions (e.g., liposomes), or by other method or any combination of the foregoing as would be known to one of ordinary skill in the art (see, for example, Remington's Pharmaceutical Sciences, 1990).

A composition comprising a compound of the present invention may be formulated for topical administration, for example, in a cream as mentioned, or in an ointment, salve, spray, gel, lotion, or emulsion. The composition may be formulated for transmucosal, transepithelial, transendothelial, or transdermal administration. One example of transdermal formulation is a patch. The composition may farther comprise a chemical penetration enhancer, a membrane permeability agent, a membrane transport agent, a preservative, a surfactant, or a stabilizer, as these terms are known to those of skill in the art.

In one topical embodiment, the present invention can utilize a patch. A transdermal or "skin" patch is a medicated adhesive patch that is placed on the skin to deliver a time released dose of medication through the skin and into the bloodstream. A wide variety of pharmaceuticals can be delivered by transdermal patches. The first commercially available prescription patch was approved by the U.S. Food and Drug Administration in December 1979, which administered scopolamine for motion sickness.

The main components to a transdermal patch are (a) a liner to protect the patch during storage (removed prior to use); (b) the active agent; (c) an adhesive that serves to adhere the components of the patch together along with adhering the patch to the skin; (d) a membrane to control the release of the drug from the reservoir and multi-layer patches; and (e) a backing that protects the patch from the outer environment.

There are four main types of transdermal patches. Single-layer Drug-in-Adhesive patches have an adhesive layer that also contains the agent. In this type of patch the adhesive layer not only serves to adhere the various layers together, along with the entire system to the skin, but is also responsible for the releasing of the drug. The adhesive layer is surrounded by a temporary liner and a backing. Multi-layer Drug-in-Adhesive patches are similar to the single-layer system in that both adhesive layers are also responsible for the releasing of the drug. The multi-layer system is different however that it adds another layer of drug-in-adhesive, usually separated by a membrane (but not in all cases). This patch also has a temporary liner-layer and a permanent backing. Reservoir patches are unlike the Single-layer and Multi-layer Drug-in-Adhesive systems in that the reservoir transdermal system has a separate drug layer. The drug layer is a liquid compartment containing a drug solution or suspension separated by the adhesive layer. This patch is also backed by the backing layer. In this type of system the rate of release is zero order. Matrix patches have a drug layer of a semisolid matrix containing a drug solution or suspension. The adhesive layer in this patch surrounds the drug layer partially overlaying it.

In another form of treatment, a topical application of a compound of the present invention is targeted at a natural body cavity such as the mouth, pharynx, esophagus, larynx, trachea, pleural cavity, peritoneal cavity, or hollow organ cavities including the bladder, colon or other visceral organs. A variety of methods may be employed to affect the topical application into these visceral organs or cavity surfaces. For example, the pharynx may be affected by simply oral swishing and gargling with solutions comprising a compound of the present invention.

In particular embodiments, the composition is administered to a subject using a drug delivery device. Any drug delivery device is contemplated for use in delivering a pharmaceutically effective amount of a compound of the present invention.

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

The dose can be repeated as needed as determined by those of ordinary skill in the art. Thus, in some embodiments of the methods set forth herein, a single dose is contemplated. In other embodiments, two or more doses are contemplated. Where more than one dose is administered to a subject, the time interval between doses can be any time interval as determined by those of ordinary skill in the art. For example, the time interval between doses may be about 1 hour to about 2 hours, about 2 hours to about 6 hours, about 6 hours to about 10 hours, about 10 hours to about 24 hours, about 1 day to about 2 days, about 1 week to about 2 weeks, or longer, or any time interval derivable within any of these recited ranges.

In certain embodiments, it may be desirable to provide a continuous supply of a pharmaceutical composition to the patient. This could be accomplished by catheterization, followed by continuous administration of the therapeutic agent. The administration could be intra-operative or post-operative.

In certain embodiments, pharmaceutical compositions may comprise, for example, at least about 0.1% of a compound of the present invention. In other embodiments, a compound of the present invention may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg body weight, about 50 microgram/kg body weight, about 100 microgram/kg body weight, about 200 microgram/kg body weight, about 350 microgram/kg body weight, about 500 microgram/kg body weight, about 1 milligram/kg/body weight, about 5 milligram/kg body weight, about 10 milligram/kg/body weight, about 20 milligram/kg body weight, about 50 milligram/kg body weight, about 100 milligram/kg body weight, about 200 milligram/kg body weight, about 350 milligram/kg body weight, about 500 milligram/kg body weight, to about 1000 mg/kg body weight or more per administration, and any range derivable therein. In non-limiting examples of a derivable range from the numbers listed herein, a range of about 5 mg/kg body weight to about 100 mg/kg body weight, about 5 microgram/kg/body weight to about 500 milligram/kg body weight, etc., can be administered, based on the numbers described above.

In certain embodiments, the dosage administered is less than an amount that would be administered of a bacteriostatic or bacteriocidal agents, if such an agent were administered instead. For example, in many types of experiments, bacteriostatic or bacteriocidal agents are administered at a mM range, whereas compounds of the present invention may, in certain embodiments, be administered at about a nM range or lower (e.g., about 100 nM or less) such that they achieve methods of the present invention as described herein (e.g., methods of treating or preventing bacterial infection) without killing bacteria. Accordingly, methods of the present invention contemplate administering a compound of the present invention in an amount that is effective to prevent virulence, or pathogenesis, but that is not a bacteriocidal or bacteriostatic amount.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal, or combinations thereof.

The candidate substance may be formulated into a composition in a free base, neutral, or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, glycolic, lactic, tartaric, or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine, TRIS, or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. It may be preferable to include isotonic agents, such as, for example, sugars, sodium chloride, or combinations thereof.

In other embodiments, one may use eye or ear drops, nasal solutions or sprays, aerosols or inhalants in the present invention. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in certain embodiments the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation. For example, various commercial nasal preparations are known and include drugs such as antibiotics or antihistamines.

In certain embodiments the candidate substance is prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. In certain embodiments, carriers for oral administration comprise inert diluents, assimilable edible carriers or combinations thereof. In other aspects of the invention, the oral composition may be prepared as a syrup or elixir. A syrup or elixir, and may comprise, for example, at least one active agent, a sweetening agent, a preservative, a flavoring agent, a dye, a preservative, or combinations thereof.

Dosage formulations of the present pharmaceutical compositions can be prepared by combining them with a pharmaceutically acceptable carrier, such as a slow release agent, to make either immediate or slow release formulations as is well known in the art. Such compositions could be used, for example, in the treatment of periodontal disease and other oral care indications. Such pharmaceutically acceptable carriers may be either solid or liquid in form such as, for example, cornstarch, lactose, sucrose, peanut oil, olive oil, sesame oil, propylene glycol and water. If a solid carrier is used, the dosage formulation of the present pharmaceutical compositions may be in, for example, powder, troche, or lozenges form. If a liquid carrier is used, the dosage formulation of the present pharmaceutical compositions may be in, for example, soft gelatin capsule, syrup liquid suspension, emulsion, or solution form. The dosage formulations may also contain adjuvants, such as preserving, stabilizing, wetting or emulsifying agents, or solution promoters. Immediate and slow release formulations are well known in the art and have been described, for example, in U.S. Pat. No. 4,764,377 (the disclosure of which is incorporated herein by reference), which describes a method for treating periodontal disease by means of a delivery device placed within the periodontal pocket so that release of a therapeutic agent occurs in the immediate vicinity of the disease process. Other means of treating periodontal disease are described in U.S. Pat. No. 5,324,756, the entire contents of which are incorporated herein by reference.

In certain embodiments an oral composition may comprise one or more binders, excipients, disintegration agents, lubricants, flavoring agents, or combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar, or both.

Certain coating materials are those which dissolve at about or at least about a pH of 5 or above, such as at about pH 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0 or above, such as pH of about 6.5 or above. Such coatings therefore only begin to dissolve when they have left the stomach and entered the small intestine. Accordingly, these coatings may be considered enteric coatings. A thick layer of coating is provided which will dissolve in minutes to hours, thereby allowing the capsule underneath to breakup only when it has reached the terminal ileum or the colon. Such a coating can be made from a variety of polymers such as cellulose acetate trimellitate (CAT), hydroxypropylmethyl cellulose phthalate (HPMCP), polyvinyl acetate phthalate (PVAP), cellulose acetate phthalate (CAP) and shellac as described by Healy, 1989. For coatings of cellulose esters, a thickness of 200-250 μm would be suitable.

Non-limiting exemplary coating materials are methyl methacrylates or copolymers of methacrylic acid and methyl methacrylate. Such materials are available as EUDRAGIT™ polymers (Rohm Pharma, Darmstadt, Germany). Eudragits are copolymers of methacrylic acid and methyl methacrylate. Compositions may be based on EUDRAGIT™ L100 and Eudragit S100. EUDRAGIT™ L100 dissolves at pH 6 and upwards and comprises 48.3% methacrylic acid units per g dry substance; EUDRAGIT™ S100 dissolves at pH 7 and upwards and comprises 29.2% methacrylic acid units per g dry substance. Certain coating compositions are based on EUDRAGIT™ L100 and EUDRAGIT™ S100 in the range 100 parts L100:0 parts S100 to 20 parts L100:80 parts S100. A non-limiting exemplary range is 70 parts L100:30 parts S100 to 80 parts L100:20 parts S100. For formulations where the ratio of EUDRAGIT™ L100:S100 is high, a coat thickness of the order 150-200 μm is preferable. This is equivalent to 70-110 mg of coating for a size 0 capsule. For coatings where the ratio EUDRAGIT™ L100:S100 is low, a coat thickness of the order 80-120 μm is preferable, equivalent to 30 to 60 mg coating for a size 0 capsule.

It is specifically contemplated that compounds of the present invention may be incorporated into the polymers that act as carriers that are nonabsorbable. Compounds of the present invention may be, for example, covalently bonded to such polymers. Such polymers may be, for example, the polymers mentioned above and/or the polymer tails and polymer backbones discussed herein.

Additional formulations which are suitable for other modes of administration include suppositories. Suppositories are solid dosage forms of various weights and shapes, usually medicated, for insertion into the rectum, vagina, or urethra. After insertion, suppositories soften, melt or dissolve in the cavity fluids. In general, for suppositories, traditional carriers may include, for example, polyalkylene glycols, triglycerides, or combinations thereof. In certain embodiments, suppositories may be formed from mixtures containing, for example, the active ingredient in the range of about 0.5% to about 10%, and preferably about 1% to about 2%.

Sterile injectable solutions are prepared by incorporating the active compounds in the required amount in the appropriate solvent with various other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsions, certain methods of preparation may include vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin, or combinations thereof.

2. Combination Therapy

In order to increase the effectiveness of a compound of the present invention, a compound of the present invention may be combined with traditional drugs. For example, an antibacterial agent, an anti-diarrhea agent, and/or an adrenergic antagonist may be administered in combination with a compound with the present invention. It is contemplated that this type of combination therapy may be used in vitro or in vivo.

For example, a compound of the present invention may be provided in a combined amount with an effective amount of a second agent (or more) to inhibit bacterial virulence, such as by inhibiting quorum signaling. This process may involve administering the agents at the same time or within a period of time wherein separate administration of the substances produces a desired therapeutic benefit. This may be achieved by contacting the cell, tissue, biofilm, or organism with a single composition or pharmacological formulation that includes two or more agents, or by contacting the cell with two or more distinct compositions or formulations, wherein one composition includes one agent and the other includes another.

The compounds of the present invention may precede, be co-current with and/or follow the other agents by intervals ranging from minutes to weeks. In embodiments where the agents are applied separately to a cell, tissue, biofilm, or organism, one would generally ensure that a significant period of time did not expire between the time of each delivery, such that the agents would still be able to exert an advantageously combined effect on the cell, tissue or organism. For example, in such instances, it is contemplated that one may contact the cell, tissue or organism with two, three, four or more modalities substantially simultaneously (i.e., within less than about a minute) as the candidate substance. In other aspects, one or more agents may be administered within of substantially simultaneously, about 1 minute, about 5 minutes, about 10 minutes, about 20 minutes about 30 minutes, about 45 minutes, about 60 minutes, about 2 hours, about 3 hours, about 4 hours, about 5 hours, about 6 hours, about 7 hours about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 22 hours, about 23 hours, about 24 hours, about 25 hours, about 26 hours, about 27 hours, about 28 hours, about 29 hours, about 30 hours, about 31 hours, about 32 hours, about 33 hours, about 34 hours, about 35 hours, about 36 hours, about 37 hours, about 38 hours, about 39 hours, about 40 hours, about 41 hours, about 42 hours, about 43 hours, about 44 hours, about 45 hours, about 46 hours, about 47 hours, about 48 hours, about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 1, about 2, about 3, about 4, about 5, about 6, about 7 or about 8 weeks or more, and any range derivable therein, prior to and/or after administering the candidate substance.

Various combination regimens of the agents may be employed. Non-limiting examples of such combinations are shown below, wherein a compound of the present invention is "A" and a second agent, such as an antibacterial agent, an anti-diarrhea agent, and/or an adrenergic antagonist (such as phentolamine, propranolol, or yombine) is A/B/A B/A/B B/B/A A/A/B A/B/B B/A/A A/B/B/B B/A/B/B B/B/B/A B/B/A/B A/A/B/B A/B/A/B A/B/B/A B/B/A/A B/A/B/A B/A/A/B A/A/A/B B/A/A/A A/B/A/A A/A/B/A

G. Plant Applications

A compound of the present invention may be administered to a plant via any method known to those of skill in the art. For example, in a method of using a composition of the invention to treat a bacterial plant infection, the composition may be diluted in a suitable volume of water to provide an application solution which is then applied to foliage of a plant or plants at an application rate sufficient to give a desired effect (e.g., reduction of bacterial infection). Compounds of the present invention that are water-soluble are particularly suited for spraying, for example. Compounds that are not water-soluble or have limited water solubility may be applied as an emulsion or microemulsion, for example.

Components such as solvents and organic acids may be added to emulsions of the invention to enhance emulsion stability; These additives generally function to increase solubility or dispersability of the surfactants in the aqueous carrier phase thus enabling the formulation of robust emulsions exhibiting enhanced thermal and pH stability, reduced viscosity, and high active agent loading. Solvents may be added to the compositions to increase the solubility or dispersibility of the surfactants in the aqueous carrier phase and thereby attain appropriate stability of the emulsion. Water soluble solvents may be added to increase the solubility of surfactants with a hydrophilic moiety in the aqueous carrier phase. Non-limiting examples of water soluble solvents include acetates, $C_{1-6}$ alkanols, $C_{1-6}$ diols, $C_{1-6}$ alkyl ethers of alkylene glycols and polyalkylene glycols, and mixtures thereof The alkanol can be selected from methanol, ethanol, n-propanol, isopropanol, the various positional isomers of butanol, pentanol, and hexanol, and mixtures thereof. It may also be possible to utilize in addition to, or in place of, said alkanols, the diols such as methylene, ethylene, propylene and butylene glycols, and mixtures thereof, and including polyalkylene glycols. Mixtures of hydrophobic and hydrophilic solvents may also be used. Organic acids may be added to the compositions to enhance the stability of the emulsion, such as acetic, dichloroacetic, citric, malic, oxalic, salicylic, or tartaric acid. Other additives including inorganic acids and oxidizing agents may be added to the compositions of the invention to enhance emulsion stability. Non-limiting examples include boric acid, perchloric acid, phosphoric acid, sulfuric acid, hydrogen peroxide, lithium perchlorate, sodium phosphate, sodium chlorate and sodium iodide.

A plant treatment composition is preferably dilute enough to be readily sprayed using standard agricultural spray equipment. The selection of application rates that are effective for a composition of the invention is within the skill of an ordinary artisan. Those of skill in the art will likewise recognize that individual plant conditions, weather and growing conditions, as well as the specific active ingredients and their weight ratio in the composition, will influence the degree of effectiveness of treating plant bacterial infections as achieved in practicing this invention.

1. Foliar Application

The term "foliar application" refers to the application of substances to the foliage, or above-ground portions, of plants, and especially application to the leaves of the plants. It is understood in the art that incidental amounts of substances used in foliar applications may filter to or contact the soil, but not in quantities which will permit penetration of the soil and significant contacting of the plant's roots compared to the amount contacting the leaves and other above-ground structures.

Foliar application has been performed on farms, in greenhouses, on flowers, and in other agricultural settings for decades, and is performed in any of a variety of ways known in the art. For example, farmers routinely apply pesticides and other agents to their crops by means of tractor mounted sprayers, by crop dusting, through pressurized sprinklers, and through systems such as elevated hoses used to spray grapevines.

Typically, a compound of the present invention is dissolved or diluted in water, as appropriate, before use. Since farmers have been accustomed for years to mixing pesticides, fertilizers, and other agricultural chemicals for use in their fields, the mixing and application of a compound of the present invention is well within a farmer's skill.

The amount of the mixture to be applied to the fields will depend on several variables. In foliar application, the goal is to moisten the foliage. How much water is necessary to accomplish this will depend largely on the amount of foliage to be covered and the precision of the method of application in directing the mixture to the foliage without also wetting the surrounding area. The amount of foliage will depend, for example, on the amount of age of the plants (young plants typically have smaller leaves than mature plants), the type of plant (different types of plants differ in the amount and density of their foliage) and the health of the plants. Farmers have, of course, applied various chemicals to their crops for years, and are well familiar with judging the amount of liquid needed for foliar application on crops of different ages and types. Once the amount of liquid to be used is determined, the amount of a composition of the present invention to be added to achieve any desired concentration in parts per million is readily determined. The determination of whether the rate of application is sufficient to moisten the foliage is also easily made and the amount readily adjusted until a satisfactory rate is achieved.

It should be noted that some systems, such as sprinkler systems, spray the whole plant while they water the soil. In the art, and as used herein, such methods are considered soil applications since their purpose is to soak the ground and not merely to wet the leaves or other portions above the ground 2. Soil Application The term "soil application" refers to the application of a substance to the soil around a plant, where the intent is either to affect the soil directly or to place the roots of the plant in contact with the substance. Generally, substances applied through a soil application will not contact the foliage, but it is possible that incidental amounts of substances used in soil applications may contact the foliage in quantities which will not significant compared to the amount contacting the roots and other below-ground structures. *Ralstonia solanacearum* infections may, for example, be treated via soil applications since the route of infection is typically through the roots (Daughtery, 2003).

In soil application, the soil is preferably first saturated to wet the particles of the soil so that the composition of the present invention can move freely in the soil and reach the roots of the plants. Therefore, preferably the soil is saturated to 70-80% field capacity with ordinary water prior to agent application. The particular concentration to be chosen varies primarily according to the flow rate of water permitted by the method of application. Methods having a higher flow rate generally require a lower concentration of a compound of the present invention, perhaps because more water containing the mixture reaches the roots of the plants. Conversely, lower flow rates will generally require higher concentrations of a compound of the present invention. Alternatively, the time of the application of the mixture can be altered. Thus, use of a low flow rate and low concentration of mixture can be balanced by increasing the time in which the water containing the mixture is applied. Thus, halving the flow rate or concentration of mixture can be compensated for by doubling the application time of the water-mixture solution. While flow rate is a particularly important variable, the crop to which the mixture is being applied may also help determine the concentration of mixture to be applied. Typically, perennials take higher concentrations than do annuals.

It should be noted that the farmer is usually well aware of the flow rate per acre of the irrigation or other soil application system in place on his or her property, as well as the acreage to be covered. The farmer can calculate the amount of water which will be used in watering the land for any particular amount of time (for example, 300 gallons per minute times 50 acres times 30 minutes is 450,000 gallons of water). The farmer can then calculate how much of a composition of the present invention is needed to result in an application of the desired concentration of the mixture.

A composition of the present invention is applied for a period of time, such as minutes to hours to days. In some cases, the practitioner may want to apply the mixture at a lower concentration, but for a longer period, such as overnight or over several days. Such applications are within the purview of the invention, so long as they result in a decrease in bacterial infection or symptoms thereof. The time of the application will also vary according to the particular method employed.

The practitioner will appreciate that different systems of application have different flow rates. For example, overhead sprinklers generally have relatively higher flow rates than do drip systems. Microsprinkler systems such as Fan Jet™ typically have flow rates between that of drip systems and that of sprinklers, and accordingly have application times somewhat higher than that of sprinklers.

Compositions of the present invention may be applied to soil by being run through a hose, pipe, drip, sprinkler, irrigation channel, or other mechanism. In practice, the devices used are not necessarily precision equipment. Accordingly, when the water flow is turned off, water will typically continue to drip or run from the hose or through the irrigation channel or other applicator for some time. It is therefore understood that the times of application will generally be an approximation and will be measured from the start of the flow of the mixture to when the flow of the mixture is turned off, whether or not some of the mixture continues to drip or run from the applicator.

Following application of a composition of the present invention, the mixture will typically be in the top few inches of soil. For many plants, the root system is deeper in the soil. It is therefore desirable to help move the mixture 6 to 12 inches into the soil to reach the root structures involved in active uptake. To achieve this, it may be desirable to use a "water push" to create a concentration gradient after application of the agent. This is achieved by following the agent application with an application of water. The water application can be as short as a few minutes or as long as several hours. Such "water pushes" to create concentration gradients are commonly used by farmers in applying agricultural chemicals and are accordingly well known in the art.

3. Application to Harvested Plants

A composition of the present invention may be employed to extend the shelf life of harvested plant matter by reducing or preventing bacterial infection of the plant matter after it has been harvested. For example, a solution or emulsion comprising a compound of the present invention may be employed for this purpose.

Applying a composition of the present invention onto the harvested plant matter may be performed using any method known to those of skill in the art, such as using a dipping or spraying procedure performed at room temperature, during which the harvested plant matter is subjected or exposed to the applied composition for a time period of seconds to minutes and possibly hours. Alternatively, the composition may be brushed on the harvested plant matter using a suitable brush for such an application.

H. Examples

The following examples are included to demonstrate certain preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Screening for Inhibitors of Bacterial Virulence

Overview

A library of 150,000 small organic molecules from UT Southwestern Medical Center, Dallas, Tex., was screened at 5 μM in a high throughput assay to identify inhibitors of QseC-dependent virulence gene activation in EHEC (FIG. 5). The first round of positive "hits," represented a diverse range of molecular architecture, was subjected to additional rounds of screening followed by preliminary evaluations for toxicity against bacterial cells in vitro. This yielded a pool of 75 potential inhibitors with $IC_{50}$ values at or below $10^{-5}$ M. One compound was selected based upon its potency compared with other lead molecules, its minimal toxicity towards bacterial and human cell lines, and potential for chemical modification. This molecule was subjected to structure-activity studies to identify ways to improve its potency. The result, LED209 (compound 5) (N-phenyl-4-[[(phenylamino)thioxomethyl]amino]-benzenesulfonamide), was prepared in three steps (see Example 2).

Experimental

In EHEC, the genes involved in the formation of the AE lesion are encoded within a chromosomal pathogenicity island named the Locus of Enterocyte Effacement (LEE). The LEE region contains five major operons: LEE1, LEE2, LEE3, LEE4 and LEE5, which encode a type III secretion system (TTSS), an adhesin (intimin), and this adhesin's receptor (Tir), which is translocated to the epithelial cell through the bacterial TTSS. The LEE genes are directly activated by the LEE-encoded regulator (Ler), which is the first gene in the LEE1 operon (Kaper et al., 2004). Transcriptional activation of LEE1 can be achieved using spent supernatant (bacteria producing AI-3 are grown to late exponential phase to an $OD_{600}$ 1.0, bacterial cells are pelleted by centrifugation, the supernatant is filtered through a 0.22 μM filter to ensure it is free from bacterial cells; this is now the spent supernatant) from bacterial strains that produce AI-3 (Sperandio et al., 2003; Walters et al., 2006).

To develop an assay for inhibitors of LEE1 transcriptional activation by AI-3, conditions were identified in which the TEVS232 bacterial strain containing the chromosomal LEE1::lacZ reporter (Sperandio et al., 1999) would respond to the addition of conditioned medium from EHEC 8624 cultures (containing AI-3). After trying a number of different growth conditions, including varying the aeration of overnight cultures, a successful protocol was developed in which fresh TEVS232 were grown in Luria broth to a concentration having 1.1-1.3 O.D. units and were diluted into Dulbecco's Modified Essential Medium (DMEM) and cultured overnight in a shaking incubator at 37° C. In the morning, cultures having an optical density of 0.2 to 0.3 are diluted into DMEM (negative control) or into DMEM containing 10% EHEC preconditioned medium. These bacteria were dispensed in 40 μl volume into the wells of 384 well plates, with the negative control bacterial added to wells of column 24. Wells in columns 2 and 23 received bacteria in conditioned medium and DMSO, wells in columns 3-22 received bacteria in conditioned medium and compounds from the UT Southwestern 150,000 compound file. Compounds were added at a final concentration of 5 μM and 1% DMSO, using a Biomek FX liquid handler.

The plates of bacteria were incubated 5 hours at 37° C. in a 5% $CO_2$ atmosphere. At the end of the incubation, cells were incubated with lysozyme at a final concentration of 0.3 mg/ml for 15 min at 32° C. Beta-Glo™ reagent (Promega) was added, which couples the β-galactosidase produced by the LEE1::LacZ fusion gene to a luciferase reaction, producing an assay that can be read by luminescence after a 4 min incubation at room temperature. The results of a plate treated with DMSO instead of compounds (plate 1) and another plate (plate 2) treated with compounds are shown in FIG. 5. The luminescence value of each well is plotted as a function of the number of the well in each column. The hit rate for this initial screen was 7,000, with an error rate of 20%, which upon re-screening yielded a hit rate of 5,600 compounds, which includes compounds that inhibits AI-3 activation of LEE1 transcription, general inhibitors of bacterial transcription, and compounds that are simply toxic. To eliminate the toxic compounds, as well as compounds that were general inhibitors of transcription from the collection of compounds of interest, a secondary screen was performed utilizing a β-lactamase bla::lacZ chromosomal reporter in the same genetic background as the LEE1::lacZ (strain MCAmp (Sperandio et al., 1999)). This secondary screen validated 75 compounds as specific AI-3 inhibitors and from this, LED209 (compound 5) was chosen due to its efficacy, no toxicity against bacterial cells, and potential for meaningful chemical modification.

Example 2

Preparation of Certain Compounds of the Present Invention

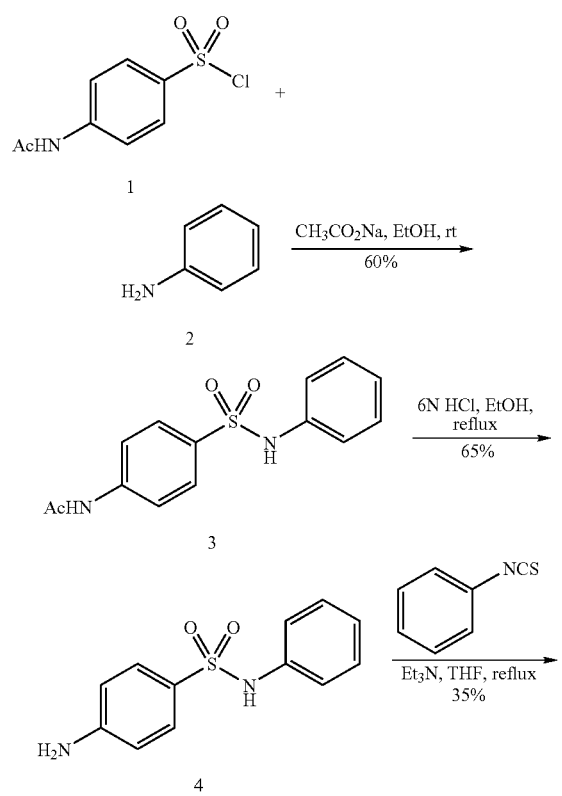

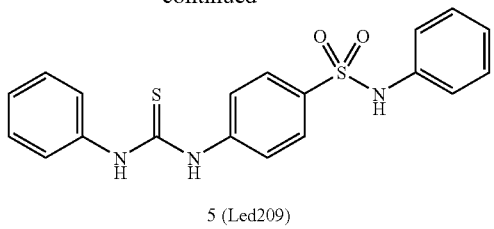

5 (Led209)

N-Acetylsulfanilyl chloride 1 (55 g, 236 mmol) was added in portion to a stirring, 0° C. suspension of sodium acetate (48.4 g, 590 mmol) and aniline 2 (22 mL, 236 mmol) in ethanol (300 mL). The reaction mixture was stirred at room temperature overnight and then poured into ice-cold water (1.5 L) with vigorous stirring. After stirring for 1 h, the white solid that gradually precipitated was collected by filtration. The filter cake was washed with ice-cold water, dried under vacuum, and recrystallized from hot ethanol to give N-[4-[(phenylamino)sulfonyl]phenyl]acetamide (3) (also called 137-19 or LED137) (41 g, 60%) as a white solid, mp 209-210° C. $^1$H NMR (CD$_3$OD, 400 MHz) δ 7.64 (br s, 4H), 7.18 (t, J=7.6 Hz, 2H), 7.06-7.00 (m, 3H), 2.10 (s, 3H).

An aqueous 6N solution of HCl (40 mL) was cautiously added with stirring to a solution of 3 (20 g, 68 mmol) in ethanol (80 mL). After heating under reflux for 3 h, the reaction mixture was evaporated to dryness in vacuo and the residue was dissolved in water. The pH of the solution was adjusted to 8-9 using 1N aq. NH$_4$OH. After stirring for 1 h, the white solid that gradually precipitated was collected by filtration. The filter cake was washed with ice-cold water, dried under vacuum, and recrystallized from hot ethanol to give to give 4-amino-N-phenyl-benzenesulfonamide (4) (also called 207-33 or LED207) (10.9 g, 65%) as a white solid, mp 194-195° C. $^1$H NMR (CD$_3$COCD$_3$, 300 MHz) δ 8.64 (br s, 1H), 7.50-7.45 (m, 2H), 7.25-7.18 (m, 4H), 7.04-6.98 (m, 1H), 6.67-6.62 (m, 2H), 5.44 (br s, 2H); $^{13}$C NMR (CD$_3$COCD$_3$, 75 MHz) δ 152.9, 138.8, 129.3 (2C), 129.1 (2C), 126.3, 124.0, 120.5 (2C), 113.1 (2C).

Triethylamine (0.07 mL, 0.5 mmol) and phenyl isothiocyanate (2.1 mL, 11 mmol) were added sequentially to a solution of 4 (2.48 g, 10 mmol) in dry THF (10 mL). After heating under reflux for 48 h, all volatiles were removed under vacuum, and the resulting crude material was purified by flash chromatography on silica gel (hexanes/acetone, 3:1) to afford N-phenyl-4-[[(phenylamino)thioxomethyl]amino]benzenesulfonamide (5, also called LED209) (1.34 g, 35%) as a white solid, mp 160-162° C. $^1$H NMR (CD$_3$COCD$_3$, 300 MHz) δ 9.35 (br s, 1H), 9.30 (br s, 1H), 8.98 (br s, 1H), 7.80-7.72 (m, 4H), 7.51-7.47 (m, 2H), 7.38-7.33 (m, 2H), 7.28-7.16 (m, 5H), 7.08-7.04 (m, 1H); $^{13}$C NMR (CD$_3$COCD$_3$, 75 MHz) δ 180.2, 143.9, 138.9, 138.2, 135.2, 129.3 (2C), 129.1 (2C), 127.9 (2C), 125.8, 124.6 (3C), 122.8 (2C), 120.8 (2C).

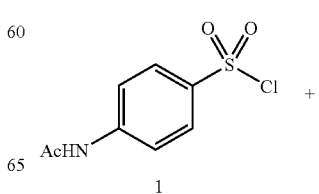

1

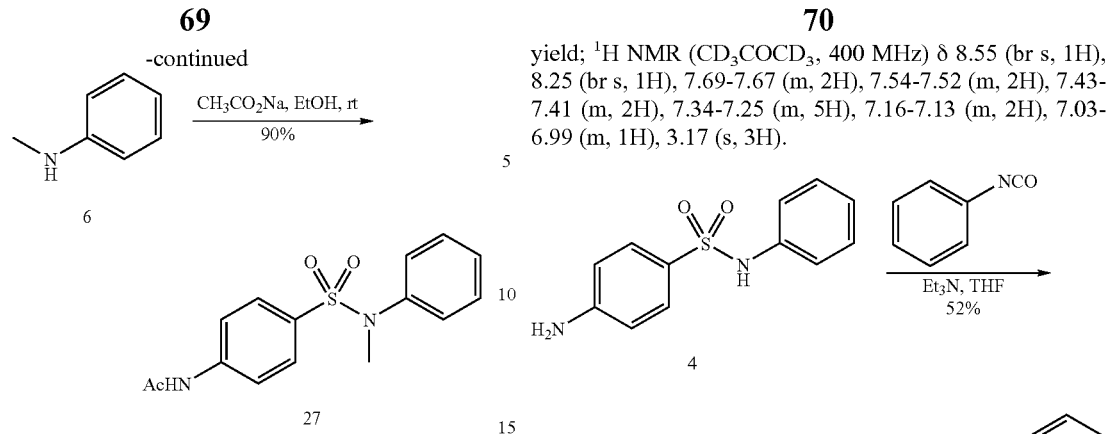

Compound 27 was prepared in a similar manner as compound 3 in 90% yield; $^1$H NMR (CD$_3$COCD$_3$, 300 MHz) δ 9.63 (br s, 1H), 7.80-7.77 (m, 2H), 7.46-7.42 (m, 2H), 7.35-7.27 (m, 3H), 7.15-7.12 (m, 2H), 3.17 (s, 3H), 2.14 (s, 3H).

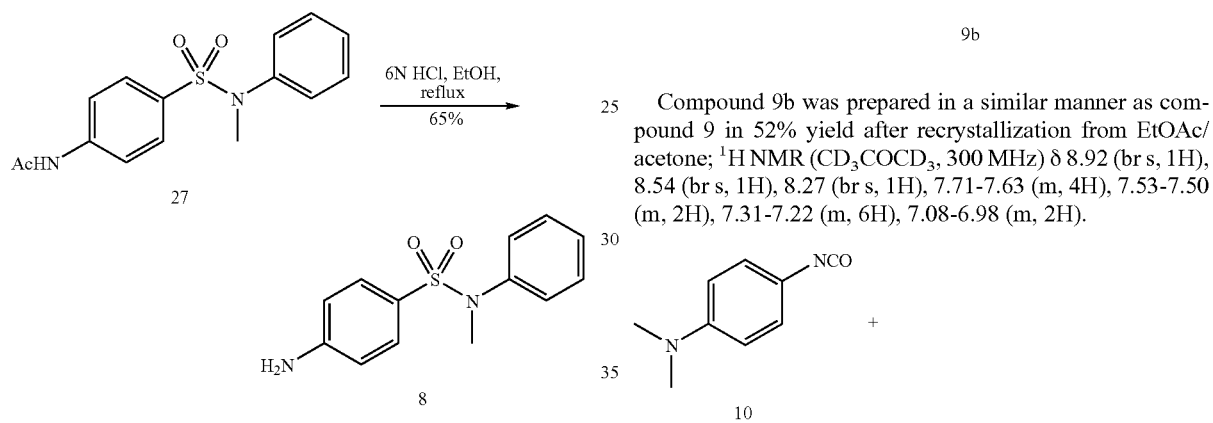

Compound 8 was prepared in a similar manner as compound 4 in 65% yield; $^1$H NMR (CD$_3$COCD$_3$, 300 MHz) 67.32-7.13 (m, 7H), 6.68-6.65 (m, 2H), 5.53 (br s, 2H), 3.10 (s, 3H).

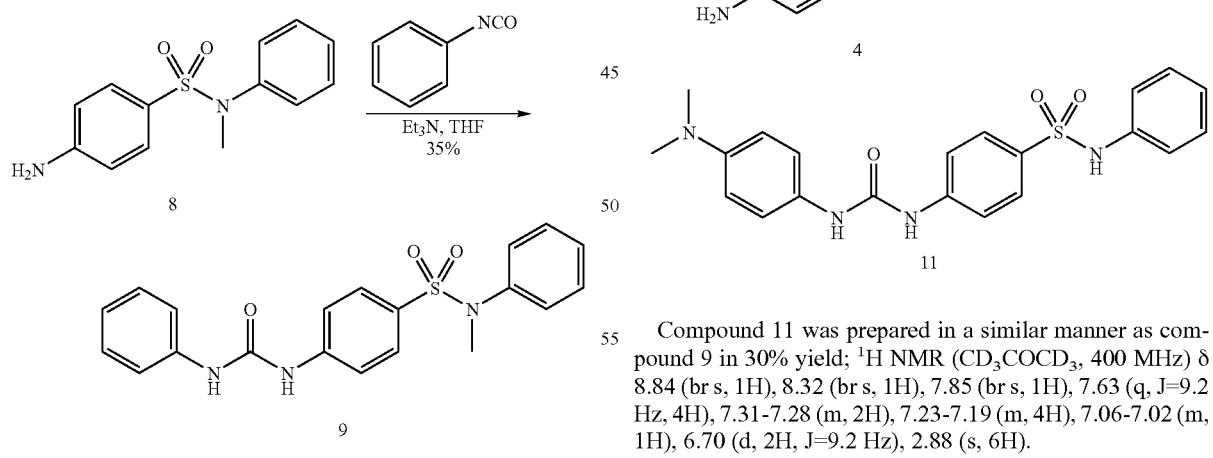

To a solution of 8 (150 mg, 0.572 mmol) in THF (3 ml) was added phenyl isocyanate (0.082 ml, 0.687 mmol) and triethylamine (0.16 ml, 1.14 mmol). The reaction mixture was stirred at ambient temperature for 48 h and evaporated to dryness. The resulting crude material was purified by flash chromatography on silica gel (CH$_2$Cl$_2$/MeOH 97:3) and recrystallized from ethanol to afford compound 9 in 35% yield; $^1$H NMR (CD$_3$COCD$_3$, 400 MHz) δ 8.55 (br s, 1H), 8.25 (br s, 1H), 7.69-7.67 (m, 2H), 7.54-7.52 (m, 2H), 7.43-7.41 (m, 2H), 7.34-7.25 (m, 5H), 7.16-7.13 (m, 2H), 7.03-6.99 (m, 1H), 3.17 (s, 3H).

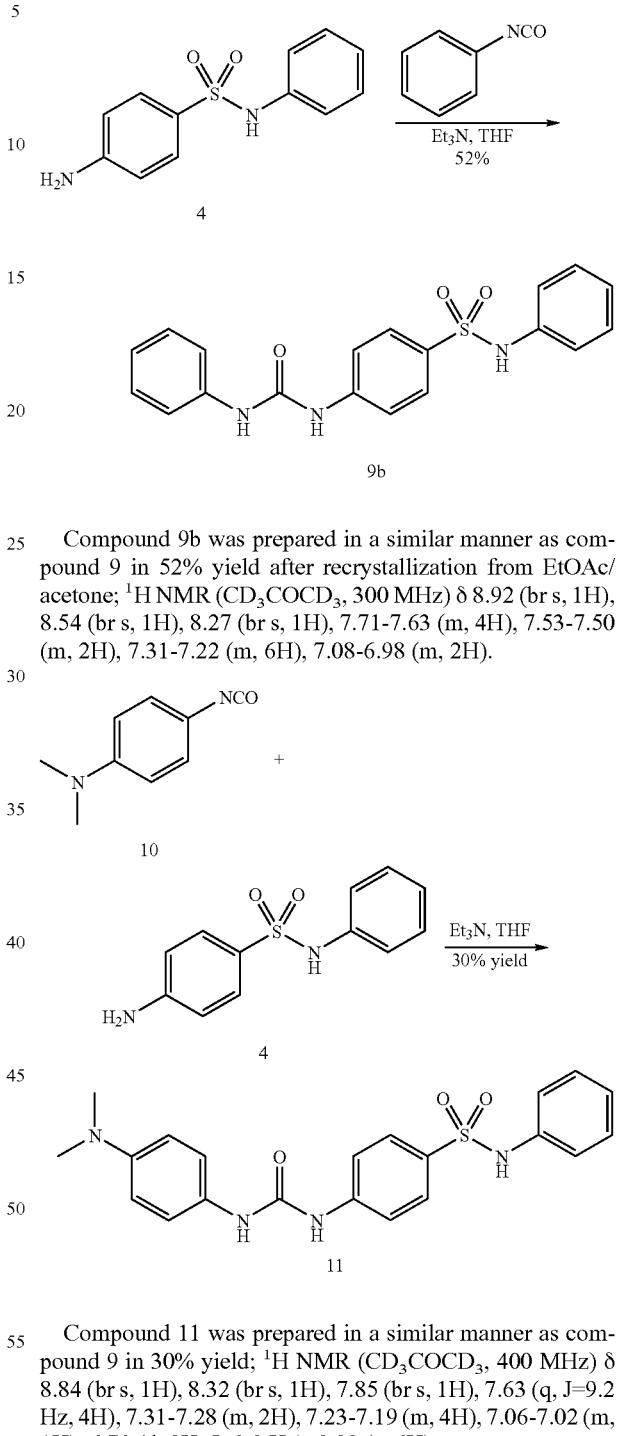

Compound 9b was prepared in a similar manner as compound 9 in 52% yield after recrystallization from EtOAc/acetone; $^1$H NMR (CD$_3$COCD$_3$, 300 MHz) δ 8.92 (br s, 1H), 8.54 (br s, 1H), 8.27 (br s, 1H), 7.71-7.63 (m, 4H), 7.53-7.50 (m, 2H), 7.31-7.22 (m, 6H), 7.08-6.98 (m, 2H).

Compound 11 was prepared in a similar manner as compound 9 in 30% yield; $^1$H NMR (CD$_3$COCD$_3$, 400 MHz) δ 8.84 (br s, 1H), 8.32 (br s, 1H), 7.85 (br s, 1H), 7.63 (q, J=9.2 Hz, 4H), 7.31-7.28 (m, 2H), 7.23-7.19 (m, 4H), 7.06-7.02 (m, 1H), 6.70 (d, 2H, J=9.2 Hz), 2.88 (s, 6H).

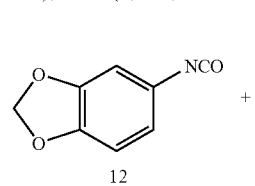

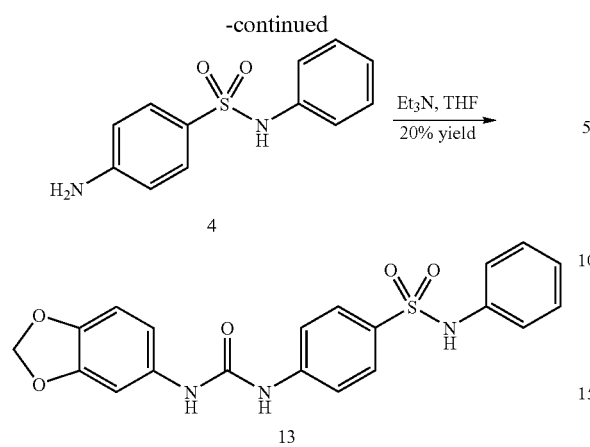

Compound 13 was prepared in a similar manner as compound 9 in 20% yield; ¹H NMR (CD₃COCD₃, 400 MHz) δ 8.86 (br s, 1H), 8.42 (br s, 1H), 8.13 (br s, 1H), 7.68-7.60 (m, 4H), 7.25-7.19 (m, 5H), 7.06-7.02 (m, 1H), 6.79 (dd, 1H, J=8.8 Hz, 2.0 Hz,), 6.73 (d, 1H, J=8.8 Hz), 5.94 (s, 2H).

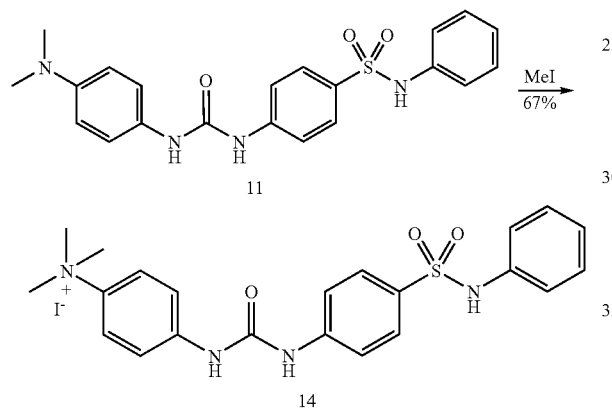

To a solution of 11 (10 mg, 0.0244 mmol) in acetone (1 ml) was added MeI (0.015 ml, 10 equiv). The reaction mixture was stirred at ambient temperature for 40 h and diluted with hexanes (10 ml). The pale yellow precipitate was filtered and dried under vacuum to give the product 14, 9 mg, 67% yield, ¹H NMR (CD₃COCD₃, 300 MHz) δ 9.86 (br s, 1H), 9.74 (br s, 1H), 8.86 (br s, 1H), 7.93 (d, 2H, J=9.6 Hz), 7.85-7.81 (m, 2H), 7.76-7.68 (m, 4H), 7.26-7.22 (m, 4H), 7.07-7.02 (m, 1H), 3.88 (s, 9H).

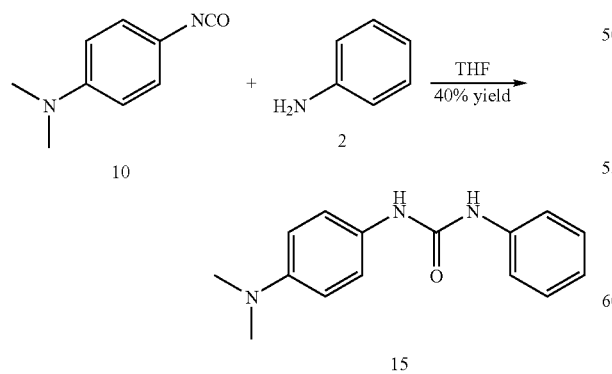

To a solution of 2 (0.087 ml, 1.15 mmol) in THF (3 ml) was added isocyanate 10 (156 mg, 0.96 mmol). The reaction mixture was stirred at ambient temperature for 48 h and evaporated to dryness. The resulting crude material was purified by flash chromatography on silica gel (Hexane/Acetone 2:1) and recrystallized from ethanol to afford compound 15 in 40% yield; ¹H NMR (CD₃COCD₃, 300 MHz) δ 7.93 (br s, 1H), 7.72 (br s, 1H), 7.53-7.49 (m, 2H), 7.34-7.30 (m, 2H), 7.27-7.21 (m, 2H), 6.97-6.91 (m, 1H), 6.73-6.68 (m, 2H), 2.87 (s, 6H).

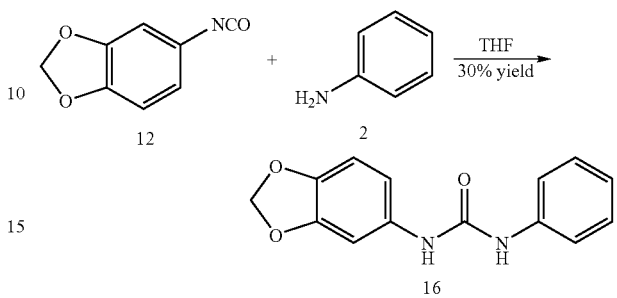

Compound 16 was prepared in a similar manner as compound 15 in 30% yield; ¹H NMR (CD₃COCD₃, 300 MHz) δ 8.01 (br s, 1H), 7.98 (br s, 1H), 7.52-7.49 (m, 2H), 7.30-7.22 (m, 3H), 6.99-6.94 (m, 1H), 6.80 (dd, 1H, J=8.4 Hz, 2.1 Hz), 6.73 (d, 1H, J=8.4 Hz), 5.94 (s, 2H), 3.17 (s, 3H).

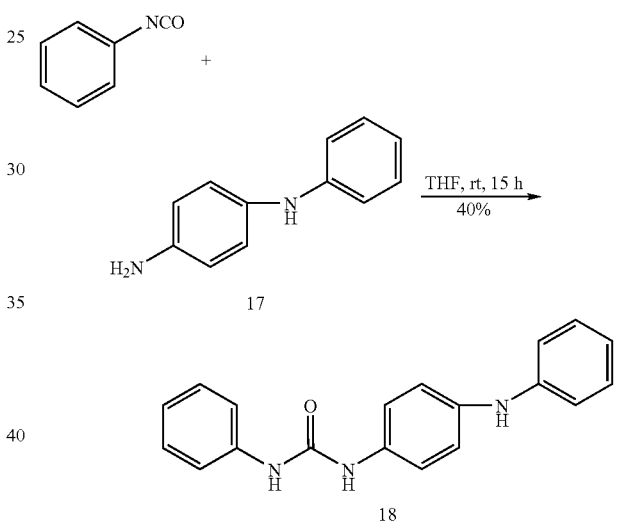

Compound 18 was prepared in a similar manner as compound 15 in 40% yield; ¹H NMR (CD₃COCD₃, 300 MHz) δ 8.01 (br s, 1H), 7.92 (br s, 1H), 7.55-7.51 (m, 2H), 7.45-7.40 (m, 2H), 7.29-7.16 (m, 4H), 7.11-7.69 (m, 5H), 6.77 (tt, 1H, J=7.5 Hz, 1.2 Hz).

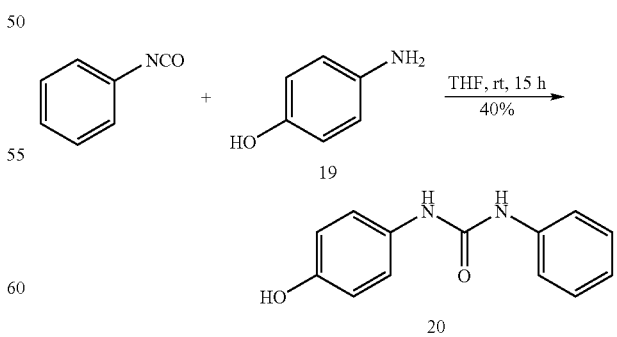

Compound 20 was prepared in a similar manner as compound 15 in 40% yield; ¹H NMR (CD₃COCD₃, 300 MHz) δ 8.01 (br s, 1H), 7.85 (br s, 1H), 7.54-7.50 (m, 2H), 7.36-7.22 (m, 4H), 6.98-6.92 (m, 1H), 6.79-6.74 (m, 2H).

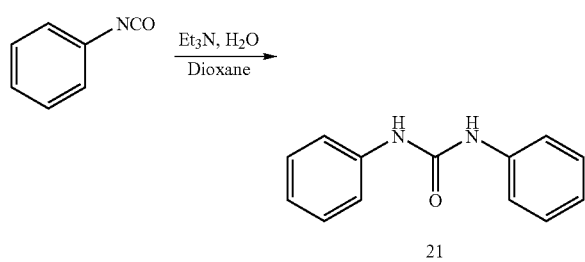

To a solution of phenylisocyanate (1 ml, 8.4 mmol) in dioxane (2 ml) was added triethylamine (8.25 ml, 58.8 mmol) at ambient temperature. The reaction mixture was stirred at ambient temperature overnight, and then poured into ice-cold water (200 ml) while stirring. White precipitate gradually came out and the mixture was stirred for 1 h and then filtered. The filter cake was washed with ice-cold water, dried under vacuum, recrystallized from hot ethanol to give 21 as white solid in 30% yield; (Perveen et al., 2007); $^1$H NMR (CD$_3$COCD$_3$, 400 MHz) δ 8.07 (br s, 2H), 7.52 (d, 4H, J=7.6 Hz), 7.26 (t, 4H, J=6.0 Hz), 6.99-6.95 (m, 2H).

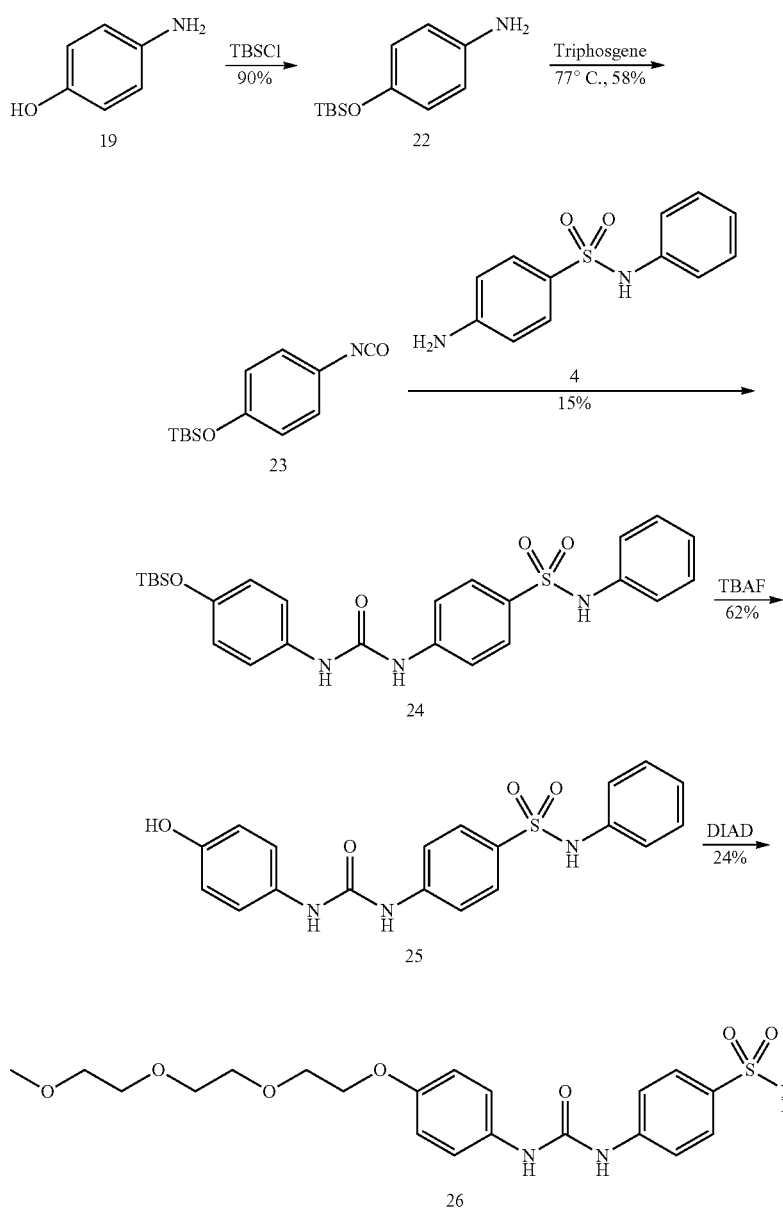

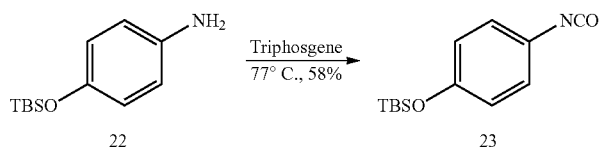

To a solution of 22 (300 mg, 1.29 mmol) in EtOAc (10 ml) was added triphosgene (382 mg, 1.29 mmol). Knaggs, et al., 2005. The reaction mixture was stirred at 77° C. for 6 h and directly loaded on silica gel, eluting with Hexane/EtOAc (14/1) gave the product 23 as colorless oil (193 mg, 58% yield), $^1$H NMR (CDCl$_3$, 300 MHz) δ 6.94 (d, 2H, J=8.7 Hz), 6.75 (d, 2H, J=8.7 Hz,), 0.96 (s, 9H), 0.18 (s, 6H); IR (thin film) v cm$^{-1}$ 2267 s (NCO).

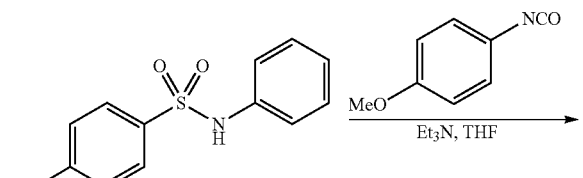

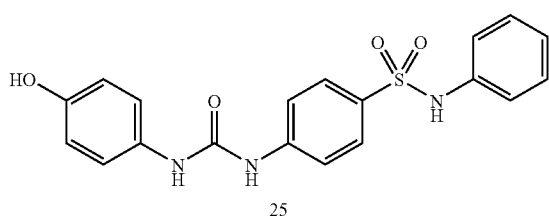

To a solution of 24 (52 mg, 0.1 mmol) in anhydrous THF (1.5 ml) was added TBAF (0.12 ml, 1.0M in THF). The reaction was stirred overnight and purified by PTLC to give the product 25 as pink solid, 24 mg, 62% yield, $^1$H NMR (CD$_3$OD, 300 MHz) δ 7.65-7.61 (m, 2H), 7.51-7.46 (m, 2H), 7.20-7.15 (m, 4H), 7.08-6.97 (m, 3H), 6.75-6.69 (m, 2H).

Compound 27 was prepared in a similar manner as compound 9: Solid, TLC: EtOAc/Hexanes 4:6, R$_f$~0.3; $^1$H NMR (CD$_3$COCD$_3$, 400 MHz) δ 8.86 (br s, 1H), 8.46 (br s, 1H), 8.08 (br s, 1H), 7.65 (q, 4H, J=18.4, 8.8 Hz), 7.4 (d, 2H, J=8.8 Hz), 7.26-7.20 (m, 5H), 7.07-7.03 (m, 1H), 6.85 (d, 2H, J=8.8 Hz), 3.75 (s, 3H).

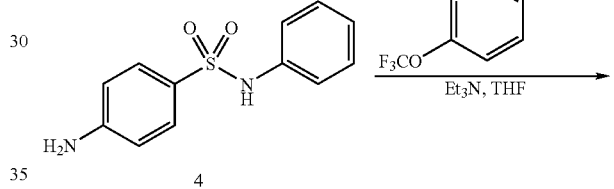

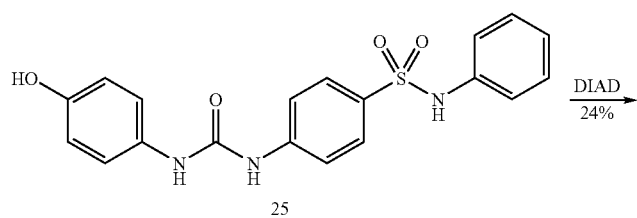

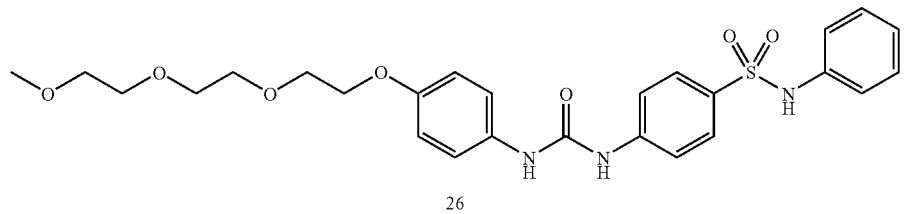

To a solution of 25 (30 mg, 0.078 mmol) in anhydrous THF (3 ml) was added PPh$_3$ (25 mg, 0.094 mmol), triethylene glycol monomethyl ether (13 mg, 0.078 mmol) and DIAD (0.019 ml, 0.094 mmol). The reaction was stirred overnight under argon and purified by prep-TLC (Si-gel) to give the product 26 as a colorless oil, 10 mg, 24% yield, $^1$H NMR (CD$_3$OD, 500 MHz) δ 7.57 (d, 2H, J=8.5 Hz), 7.50 (d, 2H, J=9.0 Hz), 7.34-7.32 (m, 3H), 7.19 (d, 2H, J=8.5 Hz), 7.11-7.10 (m, 2H), 6.73 (d, 2H, J=8.5 Hz), 3.78 (t, 2H, J=6.0 Hz), 3.58-3.56 (m, 2H), 3.52-3.48 (m, 8H), 3.34 (s, 3H).

-continued

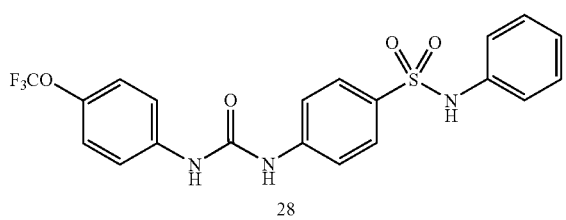

Compound 28 was prepared in a similar manner as compound 9: Solid, TLC: EtOAc/Hexanes 4:6, $R_f$~0.44; $^1$H NMR (CD$_3$COCD$_3$, 400 MHz) δ 8.87 (br s, 1H), 8.52 (br s, 1H), 8.41 (br s, 1H), 7.70-7.62 (m, 6H), 7.26-7.21 (m, 6H), 7.06-7.03 (m, 1H).

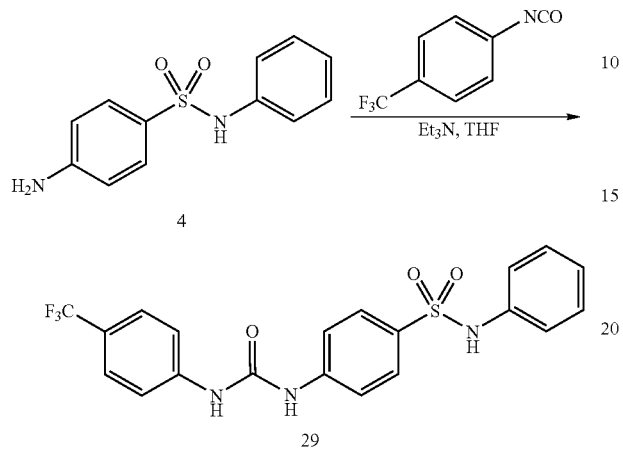

Compound 29 was prepared in a similar manner as compound 9 Solid, TLC: EtOAc/Hexanes 1:1, $R_f$~0.46; $^1$HNMR (CD$_3$COCD$_3$, 300 MHz) δ 8.89 (br s, 1H), 8.67 (br s, 2H), 7.75-7.60 (m, 7H), 7.27-7.20 (m, 4H), 7.18-7.03 (m, 2H).

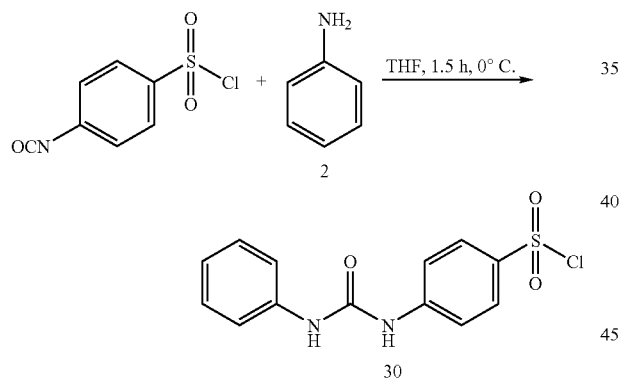

Preparation of Compound 30: To a solution of 41.8 μL (0.46 mmol) of aniline in 5 mL dry THF was added 100 mg (0.46 mmol) of 4-(chlorosulfonyl)phenyl isocyanate at 0° C. after being stirred for 1.5 h, the mixture was poured in to water and extracted with EtOAc (3×15 mL). The combined organic extracts were washed with brine, dried (Na$_2$SO$_4$) and concentrated. The residue was crystallized from hexane gave pinkish white solid 108 mg, 74% yield.

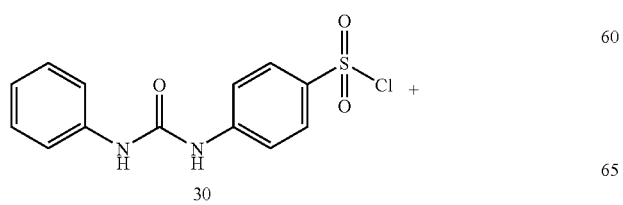

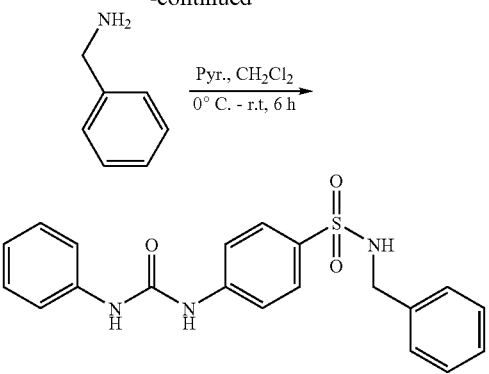

General procedure for the syntheses of sulfonamides from 30: To a solution of sulfonyl chloride 30 (0.14 mmol) in dry THF (3 mL) at 0° C. was added amine 2 (0.14 mmol) and pyridine (0.16 mmol) successively and the reaction mixture was allowed stir at room temperature for 6-10 h. The reaction mixture was quenched with water, extracted with EtOAc, washed with brine, dried and concentrated. The residue was purified by column chromatography or by PTLC to furnish sulfonamide derivatives in good yields.

Compound 31: 24 mg, 49% yield. Solid, TLC: EtOAc/Hexanes 1:1, $R_f$~0.38; $^1$H NMR (CD$_3$COCD$_3$, 300 MHz) δ 9.01 (br s, 1H), 8.64 (br s, 1H), 7.97-7.69 (m, 4H), 7.56-7.53 (m, 2H), 7.31-7.24 (m, 7H), 6.99 (t, 1H, J=8.7 Hz), 4.11 (d, 2H, J=5.7 Hz).

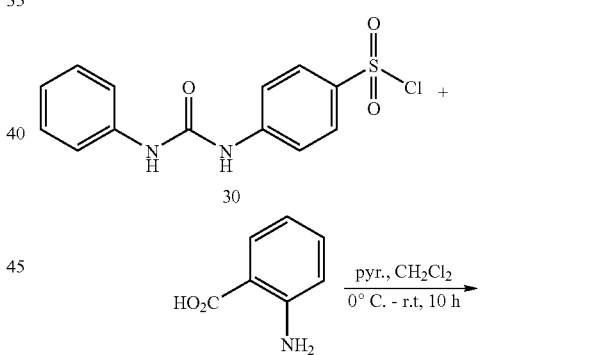

Compound 32 was prepared in a similar manner as compound 31 in 26% yield; Solid, TLC: CH$_3$OH/CH$_2$Cl$_2$ 5:95, $R_f$~0.2; $^1$H NMR (CD$_3$COCD$_3$, 300 MHz) δ 10.27 (br s, 1H), 10.13 (br s, 1H), 8.07 (d, 2H, J=8.7 Hz), 7.98-7.72 (m, 6H), 7.62 (d, 2H, J=7.8 Hz), 7.36 (t, 1H, J=7.5 Hz), 7.21 (t, 2H, J=7.5 Hz), 6.98-6.89 (m, 2H).

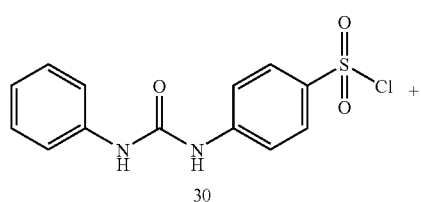

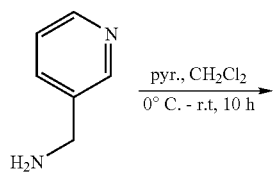

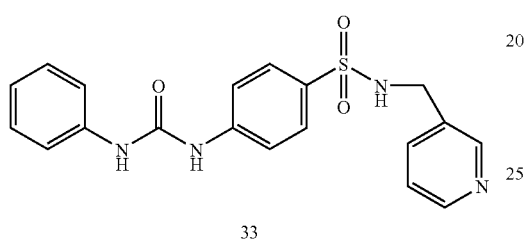

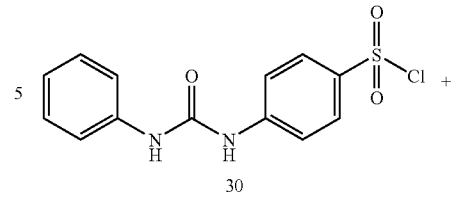

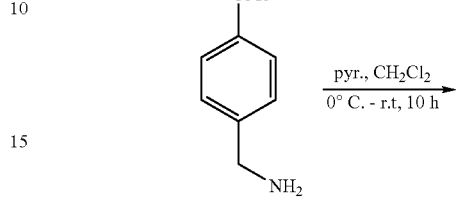

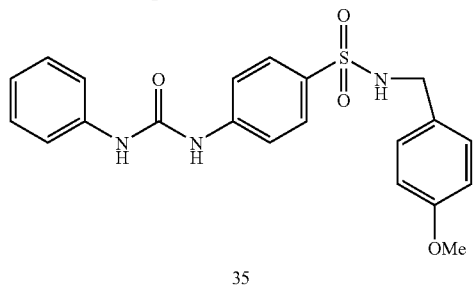

Compound 33 was prepared in a similar manner as compound 31 in 55% yield; Solid, TLC: CH$_3$OH/CH$_2$Cl$_2$ 5:95, R$_f$~0.4; $^1$H NMR (DMSO-d$_6$, 300 MHz) δ 9.12 (br s, 1H), 8.81 (br s, 1H), 8.40 (br s, 1H), 7.70-7.58 (m, 5H), 7.47-7.44 (m, 2H), 7.31-7.26 (m, 3H), 6.98 (t, 1H, J=7.2 Hz), 4.03 (d, 2H, J=7.5 Hz).

Compound 35 was prepared in a similar manner as compound 31 in 28.3% yield; Solid, TLC: EtOAc/Hexanes 1:1, R$_f$~0.42; $^1$H NMR (DMSO-d$_6$, 300 MHz) δ 9.13 (br s, 1H), 8.82 (br s, 1H), 8.12 (t, 1H, NH, J=6.3 Hz), 7.69-7.58 (m, 4H), 7.48-7.44 (m, 3H), 7.31-7.26 (m, 5H), 7.01-6.96 (m, 1H), 4.08 (d, 2H, J=5.7 Hz), 3.75 (s, 3H).

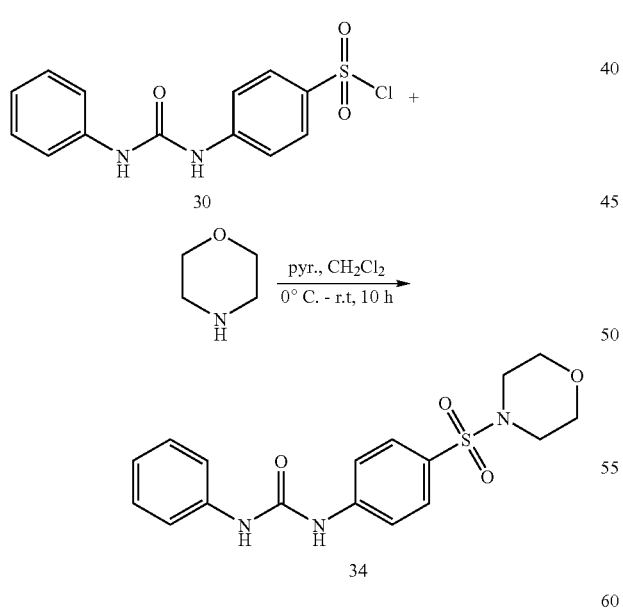

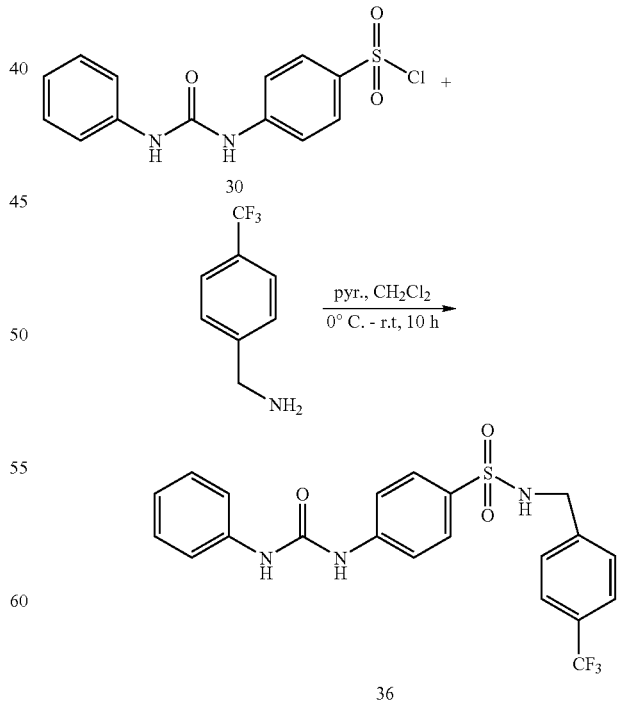

Compound 34 was prepared in a similar manner as compound 31 in 62% yield; solid, TLC: EtOAc/Hexanes 4:6, R$_f$~0.42; $^1$H NMR (DMSO-d$_6$, 300 MHz) δ 9.21 (br s, 1H), 8.82 (br s, 1H), 7.71-7.61 (m, 4H), 7.47-7.49 (m, 2H), 7.29 (t, 2H, J=8.7 Hz), 7.02-6.96 (m, 1H), morpholine nmr values are missing.

Compound 36 was prepared in a similar manner as compound 31 in 52% yield; solid, TLC: EtOAc/Hexanes 1:1, $R_f$-0.38; $^1$H NMR (DMSO-$d_6$, 300 MHz) δ 9.13 (br s, 1H), 8.82 (br s, 1H), 8.12 (t, 1H, NH, J=6.3 Hz), 7.69-7.58 (m, 4H), 7.48-7.44 (m, 3H), 7.31-7.26 (m, 6H), 7.01-6.96 (m, 1H), 4.08 (d, 2H, J=5.7 Hz).

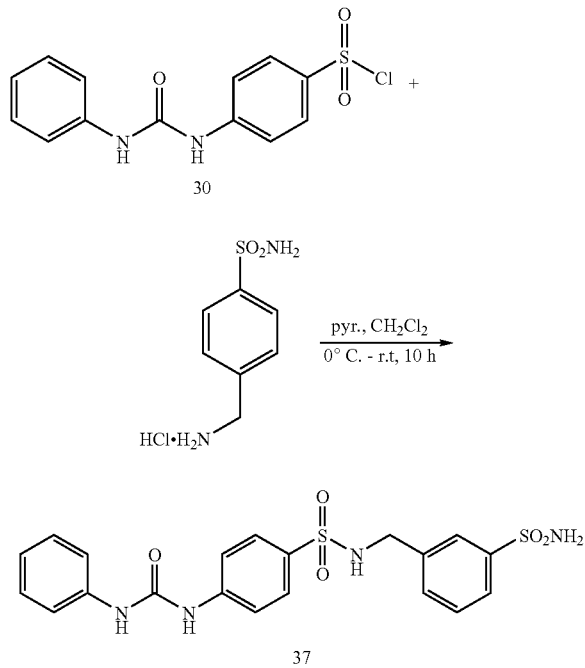

Compound 37 was prepared in a similar manner as compound 31 in 19% yield; Solid, TLC: CH$_3$OH/CH$_2$Cl$_2$ 5:95, $R_f$-0.27; $^1$H NMR (DMSO-$d_6$, 300 MHz) δ 8.73 (br s, 1H), 8.67 (br s, 1H), 8.17 (br s, 1H), 7.84 (d, 2H, J=8.2 Hz), 7.60 (d, 2H, J=8.2 Hz), 7.49-7.34 (m, 5H), 7.26 (t, 2H, J=7.5 Hz), 6.95 (t, 2H, J=7.2 Hz), 4.1 (d, 2H, J=5.7 Hz).

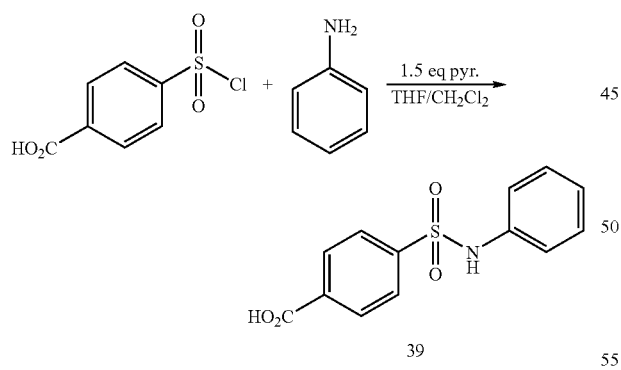

Synthesis of Compound 39. To a solution of 4-(chlorosulfonyl)benzoic acid (100 mg, 0.45 mmol) in a mixture of dry THF/CH$_2$Cl$_2$ (1/4) (5 mL), aniline (45.4 μL, 0.49 mmol) and py (55 μL, 0.67 mmol) were added at 0 C. and the was allowed to stir at r.t for 4 h. The solvent was concentrated and the residue was purified by triturating with CH$_2$Cl$_2$, and decanting to give sulfonamide 39 as a white solid in (0.11 g, 88% yield: TLC: EtOAc/Hexanes 1:1, $R_f$-0.39; $^1$H NMR (DMSO-$d_6$, 300 MHz) δ 10.44 (br s, 1H), 8.04 (d, 2H, J=9.0 Hz), 7.83 (d, 2H, J=9.0 Hz), 7.24-7.19 (m, 2H), 7.08-7.02 (m, 3H).

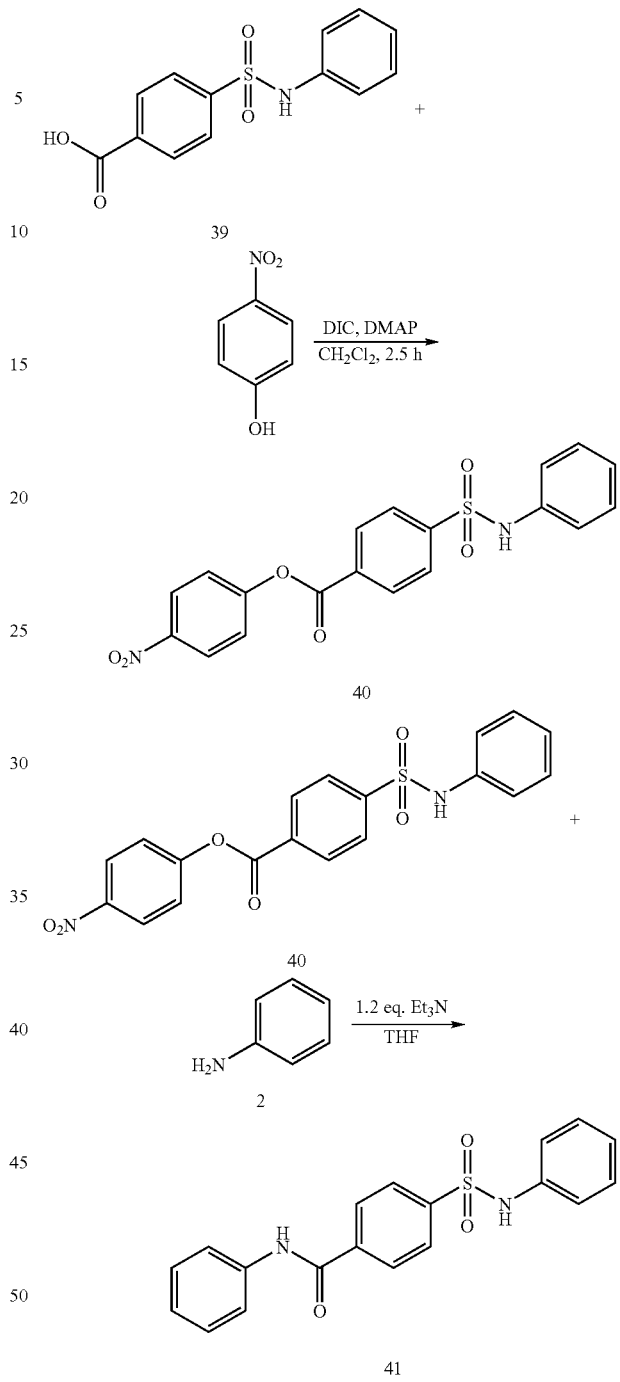

Compound 40: To solution of 39 (0.2 g, 0.722 mmol) in dry CH$_2$Cl$_2$ (5 mL), DIC (134 μL, 0.86 mmol) and cat. DMAP were added and was stirred at room temperature for 2 h. The reaction mixture was diluted with water and extracted with CH$_2$Cl$_2$ (3×5 mL). The combined organic extracts were dried, concentrated and purified by eluting with 1:9 EtOAc/hexanes on silica gel column to give 40 (0.26 g, 92%) as solid. $^1$H NMR spectrum was consistent with its structure and used in the syntheses of 41-46.

Compound 41: A solution of active ester 40 (60 mg, 0.15 mmol) amine 2 (16.8 mg, 0.18 mmol), and Et$_3$N (18.2 mg, 0.18 mmol) in dry THF (5 mL) were stirred at ambient temperature for 6 h. The solvent was concentrated and the residue was purified by prep-TLC to give 39 mg of a solid (73% yield); TLC: EtOAc/Hexanes 2:3, $R_f$~0.46; $^1$H NMR (CD$_3$OD, 300 MHz) δ 7.97 (d, 2H, J=8.7 Hz), 7.86 (d, 2H, J=8.7 Hz), 7.67-7.64 (m, 2H), 7.34 (t, 2H, J=6.9 Hz), 7.24-7.03 (m, 6H).

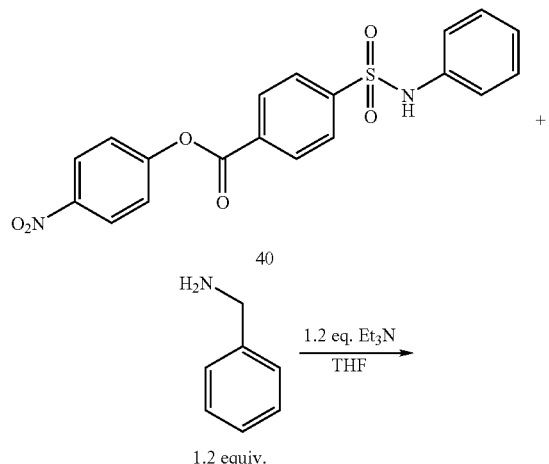

Compound 42 was prepared in a similar manner as compound 41 in 73% yield; solid; TLC: EtOAc/Hexanes 2:3, $R_f$~0.4; $^1$H NMR (CD$_3$OD, 300 MHz) δ 7.89 (d, 2H, J=8.7 Hz), 7.81 (d, 2H, J=8.7 Hz), 7.31-7.17 (m, 8H), 7.09-7.02 (m, 2H), 4.54 (s, 2H).

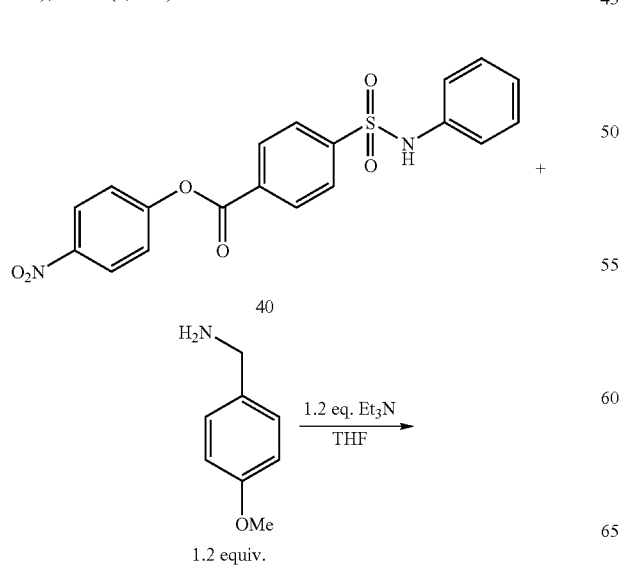

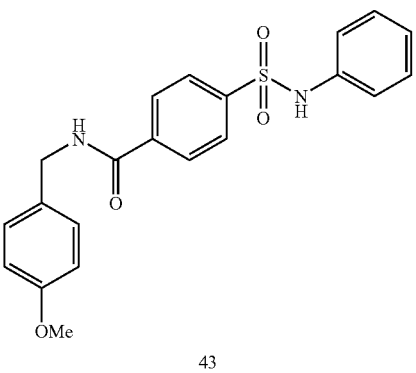

43

Compound 43 was prepared in a similar manner as compound 41 in 77% yield; solid; TLC: EtOAc/Hexanes 3:2, $R_f$~0.65; $^1$H NMR (CD$_3$OD, 300 MHz) δ 7.87 (d, 2H, J=8.8 Hz), 7.80 (d, 2H, J=8.8 Hz), 7.26-7.17 (m, 4H), 7.08-7.04 (m, 3H), 6.86 (d, 2H, J=7.5 Hz), 4.47 (s, 2H), 3.76 (s, 3H).

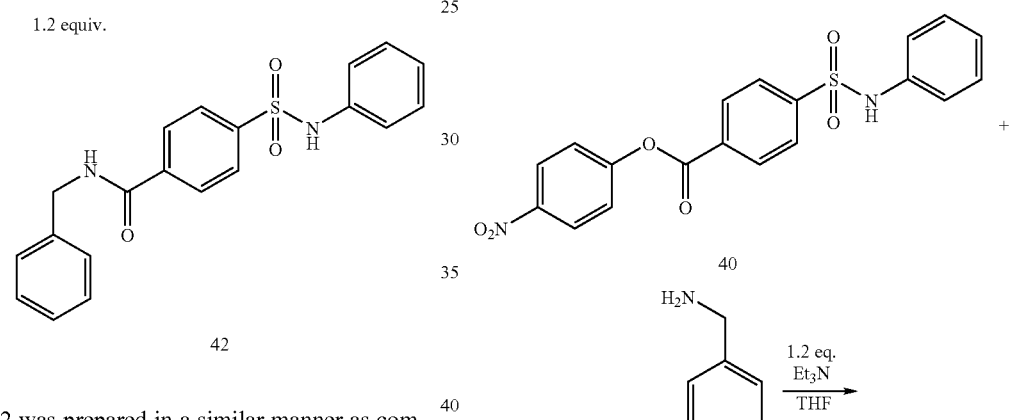

44

Compound 44 was prepared in a similar manner as compound 41 in 71% yield; solid; TLC: EtOAc/Hexanes 2:3, $R_f$~0.45; $^1$H NMR (CD$_3$OD, 300 MHz) δ 7.91 (d, 2H, J=8.4 Hz), 7.82 (d, 2H, J=8.4 Hz), 7.62 (d, 2H, J=8.4 Hz), 7.51 (d, 2H, J=8.4 Hz), 7.20 (t, 2H, J=8.4 Hz), 7.09-7.05 (m, 3H), 4.60 (s, 2H).

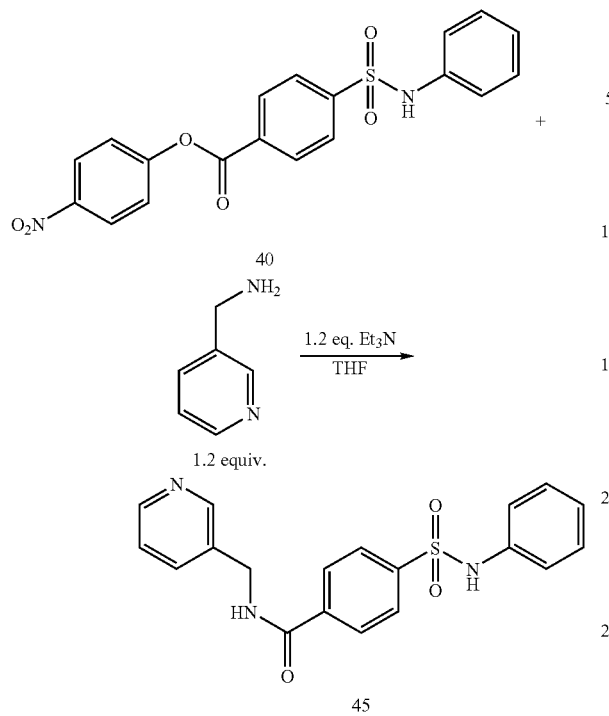

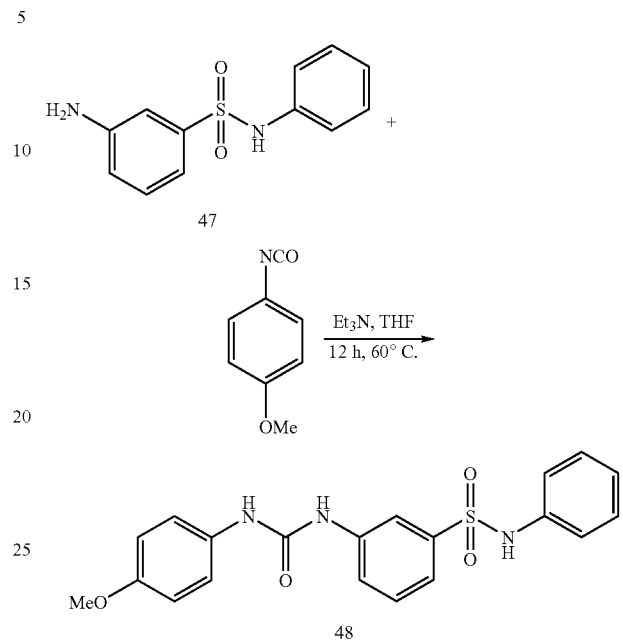

7.22-7.17 (m, 2H), 7.09-7.03 (m, 3H), 4.85-3.78 (m, 1H), 1.94-1.90 (m, 2H), 1.81-1.78 (m, 2H), 1.70-1.65 (m, 1H), 1.42-1.17 (m, 5H).

Compound 45 was prepared in a similar manner as compound 41 in 44% yield; solid; TLC: CH$_3$OH/CH$_2$Cl$_2$ 5:95, R$_f$~0.2; $^1$H NMR (CD$_3$OD, 300 MHz) δ 8.53 (br s, 1H), 8.42 (br s, 1H), 7.91-7.79 (m, 6H), 7.40-7.36 (m, 1H), 7.22-7.16 (m, 2H), 7.09-7.01 (m, 4H), 4.57 (s, 2H).

Compound 48 was prepared in a similar manner as compound 9 in 53% yield; solid, TLC: EtOAc/Hexanes 4:6, R$_f$~0.4; $^1$H NMR (CD$_3$OD, 300 MHz) δ 7.98 (br s, 1H), 7.59-7.55 (m, 1H), 7.33-7.27 (m, 5H), 7.23-7.17 (m, 2H), 7.11-7.01 (m, 3H), 6.88-6.85 (m, 2H), 3.75 (s, 3H).

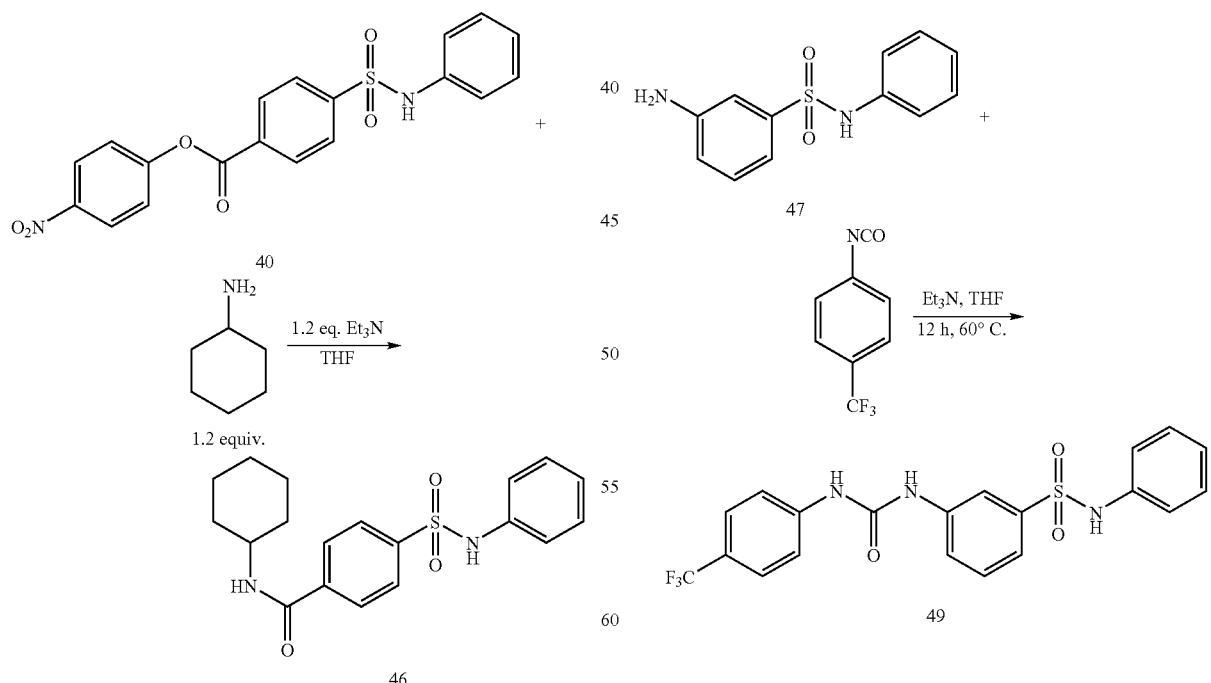

Compound 46 was prepared in a similar manner as compound 41 in 67% yield: solid, TLC: EtOAc/Hexanes 50%, Rf 0.4; $^1$H NMR (CD$_3$OD, 300 MHz) δ 7.85-7.78 (m, 4H), Compound 49 was prepared in a similar manner as compound 9 in 49% yield; solid, TLC: EtOAc/Hexanes 4:6, R$_f$~0.41 (2 elutions); $^1$H NMR (CD$_3$OD, 300 MHz) δ 7.97 (br s, 1H), 7.64-7.56 (m, 5H), 7.38 (d, 2H, J=6.0 Hz), 7.23-7.18 (m, 3H), 7.11-7.02 (m, 3H).

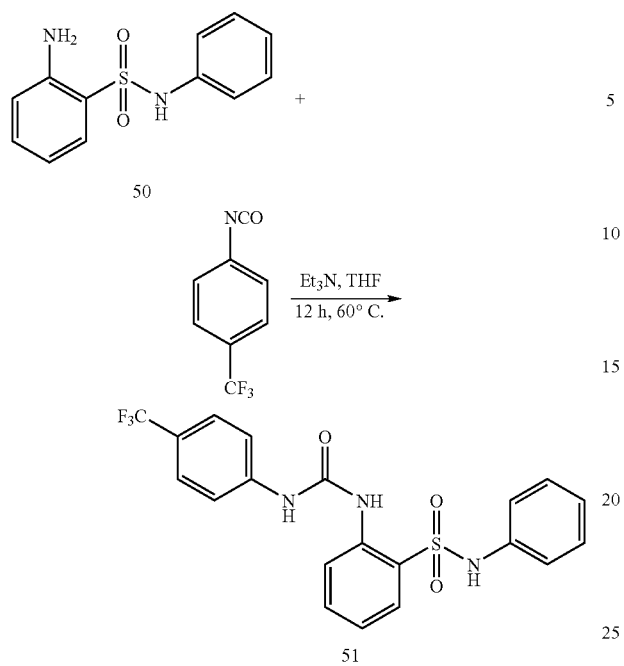

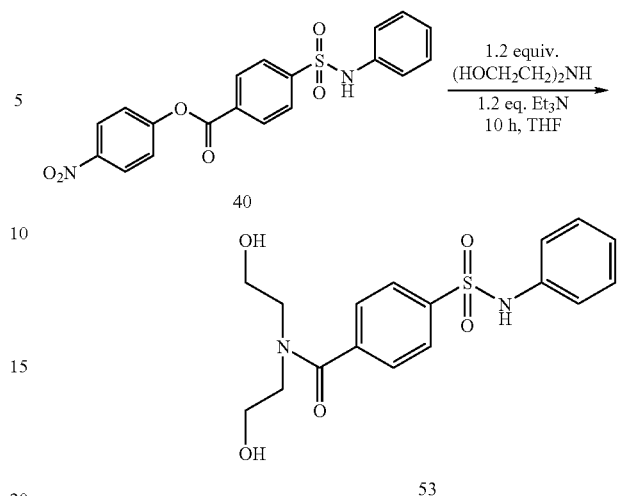

Compound 51 was prepared in a similar manner as compound 9 in 28% yield; solid, TLC: EtOAc/Hexanes 4:6, $R_f$~0.46; $^1$H NMR (CD$_3$OD, 300 MHz) δ 7.93 (dd, 1H, J=8.7, 1.2 Hz), 7.08 (dd, 1H, J=8.1, 1.5 Hz), 7.62-7.48 (m, 5H), 7.16-7.08 (m, 5H), 6.96-6.90 (m, 1H).

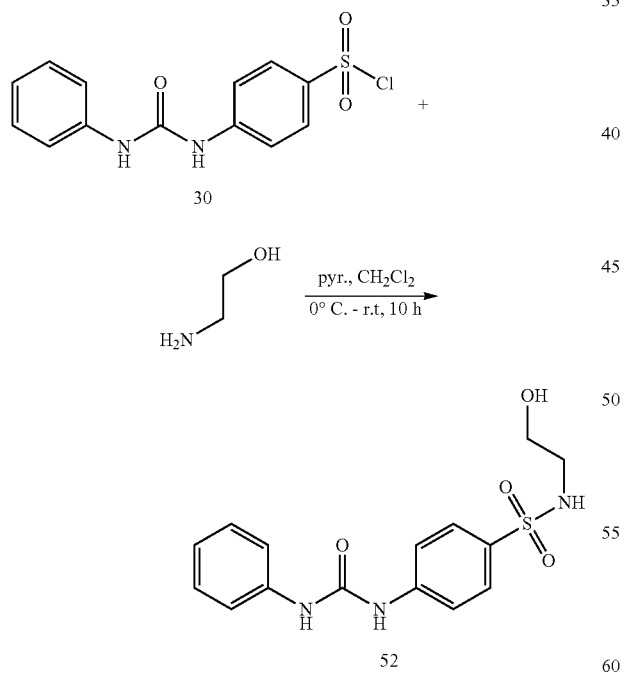

Compound 52 was prepared in a similar manner as compound 31 in 65% yield; syrup, TLC: EtOAc/Hexanes 7:3, $R_f$~0.36; $^1$H NMR (CD$_3$OD, 300 MHz) δ 7.78-7.52 (m, 2H), 7.64-7.61 (m, 2H), 7.45-7.41 (m, 2H), 7.32-7.26 (m, 2H), 7.31-6.98 (m, 1H), 3.56-3.51 (m, 2H), 2.95-2.91 (m, 2H).

Compound 53 was prepared in a similar manner as compound 31 in 62% yield; syrup; TLC: EtOAc/Hexanes 4:1, $R_f$~0.2; $^1$H NMR (CD$_3$OD, 300 MHz) δ 7.80 (d, 2H, J=8.4 Hz), 7.55 (d, 2H, J=8.4 Hz), 7.23-7.17 (m, 2H), 7.09-7.03 (m, 3H), 3.81 (t, 2H, J=5.4 Hz), 3.67 (t, 2H, J=5.4 Hz), 3.56 (t, 2H, J=5.4 Hz), 3.36 (d, 2H, J=5.4 Hz).

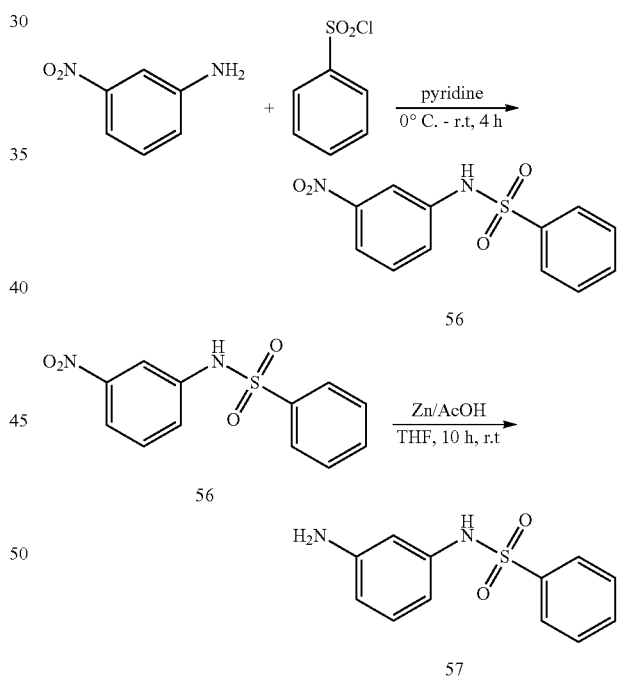

To compound 54 (3.0 g, 21.6 mmol) in pyridine at 0° C. was added 55 (3.32 mL, 26.0 mmol). After warming to ambient temperature over 4 h the solvent was removed in vacuo, and the residue was extracted with EtOAc and 1N HCl. The EtOAc layer was washed successively with water, NaHCO$_3$, and water. After drying with NaSO$_4$ the solvent was removed in vacuo. The crude product was purified by silica gel chromatography to give 71% of 56: solid; TLC: EtOAc/Hexanes 3:7, $R_f$~0.3; $^1$H NMR (CDCl$_3$, 300 MHz) δ 8.35-8.31 (m, 1H), 7.93 (d, 2H, J=8.1 Hz), 7.87 (t, 1H, J=2.1 Hz), 7.76-7.70 (m, 1H), 7.62-7.54 (m, 3H), 7.39-7.36 (m, 1H).

To compound 56 (2.0 g, 7.1 mmol) was stirred with zinc powder (4.7 g, 72 mmol) and extractive workup and preparative chromatography to give 76% of 57: solid; TLC: EtOAc/Hexanes 1:1, $R_f$~0.4; $^1$H NMR (CDCl$_3$, 300 MHz) δ 7.83-7.80 (m, 2H), 7.61-7.47 (m, 3H), 7.39-7.33 (m, 2H), 7.20-7.03 (m, 2H).

Compound 59 was prepared in a similar manner as compound 9 in 44% yield; solid; TLC: EtOAc/Hexanes 1:1, $R_f$~0.42; $^1$H NMR (CD$_3$COCD$_3$, 300 MHz) δ 8.97 (br s, 1H), 8.07 (br s, 1H), 7.86-7.83 (m, 3H), 7.62-7.49 (m, 3H), 7.44-7.38 (m, 2H), 7.23-7.20 (m, 2H), 7.10 (t, 1H, J=8.1 Hz), 6.88-6.81 (m, 2H).

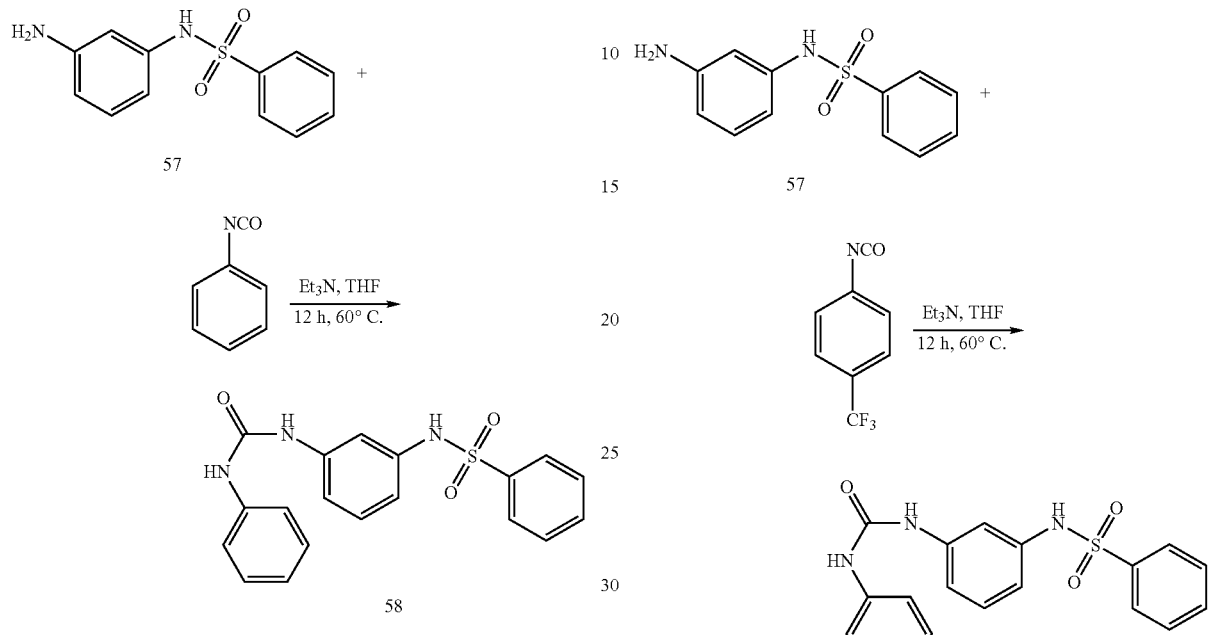

Compound 58 was prepared in a similar manner as compound 9 in 52% yield; solid; TLC: EtOAc/Hexanes 1:1, $R_f$~0.5; $^1$H NMR (CD$_3$COCD$_3$, 300 MHz) δ 8.99 (br s, 1H), 8.19 (br s, 1H), 8.10 (br s, 1H), 7.85 (d, 2H, J=6.9 Hz), 7.59-7.49 (m, 5H), 7.29-7.21 (m, 3H), 7.12 (t, 1H, J=8.1 Hz), 6.98 (t, 1H, J=7.4 Hz), 6.86-6.82 (m, 2H).

Compound 60 was prepared in a similar manner as compound 9 in 46% yield; solid; TLC: EtOAc/Hexanes 3:7, $R_f$~0.4; $^1$H NMR (CD$_3$COCD$_3$, 300 MHz) δ 9.03 (br s, 1H), 8.46 (br s, 1H), 8.29 (br s, 1H), 7.85 (d, 2H, J=6.9 Hz), 7.67 (d, 2H, J=13.8 Hz), 7.61-7.50 (m, 4H), 7.26-7.21 (m, 2H), 7.14 (t, 1H, J=7.8 Hz), 6.88-6.85 (m, 2H).

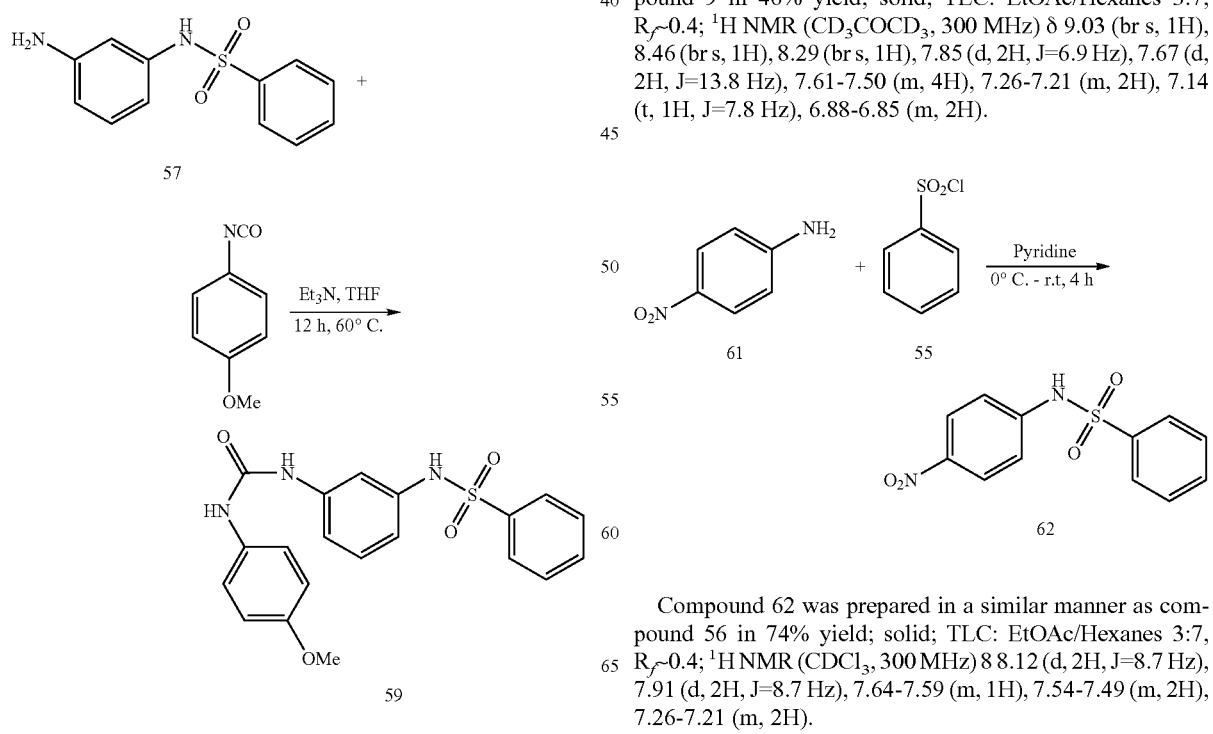

Compound 62 was prepared in a similar manner as compound 56 in 74% yield; solid; TLC: EtOAc/Hexanes 3:7, $R_f$~0.4; $^1$H NMR (CDCl$_3$, 300 MHz) δ 8.12 (d, 2H, J=8.7 Hz), 7.91 (d, 2H, J=8.7 Hz), 7.64-7.59 (m, 1H), 7.54-7.49 (m, 2H), 7.26-7.21 (m, 2H).

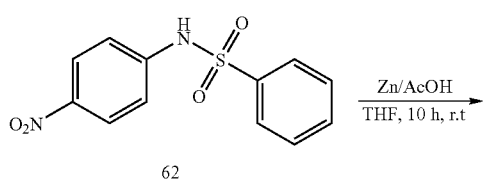

62

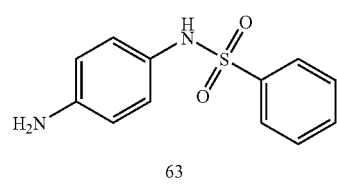

63

Compound 63 was prepared in a similar manner as compound 57 in 71% yield; solid; TLC: EtOAc/Hexanes 7:3, $R_f$~0.4; $^1$H NMR (CD$_3$COCD$_3$, 300 MHz) δ 8.53 (br s, 1H), 7.70-7.67 (m, 2H), 7.61-7.46 (m, 3H), 6.82 (d, 2H, J=8.4 Hz), 6.52 (d, 2H, J=8.4 Hz), 4.06 (br s, 2H).

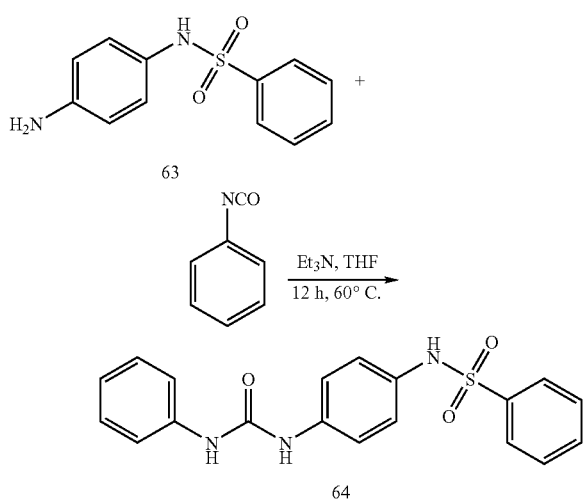

64

Compound 64 was prepared in a similar manner as compound 9 in 39% yield; solid; TLC: EtOAc/Hexanes 1:1, $R_f$~0.55; $^1$H NMR (CD$_3$COCD$_3$, 300 MHz) δ 8.78 (br s, 1H), 8.12 (br s, 2H), 7.77-7.42 (m, 2H), 7.60-7.49 (m, 5H), 7.42 (d, 2H, J=9.0 Hz), 7.26 (t, 2H, J=7.2 Hz), 7.09 (d, 2H, J=8.7 Hz), 6.99 (t, 1H, J=7.2 Hz).

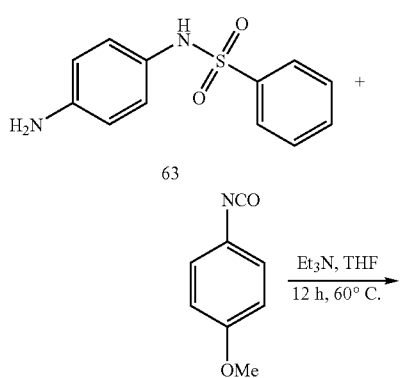

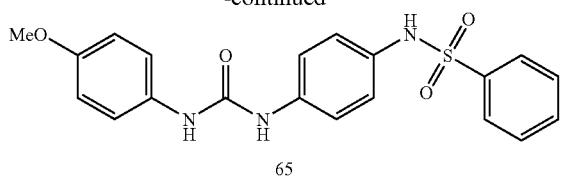

65

Compound 65 was prepared in a similar manner as compound 9 in 32% yield; solid; TLC: EtOAc/Hexanes 1:1, $R_f$~0.3; $^1$H NMR (CD$_3$OD, 300 MHz) δ 7.94 (s, 1H), 7.59-7.55 (m, 1H), 7.35-7.27 (m, 4H), 7.23-7.17 (m, 3H), 7.11-7.01 (m, 2H), 6.88-6.85 (m, 2H), 3.79 (s, 3H).

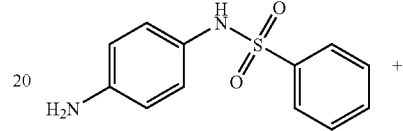

63

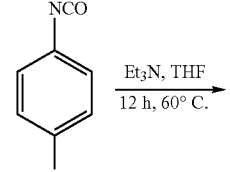

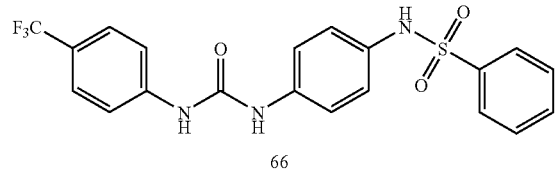

66

Compound 66 was prepared in a similar manner as compound 9 in 45% yield; solid; TLC: EtOAc/Hexanes 3:7, $R_f$~0.4; $^1$H NMR (CD$_3$OD, 300 MHz) δ 7.97 (s, 1H), 7.64-7.55 (m, 5H), 7.39-7.37 (m, 2H), 7.23-7.18 (m, 2H), 7.11-7.01 (m, 3H).

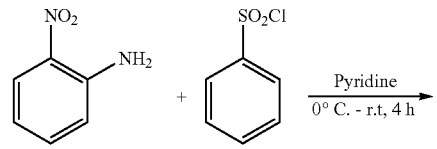

67    55

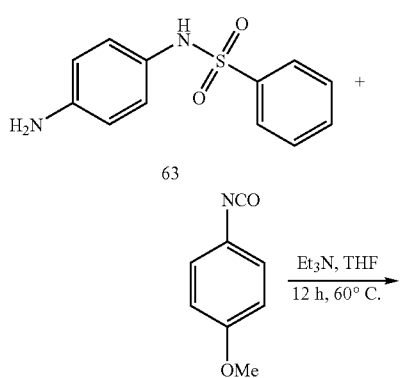

68

Compound 68 was prepared in a similar manner as compound 56 in 64% yield; solid; TLC: EtOAc/Hexanes 3:7, $R_f$~0.4 (3 elutions); $^1$H NMR (CDCl$_3$, 300 MHz) δ 8.05-8.03 (m, 1H), 7.98-7.95 (m, 2H), 7.73-7.67 (m, 1H), 7.64-7.53 (m, 4H), 7.16-7.13 (m, 1H).

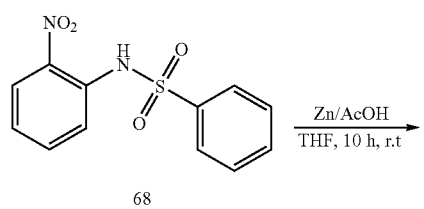

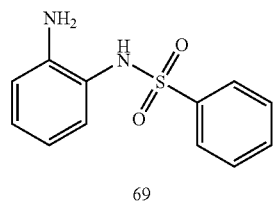

Compound 69 was prepared in a similar manner as compound 57 in 71% yield; solid; TLC: EtOAc/Hexanes 3:7, $R_f$~0.4 (3 elutions); $^1$H NMR (CDCl$_3$, 300 MHz) δ 8.05-8.03 (m, 1H), 7.98-7.95 (m, 2H), 7.73-7.67 (m, 1H), 7.64-7.53 (m, 4H), 7.16-7.13 (m, 1H).

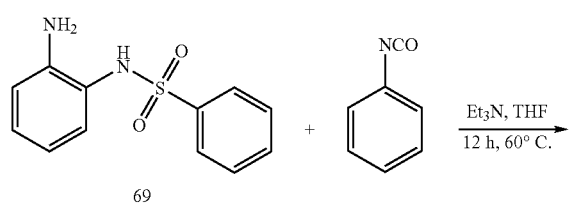

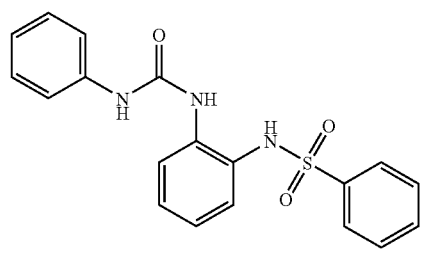

Compound 70 was prepared in a similar manner as compound 9 in 44% yield; solid; TLC: EtOAc/Hexanes 1:1, $R_f$~0.35; $^1$H NMR (CD$_3$COCD$_3$, 300 MHz) δ 8.78 (br s, 1H), 8.70 (br s, 1H), 8.05 (br s, 1H), 7.92 (dd, 1H, J=8.4, 1.2 Hz), 7.71-7.57 (m, 3H), 7.56-7.50 (m, 4H), 7.30 (t, 2H, J=7.2 Hz), 7.21 (dt, 1H, J=8.7, 1.5 Hz),7.01 (dt, 1H, J=8.7, 1.5 Hz), 6.88 (dt, 1H, J=8.7, 1.5 Hz), 6.77 (dd, 1H, J=7.8, 1.2 Hz).

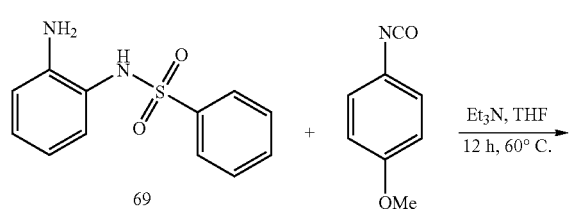

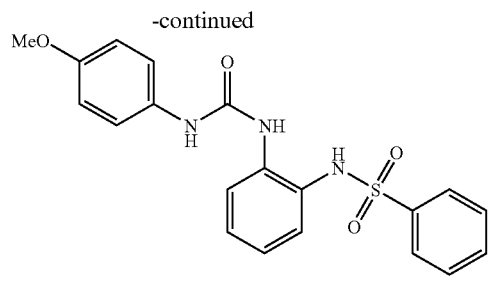

Compound 71 was prepared in a similar manner as compound 9 in 33% yield; solid; TLC: EtOAc/Hexanes 1:1, $R_f$~0.2; $^1$H NMR (CD$_3$COCD$_3$, 300 MHz) δ 8.79 (br s, 1H), 8.54 (br s, 1H), 7.96 (br s, 1H), 7.83 (dd, 1H, J=8.1, 1.5 Hz), 7.76-7.62 (m, 3H), 7.55-7.43 (m, 4H), 7.19 (dt, 1H, J=7.2, 1.8 Hz),6.92-6.87 (m, 3H), 6.81 (dd, 1H, J=7.8, 1.5 Hz), 3.77 (s, 3H).

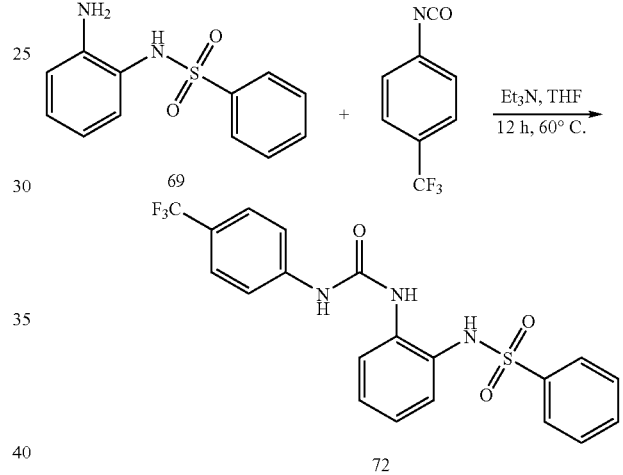

Compound 72 was prepared in a similar manner as compound 9 in 39% yield; solid; TLC: EtOAc/Hexanes 1:1, $R_f$~0.43; $^1$H NMR (CD$_3$COCD$_3$, 300 MHz) δ 9.25 (br s, 1H), 8.58 (br s, 1H), 8.17 (br s, 1H), 8.03 (dd, 1H, J=8.4, 1.2 Hz), 7.78 (d, 2H, J=8.4 Hz), 7.72-7.62 (m, 5H), 7.57 (apparent t, 2H, J=7.5 Hz), 7.24 (dt, 1H, J=8.4, 1.5 Hz), 6.88 (dt, 1H, J=7.5, 1.2 Hz), 6.82 (dd, 1H, J=8.1, 1.5 Hz).

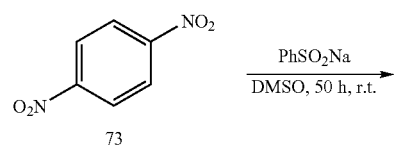

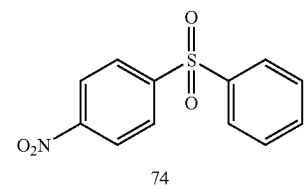

To compound 73 (500 mg, 3.0 mmol) in DMSO was added PhSO$_2$Na (509 mg, 3.1 mmol) and the mixture stirred at ambient temperature. After 50 h, the mixture was poured into water and extracted with EtOAc (3×50 mL). The EtOAc extracts were combined and washed with bicarbonate, water, and brine then dried with Na₂SO₄. The compound was purified by chromatography (0.61 g, 78%). Spectral measurement were consistent with it structure.

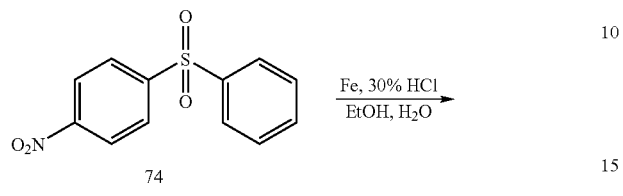

74

To 74 (200 mg, 0.76 mmol) in EtOH-water (9:1) and iron powder (424 mg, 7.6 mmol) was added 8 mmol HCl (30%) and stirred overnight at ambient temperature. The reaction mixture was stripped in vacuo, and purified by column chromatography to give 75 in 61% yield: ¹H NMR (CDCl₃, 300 MHz) δ 7.89 (d, 2H, J=7.5 Hz), 7.71 (d, 2H, J=8.7 Hz), 7.51-7.46 (m, 3H), 6.66 (d, 2H, J=8.7 Hz).

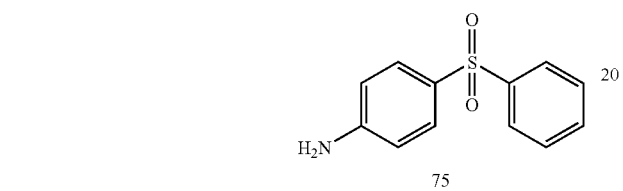

75

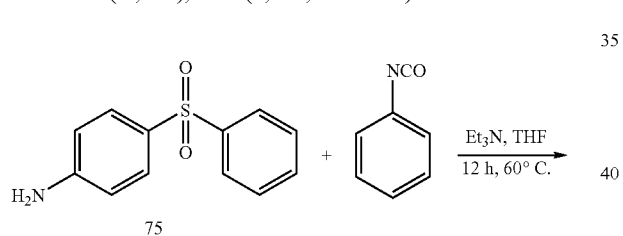

76

Compound 76 was prepared in a similar manner as compound 9 in 36% yield; Solid, TLC: EtOAc/Hexanes 30%, Rf 0.5; ¹H NMR (CD₃OD, 300 MHz) δ 7.43-7.39 (m, 4H), 7.31-7.25 (m, 8H), 7.03-6.99 (m, 2H).

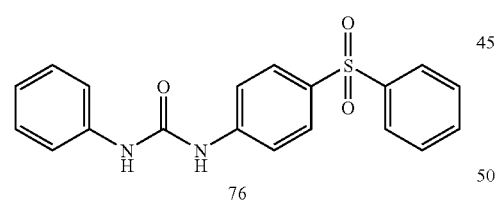

30

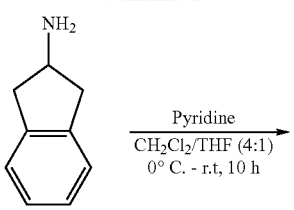

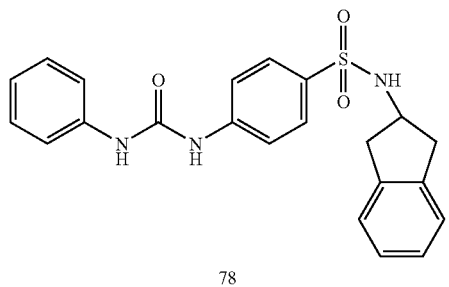

78

Compound 78 was prepared in a similar manner as compound 31 in 36% yield; solid, TLC: EtOAc/Hexanes 1:1, R$_f$~0.46 (2 elutions); ¹H NMR (CD₃COCD₃, 300 MHz) δ 8.58 (br s, 1H), 8.28 (br s, 1H), 7.88 (d, 2H, J=9.0 Hz), 7.78 (d, 2H, J=9.0 Hz), 7.56 (d, 2H, J=8.4 Hz), 7.30 (t, 2H, J=2.0 Hz), 7.18-7.16 (m, 4H), 7.03-6.96 (m, 1H), 6.74 (d, 2H,NH, J=1.5 Hz), 4.82 (q, 1H, J=10.2 Hz), 2.88-2.62 (m, 2H), 2.29-2.18 (m, 1H), 1.78-1.68 (m, 1H).

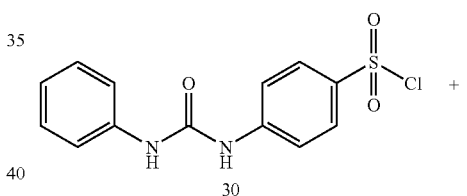

30

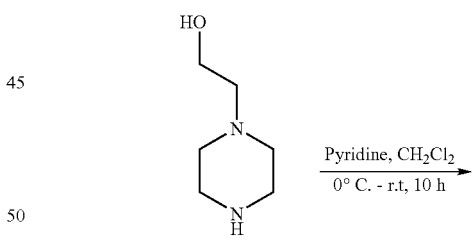

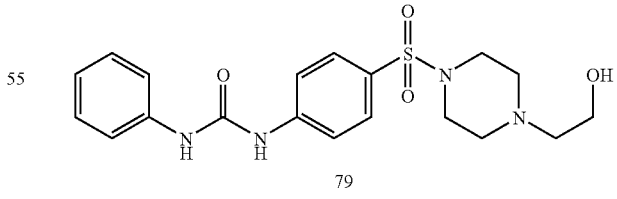

79

Compound 79 was prepared in a similar manner as compound 31 in 46% yield; solid, TLC: CH₃OH/CH₂Cl₂ 5:95, R$_f$~0.27; ¹H NMR (CD₃COCD₃, 300 MHz) δ 8.64 (br s, 1H), 8.31 (br s, 1H), 7.82-7.78 (m, 2H), 7.70-7.66 (m, 2H), 7.57-7.54 (m, 1H), 7.05-6.97 (m, 4H), 3.54 (br s, 2H), 3.38 (br s, 1H), 2.95-2.28 (br m, 4H), 2.56-2.46 (br m, 6H).

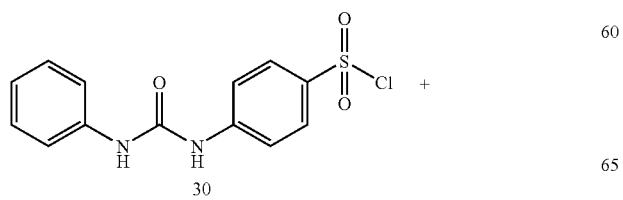

30

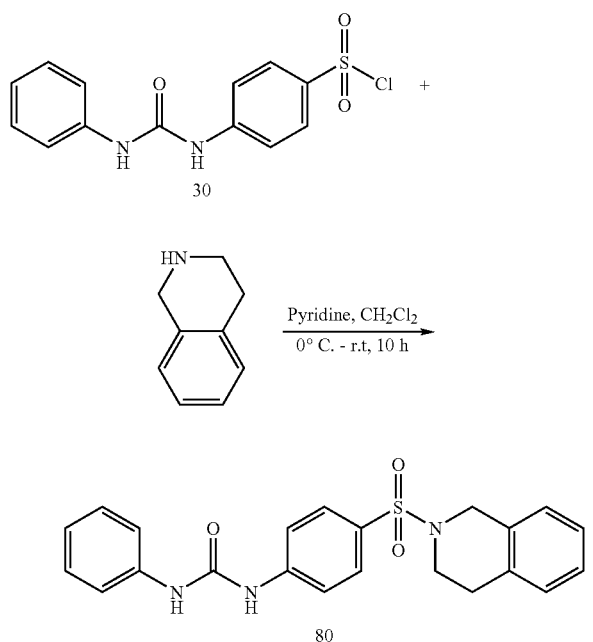

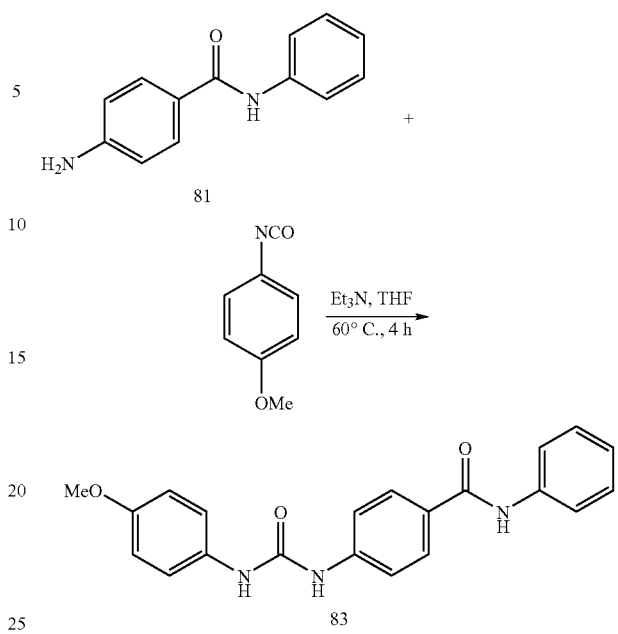

Compound 80 was prepared in a similar manner as compound 31 in 41% yield; solid, TLC: EtOAc/Hexanes 1:1, $R_f$~0.4; $^1$H NMR (CD$_3$COCD$_3$, 300 MHz) δ 8.58 (br s, 1H), 8.24 (br s, 1H), 7.78 (m, 5H), 7.56-7.53 (m, 2H), 7.34-7.26 (m, 2H), 7.15-7.11 (brm, 3H), 7.06-6.98 (m, 1H), 4.23 (s, 2H), 3.36-3.32 (m, 2H), 2.98-2.78 (m, 2H).

Compound 83 was prepared in a similar manner as compound 9 in 35% yield; solid; $^1$H NMR (DMSO-d$_6$, 300 MHz) δ 10.01 (br s, 1H), 8.92 (br s, 1H), 8.58 (br s, 1H), 7.89 (d, 2H, J=8.1 Hz), 7.75 (d, 2H, J=7.8 Hz), 7.56 (d, 2H, J=8.1 Hz), 7.37-7.30 (m, 4H), 7.06 (t, 1H, J=7.2 Hz), 6.87 (d, 2H, J=7.8 Hz).

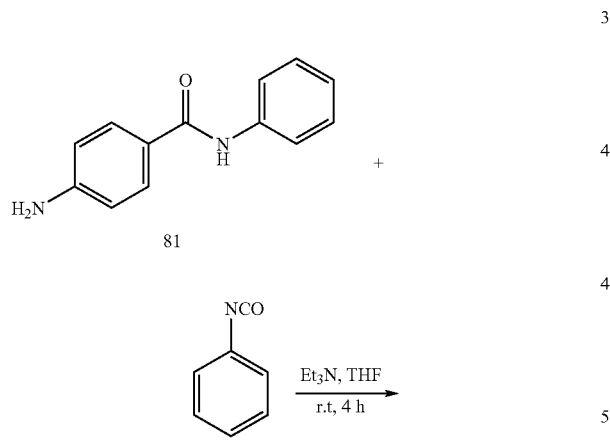

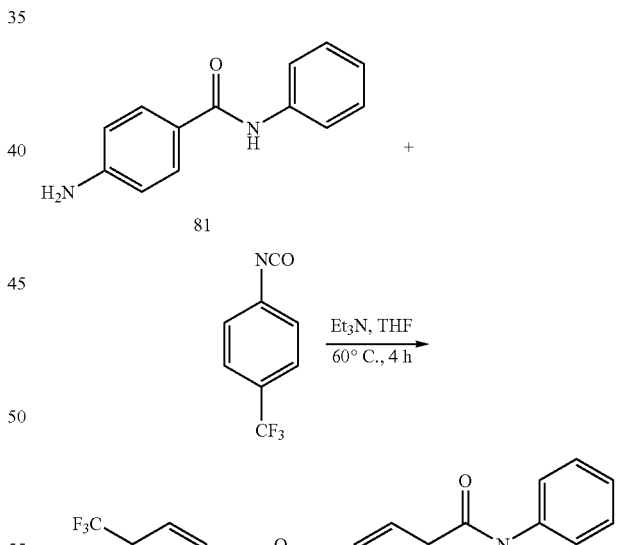

Compound 82 was prepared in a similar manner as compound 9 in 46% yield; solid; $^1$H NMR (DMSO-d$_6$, 300 MHz) δ 10.08 (br s, 1H), 9.01 (br s, 1H), 8.78 (br s, 1H), 7.93-7.89 (m, 2H), 7.77-7.74 (m, 2H), 7.60-7.57 (m, 2H), 7.48-7.45 (m, 2H), 7.36-7.26 (m, 4H), 7.07-6.92 (m, 2H).

Compound 84 was prepared in a similar manner as compound 9 in 36% yield; solid; $^1$H NMR (DMSO-d$_6$, 300 MHz) δ 10.43 (br s, 1H), 9.59 (br s, 1H), 9.50 (br s, 1H), 8.44 (d, 2H, J=8.7 Hz), 8.31 (d, 2H, J=8.7 Hz), 8.20 (d, 2H, J=8.7 Hz), 7.37-7.30 (m, 5H), 7.77 (t, 1H, J=8.1 Hz), 7.51 (t, 1H, J=8.1 Hz).

Example 3

LED209 Minimally Affects Adrenergic Signaling

The observation that epinephrine (epi) binds to the QseC membrane receptor triggering expression of key virulence genes raises obvious concerns that any drug targeting this interaction may also interfere with adrenergic signaling systems operating in the host. Mammalian adrenergic receptors are a class of G protein-coupled receptors that are targets of their endogenous ligands, the catecholamines epinephrine (epi) and norepinephrine (NE) and are activated by these. There are three classes of adrenergic receptors (α1, α2 and β), each containing three members; each class of adrenergic receptors in turn activates a unique isoform of heterotrimeric G proteins that subsequently modulates the activity of key signaling proteins regulating intracellular second messengers.

Figure 6A:
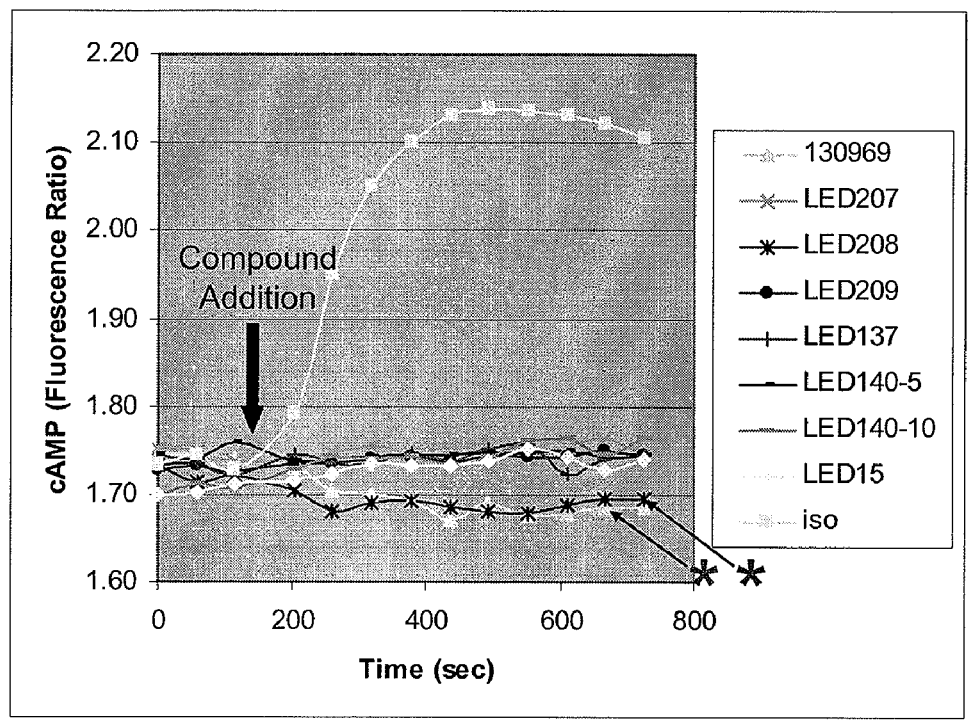
FIGS. 6A-6B. LED209 (1 μM) does not interfere with signaling through human adrenergic receptors.
Figure 6B:
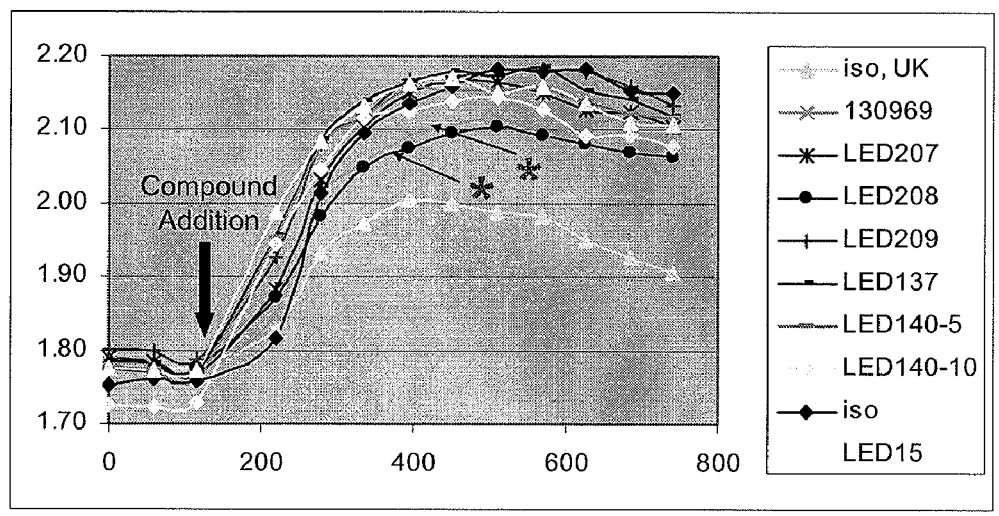

As tested in the assay described by Ross et al., 2007, compounds 130969 (*) and LED208 (*) but not LED209 reduce both basal (shown in FIG. 6A) and Iso (β2 adrenergic)-stimulated (FIG. 6B) cAMP levels when tested at 1 μM concentrations. Structures of the compounds used in this assay are shown below:

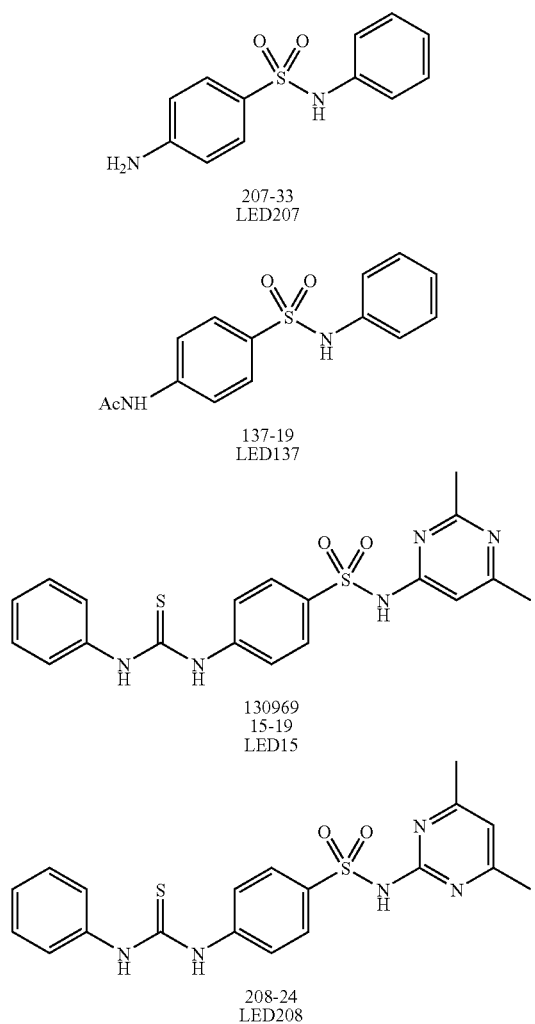

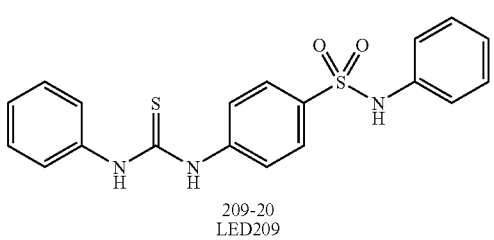

209-20
LED209

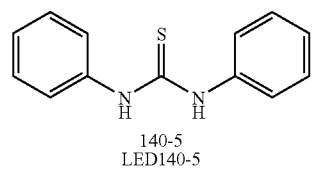

140-5
LED140-5

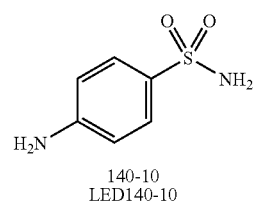

140-10
LED140-10

Example 4

QseC Autophosphorylation Studies

Experimental

QseC autophosphorylation. QseC autophosphorylation experiments were performed as described by Clarke et al. (2006). Briefly, As described previously (Clarke and Sperandio, 2005), the E. coli strain containing pVS155 (qseC::MycHis) was grown at 37° C. in LB to an O.D.$_{600}$ of 0.7, at which point arabinose was added to a final volume of 0.2% and allowed to induce for three hours (Clarke and Sperandio, 2005). Nickel columns were utilized, according to manufacturer's instructions (Qiagen). Autophosphorylation experiments were performed with QseC embedded in liposomes. Liposomes were reconstituted as described by Janausch et al (2004). Briefly, 50 mg of E. coli phospholipids (Avanti Polar Lipids, 20 mg/ml in chloroform) were evaporated and then dissolved into 5 ml potassium phosphate buffer containing 80 mg N-octyl-β-D-glucopyranoside. The solution was dialyzed overnight against potassium phosphate buffer. The resulting liposome suspension was subjected to freeze/thaw in liquid N$_2$. Liposomes were then destabilized by the addition of 26.1 mg dodecylmaltoside, and 2.5 mg of QseC-MycHis was added, followed by stirring at room temperature for 10 minutes. Biobeads (261 mg) were then added to remove the detergent, and the resulting solution was allowed to incubate at 4° C. overnight. The supernatant was then incubated with fresh Biobeads for 1 hour in the morning. The resulting liposomes containing reconstituted QseC-MycHis were frozen in liquid N$_2$ and stored at −80° C. until used. Orientation of HKs in the liposome system has been established by previous groups (Dioum et al., 2002) and can be concluded from the accessibility of ATP to the kinase site, and anti-Myc antisera to the C-terminal QseC-MycTag without disruption of the liposomes. 20 μl of the liposomes containing QseC-MycHis were adjusted to 10 mM MgCl$_2$ and 1 mM DTT, no signal, or 50 μM of epinephrine, or 50 μM of epinephrine and 5 pM LED209 (compound 5), frozen and thawed rapidly in liquid N$_2$, and kept at room temperature for 1 hour. 0.625 µl of [γ$^{32}$P] dATP (110 TBq/mmol) was added to each reaction. At a 10 minute time point, 20 µl of SDS loading buffer was added. The samples were run on SDS-PAGE without boiling according to standard procedures (Sambrook et al, 1989) and visualized via phosphorimager. The bands were quantitated using ImageQuant version 5.0 software (Amersham).

Binding of tritiated norepinephrine to QseC. Binding of tritiated NE to QseC was performed as described by Clarke et al. (5) with modifications. QseC loaded liposomes were prepared as described above, and signals loaded by freeze thawing in liquid N$_2$ as described above. However, the liposomes were incubated at room temperature for only 10 minutes, to allow only partial reconstitution of the lipids, so unbound signal could diffuse out from the liposome. These liposomes were then centrifuged at 12,000 g for 5 minutes (to pellet the lipids), and the supernatant was discarded. The signal bound to QseC in these liposomes was measured using a scintillation counter, reading for tritium. To normalize against unbound tritium, readings were normalized against liposomes loaded with 5 µM tyrosine (which has a similar molecular weight to norepinephrine, and is not a signal to QseC). As controls, binding of norepinephrine was performed in the presence of 50 µM phentolamine, previously shown to inhibit binding to QseC, and 50 µM propranolol, which does not inhibit binding of norepinephrine to QseC (5). Binding to 5 µM norepinephrine was also performed in the presence 5 pM and 5 fM of LED209.

Results

Figure 7A:
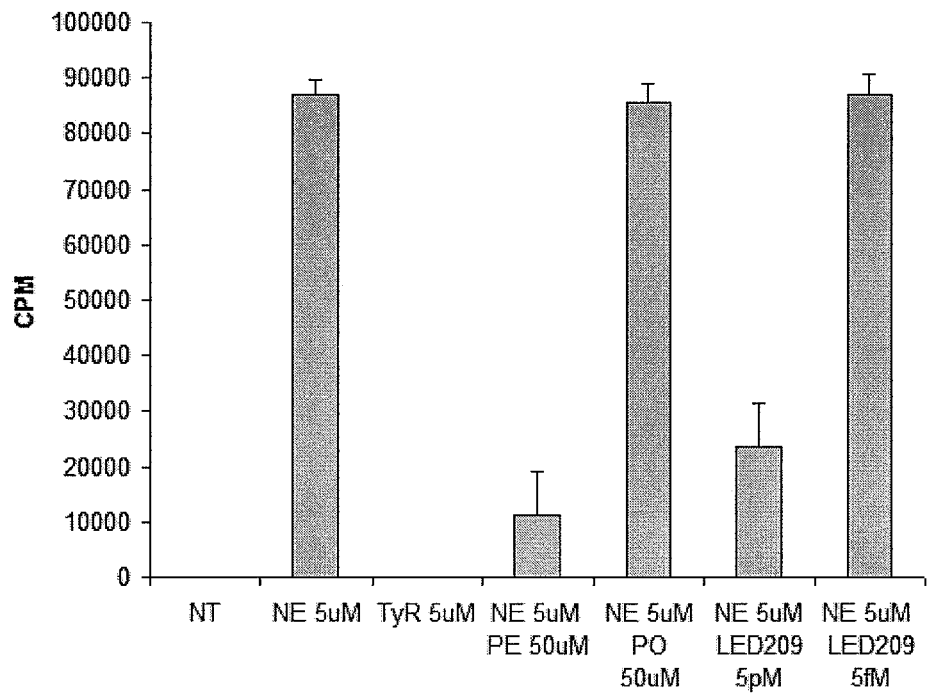
FIGS. 7A and 7B.
Figure 7B:
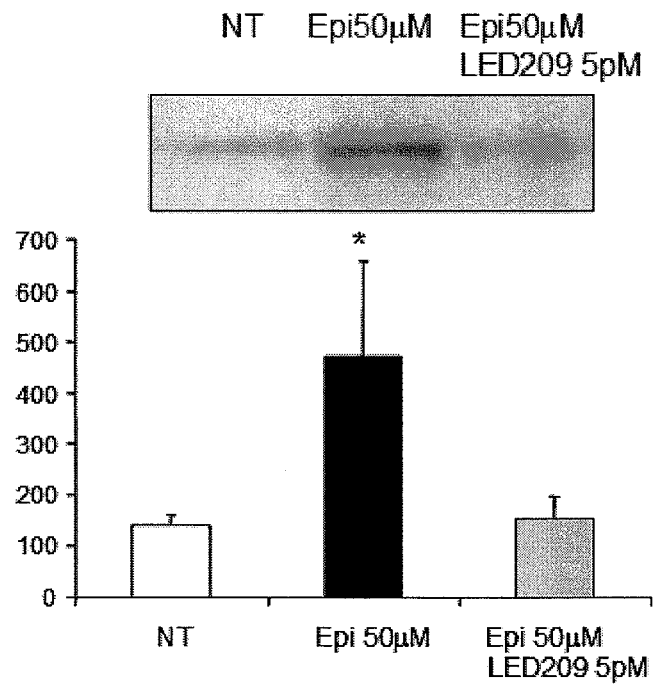

It was reported (Clarke et al., 2006), and the inventors confirmed that purified QseC in a liposome binds to tritiated norepinephrine, and that phentolamine (an alpha-adrenergic antagonist) antagonizes this binding to block QseC autophosphorylation. In contrast, propranolol (a beta-adrenergic antagonist) has no effect on QseC (FIG. 7A). As shown by the present inventors, norepinephrine binding can be directly antagonized by 5 pM of LED209 (compound 5), but not 5 fM. Autophosphorylation of QseC in response to 50 µM epinephrine is also inhibited in the presence of 5 pM of LED209 (FIG. 7B).

Example 5

Quantitative Real-Time (RT)-PCR

Quantitative real-time (RT)-PCR was used in a variety of the following Examples, and the general protocol is as follows.

Overnight cultures grown aerobically in LB for *Salmonella typhimurium*, DMEM for EHEC (WT and qseC mutant (Sperandio et al., 2002)) and Mueller Hinton for *F. tularensis* at 37° C. to either mid-exponential growth phase (OD$_{600}$ 0.5) or late-exponential growth phase (OD$_{600}$ 1.0). For the epinephrine studies, a stock epinephrine solution of 50 mM in water was made and diluted 10$^{-3}$ in overnight cultures that were diluted 1:100 in DMEM for a final concentration of 50 µM. RNA from three biological replicate cultures of each strain was extracted using the RiboPure™—Bacteria RNA isolation kit (Ambion) following manufacturer's guidelines. The primers used in the Real-Time assays were designed using Primer Express v1.5 (Applied Biosystems) (Table 2). Real-Time RT-PCR was performed in a one-step reaction using an ABI 7500 sequence detection system (Applied Biosystems).

TABLE 2

Oligonucleotides used in this study

| | Forward Primer | Reverse Primer |
|---|---|---|
| *escherichia coli* | | |
| ler | CGACCAGGTCTGCCCTTCT (SEQ ID 1) | GCCGGAACTCATCGAAA (SEQ ID 2) |
| flicC | TCCATCGACAAATTCCGTTCT (SEQ ID 3) | TGGTGACTGCGGAATCCA (SEQ ID 4) |
| stx2A | ACCCCACCGGGCAGTT (SEQ ID 5) | GGTCAAAACGCGCCTGATA (SEQ ID 6) |
| flhD | TTTCGTCTCGGCATAAATGAA (SEQ ID 7) | TCATTCAGCAAGCGTGTTGAC (SEQ ID 8) |
| eae | GCTGGCCTTGGTTTGATCA (SEQ ID 9) | GCGGAGATGACTTCAGCACTT (SEQ ID 10) |
| rpoA | GCGCTCATCTTCTTCCGAAT (SEQ ID 11) | CGCGGTCGTGGTTATGTG (SEQ ID 12) |
| *Salmonella typhimurium* | | |
| flhDC | GTCAAACCGGAAATGACAAACTAA (SEQ ID 13) | ACCCTGCCGCAGATGGT (SEQ ID 14) |
| sifA | GTTGTCTAATGGAACCGATAATATCG (SEQ ID 15) | CTACCCCCTCCCTTCGACAT (SEQ ID 16) |
| mgtBC | ACTTCATTGCGCCCATACACT (SEQ ID 17) | CGTCAGGGCCTCACGATAGA (SEQ ID 18) |
| rpoA | GCGCTCATCTTCTTCCGAAT (SEQ ID 19) | CGCGGTCGTGGTTATGTG (SEQ ID 20) |

TABLE 2-continued

Oligonucleotides used in this study

| | Forward Primer | Reverse Primer |
|---|---|---|
| *Francisella tularensis* | | |
| qseC | CGTACCTCAAGAGAATATCGAACGT (SEQ ID 21) | TGCGACGATTGCTAAACCTAGTC (SEQ ID 22) |
| iglC | AAAAAGGAGAATGATTATGAGTGAG ATG (SEQ ID 23) | TGCAGTAGGATCAGTTCTCACATG (SEQ ID 24) |
| pdpA | TGAGTTAATTTCAAACTCTGCCATATC (SEQ ID 25) | GTTTGGGTATATGCCATTTCACAG (SEQ ID 26) |
| MIP | CTCGAGTGATAGCGCAACATTC (SEQ ID 27) | TGTTGATCCATTAGGTATTTGAGGAA (SEQ ID 28) |
| rpoA | CGATACCAACCGAGCTTGAGA (SEQ ID 29) | CCTCAAAAGCAACTCTTTTTAATAGGATT (SEQ ID 30) |

For each 20 μl reaction, 10 μl 2× SYBR master mix, 0.1 μl Multi-scribe reverse transcriptase (Applied Biosystems), and 0.1 μl RNase inhibitor (Applied Biosystems) were added. Amplification efficiency of each of the primer pairs was verified using standard curves of known RNA concentrations. Melting curve analysis was used to ensure template specificity by heating products to 95° C. for 15 s, followed by cooling to 60° C., and heating to 95° C. while monitoring fluorescence. Once amplification efficiency and template specificity were determined for each primer pair, relative quantification analysis was used to analyze the unknown samples using the following conditions for cDNA generation and amplification: 1 cycle at 48° C. for 30 min, 1 cycle at 95° C. for 10 min, 40 cycles at 95° C. for 15 s and 60° C. for 1 min. The rpoA (RNA polymerase subunit A) gene from each species was used as the endogenous control.

Data collection was performed using the ABI Sequence Detection 1.3 software (Applied Biosystems). Data were normalized to levels of rpoA and analyzed using the comparative critical threshold ($C_T$) method previously described (Anonymous, 1997). The expression level of the target genes at the different growth phases was compared using the relative quantification method (Anonymous, 1997). Real-time data is presented as fold change compared to WT levels at early-exponential growth phase. Error bars represent the standard deviation of the $\Delta\Delta C_T$ value (Anonymous, 1997). Statistical significance was determined by Students t test. A P value of <0.05 was considered significant.

Example 6

Virulence Expression Studies

Experimental

Quantitative real-time (RT)-PCR protocol. See Example 5.

Preparation of Secreted Proteins. Secreted proteins from EHEC strain 8624 with 50 μM epinephrine, 50 μM epinephrine plus 5 nM LED209 (compound 5), and 50 μM epinephrine plus 5 μM LED209 were harvested as previously described by Jarvis et al. (1995). Briefly, bacteria were grown aerobically in DMEM at 37° C. and collected at late-exponential ($OD_{600}$ 1.0) growth. Total secreted protein from culture supernatants was separated by removing bacteria using centrifugation and filtration and then precipitating the secreted proteins present in the supernatant with trichloroacetic acid. The samples were then subjected to immunoblotting with rabbit polyclonal antisera to EspA and EspB and visualized with ECL.

Fluorescein actin staining (FAS) test. FAS assays were performed as previously described by Knutton et al. (1989). In brief, overnight bacterial cultures grown aerobically in LB at 37° C. were diluted 1:100 and used to infect confluent monolayers of HeLa cells grown on glass coverslips at 37° C. and 5% $CO_2$. Cells were grown for 6 hours at 37° C. and 5% $CO_2$. The coverslips were then washed, permeabilized with 0.2% Triton X-100, treated with FITC-phalloidin to visualize actin accumulation, and propidium iodide was added to stain bacteria. Samples were visualized by immunofluorescence using a Zeiss Axiovert microscope. The entire field of at least six coverslips from each strain was examined and images taken of AE lesions.

Results

Figure 8A:
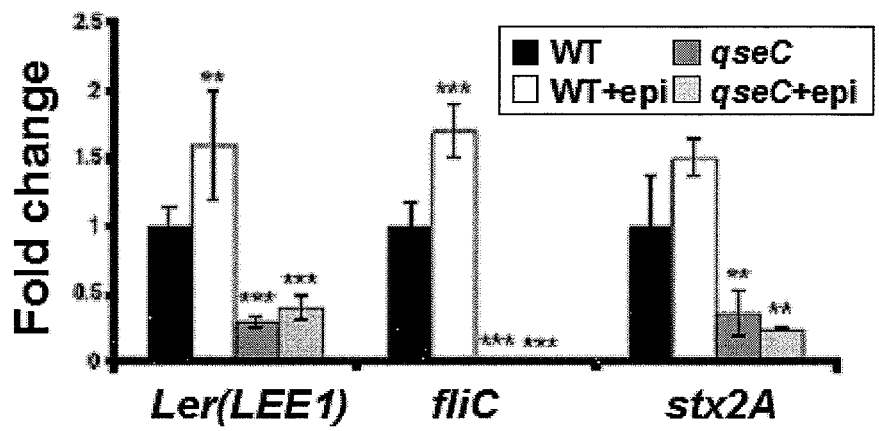

New types of antimicrobial agents are needed for enterohemorrhagic *E. coli* (EHEC) infections, since treatments based on conventional antibiotics have been associated with worse clinical outcomes (Tarr et al., 2002), probably because antibiotics induce an SOS response that enhances EHEC virulence (Zhang et al, 2000). The genes encoding Shiga-toxin are located within the late genes of a λ bacteriophage, and are transcribed when the phage enters its lytic cycle upon induction of an SOS response in EHEC (Wagner et al., 2001). Shiga-toxins are responsible for the morbidity and mortality of these infections. Transcription of EHEC virulence genes is induced by AI-3 and epinephrine. Neither AI-3 nor epinephrine had any effect on promoting virulence in a qseC mutant (FIG. 8A).

Figure 8B:
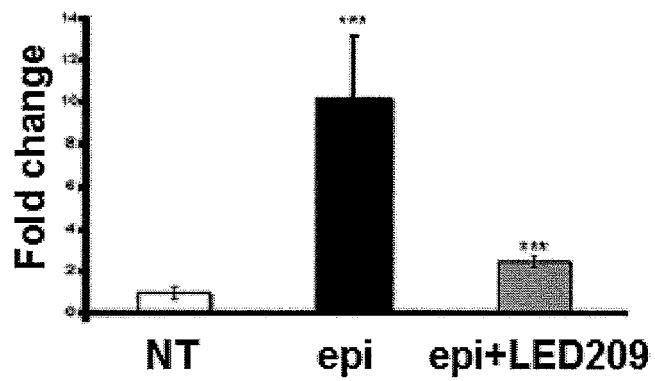
Figure 8C:
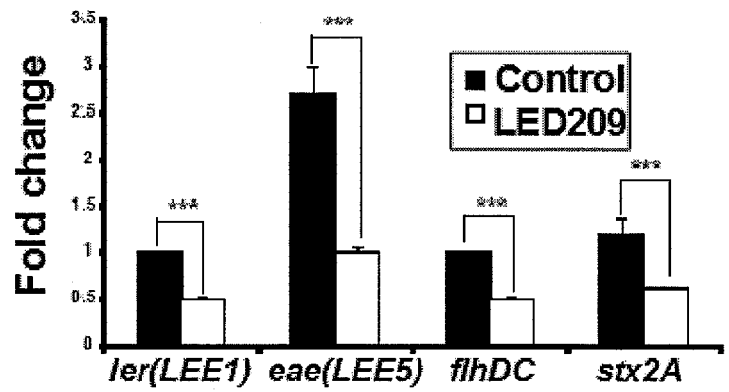
Figure 8D:
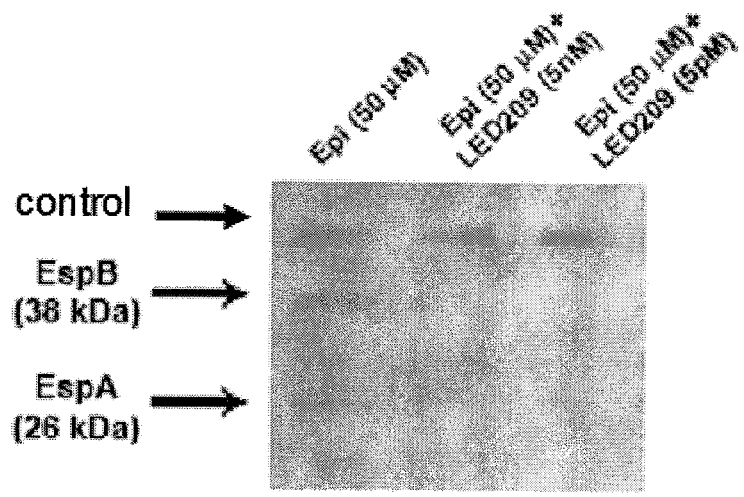
Figure 8E:
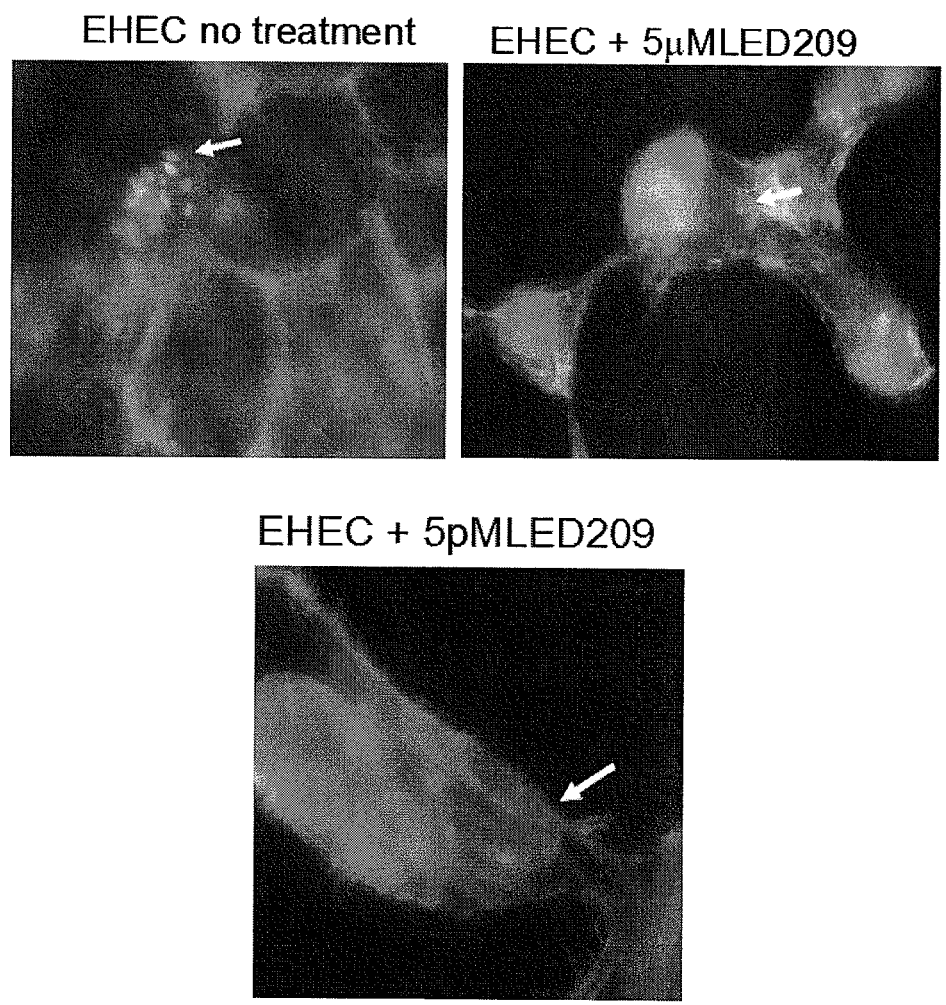

QseC-dependent virulence gene expression in response to epinephrine (FIG. 8B) and AI-3 (FIG. 8C) was inhibited in the presence of 5 pM LED209 (compound 5). LED209-mediated inhibition of virulence gene expression also inhibited the secretion of EspA and EspB, two proteins encoded within the locus of enterocyte effacement (LEE) that are required for EHEC to translocate bacterial proteins into host cells and cause attaching-effacing (AE) lesions (FIG. 8D). Remarkably, at 5 pM LED209 abolished EHEC AE lesion formation on cultured epithelial cells (FIG. 8E). Unlike conventional antibiotics, LED209 does not kill or hinder EHEC growth (FIG. 8F), or trigger the EHEC SOS response. Consequently it does not promote expression of Shiga-toxin; indeed, it decreases the expression of the stxAB genes that encode this toxin (FIG. 8C).

Example 7

In vivo Rabbit Studies

Experimental

To prepare the inoculum, bacteria were grown overnight in LB broth at 37° C. with appropriate antibiotics, harvested by centrifugation and resuspended in sterile PBS (pH 7.2) and adjusted to a cell density of ~$10^9$ cfu ml$^{-1}$. Infant rabbit experiments were carried out as described previously (Ritchie et al, 2003). Briefly, 3-day-old New Zealand White rabbits were intragastrically inoculated with ~$5 \times 10^8$ cfu of 8624 or one of its derivatives using a size 5 French catheter. Rabbits were monitored twice daily for signs of illness or diarrhea. Diarrhea was described as i) none—normal pellets are dark green, hard and formed, ii) mild—diarrhea consisting of a mix of soft yellow-green unformed and formed pellets resulting in light staining of the hind legs, or iii) severe—diarrhea consisting of unformed or liquid feces, resulting in significant staining of the hind legs. Rabbits were euthanized at 7 days post-infection. At necropsy, the intestinal tract from the duodenum to the anus was removed and samples obtained for histologic and microbiologic analyses. To limit any litter-specific effects, at least two different litters were used to test each bacterial strain.

Results

Figure 9:
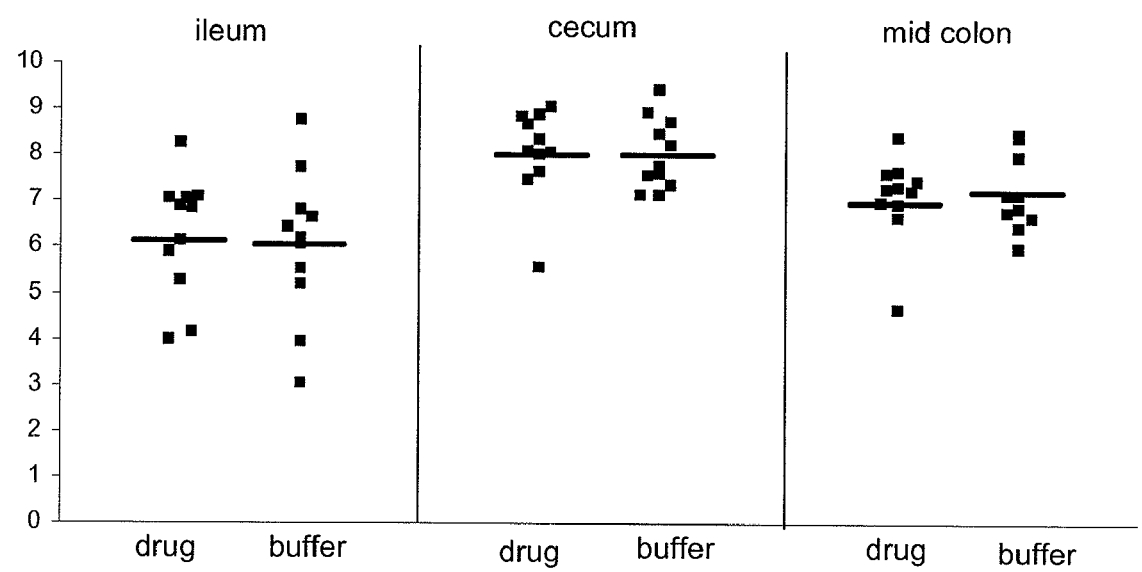
FIG. 9. Colonization of infant rabbits by EHEC treated with buffer (5% DMSO, 23% PEG400, 70% sodium bicarbonate pH 9, 2% Tween 80), or 20 mg/kg of LED209 in buffer. LED209 treatment was administered 3 hours prior, along, 3 hours and 24 hours post infection with EHEC. There were no differences between treated and untreated animals in the ileum and cecum. There was only a mild non-statistically significance difference in drug treated animals in the colon.
Figures 10A, 10B, 10C:
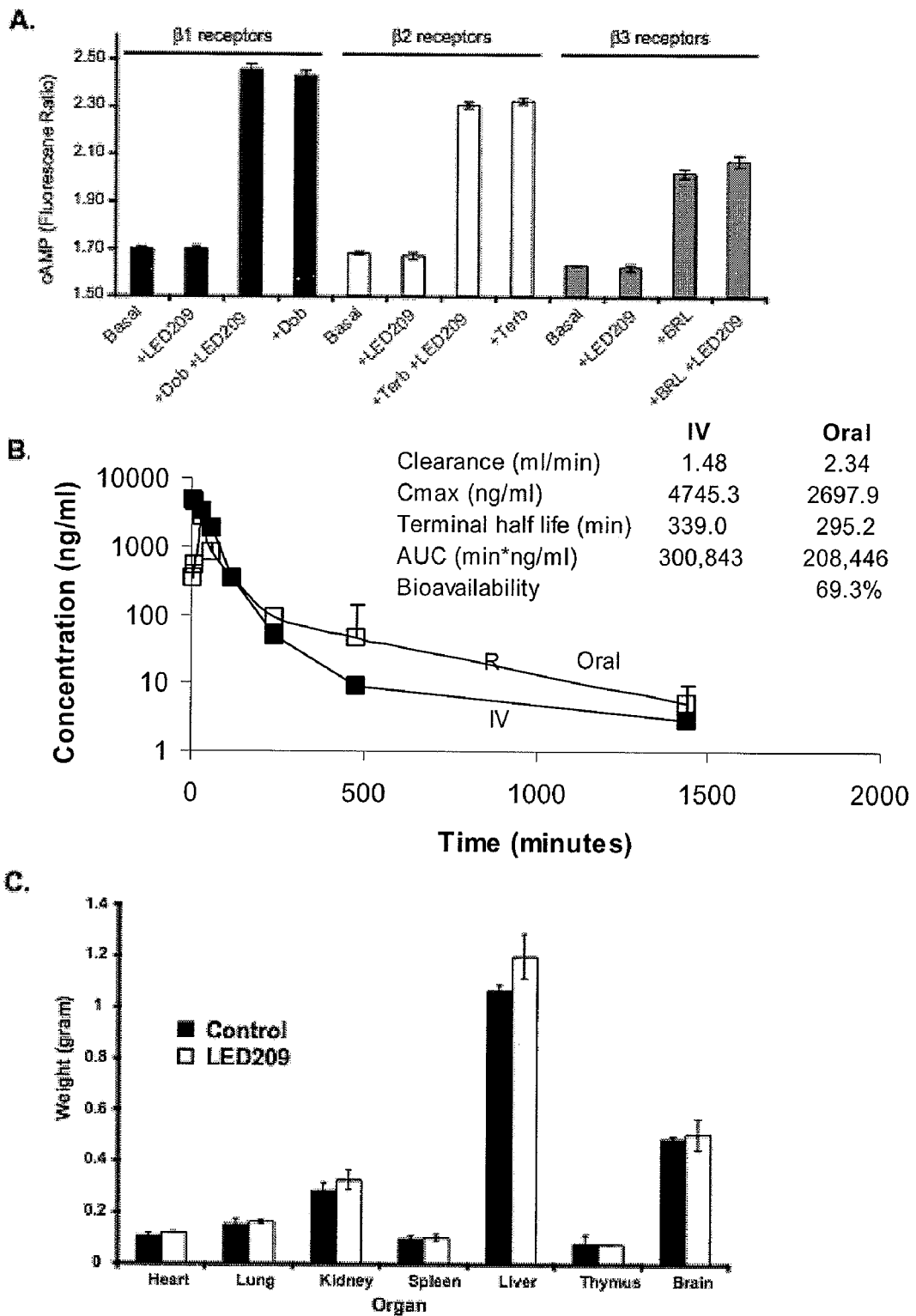
FIGS. 10A-10C. LED209 does not interfere with mammalian adrenergic signaling, is orally bioavailable, and is non toxic to mice.

Administration of LED209 (compound 5) to infant rabbits before, after or along with EHEC only resulted in a modest (and non-statistically significant) reduction in EHEC colonization of the intestine (FIG. 9). The failure of LED209 to reduce EHEC colonization in this animal model may be attributable to rapid absorption from the gastrointestinal (GI) tract (FIGS. 10A-10C). A non-absorbable formulation may be required for non-invasive human pathogens like EHEC.

Example 8

Salmonella typhimurium Experiments—In vitro and In vivo

Experimental

Mutagenesis of qseC in S. typhimurium. Construction of an isogenic S. typhimurium SL1344 qseC mutant was carried out as previously described (Datsenko and Wanner, 2000). Briefly, SL11344 cells containing pKD46 were prepared for electroporation. A qseC PCR product was generated using primers depicted in Table 2 and pKD3 as a template and gel purified. Electroporation of the PCR product into these cells was performed, cells were incubated at 37° C. for 2 hours, and plated on media containing 30 µg ml$^{-1}$ chloramphenicol overnight at 37° C. Resulting colonies were patched for chloramphenicol resistance and ampicillin sensitivity, and PCR verified for the absence of the gene. The chloramphenicol cassette was then resolved from the mutant in order to create a non-polar, isogenic qseC mutant. Plasmid pCP20, encoding a resolvase, was electroporated into the mutant strain, and resulting colonies were patched for chloramphenicol sensitivity.

Mice survival experiments with S. typhimurium. Mice (129x1/SvJ 7 to 9 weeks old, female) were either treated orally with LED209 (compound 5) (20 mg/kg in 5% DMSO, 23% PEG400, 70% sodium bicarbonate pH9, 2% Tween 80), intraperitonially infected with $10^8$ cfu of S. typhimurium strain SL1344, or treated orally with LED209 (3 hours pre and post infection) and infected with $10^8$ cfu of S. typhimurium strain SL1344. Ten mice per treatment were used, and these experiments were repeated twice to ensure reproducibility. Mice were returned to their cages and monitored daily for signs of morbidity (anorexia, rapid shallow breathing, scruffy fur, decreased muscle tone, and lethargy) and death. At 12 days post infection the animals that survive were euthanized by $CO_2$ asphyxiation. Liver and spleens were harvested, homogenized and plated on LB agar plates for bacterial cell counts (cfus).

Results

Figure 11A:
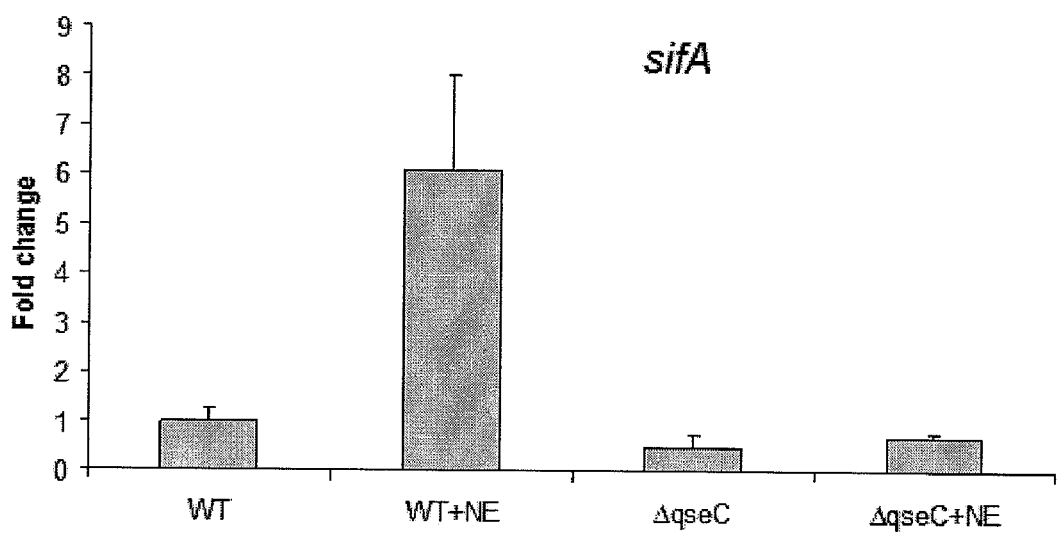
FIGS. 11A-11B.
Figure 11B:
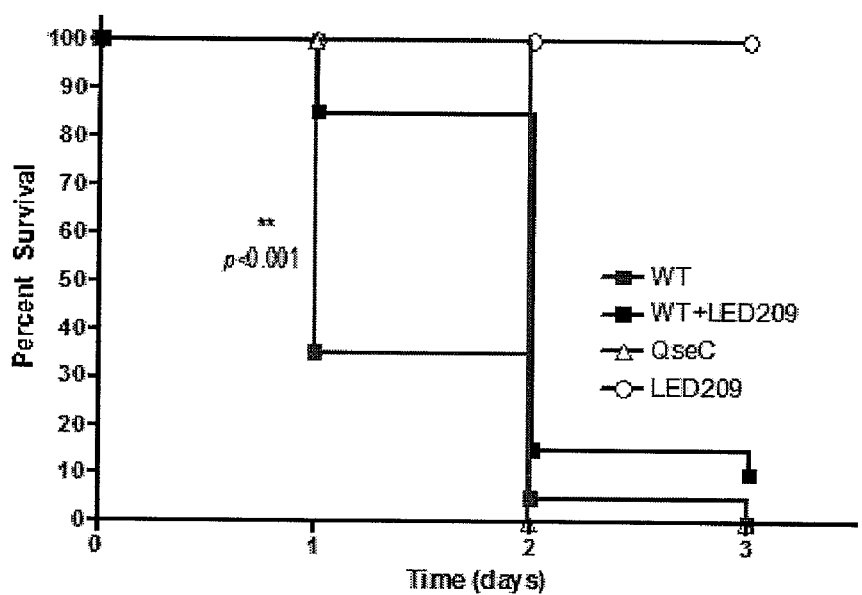
Figure 12:
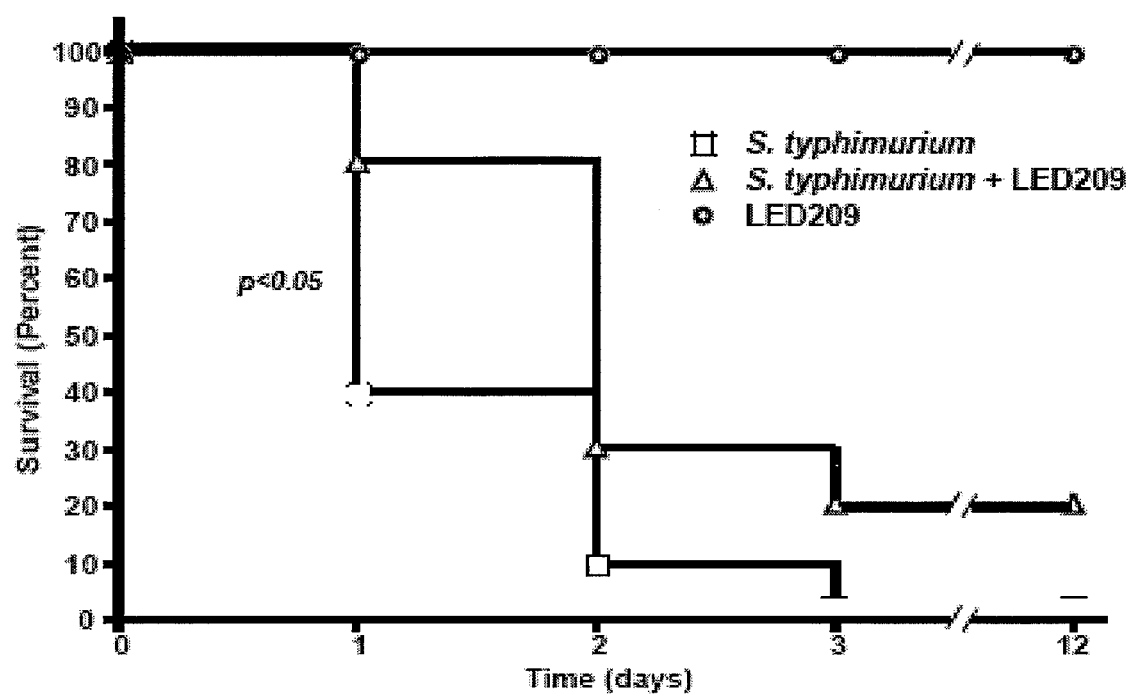
FIG. 12. LED209 inhibits S. typhimurium virulence in vivo. Mice (129×1/SvJ) survival plot upon oral treatment with LED209 (20 mg/kg) alone, intraperitonial infection with $10^8$ cfu of S. typhimurium strain SL1344, and intraperitonial infection with $10^8$ cfu of S. typhimurium strain SL1433 plus LED209 (20 mg/kg). By 24 hours post infection only 40% of the untreated infected mice survived, while 80% of the treated and infected mice survived. Importantly, although 100% of the infected untreated infected mice died, 20% of the treated and infected mice survived until day 12 when they were sacrificed.
Figure 13A:
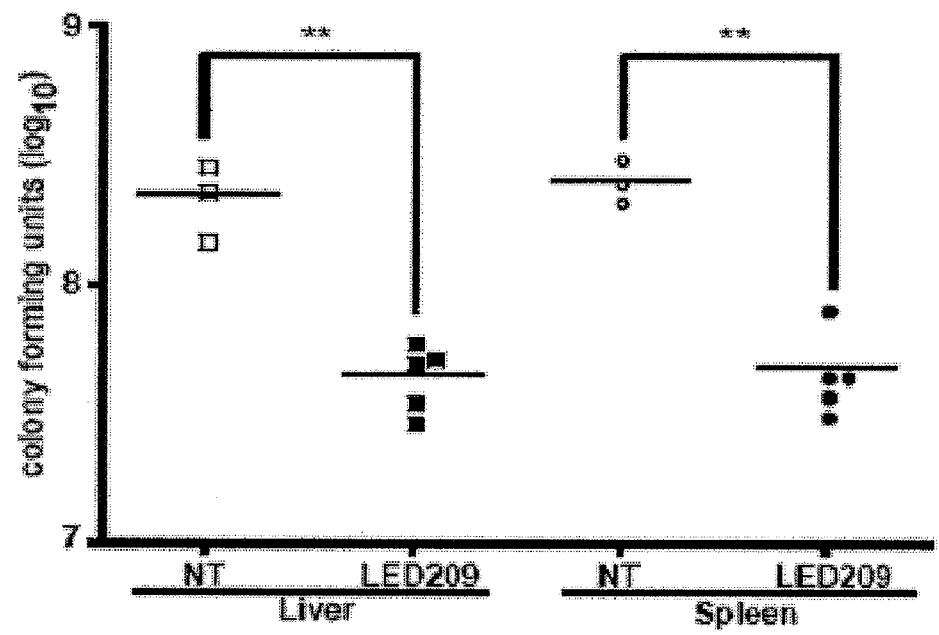
FIGS. 13A-13B.
Figure 13B:
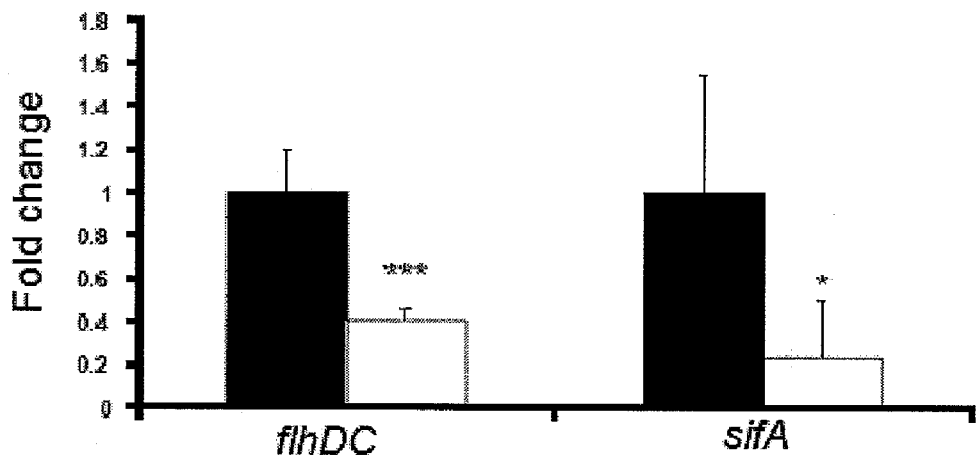

Salmonella typhimurium encodes a homologue of the EHEC QseC (87% similarity) sensor kinase that also controls virulence gene expression (Merighi et al, 2006) (FIG. 11A). EHEC and S. typhimurium QseC are functionally interchangeable (Merighi et al., 2006) and a S. typhimurium qseC mutant was found to be defective for colonization of the swine GI tract (Bearson and Bearson, 2007) and attenuated for systemic disease in mice (FIG. 11B). LED209 (compound 5) (20 mg/kg) was given orally to mice 3 hours before and 3 hours after intraperitoneal injection of a lethal dose of S. typhimurium. Twenty four hours after infection, only 30% of untreated mice remained alive whereas 80% of the LED209 treated mice were still alive (FIG. 11B). All the S. typhimurium-infected mice died within 72 hours of infection, and 20% of LED209 treated mice survived up to 12 days (FIG. 11B; FIG. 12). Even though LED209 did not influence S. typhimurium growth in vitro (FIG. 8F), there were ~10-fold fewer S. typhimurium cfus recovered from the spleens and livers of treated animals (FIG. 13A). Addition of LED209 to cultures in vitro diminished expression of the sifA virulence gene (FIG. 13B), which is important for the development of systemic disease by S. typhimurium (Beuzon et al, 2000). Importantly, transcription of sifA is activated by norepinephrine in a QseC-dependent manner (FIG. 11A). Together, these observations suggest that LED209 inhibition of S. typhimurium virulence gene expression in vivo compromises the survival of the pathogen in the host.

Example 9

Francisella tularensis Experiments—In vitro and In vivo

Experimental

β-galactosidase experiments. Plasmid pVS175 containing the E. coli fliC::lacZ fusion (Weiss et al., 2007) was introduced into WT E. coli MC4100, the isogenic qseC mutant VS184 (Weiss et al., 2007), and the qseC complemented strains with the EHEC qseC (strain VS185 (Weiss et al., 2007)), and F. tularensis qseC genes (pFTQseC). Cultures were diluted 1:100 and grown in either LB or tryptone media (1% tryptone and 0.25% NaCl) supplemented with 0.2% arabinose to an O.D.$_{600}$ of 0.8 at 37° C. These cultures were then assayed for β-galactosidase activity using o-nitrophenyl-beta-D-galactopyranoside (ONPG).

pFTQseC was constructed by cloning the Eco RV/Bgl II fragment from pFTQseC_Full42 (FTT0094c cloned into pET-DEST42 (Invitrogen; C-terminal 6His tag)) into a Bam HI/Hinc II digested pACYC184. Plasmid contains only the chloramphenicol resistance.

Macrophage infection. J774 murine macrophages ($1 \times 10^4$) were infected with $10^6$ cfu of F. tularensis SCHU S4 (multiplicity of infection 1:100) for 2 h at 37° C. 5% $CO_2$. They were treated with 40 µg/ml of gentamycin for 1 hour to kill extracellular bacteria and lysed with octglucoside. Bacteria were diluted and plated in Mueller Hinton plates for cfu counts.

Mice survival experiments with F. tularensis. All animal work performed with the SCHU S4 strain was conducted in a federally-licensed small animal containment level 3. Mice (C3H HeN, female) were either treated orally with LED209 (compound 5) (20 mg/kg in 5% DMSO, 23% PEG400, 70% sodium bicarbonate pH 9, 2% Tween 80), intranasally infected with 30 cfu of *F. tularensis* strain SCHU S4, or treated orally with LED209 (3 hours post infection in a single dose) and infected with 30 cfu of *F. tularensis* strain SCHU S4. Ten mice per treatment were used, and these experiments were repeated twice to ensure reproducibility. Mice were returned to their cages and monitored daily for signs of morbidity (anorexia, rapid shallow breathing, scruffy fur, decreased muscle tone, and lethargy) and death. At 9 days post infection the animals that survive were euthanized by $CO_2$ asphyxiation.

Results

Figure 14A:
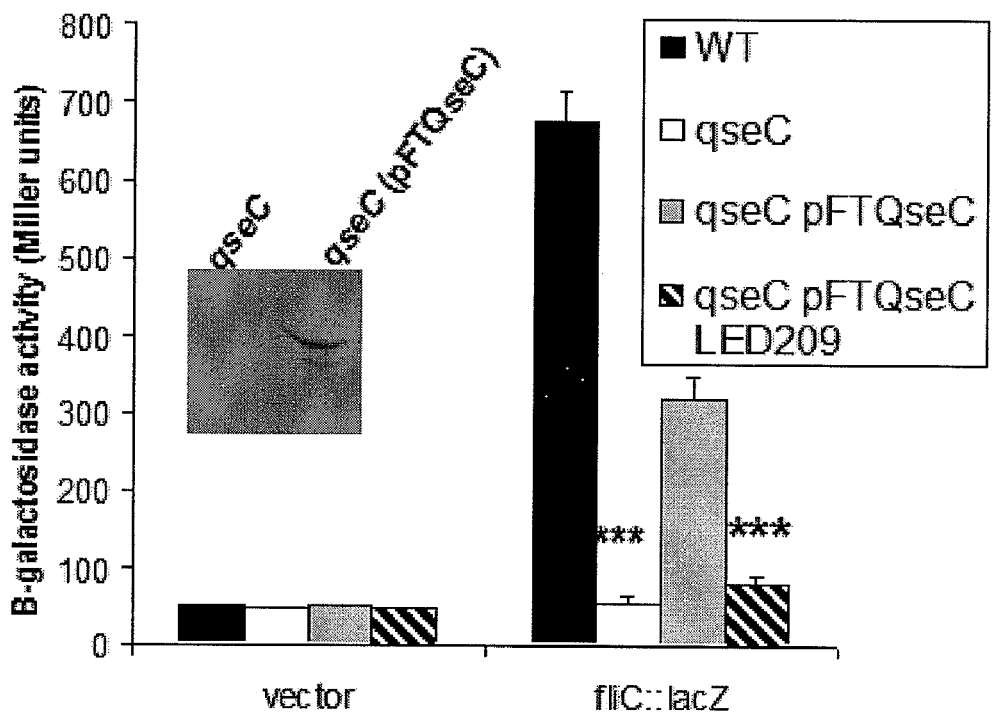
FIGS. 14A-14E.
Figure 14B:
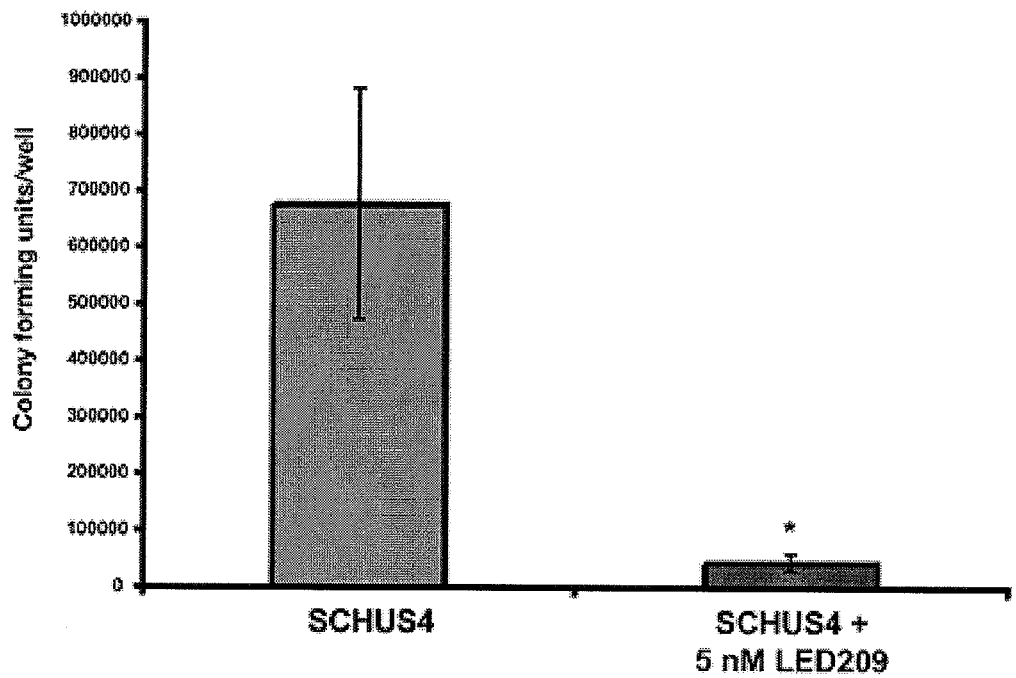
Figure 14C:
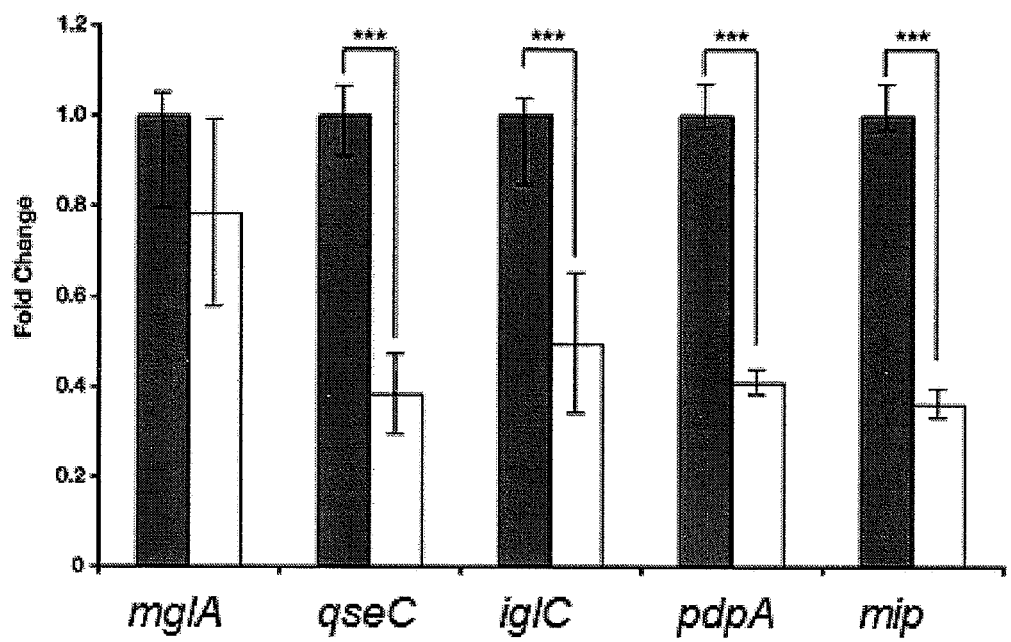

*Francisella tularensis* has one histidine sensor kinase, QseC (57% similarity), encoded in its genome, and a qseC mutant is attenuated for mouse infection (Weiss et al., 2007). The *F. tularensis* and EHEC QseC proteins are also functionally interchangeable, and the *F. tularensis* QseC can rescue expression of a QseC-dependent gene in an *E. coli* qseC mutant (FIG. 14A). LED209 (compound 5) reduced the number of *F. tularensis* strain SCHU-S4 recovered from macrophages 10-fold (FIG. 14B). Furthermore, LED209 decreased expression of several *F. tularensis* virulence genes in vitro (FIG. 14C), including qseC itself.

Figure 14D:
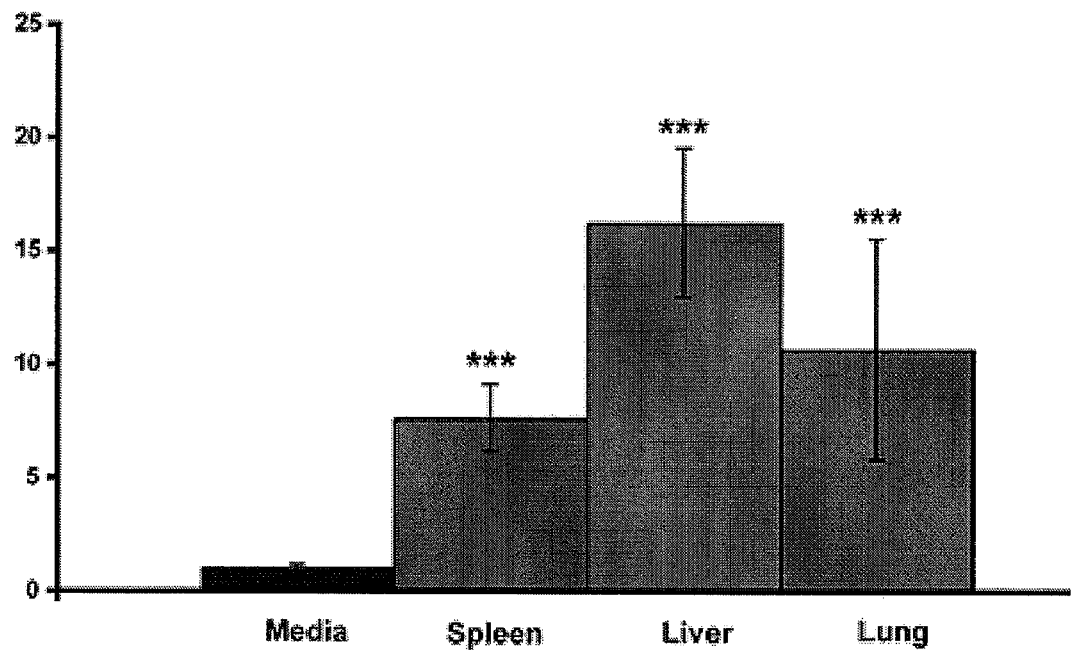
Figure 14E:
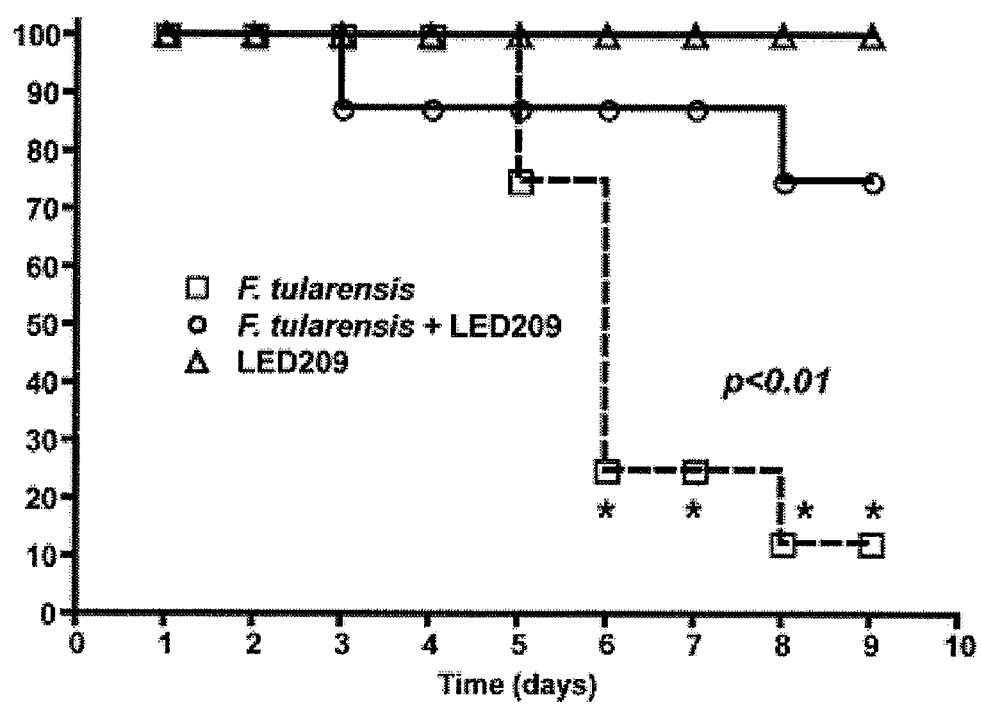

Quantitative-RT-PCR assays (see Example 6) demonstrated that qseC expression is up-regulated during infection of mice by SCHU-S4 (FIG. 14D). LED209 was administered orally in a single dose three hours post-infection with SCHU-S4. While 80% of LED209 treated mice remained alive 9 days post-infection, only 10% of the untreated mice survived till this point (FIG. 14E). Thus a single oral dose of LED209 can protect mice already exposed to aerosolized *F. tularensis*. There was no overt toxicity of the LED209 and none of the mice treated with LED209 alone died (FIG. 14E).

Figure 15:
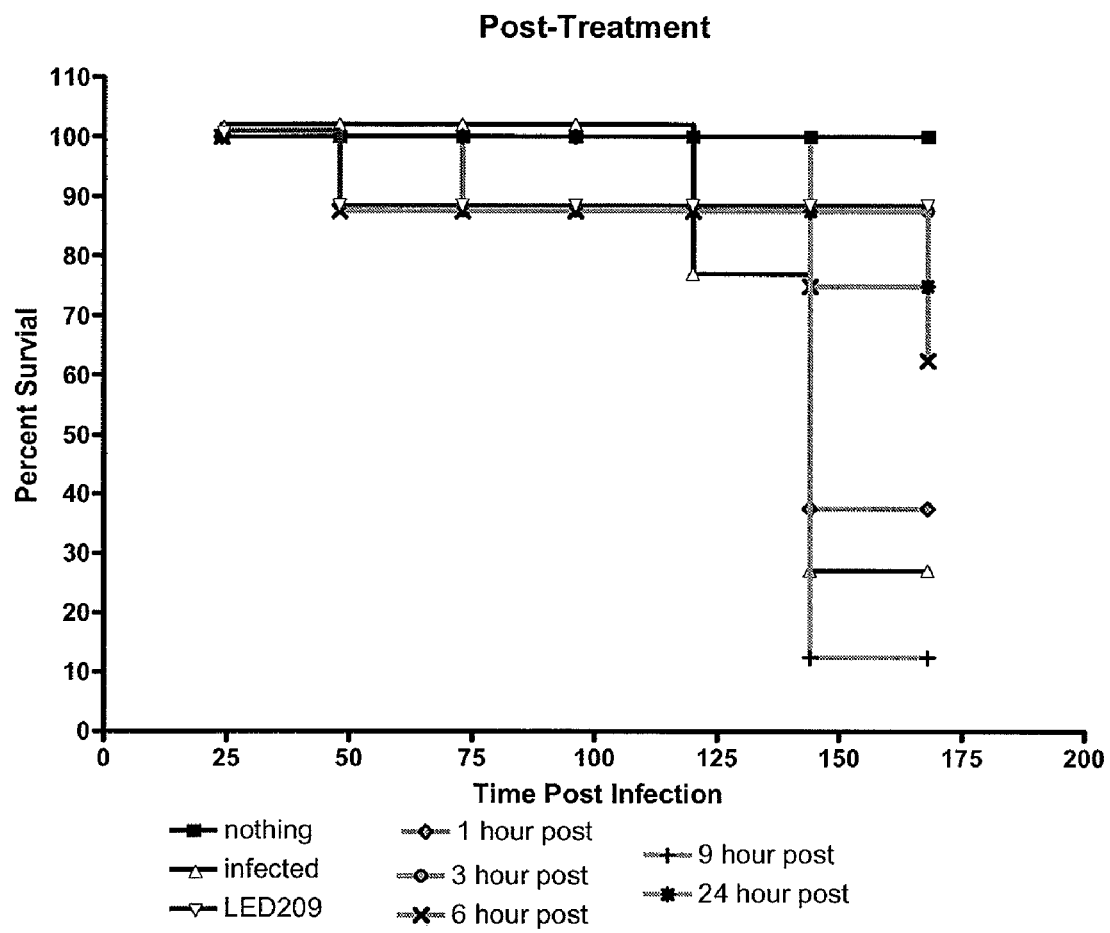
FIG. 15. In vivo inhibition of *Francisella tularensis* by LED209.

In a separate experiment, eight mice were infected with 30 colony forming units (cfu) of *Francisella tularensis* type A strain SCHU S4. The mice were then treated with 20 mg/kg of LED209 (compound 5) several time points after infections (1, 3, 6, 9 and 24 hours). At 175 hours post-infection, only 20% of the untreated mice infected with *F. tularensis* were alive, while 60% of the mice treated with LED209 6 hours post infection were alive, and 75% of the mice treated with LED209 post-infection were alive. See FIG. 15. These data show that LED209 can treat infection by the biothreat agent *F. tularensis*.

Example 10

Toxicology and Bioavailability Studies

Experimental

Intracellular cAMP measurements. Live-cell intracellular cAMP determinations were performed using an EPAC-based cAMP BRET reporter as described by Jiang et al. (2007). HEK293 cells expressing either β2 (endogenous) or exogenously expressed β1 or β3 adrenergic receptors were treated with β-adrenergic-specific agonist (1 nM dobutamine, 100 nM terbutaline, or 10 nM BRL37344) alone or in combination with 5 µM LED209 (compound 5). Each cell line was also assessed for its ability to respond to 5 µM LED209 in the absence of β adrenergic receptor agonists. Following addition of compounds, cAMP measurements were made at 100 second intervals over a time course of 25 minutes. Peak intracellular cAMP levels were identified for each experimental condition and plotted. Each value is an average of triplicate determinations are representative of 3 experiments.

Pharmacokinetic Analysis. Female CD-1 mice (18-21 g) were purchased from Charles River laboratories. Animals were allowed to acclimate to the animal facility at UT Southwestern Medical Center for approximately 1 week prior to use and all animal work was approved by the Institutional Animal Care and Use Committee at UT Southwestern. Mice were either injected with 20 mg/kg LED209 i.v. as a bolus in 0.2 ml of 5% DMSO/23% PEG400/2% Tween 80/70% 0.1 M sodium bicarbonate, pH 9 or given compound by oral gavage (0.2 ml) in the same formulation. At the indicated time points, animals were given an inhalation overdose of $CO_2$ and blood was harvested by cardiac puncture with a sodium citrate-coated needle and syringe containing 50 µl of sodium citrate. Plasma was isolated by centrifugation of the blood for 10 min at 8,0000×g and frozen at −80° C. until analysis. One hundred microliters of plasma was spiked with 20 ng of an internal standard, "K6" (2,4-dihydroxybenzaldehyde (5-phenyl-2-pyrimidinyl)hydrazone). Proteins were precipitated by 200 µl of acetonitrile, and the samples spun at 10,000×g. The supernatant was resuspended to a final volume of 1 ml in 50:50 methanol:water containing 0.1% formic acid and filtered through a 0.45 micron filter. Samples were analyzed on an ABI/MDS Sciex 3200-Qtrap LC/MS/MS in positive MRM mode. The MRM transition monitored for LED209 was 384.0 to 94.1 for LED209 and 307.0 to 171.1 for the K6 internal standard. Electrospray ionization was used. A Shimadzu Prominence LC system was used with a 75×2 mm, 4 micron Phenomenex Synergi Fusion RP column. The flow rate was set at 0.5 ml/min. Forty five microliters of sample were injected and compound eluted with a stepwise gradient from 0-100% methanol in water. A standard curve was prepared by using blank murine plasma (Biomeda, Foster City, Calif.) spiked with various concentrations of LED209. The lower limit of detection was set at a signal to noise ratio of 3:1 when comparing spiked samples to blank plasma. Standard curves were constructed by plotting the analyte-to-internal standard ratio versus the concentration of LED209 in each samples and a power curve fit to the data. Back-calculation of concentrations indicated the curve was accurate to within 10% over 3 logs from 1000 to 10 ng/ml. Pharmacokinetic parameters for plasma were determined by using the noncompartmental analysis tool on the WinNonlin software package (Pharsight, Mountain View, Calif.).

Toxicology Studies. Three female CD-1 mice (~22 g) were treated qdX5 with 20 mg/kg LED209 by oral gavage in 0.2 ml of 5% DMSO/23% PEG400/2% Tween 80/70% 0.1 M sodium bicarbonate, pH 9. Three separate female CD-1 mice (~22 g) were treated qdX5 with vehicle only. Mice were weighed and observed daily. Three days after the final dose, the animals were weighed and sacrificed. Blood was taken for chemistry and complete blood counts (Charles River Laboratories, Wilmington, Mass.) and the organs weighed.

Preliminary toxicology assessment of LED209. LED209 (in 5% DMSO, 23% PEG400, 70% sodium bicarbonate pH 9, 2% Tween 80) was dosed daily for 5 days by oral gavage at 20 mg/kg in 3 female CD-1 mice in comparison to 3 mice given vehicle (5% DMSO, 23% PEG400, 70% sodium bicarbonate pH 9, 2% Tween 80) only. Mice weights (FIG. 16) and weights of organs (FIG. 10C) showed no significant differences between treated and untreated animals, with the exception of 4 on which the compound treated group failed to gain weight at the same rate as the vehicle treated group. Blinded review by a veterinary pathologist of hemotoxylin and eosin stained sections from duodenum, colon, liver, kidney, spleen, and heart did not reveal any observable pathology in either vehicle or compound treated mice.

Results

Figure 16:
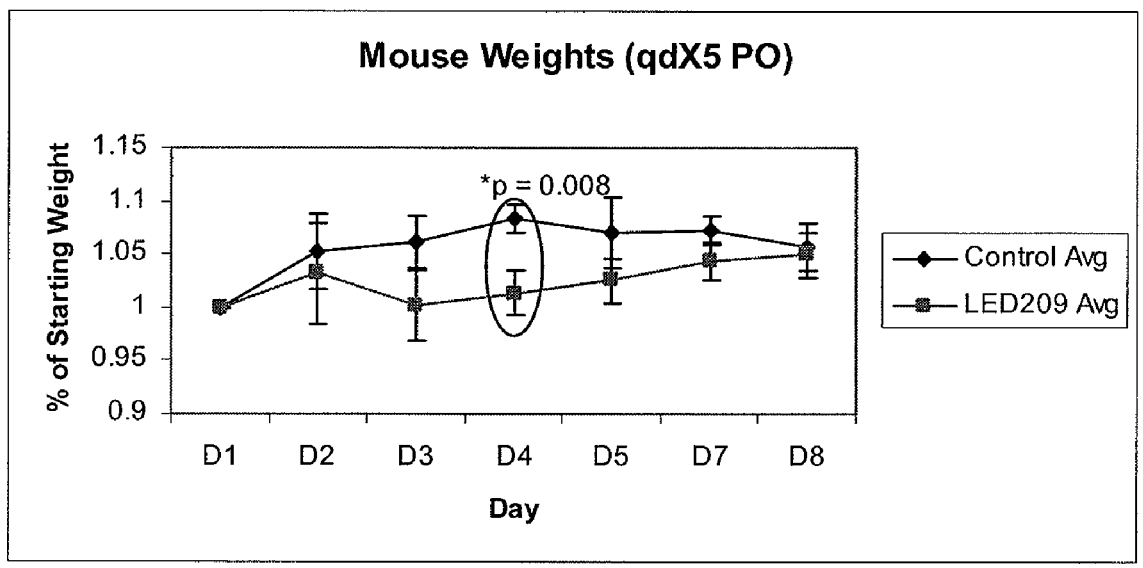
FIG. 16. Weights of mice treated with either vehicle alone or LED209 in a toxicology experiment.
Figure 17:
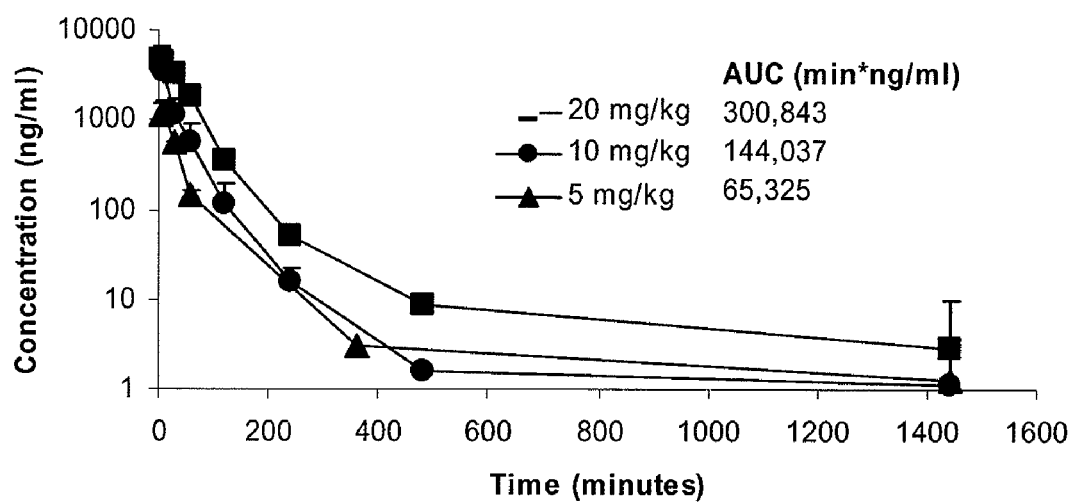
FIG. 17. The pharmacokinetics of LED209 are linear. CD-1 female mice were dosed with 20 mg/kg, 10 mg/kg, and 5 mg/kg LED209 as an IV bolus. At various times post-dosing, groups of three animals each were subject to a terminal bleed. Plasma was isolated and frozen at $-80°$ C. for later analysis. Protein was precipitated from 100 µl of plasma with 200 µl acetonitrile containing 20 ng of an internal standard. Samples were spun to isolate free compound and subject to electrospray LC/MS/MS analysis. Samples were quantitated using a standard curve prepared as described above in blank plasma. The data were evaluated using the noncompartmental model in WinNonLin (Pharsight). AUC increases proportionally with dose.

Since LED209 (compound 5) blocks epinephrine and NE triggering of QseC-mediated activation of virulence gene expression, there was a concern that this compound might also interfere with adrenergic signaling systems in the host. Using live cell-based assays (Jiang et al., 2007), LED209 was shown to not influence signaling through human β-adrenergic receptor isoforms (FIG. 10). Pharmacokinetic studies suggested that there are no inherent structural features that might limit its bioavailability or biocompatibility and revealed that LED209 is approximately 70% bioavailable when administered orally to mice (FIG. 10). Moreover, studies of LED209 in mice did not reveal any evidence of toxicity (FIGS. 16-18).

All of the methods and apparatuses disclosed and claimed herein can be made and executed without undue experimentation in light of the present disclosure. While the compositions and methods of this invention have been described in terms of preferred embodiments, it will be apparent to those of skill in the art that variations may be applied to the methods and apparatuses and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

JP Patent 03843586B2
JP Patent 11268421A2
U.S. Pat. No. 4,764,377
U.S. Pat. No. 5,324,746
U.S. Pat. No. 5,811,151
U.S. Pat. No. 5,281,170
U.S. Pat. No. 6,024,918
U.S. Pat. No. 6,737,247
U.S. Pat. No. 7,256,259
WO 2002/070467
WO 2003/028762
WO 2005/016873
Anonymous, In: *Applied Biosystems Prism* 7700 *Sequence Detection System*, User Bulletin #2. The Perkin-Elmer Corp., Norwalk, Conn., 1997.
Artusson and Karlsson, *Biochem. Biophys. Res. Commun.*, 175:880-885, 1991.
Azzi et al., *Mol. Pharmacol.*, 60:999-1007, 2001.
Bearson and Bearson, *Microb. Pathog.*, Oct. 12, 2007.
Beuzon et al., *Embo J.*, 19:3235, 2000.
Boyle et al., *J. Bacteriol.*, 189:1489-1495, 2007.
Bundgaard, *Drugs of the Future*, 16:443-458, 1991.
Bundgaard, In: *Design of Prodrugs*, 7-9, 21-24, Elsevier, Amsterdam, 1985.
Checroun et al, *Proc. Natl. Acad. Sci. USA*, 103:14578-14583, 2006.
Clarke and Sperandio, *Microbiology*, 57:1734-1749, 2005.
Clarke and Sperandio, *Molec. Microbiology*, 58:441-445, 2005.
Clarke et al., *Proc. Natl. Acad. Sci. USA*, 103:10420-10425, 2006.
Clemens et al., *Infect. Immun.*, 72:3204-3217, 2004.
Clemens et al., *Infect. Immun.*, 73:5892-5902, 2005.
Collmer and Keen, *Rev. Phytopathol.*, 24:383-409, 1986.
Crump et al., *Clin. Infect. Dis.*, 37:75-81, 2003.
Datsenko and Wanner, *Proc. Natl. Acad. Sci. USA*, 97:6640, 2000.
Daughtrey, M., Mar. 4, 2003 update of material presented by M. Daughtrey, Dept. of Plant Pathology, Cornell University in talk on "New and Re-emerging Diseases in 2003" at the Society of American Florists' 19th Annual Conference on Insect and Disease Management on Ornamentals on Feb. 23, 2003.
Davis et al., *Emerg. Infect. Dis.*, 5:802-806, 1999.
Dioum et al., *Science*, 298:2385, 2002.
Fortier et al., *Infect. Immun.*, 63:1478-1483, 1995.
Fuqua et al., *Annu Rev Microbiol.*, 50:727-751, 1996.
Glynn et al, *N. Engl. J. Med.*, 338:1333-1338, 1998.
Golovliov et al., *Infect. Immun.*, 65:2183-2189, 1997.
Greene and Wuts, In: *Protecting Groups in Organic Synthesis*, 3rd ed., John Wiley & Sons, Inc., 1999.
Hardy et al., In: *Drug Delivery to the Gastrointestinal Tract*, Chapter 7, Hardy et al. (Eds.), Ellis Horwood, Chichester, 1989.
Haywood et al., In: *Bacterial Wilt Disease: Molecular and Ecological Aspects*, Prior et al., Eds. Springer Verlag, Berlin, Germany, 1998.
Haywood, *Ralstonia solanacearum*. Encyclopedia of Microbiology, Vol. 4, Second Edition, Academic Press, NY, 2000.
Hidalgo, *Curr. Top. Med. Chem.*, 1:385-401, 2001.
Igo et al, *Genes Dev.*, 3:1725-1734, 1989.
Janausch et al., *Microbiology*, 150:877, 2004.
Jarvis et al., *Proc. Natl. Acad. Sci. USA*, 92:7996, 1995.
Jiang et al., *J. Biol. Chem.*, 282:10576, 2007.
Kaper et al., *Nat. Rev. Microbiol.*, 2:123, 2004.
Kaper and O'Brien, In: *Escherichia coli O157:H7 and other Shiga toxin-producing E. coli strains*, 1st Ed., ASM Press, Washington, D.C., 1998.
Kelman, North Carolina Agric. Exp. Stn. Tech. Bull. No. 99, 1953.
Kim et al., *Phytopathol.*, 92:S42, 2002.
Kimmitt et al., *Emerg. Infect. Dis.*, 6:458-465, 2000.
Kimmitt et al., *Lancet*, 353:1588-1589, 1999.
Knaggs et al, *Org. Biomol. Chem.*, 3:4002-4010, 2005.
Knutton et al., *Infect. Immun.*, 57:1290-1298, 1989.
Lee et al., *Infect. Immun.*, 74:4002-4013, 2006.
Lyon and Muir, *Chem. Biol.*, 10:1007-1021, 2003.
Merighi et al., *J. Bacteriol.*, 188:141, (2006).
Moreira et al., *J. Bacteriol.*, 188:3952-3961, 2006.
Nakaya et al, *Emerg. Infect. Dis.*, 9:255-257, 2003.
Official J. Eur. Communities L-235: 1 39, 1998.
Perna et al., *Nature*, 409:529-533, 2001.
Perveen et al., *Syn. Comm.*, 35:1663-1674, 2005.
Pirhonen, et al., *EMBO J.* 12:2467-2476, 1993.
Plant et al., *Nature*, 297:510-511, 1982.
Prior et al., *J. Appl. Microbiol.*, 91:614-620, 2001.
Pullen and Stuart, *JAMA*, 129:495-500, 1945.
Rasko et al. *Science*, 321:1078-1080, 2008.
Rasmussen and Givskov, *Microbiol.*, 152:895-904, 2006.
Reading et al., *J. Bacteriol.*, 189:2468-2476, 2007.
Remington's Pharmaceutical Sciences, 18th Ed. Mack Printing Company, pp. 1289-1329, 1990.
Ritchie et al., *Infect. Immun.*, 71:7129, 2003.
Robson et al., *Trends Biotechnol.*, 15:458-464, 1997.

Roychoudhury et al., *Proc. Natl. Acad. Sci. USA*, 90:965-969, 1993.
Russell et al., *J. Bacteriol.*, 189:5387-5392, 2007.
Samrakandi et al., *FEMS Microbiol. Lett.*, 237:9-17, 2004.
Sandstrom, *J. Chem. Technol. Biotechnol.*, 59:315-320, 1994.
Shehata et al., *Proc. Indian Natl Sci. Acad., Part A: Phys. Sci.*, 52:1413-19, 1986.
Sen et al., *Anal. Biochem.*, 307:280-286, 2002.
Sharp and Sperandio, *Infect. Immun.*, 75:2432-2440, 2007.
Sperandio et al, *Proc. Natl. Acad. Sci. USA*, 96:15196-15200, 2003.
Stead et al., In: *Brighton Crop Protection Conference—Pests and Diseases*, British Crop Protection Council, Farnham, Surrey, United Kingdom, Pages 1145-1152, 1996.
Stuart and Pullen, *Am. J Med. Sci.*, 210:223-236, 1945.
Syrjala et al., *J. Laryngol. Otol.*, 100:1169-1176, 1986.
Tannock et al., *Appl. Environ. Microbiol.*, 71:8419-25, 2005.
Tarnvik, *Rev. Infect. Dis.*, 11:440-451, 1989.
Ross, et al., *J. Biol. Chem.*, 282:10576-84, 2007.
Sambrook et al., *Molecular cloning: a laboratory manual*, Cold Spring Harbor Laboratory Press, 2$^{nd}$ Ed., 1989
Sperandio et al, *Proc. Natl. Acad. Sci. USA*, 100:8951-8956, 2003.
Sperandio et al., *Mol. Microbiol.*, 43:809, 2002.
Sperandio et al., *Proc. Natl. Acad. Sci. USA*, 96:15196, 1999.
Tarr et al., *N. Engl. J. Med.*, 347:2171, 2002.
Van Breemen and Li, *Expert Opin. Drug Metab. Toxicol.*, 1:175-185, 2005.
von Bodman et al, *Ann. Rev. Phytopath.*, 41:455-482, 2003.
Wagner et al., *J. Bacteriol.*, 183:2081, 2001.
Walter and Sperandio, *Infect. Immun.*, 74:5445-5455, 2006.
Walters et al., *J. Bacter.*, 188:5668-5681, 2006.
Weill et al., *Emerg. Infect. Dis.*, 12:1611-1612, 2006.
Weiss et al., *Proc. Natl. Acad. Sci. USA*, 104:6037-6042, 2007.
Williamson et al., *Phytopathol.*, 91:S75, 2001.
Yee, *Pharm. Res.*, 14:763-766, 1997.
Zhang et al., *J. Infect. Dis.*, 181:644, 2000.
Zimmerman et al, *J. Biol. Chem.*, 273:19650-5, 1998.

---

What is claimed is:

1. A method of treating a bacterial infection in a subject, comprising administering to the subject an effective amount of a compound having the formula:

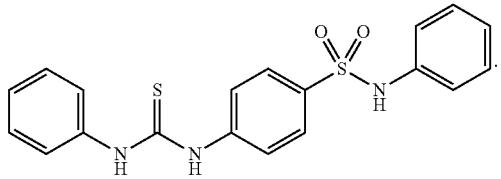

2. The method of claim 1, wherein the bacterial infection is caused by a mammalian bacterial or a plant bacterial pathogen.

3. The method of claim 1, wherein the bacterial infection is caused by at least one of the organisms *Actinobacillus pleuropneumoniae, Burkholderia cepacia, Chromobacter violaceum, Coxiella burnetti, E. coli, Erwinia carotovora, Francisella tularensis, Haemophilus influenzae, Pasteurella multocida, Pseudomonas aeruginosa, Pseudomonas fluorescens, Ralstonia solanacearum, Shigella flexneri, Salmonella typhi, Salmonella typhimurium, Vibrio cholerae, Vibrio parahaemoliticus, Vibrio vulnificus, Yersinia pestis,* or *Yersinia pseudotuberculosis.*

4. The method of claim 3, wherein the *E. coli* organism is a pathogenic *E. coli.*

5. The method of claim 4, wherein the *E. coli* organism is enterohemorrhagic *E. coli.*

6. The method of claim 4, wherein the *E. coli* organism is uropathogenic *E. coli.*

7. The method of claim 1, wherein the bacterial infection is caused by at least one of the organisms enterotoxigenic *E. coli,* enteropathogenic *E. coli.,* enteroaggregative *E. coli,* enteroinvasive *E. coli,* diffuse adhering *E. coli, E. coli* K1, *Acinetobacter, Bordetella parapertussis, Burkolderia phymatum, Citrobacter, Enterobacter, Klebsiella pneumonia, Legionella pneumophila, Ralstonia euthropha, Yersinia enterocolitica,* or *Yersinia mollareti.*

8. The method of claim 7, wherein the *Acinetobacter* organism is *Acinetobacter baumannii.*

9. The method of claim 1, wherein the bacterial infection is caused by a bacteria that is a multi-drug resistant bacteria.

10. The method of claim 1, wherein the compound is comprised in a pharmaceutically acceptable composition.

11. The method of claim 10, wherein the composition is absorbable.

12. The method of claim 10, wherein the composition is nonabsorbable.

13. The method of claim 10, wherein the pharmaceutically acceptable composition comprises an enteric coating.

14. The method of claim 1, wherein the compound is administered orally, via inhalation, intraperitoneally, intravenously, intramuscularly, rectally, buccally, transdermally, vaginally, or via eye or ear drops.

15. The method of claim 14, wherein the compound is administered in an amount of about 0.1 to about 50 mg/kg body weight.

16. The method of claim 15, wherein the compound is administered in an amount of about 10 to about 30 mg/kg body weight.

17. A method of treating bacterial infection in a subject, comprising administering to the subject an effective amount of a compound having the formula:

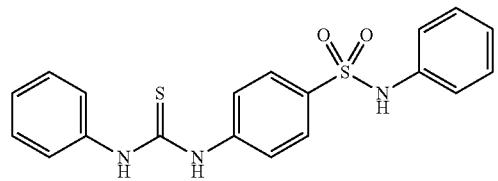

wherein the bacterial infection is caused by a bacterium that has a QseC kinase or QseC kinase homolog.

18. A method of treating bacterial infection in a subject, comprising administering to the subject an effective amount of a compound having the formula:

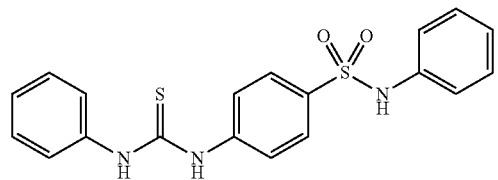

wherein the compound minimally affects adrenergic receptor activity.

* * * * *

SEQUENCE LISTING

```
<160> NUMBER OF SEQ ID NOS: 30

<210> SEQ ID NO 1
<211> LENGTH: 19
<212> TYPE: DNA
<213> ORGANISM: Artificial
<220> FEATURE:
<223> OTHER INFORMATION: Synthetic primer

<400> SEQUENCE: 1
cgaccaggtc tgcccttct                                                   19

<210> SEQ ID NO 2
<211> LENGTH: 17
<212> TYPE: DNA
<213> ORGANISM: Artificial
<220> FEATURE:
<223> OTHER INFORMATION: Synthetic primer

<400> SEQUENCE: 2
gccggaactc atcgaaa                                                     17

<210> SEQ ID NO 3
<211> LENGTH: 21
<212> TYPE: DNA
<213> ORGANISM: Artificial
<220> FEATURE:
<223> OTHER INFORMATION: Synthetic primer

<400> SEQUENCE: 3
tccatcgaca aattccgttc t                                                21

<210> SEQ ID NO 4
<211> LENGTH: 18
<212> TYPE: DNA
<213> ORGANISM: Artificial
<220> FEATURE:
<223> OTHER INFORMATION: Synthetic primer

<400> SEQUENCE: 4
tggtgactgc ggaatcca                                                    18
```

```
<210> SEQ ID NO 5
<211> LENGTH: 16
<212> TYPE: DNA
<213> ORGANISM: Artificial
<220> FEATURE:
<223> OTHER INFORMATION: Synthetic primer

<400> SEQUENCE: 5
accccaccgg gcagtt                                                    16

<210> SEQ ID NO 6
<211> LENGTH: 19
<212> TYPE: DNA
<213> ORGANISM: Artificial
<220> FEATURE:
<223> OTHER INFORMATION: Synthetic primer

<400> SEQUENCE: 6
ggtcaaaacg cgcctgata                                                 19

<210> SEQ ID NO 7
<211> LENGTH: 21
<212> TYPE: DNA
<213> ORGANISM: Artificial
<220> FEATURE:
<223> OTHER INFORMATION: Synthetic primer

<400> SEQUENCE: 7
tttcgtctcg gcataaatga a                                              21

<210> SEQ ID NO 8
<211> LENGTH: 21
<212> TYPE: DNA
<213> ORGANISM: Artificial
<220> FEATURE:
<223> OTHER INFORMATION: Synthetic primer

<400> SEQUENCE: 8
tcattcagca agcgtgttga c                                              21

<210> SEQ ID NO 9
<211> LENGTH: 19
<212> TYPE: DNA
<213> ORGANISM: Artificial
<220> FEATURE:
<223> OTHER INFORMATION: Synthetic primer

<400> SEQUENCE: 9
gctggccttg gtttgatca                                                 19

<210> SEQ ID NO 10
<211> LENGTH: 21
<212> TYPE: DNA
<213> ORGANISM: Artificial
<220> FEATURE:
<223> OTHER INFORMATION: Synthetic primer

<400> SEQUENCE: 10
gcggagatga cttcagcact t                                              21

<210> SEQ ID NO 11
<211> LENGTH: 20
<212> TYPE: DNA
<213> ORGANISM: Artificial
<220> FEATURE:
<223> OTHER INFORMATION: Synthetic primer
```

<400> SEQUENCE: 11
gcgctcatct tcttccgaat                                           20

<210> SEQ ID NO 12
<211> LENGTH: 18
<212> TYPE: DNA
<213> ORGANISM: Artificial
<220> FEATURE:
<223> OTHER INFORMATION: Synthetic primer

<400> SEQUENCE: 12
cgcggtcgtg gttatgtg                                             18

<210> SEQ ID NO 13
<211> LENGTH: 24
<212> TYPE: DNA
<213> ORGANISM: Artificial
<220> FEATURE:
<223> OTHER INFORMATION: Synthetic primer

<400> SEQUENCE: 13
gtcaaaccgg aaatgacaaa ctaa                                      24

<210> SEQ ID NO 14
<211> LENGTH: 17
<212> TYPE: DNA
<213> ORGANISM: Artificial
<220> FEATURE:
<223> OTHER INFORMATION: Synthetic primer

<400> SEQUENCE: 14
accctgccgc agatggt                                              17

<210> SEQ ID NO 15
<211> LENGTH: 26
<212> TYPE: DNA
<213> ORGANISM: Artificial
<220> FEATURE:
<223> OTHER INFORMATION: Synthetic primer

<400> SEQUENCE: 15
gttgtctaat ggaaccgata atatcg                                    26

<210> SEQ ID NO 16
<211> LENGTH: 20
<212> TYPE: DNA
<213> ORGANISM: Artificial
<220> FEATURE:
<223> OTHER INFORMATION: Synthetic primer

<400> SEQUENCE: 16
ctaccccctc ccttcgacat                                           20

<210> SEQ ID NO 17
<211> LENGTH: 21
<212> TYPE: DNA
<213> ORGANISM: Artificial
<220> FEATURE:
<223> OTHER INFORMATION: Synthetic primer

<400> SEQUENCE: 17
acttcattgc gcccatacac t                                         21

```
<210> SEQ ID NO 18
<211> LENGTH: 20
<212> TYPE: DNA
<213> ORGANISM: Artificial
<220> FEATURE:
<223> OTHER INFORMATION: Synthetic primer

<400> SEQUENCE: 18
cgtcagggcc tcacgataga                                          20

<210> SEQ ID NO 19
<211> LENGTH: 20
<212> TYPE: DNA
<213> ORGANISM: Artificial
<220> FEATURE:
<223> OTHER INFORMATION: Synthetic primer

<400> SEQUENCE: 19
gcgctcatct tcttccgaat                                          20

<210> SEQ ID NO 20
<211> LENGTH: 18
<212> TYPE: DNA
<213> ORGANISM: Artificial
<220> FEATURE:
<223> OTHER INFORMATION: Synthetic primer

<400> SEQUENCE: 20
cgcggtcgtg gttatgtg                                            18

<210> SEQ ID NO 21
<211> LENGTH: 25
<212> TYPE: DNA
<213> ORGANISM: Artificial
<220> FEATURE:
<223> OTHER INFORMATION: Synthetic primer

<400> SEQUENCE: 21
cgtacctcaa gagaatatcg aacgt                                    25

<210> SEQ ID NO 22
<211> LENGTH: 23
<212> TYPE: DNA
<213> ORGANISM: Artificial
<220> FEATURE:
<223> OTHER INFORMATION: Synthetic primer

<400> SEQUENCE: 22
tgcgacgatt gctaaaccta gtc                                      23

<210> SEQ ID NO 23
<211> LENGTH: 28
<212> TYPE: DNA
<213> ORGANISM: Artificial
<220> FEATURE:
<223> OTHER INFORMATION: Synthetic primer

<400> SEQUENCE: 23
aaaaaggaga atgattatga gtgagatg                                 28

<210> SEQ ID NO 24
<211> LENGTH: 24
<212> TYPE: DNA
<213> ORGANISM: Artificial
<220> FEATURE:
<223> OTHER INFORMATION: Synthetic primer
```

```
<400> SEQUENCE: 24
tgcagtagga tcagttctca catg                                            24

<210> SEQ ID NO 25
<211> LENGTH: 27
<212> TYPE: DNA
<213> ORGANISM: Artificial
<220> FEATURE:
<223> OTHER INFORMATION: Synthetic primer

<400> SEQUENCE: 25
tgagttaatt tcaaactctg ccatatc                                         27

<210> SEQ ID NO 26
<211> LENGTH: 24
<212> TYPE: DNA
<213> ORGANISM: Artificial
<220> FEATURE:
<223> OTHER INFORMATION: Synthetic primer

<400> SEQUENCE: 26
gtttgggtat atgccatttc acag                                            24

<210> SEQ ID NO 27
<211> LENGTH: 22
<212> TYPE: DNA
<213> ORGANISM: Artificial
<220> FEATURE:
<223> OTHER INFORMATION: Synthetic primer

<400> SEQUENCE: 27
ctcgagtgat agcgcaacat tc                                              22

<210> SEQ ID NO 28
<211> LENGTH: 26
<212> TYPE: DNA
<213> ORGANISM: Artificial
<220> FEATURE:
<223> OTHER INFORMATION: Synthetic primer

<400> SEQUENCE: 28
tgttgatcca ttaggtattt gaggaa                                          26

<210> SEQ ID NO 29
<211> LENGTH: 21
<212> TYPE: DNA
<213> ORGANISM: Artificial
<220> FEATURE:
<223> OTHER INFORMATION: Synthetic primer

<400> SEQUENCE: 29
cgataccaac cgagcttgag a                                               21

<210> SEQ ID NO 30
<211> LENGTH: 29
<212> TYPE: DNA
<213> ORGANISM: Artificial
<220> FEATURE:
<223> OTHER INFORMATION: Synthetic primer

<400> SEQUENCE: 30
cctcaaaagc aactcttttt aataggatt                                       29
```